(12) United States Patent
Tafesse

(10) Patent No.: US 8,759,362 B2
(45) Date of Patent: Jun. 24, 2014

(54) BICYCLOHETEROARYL COMPOUNDS AND THEIR USE AS TRPV1 LIGANDS

(75) Inventor: Laykea Tafesse, Robbinsville, NJ (US)

(73) Assignee: Purdue Pharma L.P., Stamford, CT (US)

( * ) Notice: Subject to any disclaimer, the term of this patent is extended or adjusted under 35 U.S.C. 154(b) by 905 days.

(21) Appl. No.: 12/603,719

(22) Filed: Oct. 22, 2009

(65) Prior Publication Data
US 2010/0130499 A1  May 27, 2010

Related U.S. Application Data

(60) Provisional application No. 61/108,158, filed on Oct. 24, 2008.

(51) Int. Cl.
| C07D 471/04 | (2006.01) |
| A61K 31/519 | (2006.01) |
| A61P 23/00 | (2006.01) |
| A61P 1/00 | (2006.01) |
| A61P 1/04 | (2006.01) |

(52) U.S. Cl.
USPC .................... 514/264.1; 514/264.11; 544/279

(58) Field of Classification Search
USPC .......................... 544/278; 514/264.11, 264.1
See application file for complete search history.

(56) References Cited

U.S. PATENT DOCUMENTS

| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,797,419 A | 1/1989 | Moos et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,529,998 A | 6/1996 | Habich et al. |
| 5,591,767 A | 1/1997 | Mohr et al. |
| 5,639,476 A | 6/1997 | Oshlack et al. |
| 5,674,533 A | 10/1997 | Santus et al. |
| 5,698,155 A | 12/1997 | Grosswald et al. |
| 5,733,566 A | 3/1998 | Lewis |
| 5,891,889 A | 4/1999 | Anthony et al. |
| 6,136,839 A | 10/2000 | Isakson et al. |
| 6,150,129 A | 11/2000 | Cook et al. |
| 6,239,267 B1 | 5/2001 | Duckworth et al. |
| 6,248,756 B1 | 6/2001 | Anthony et al. |
| 6,335,180 B1 | 1/2002 | Julius et al. |
| 6,406,908 B1 | 6/2002 | McIntyre et al. |
| 6,414,149 B1 * | 7/2002 | Chu-Moyer et al. ........... 544/295 |
| 6,482,479 B1 | 11/2002 | Dübal et al. |
| 6,610,677 B2 * | 8/2003 | Davies et al. ................. 514/183 |
| 6,653,300 B2 * | 11/2003 | Bebbington et al. ........... 514/183 |
| 6,723,730 B2 | 4/2004 | Bakthavatchalam et al. |
| 6,887,870 B1 | 5/2005 | Ahmad et al. |
| 6,924,290 B2 * | 8/2005 | Nagarathnam et al. ..... 514/258.1 |
| 7,105,667 B2 * | 9/2006 | Pitts et al. ..................... 544/279 |
| 7,312,330 B2 * | 12/2007 | Kelly et al. ..................... 544/279 |
| 7,432,275 B2 | 10/2008 | Bakthavatchalam et al. |
| 7,488,740 B2 | 2/2009 | Bakthavatchalam et al. |
| 7,524,852 B2 * | 4/2009 | Arai et al. ................ 514/264.11 |
| 7,531,558 B2 | 5/2009 | Macdonald et al. |
| 7,935,702 B2 | 5/2011 | Bakthavatchalam et al. |
| 2003/0104974 A1 * | 6/2003 | Pitts et al. ......................... 514/1 |
| 2003/0153568 A1 | 8/2003 | Cusack et al. |
| 2004/0102450 A1 | 5/2004 | Ewing et al. |
| 2004/0152690 A1 | 8/2004 | Balan et al. |
| 2004/0176443 A1 | 9/2004 | Bakthavatchalam et al. |
| 2004/0186111 A1 | 9/2004 | Sun et al. |
| 2005/0038023 A1 * | 2/2005 | Bebbington et al. ........ 514/227.8 |
| 2005/0085512 A1 | 4/2005 | Lee et al. |

(Continued)

FOREIGN PATENT DOCUMENTS

| DE | 19934799 A1 | 2/2001 |
| EP | WO 0132632 | * 5/2001 |

(Continued)

OTHER PUBLICATIONS

Kuznetsov, et al., Chemistry of Heterocyclic Compounds (New York, NY, US) (2007), 43(5), 640-645.*
Kuznetsov, et al., Chemistry of Heterocyclic Compounds (New York, NY, US) (2007), 43(10), 1320-1324.*
Bingham et al., "Over one hundred solvates of sulfathiazole,"*Chem. Comm.*, pp. 603-604 (2001).
Buchwald et al., "Long-term, Continuous Intravenous Heparin Administration by an Implantable Infusion Pump in Ambulatory Patients with Recurrent Venous Thrombosis,"0 *Surgery* 88:507-516 (1980).

(Continued)

*Primary Examiner* — Emily Bernhardt
*Assistant Examiner* — Cecilia M Jaisle
(74) *Attorney, Agent, or Firm* — Dechert LLP

(57) ABSTRACT

The invention relates to compounds of formula I

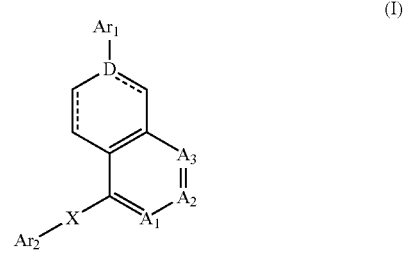

(I)

and pharmaceutically acceptable derivatives thereof, compositions comprising an effective amount of a compound of formula I or a pharmaceutically acceptable derivative thereof, and methods for treating or preventing a condition such as pain, UI, an ulcer, IBD and IBS, comprising administering to an animal in need thereof an effective amount of a compound of formula I or a pharmaceutically acceptable derivative thereof.

21 Claims, No Drawings

(56) References Cited

U.S. PATENT DOCUMENTS

| | | | |
|---|---|---|---|
| 2005/0165015 A1 | 7/2005 | Ncube et al. | |
| 2005/0165032 A1* | 7/2005 | Norman et al. | 514/264.11 |
| 2005/0192293 A1 | 9/2005 | Kelly et al. | |
| 2005/0215572 A1 | 9/2005 | Kelly et al. | |
| 2005/0277643 A1* | 12/2005 | Kelly et al. | 514/243 |
| 2006/0100245 A1 | 5/2006 | Bakthavatchalam et al. | |
| 2006/0128717 A1 | 6/2006 | Sun et al. | |
| 2006/0199824 A1 | 9/2006 | Sun et al. | |
| 2006/0235022 A1 | 10/2006 | Sun | |
| 2006/0241117 A1 | 10/2006 | Sun | |
| 2009/0170867 A1 | 7/2009 | Kurose | |
| 2009/0170868 A1 | 7/2009 | Tafesse | |
| 2009/0176796 A1 | 7/2009 | Tafesse | |
| 2011/0245209 A1 | 10/2011 | Xiao et al. | |
| 2011/0246209 A1* | 10/2011 | Jagannathan et al. | 705/1.1 |
| 2012/0040936 A1* | 2/2012 | Kanno et al. | 514/82 |
| 2012/0046300 A1* | 2/2012 | Hennequin | 514/252.17 |
| 2012/0065183 A1* | 3/2012 | Cooke et al. | 514/210.18 |

FOREIGN PATENT DOCUMENTS

| | | | |
|---|---|---|---|
| EP | WO 2005042537 | * | 5/2005 |
| EP | WO 2006062981 | * | 12/2005 |
| EP | WO 2006074057 | * | 12/2005 |
| EP | WO 2008005538 | * | 1/2008 |
| EP | WO 2009017838 | * | 2/2009 |
| JP | 11-199573 | | 7/1999 |
| WO | WO 97/28140 A1 | | 10/1997 |
| WO | WO 98/31669 A1 | | 7/1998 |
| WO | WO 98/31677 A1 | | 7/1998 |
| WO | WO 2008/133973 A1 | | 11/2008 |

OTHER PUBLICATIONS

Bundgaard et al., "Glycolamide Esters as Biolabile Prodrugs of Carboxylic Acid Agents: Synthesis, Stability, Bioconversion, and Physicochemical Properties," *J. Pharmaceut Sci.* 77(4):285-298 (1988).

Bundgaard "(C) Means to Enhance Penetration (1) Prodrugs as a means to improve the delivery of peptide drugs," *Advanced Drug Delivery Revs.* 8:1-38 (1992).

Chu-Moyer et al., "Orally-Effective: Long-Acting Sorbitol Dehydrogenase Inhibitors: Synthesis, Structure-Activity Relationships, and in Vivo Evaluations of Novel Heterocycle-Substituted Piperazino-Pyrimidines," *J. Med. Chem.* 45:511-528 (2002).

During et al., "Controlled Release of iDopamine from a Polymeric Brain Implant: In Vivo Characterization," *Ann. Neurol.* 25:351-356 (1989).

Gavva et al., "AMG 9810 [(E)-3-(4-t-Butylphenyl)-N-(2,3-dihydrobenzo[b][1,4]dioxin-6-yl)acrylamide], a Novel Vanilloid Receptor 1 (TRPV1) Antagonist with Antihyperalgesic Properties," *J. Pharmacol. Exp. Ther.* 313:474-484 (2005).

Gharat et al., "Medicinal Chemistry of the Vanilloid (Capsaicin) TRPVI Receptor: Current Knowledge and Future Perspectives," *Drug Devel. Res.* 68:477-497 (2007).

Greene et al., *Protective Groups in Organic Synthesis*, 2$^{nd}$ Ed., John Wiley & Sons, New York (1991).

Hargreaves et al., "A new and sensitive method for measuring thermal nociception in cutaneous hyperalgesia," *Pain* 31(1):77-88 (1988).

Kakeya, et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* 32:692-698 (1984).

Khadse et al., "Synthesis and Study of 2-($N^4$-substituted-$N^1$-piperazinyl)-pyrido-(3,2-d)-thiazoles, 5-nitro-2-($N^4$-substituted-$N^1$-piperazinyl)-Benzthiazoles and allied compounds as possible anthelmintic agents," *Bull. Haff. Inst.* 1(3):27-32 (1975).

Langer et al., "Classes of Systems," *Medical Applications Controlled Release* vol. 1, CRC Press, Boca Raton, FL (1984).

March, *March's Advanced Organic Chemistry: Reaction Mechanisms and Structure*, pp. 891-892, 4$^{th}$ Ed. (1992).

Sharpless et al., "The osmium-catalyzed asymmetric dihydroxylation: A new ligand class and a process improvement," *J. Org. Chem.* 57:2768-2771 (1992).

Smith et al., *March's Advanced Organic Chemistry: Reaction Mechanisms and Structure*, pp. 805-807, 5$^{th}$ Ed. (2001).

Treat et al., "Liposome Encapsulated Doxorubicin Prelimi nary Results of Phase I and Phase II Trials," pp. 317-327 and 353-365 in *Liposomes in the Therapy of Infectious Disease and Cancer* (1989).

Van Tonder et al., "Preparation and Physicochemical Characterization of 5 Niclosamide Solvates and I Hemisolvate," *AAPS Pharm. Sci. Tech.* 5(1), Article 12 (2004).

Bartho et al., "Involvement of Capsaicin-Sensitive Neurones in Hyperalgesia and Enhanced Opioid Antinociception in Inflammation," *Naunyn-Schmiedeberg's Archives Pharmacol.* 342:666-670 (1990).

Berkow et al., "Irritable Bowel Syndrome," *The Merck Manual of Medical Information*, pp. 525-526 (1997).

Berkow et al., "Crohn's Disease," *The Merck Manual of Medical Information*, pp. 528-530 (1997).

Bingham et al., "Over one hundred solvates of sulfathiazole," *Chem. Comm.*, pp. 603-604 (2001).

Buchwald et al., "Long-term, Continuous Intravenous Heparin Administration by an Implantable Infusion Pump in Ambulatory Patients with Recurrent Venous Thrombosis," *Surgery* 88:507-516 (1980).

Bundgaard, *Design of Prodrugs*, Elsevier (1985).

Bundgaard et al., "Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988).

Bundgaard, "Design and Application of Prodrugs," Chapter 5, pp. 113-191 in *A Textbook of Drug Design and Development*, Krogsgaard-Larsen and Bundgaard Eds., Harwood Academic Publishers (1991).

Bundgaard, "(C) Means to Enhance Penetration (1) Prodrugs as a means to improve the delivery of peptide drugs," *Advanced Drug Delivery Revs.* 8:1-38 (1992).

Caira et al., "Preparation and Crystal Characterization of a Polymorph, a Monohydrate, and an Ethyl Acetate Solvate of the Antifungal Fluconazole," *J. Pharmaceut. Sci.* 93(3):601-611 (2004).

D'Amour et al., "A Method for Determining Loss of Pain Sensation," *J. Pharmacol. Exp. Ther.* 72:74-79 (1941).

Di Marzo et al., "Endovanilloid signaling in pain," *Current Opinion in Neurobiology* 12:372-379 (2002).

"Drug and Enzyme Targeting, Part A," Widder et al., Eds., vol. 112 in *Methods in Enzymology*, Academic Press (1985).

During et al., "Controlled Release of Dopamine from a Polymeric Brain Implant: In Vivo Characterization," *Ann. Neurol.* 25:351-356 (1989).

Filer, "The Preparation and Characterization of Tritiated Neurochemicals," Chapter 6, pp. 155-192 in *Isotopes in the Physical and Biomedical Sciences*, vol. 1, Labeled Compounds (Part A) (1987).

Foley, "Pain," *Cecil Textbook of Medicine* pp. 100-107 (Bennett and Plum, Eds. 20$^{th}$ Ed., 1996).

Gavva et al., "AMG 9810 [(E)-3-(4-t-Butylphenyl)-N-(2,3-dihydrobenzo[b][1,4] dioxin-6-yl)acrylamide], a Novel Vanilloid Receptor 1 (TRPV1) Antagonist with Antihyperalgesic Properties," *J. Pharmacol. Exp. Ther.* 313:474-484 (2005).

Gharat et al., "Medicinal Chemistry of the Vanilloid (Capsaicin) TRPV1 Receptor: Current Knowledge and Future Perspectives," *Drug Devel. Res.* 68:477-497 (2007).

Goodson, "Dental Applications," pp. 115-138 in *Medical Applications of Controlled Release*, vol. 2, Applications and Evaluation, Langer and Wise, Eds., CRC Press (1984).

Greene et al., *Protecting Groups in Organic Synthesis*, 2$^{nd}$ Ed., John Wiley & Sons, New York (1991).

Grupp et al., "Protection against Hypoxia-reoxygenation in the Absence of Poly (ADP-ribose) Synthetase in Isolated Working Hearts," *J. Mol. Cell. Cardiol.* 31:297-303 (1999).

(56) References Cited

OTHER PUBLICATIONS

Hanson, "Analgesic, Antipyretic and Anti-Inflammatory Drugs," pp. 1196-1221 in *Remington: The Science and Practice of Pharmacy*, vol. 2 (Gennaro Ed. 19$^{th}$ Ed. 1995).

Hargreaves et al., "A new and sensitive method for measuring thermal nociception in cutaneous hyperalgesia," *Pain* 32(1):77-88 (1988).

Howard et al., "Intracerebral drug delivery in rats with lesion-induced memory deficits," *J. Neurosurg.* 71:105 (1989).

Insel, "Analgesic-Antipyretic and Anti-inflammatory Agents and Drugs Employed in the Treatment of Gout," pp. 617-657 in *Goodman & Gilman's The Pharmacological Basis of Therapeutics* (Goodman et al., Eds., 9$^{th}$ Ed., McGraw-Hill, New York 1996).

Kakeya, et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* 32:692-698 (1984).

Kim et al., "An experimental model for peripheral neuropathy produced by segmental spinal nerve ligation in the rat," *Pain* 50(3):355-363 (1992).

Langer et al., "Chemical and Physical Structure of Polymers as Carriers for Controlled Release of Bioactive Agents: A Review," *J. Macromol. Sci. Rev. Macromol. Chem.* C23(1):61-126 (1983).

Langer et al., "Classes of Systems," *Medical Applications of Controlled Release* vol. I, CRC Press, Boca Raton, FL (1984).

Langer, "New Methods of Drug Delivery," *Science* 249:1527-1533 (1990).

Levy, "Inhibition of Calcification of Bioprosthetic Heart Valves by Local Controlled-Release Diphosphonate," *Science* 228:190-192 (1985).

Ognyanov et al., "Design of Potent, Orally Available Antagonists of the Transient Receptor Potential Vanilloid 1. Structure-Activity Relationships of 2-Piperazin-1-yl-1H-benzimidazoles," *J. Med. Chem.* 49:3719-3742 (2006).

Radebough et al., "Preformulation," pp. 1447-1676 in *Remington's Pharmaceutical Sciences* (Gennaro, Ed., 19$^{th}$ Ed., 1995).

Saudek et al., "A Preliminary Trial of the Programmable Implantable Medication System for Insulin Delivery," *New Engl. J. Med.* 321:574-579 (1989).

Sefton, "Implantable Pumps," *CRC Crit. Rev. Biomed. Eng.* 14(3):201-240 (1987).

Seltzer et al., "A novel behavioral model of neuropathic pain disorders produced in rats by partial sciatic nerve injury," *Pain* 43:205-218 (1990).

Sharpless et al., "The osmium-catalyzed asymmetric dihydroxylation: A new ligand class and a process improvement," *J. Org. Chem.* 57:2768-2771 (1992).

Smolen et al., "Drug Product Design and Performance," *Controlled Drug Bioavailability* vol. 1, John Wiley & Sons, New York (1984).

Stein, et al., "Unilateral Inflammation of the Hindpaw in Rats as a Model of Prolonged Noxious Stimulation: Alterations in Behavior and Nociceptive Thresholds," *Pharmacol. Biochem. & Behavior* 31:451-455 (1988).

Szallasi et al, "The vanilloid receptor TRPV1: 10 years from channel cloning to antagonist proof-of-concept," *Nature Revs. Drug Discovery* 6:357-372 & Corrigendum (2007).

Treat et al., "Liposome Encapsulated Doxorubicin Preliminary Results of Phase I and Phase II Trials," pp. 317-327 and 353-365 in *Liposomes in the Therapy of Infectious Disease and Cancer* (1989).

Van Tonder et al., "Preparation and Physicochemical Characterization of 5 Niclosamide Solvates and 1 Hemisolvate," *AAPS Pharm. Sci. Tech.* 5(1), Article 12 (2004).

Office Action dated Jun. 3, 2011 for U.S. Appl. No. 12/603,733.

Office Action dated Jan. 13, 2012 for U.S. Appl. No. 12/603,733.

Advisory Action dated Apr. 5, 2012 for U.S. Appl. No. 12/603,733.

\* cited by examiner

SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 1
gaagatcttc gctggttgca cactgggcca ca                              32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaagatcttc ggggacagtg acggttggat gt                              32

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatccagca aggatgaaga aatgg                                      25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtctgcgtg acgtcctcac ttct                                       24
```

BICYCLOHETEROARYL COMPOUNDS AND THEIR USE AS TRPV1 LIGANDS This application claims the benefit of U.S. provisional application No. 61/108,158, filed Oct. 24, 2008, the disclosure of which is incorporated by reference herein in its entirety.

1. FIELD OF THE INVENTION

The invention relates to compounds of formulae I-IV, and pharmaceutically acceptable derivatives thereof, compositions comprising an effective amount of a compound of formulae I-IV and methods for treating or preventing a condition such as nociceptive or neuropathic pain, urinary incontinence ("UI"), an ulcer, inflammatory bowel disease ("IBD"), and irritable bowel syndrome ("IBS"), comprising administering to an animal in need thereof an effective amount of a compound of formulae I-IV.

2. BACKGROUND OF THE INVENTION

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, *Pain, in Cecil Textbook of Medicine* 100-107 (J. C. Bennett and F. Plum Eds., 20th Ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or central nervous system and is maintained by aberrant somatosensory processing. There is a large body of evidence relating activity at vanilloid receptors (V. Di Marzo et al., *Current Opinion in Neurobiology* 12:372-379 (2002)) to pain processing.

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id. In addition to the above-listed treatments, neuropathic pain, which can be difficult to treat, has also been treated with anti-epileptics (e.g., gabapentin, carbamazepine, valproic acid, topiramate, phenytoin), NMDA antagonists (e.g., ketamine, dextromethorphan), topical lidocaine (for post-herpetic neuralgia), and tricyclic antidepressants (e.g., fluoxetine, sertraline and amitriptyline).

Urinary incontinence ("UI") is uncontrollable urination, generally caused by bladder-detrusor-muscle instability. UI affects people of all ages and levels of physical health, both in health care settings and in the community at large. Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle over activity.

None of the existing commercial drug treatments for UI has achieved complete success in all classes of UI patients, nor has treatment occurred without significant adverse side effects.

Treatment of ulcers typically involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Inflammatory-bowel disease ("IBD") is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease typically affects the full thickness of the intestinal wall. Generally the disease affects the lowest portion of the small intestine (ileum) and the large intestine, but can occur in any part of the digestive tract.

Cramps and diarrhea, side effects associated with Crohn's disease, can be relieved by anticholinergic drugs, diphenoxylate, loperamide, deodorized opium tincture, or codeine.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. *The Merck Manual of Medical Information* 528-530 (R. Berkow Ed., 1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30; however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely throughout the large intestine. The cause of ulcerative colitis is unknown.

Treatment of ulcerative colitis is directed to controlling inflammation, reducing symptoms, and replacing lost fluids and nutrients. Anticholinergic drugs and low doses of diphenoxylate or loperamide are administered for treating mild diarrhea. For more intense diarrhea higher doses of diphenoxylate or loperamide, or deodorized opium tincture or codeine are administered.

Irritable-bowel syndrome ("IBS") is a disorder of motility of the entire gastrointestinal tract, causing abdominal pain, constipation, and/or diarrhea. IBS affects three-times more women than men. In IBS, stimuli such as stress, diet, drugs, hormones, or irritants can cause the gastrointestinal tract to contract abnormally. During an episode of IBS, contractions of the gastrointestinal tract become stronger and more frequent, resulting in the rapid transit of food and feces through the small intestine, often leading to diarrhea. Cramps result from the strong contractions of the large intestine and increased sensitivity of pain receptors in the large intestine.

Treatment of MS typically involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. *The Merck Manual of Medical Information* 525-526 (R. Berkow Ed., 1997).

International PCT Publication No. WO 2008/133973 A1 describes therapeutic agents useful for treating pain.

U.S. Patent Application Publication No. US 2009/0170868 A1 by Tafesse describes TRPV1 antagonists and the use thereof.

U.S. Patent Application Publication No. US 2005/0165032 A1 by Norman et al. and International PCT Publication No. WO 2005/070929 describe vanilloid receptor ligands and their use in treating pain.

U.S. Patent Application Publication No. US 2005/0215572 A1 by Kelly et al. and International PCT Publication No. WO 05/066171 describe bicycloheteroarylamine compounds as ion channel ligands and uses thereof.

There remains, however, a clear need in the art for new drugs useful for treating or preventing pain, UI, an ulcer, IBD, and IBS. Citation of any reference in Section 2 of this application is not to be construed as an admission that such reference is prior art to the present application.

3. SUMMARY OF THE INVENTION

The invention encompasses compounds of formula I:

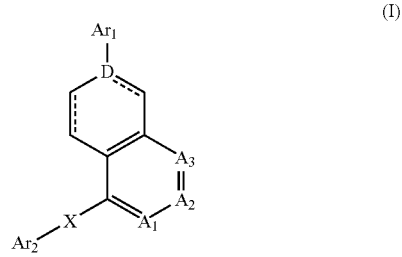

(I)

or a pharmaceutically acceptable derivative thereof, where
each dashed line independently denotes the presence or absence of a bond, and where
$A_1$, $A_2$ and $A_3$ are independently selected from $C(R_3)$ and N, provided that $A_1$ and $A_2$, or $A_2$ and $A_3$, or $A_1$, $A_2$ and $A_3$ cannot simultaneously be N;
D is N, C or $C(R_D)$, provided that when D is N or $C(R_D)$, then the dashed line connected to D is absent and when D is C, then the dashed line connected to D is present and is another bond;
$R_D$ is selected from —H, -halo, —$NO_2$, —CN, —SH, —OH, —C(O)$OR_7$, —C(halo)$_3$, —CH(halo)$_2$, —$CH_2$(halo), and —($C_1$-$C_6$)alkyl;
X is —O—, —N($R_{20}$)—, —S—, —S(O)—, or —S(O)$_2$—;

each $R_3$ is independently selected from:
(a) —H, —$N_3$, -halo, —$NO_2$, —CN, —P(O)(OH)$_2$, —S(O)$_2$(OH), —S(O)$_2$(O)—($C_1$-$C_6$)alkyl, —SH, —OH, —$COOR_7$, —C(halo)$_3$, —CH(halo)$_2$, and —$CH_2$(halo); or
(b) —($C_1$-$C_6$)alkyl, —($C_1$-$C_6$)alkoxy, —($C_3$-$C_8$)cycloalkyl, —($C_2$-$C_6$)alkenyl, —($C_2$-$C_6$)alkynyl, —($C_6$-$C_{14}$)aryl, —($C_1$-$C_6$)alkyl-N($R_7$)$_2$, —($C_1$-$C_6$)heteroalkyl, —(3- to 7-membered)heterocycle, -(5- to 10-membered)heteroaryl, —($C_6$-$C_{14}$)bicycloalkyl, —($C_1$-$C_6$)thioalkoxy, —($C_1$-$C_6$)alkyl-($C_1$-$C_6$)alkoxy, —($C_1$-$C_6$)alkyl-O—($C_6$-$C_{14}$)aryl, —($C_1$-$C_6$)alkyl-$R_7$, —($C_1$-$C_6$)alkyl-O—($C_3$-$C_8$)cycloalkyl, —($C_1$-$C_6$) alkyl-(3- to 7-membered)heterocycle, —($C_1$-$C_6$)alkyl-(5- to 10-membered)heteroaryl, —($C_1$-$C_6$)alkyl-N($R_7$)$_2$, —N($R_7$)$_2$, —N($R_7$)—($C_1$-$C_6$)alkyl-$R_{14}$, —S(O)—($C_1$-$C_6$)alkyl, —O—($C_1$-$C_6$)alkyl-$R_{14}$, —O—($C_1$-$C_6$)alkyl-S(O)$_2$—$R_{14}$, —O—($C_3$-$C_8$)cycloalkyl, —$OR_{14}$, —$SR_{14}$, —O—($C_1$-$C_6$)alkyl-O—$R_{14}$, —O—($C_1$-$C_6$)alkyl-C(O)—N($R_7$)—($C_1$-$C_6$)alkyl-$OR_7$, —O—($C_1$-$C_6$)alkyl-C(O)—$R_{14}$, —O—($C_1$-$C_6$)alkyl-C(O)—N($R_7$)$_2$, —C(O)$R_{14}$, —C(O)—($C_1$-$C_6$)alkyl, —C(O)-(3- to 7-membered)heterocycle, —C(O)-(5- to 10-membered)heteroaryl, —C(O)O—($C_1$-$C_6$)alkyl, —C(O)N($R_7$)—($C_1$-$C_6$)alkyl-(3- to 7-membered)-heterocycle, —C(O)N($R_7$)—($C_1$-$C_6$)alkyl-(5- to 10-membered)heteroaryl, —C(O)N($R_7$)$_2$, —OC(O)N($R_7$)$_2$, —C(O)N($R_7$)—($C_1$-$C_6$)alkyl-N($R_7$)$_2$, —C(O)N($R_7$)—($C_1$-$C_6$)alkyl-$R_7$, —S(O)$_2$—($C_1$-$C_6$)alkyl, and —S(O)$_2$—N($R_7$)$_2$, each of which can be unsubstituted or substituted with 1, 2, 3 or 4 independently selected $R_{14}$;
$Ar_1$ is:

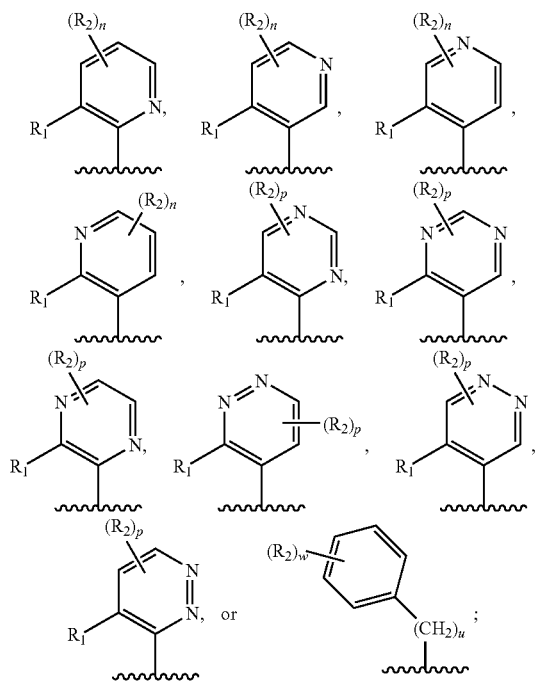

$Ar_2$ is:
(a) -(3- to 7-membered)heterocycle, -(7- to 10-membered) bicycloheterocycle, each of which can be unsubstituted or substituted with 1, 2, 3, or 4 independently selected $R_3$ groups; or (b)

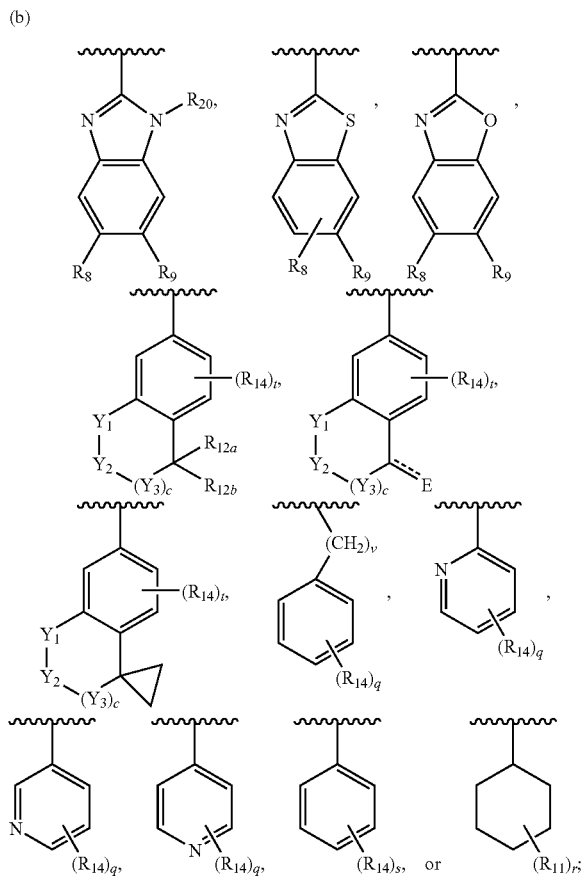

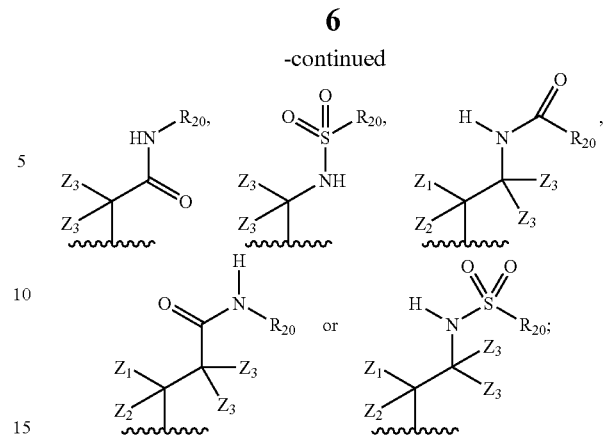

c is the integer 0, 1, or 2;

$Y_1$, $Y_2$, and $Y_3$ are each independently selected from C, N, and O, where no more than one of $Y_1$, $Y_2$, and $Y_3$ can be O, and for each $Y_1$, $Y_2$, or $Y_3$ that is N, the N is bonded to one $R_{21}$ group, and for each $Y_1$, $Y_2$, or $Y_3$ that is C, the C is bonded to two $R_{20}$ groups, provided that there are no more than a total of two $(C_1-C_6)$alkyl groups substituted on all of $Y_1$, $Y_2$, and $Y_3$;

E is =O, =S, =CH($C_1$-$C_5$)alkyl, =CH($C_2$-$C_5$)alkenyl, —NH($C_1$-$C_6$)alkyl, or =N—OR$_{20}$;

$R_1$ is —H, -halo, —($C_1$-$C_4$)alkyl, —NO$_2$, —CN, —OH, —OCH$_3$, —NH$_2$, —C(halo)$_3$, —CH(halo)$_2$, —CH$_2$(halo), —OC(halo)$_3$, —OCH(halo)$_2$, —OCH$_2$(halo), or —S(O)$_2$—($C_1$-$C_6$)alkyl;

each $R_2$ is independently selected from:
(a) -halo, —OH, —O($C_1$-$C_4$)alkyl, —CN, —NO$_2$, —NH$_2$, —($C_1$-$C_{10}$)alkyl, —($C_2$-$C_{10}$)alkenyl, —($C_2$-$C_{10}$)alkynyl, and -phenyl; or
(b) a group of formula Q, where Q is:

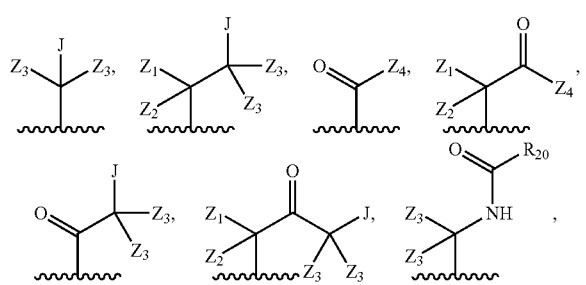

each $Z_1$ is independently selected from —H, —SR$_7$, —CH$_2$OR$_7$, —CH$_2$SR$_7$, —CH$_2$N(R$_{20}$)$_2$, and -halo;

each $Z_2$ is independently selected from —H, —($C_1$-$C_6$)alkyl, —($C_2$-$C_6$)alkenyl, —($C_2$-$C_6$)alkynyl, —CH$_2$OR$_7$, -phenyl, and -halo;

each $Z_3$ is independently selected from —H, —($C_1$-$C_6$)alkyl, —($C_2$-$C_6$)alkenyl, —($C_2$-$C_6$)alkynyl, -phenyl;

each $Z_4$ is independently selected from —H, —OH, —OR$_{20}$, —($C_1$-$C_6$)alkyl, and —N(R$_{20}$)$_2$;

each J is independently selected from —OR$_{20}$, —SR$_{20}$, —N(R$_{20}$)$_2$, and —CN;

provided that at least one $R_2$ group is a group of formula Q;

each $R_7$ is independently selected from —H, —OH, —($C_1$-$C_6$)alkyl, —($C_1$-$C_6$)alkoxy, —($C_1$-$C_6$)alkyl-($C_6$-$C_{14}$)aryl, —O—($C_6$-$C_{14}$)aryl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, —($C_1$-$C_6$)alkyl-($C_1$-$C_6$)alkoxy, —($C_1$-$C_6$)haloalkyl, —($C_1$-$C_6$)hydroxyalkyl, —($C_1$-$C_6$)alkoxy($C_1$-$C_6$)alkyl, —($C_1$-$C_6$)alkyl-N(R$_{20}$)$_2$, —C(O)N(R$_{20}$)$_2$, -(3- to 7-membered)heterocycle, -(7- to 10-membered)bicycloheterocycle, —($C_6$-$C_{14}$)bicycloalkyl, and —S(O)$_2$—($C_1$-$C_6$)alkyl;

each $R_8$ and $R_9$ is independently selected from:
(a) —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, and -phenyl, each of which is unsubstituted or substituted with 1 or 2 —OH groups; or
(b) —H, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —SC(halo)$_3$, —SCH(halo)$_2$, —SCH$_2$(halo), —CN, —O—CN, —OH, -halo, —N$_3$, —NO$_2$, —CH=NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, and —S(O)$_2$R$_7$;

each $R_{11}$ is independently selected from —CN, —OH, —($C_1$-$C_6$)alkyl, —($C_2$-$C_6$)alkenyl, -halo, —N$_3$, —NO$_2$, —N(R$_7$)$_2$, —CH=NR$_7$, —NR$_7$OH, —OR$_7$, —C(O)R$_7$, —C(O)OR$_7$, —OC(O)R$_7$, and —OC(O)OR$_7$;

$R_{12a}$ and $R_{12b}$ are each independently selected from —H and —($C_1$-$C_6$)alkyl;

each $R_{14}$ is independently selected from —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_1$-$C_6$)alkoxy, —($C_1$-$C_6$)alkoxy-($C_1$-$C_6$)alkyl, -phenyl, —C(halo)$_3$, —CH(halo)$_2$, —CH$_2$(halo), -(3- to 7-membered)heterocycle, -(5- to 10-membered)heteroaryl, —($C_1$-$C_6$)haloalkyl, —($C_2$-$C_6$)haloalkenyl, —($C_2$-$C_6$)haloalkynyl, —($C_2$-$C_6$)hydroxyalkenyl, —($C_2$-$C_6$)hydroxyalkynyl, —($C_1$-$C_6$)alkoxy($C_2$-$C_6$)alkyl, —($C_1$-$C_6$)alkoxy-($C_2$-$C_6$)alkenyl, —($C_1$-$C_6$)alkoxy($C_2$-$C_6$)alkynyl, —($C_1$-$C_6$)alkoxy-($C_3$-$C_8$)cycloalkyl, —CN, —OH, -halo, —OC(halo)$_3$, —N$_3$, —NO$_2$, —CH=NR$_7$, —N(R$_7$)$_2$, —NR₇OH, —OR₇, —SR₇, —O(CH₂)ᵦOR₇, —O(CH₂)ᵦSR₇, —O(CH₂)ᵦN(R₇)₂, —N(R₇)(CH₂)ᵦOR₇, —N(R₇)(CH₂)ᵦSR₇, —N(R₇)(CH₂)ᵦN(R₇)₂, —N(R₇)C(O)R₇, —N(R₇)—S(O)₂—(C₁-C₆)alkyl, —C(O)—N(R₇)₂, —C(O)R₇, —C(O)OR₇, —OC(O)R₇, —OC(O)OR₇, —S(O)R₇, —S(O)₂R₇, —S(O)₂N(R₇)₂, —S(O)₂—C(halo)₃, —S(O)₂-(3- to 7-membered)heterocycle, —C(O)N(R₇)₂, —(C₁-C₅)alkyl-C=NOR₇, —(C₁-C₅)alkyl-C(O)—N(R₇)₂, —(C₁-C₆)alkyl-NHS(O)₂N(R₇)₂, and —(C₁-C₆)alkyl-C(=NH)—N(R₇)₂;

each R₂₀ is independently selected from —H, —(C₁-C₆)alkyl, and —(C₃-C₈)cycloalkyl;

each R₂₁ is independently selected from —H, —(C₁-C₆)alkyl,

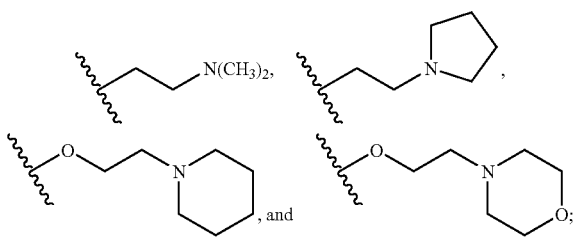

each -halo is independently selected from —F, —Cl, —Br, and —I;

each b is independently selected from the integers 1 and 2;
n is the integer 1, 2, or 3;
p is the integer 1 or 2;
q is the integer 0, 1, 2, 3 or 4;
r is the integer 0, 1, 2, 3, 4, 5, or 6;
s is the integer 0, 1, 2, 3, 4, or 5;
t is the integer 1, 2, or 3;
u is the integer 1, 2, 3 or 4;
v is the integer 1, 2, 3 or 4; and
w is the integer 1, 2, 3, 4, or 5;

provided that when A₁ and A₃ are each N, A₂ is C(R₃), R₃ is —H, and Ar₂ is substituted phenyl, then Q is not —CH₂OH.

Compounds of formula I are believed to be highly soluble in aqueous solutions, e.g., at a pH of about 6.8 and/or at a pH of about 1.2, and are believed to be very potent at the TRPV1 receptor.

A compound of formula I, or a pharmaceutically acceptable derivative thereof, is believed to be useful for treating or preventing pain, such as inflammatory or neuropathic pain, UI, an ulcer, IBD, or IBS (each being a "Condition") in an animal.

The invention also relates to compositions comprising an effective amount of a compound of formula I, or a pharmaceutically acceptable derivative thereof, and a pharmaceutically acceptable carrier or excipient. The compositions are believed to be useful for treating or preventing a Condition in an animal.

The invention further relates to methods for treating a Condition comprising administering to an animal in need thereof an effective amount of a compound of formula I, or a pharmaceutically acceptable derivative thereof.

The invention further relates to methods for preventing a Condition comprising administering to an animal in need thereof an effective amount of a compound of formula I, or a pharmaceutically acceptable derivative thereof.

The invention further relates to use of a compound of formula I in the manufacture of a medicament for treating and/or preventing a Condition.

The invention still further relates to methods for inhibiting Transient Receptor Potential Vanilloid 1 ("TRPV1," formerly known as Vanilloid Receptor 1 or VR1) function in a cell, comprising contacting a cell capable of expressing TRPV1 with an effective amount of a compound of formula I, or a pharmaceutically acceptable derivative thereof.

The invention still further relates to a method for preparing a composition comprising the step of admixing a compound of formula I, or a pharmaceutically acceptable derivative thereof, and a pharmaceutically acceptable carrier or excipient.

The invention still further relates to a kit comprising a container containing an effective amount of a compound of formula I, or a pharmaceutically acceptable derivative thereof.

The invention still further relates to a compound of formula I, or a pharmaceutically acceptable derivative thereof, for use as a medicament.

Preferred compounds of formula I are compounds of formula II:

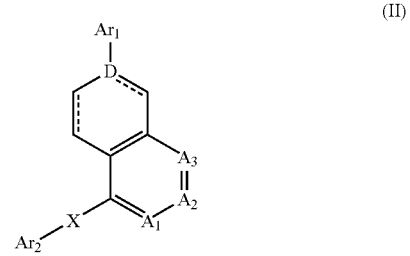

or a pharmaceutically acceptable derivative thereof, where the dashed lines, A₁, A₂, A₃, D and X are as defined above for compounds of formula I;

Ar₁ is:

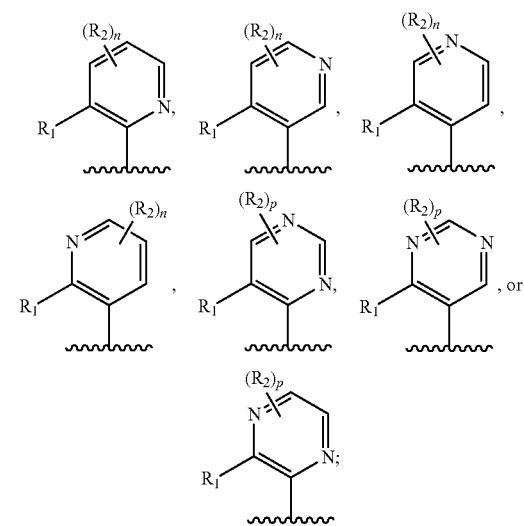

$Ar_2$ is:

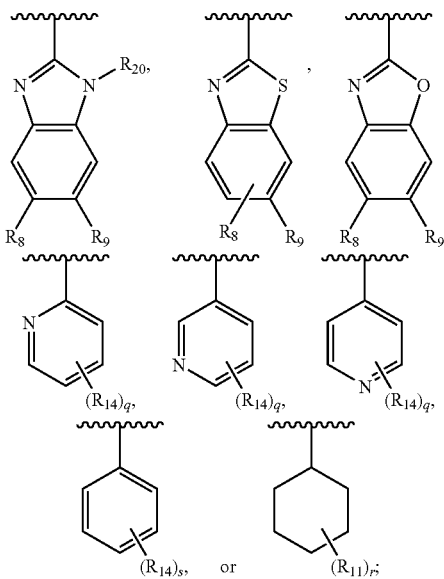

Q is:

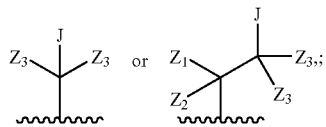

each $Z_1$ is independently selected from —H, —OR$_7$, —SR$_7$, —CH$_2$OR$_7$, —CH$_2$SR$_7$, —CH$_2$N(R$_{20}$)$_2$, and -halo;

each $Z_2$ is independently selected from —H, —(C$_1$-C$_6$)alkyl, —(C$_2$-C$_6$)alkenyl, —(C$_2$-C$_6$)alkynyl, and —CH$_2$OR$_7$, -phenyl, and -halo;

each $Z_3$ is independently selected from —H, —(C$_1$-C$_6$)alkyl, —(C$_2$-C$_6$)alkenyl, —(C$_2$-C$_6$)alkynyl, and -phenyl;

each J is independently selected from —OR$_{20}$, —SR$_{20}$, —N(R$_{20}$)$_2$, and —CN;

provided that at least one $R_2$ group is a group of formula Q.

Compounds of formula II are believed to be highly soluble in aqueous solutions at either pH 6.8 or pH 1.2 and are believed to be very potent at the TRPV1 receptor.

Preferred compounds of formula II are compounds of formula III:

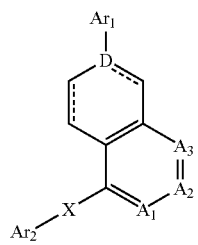

(III)

where the dashed lines, $A_1$, $A_2$, $A_3$, D and X are as defined above for compounds of formula I;

$Ar_1$ is:

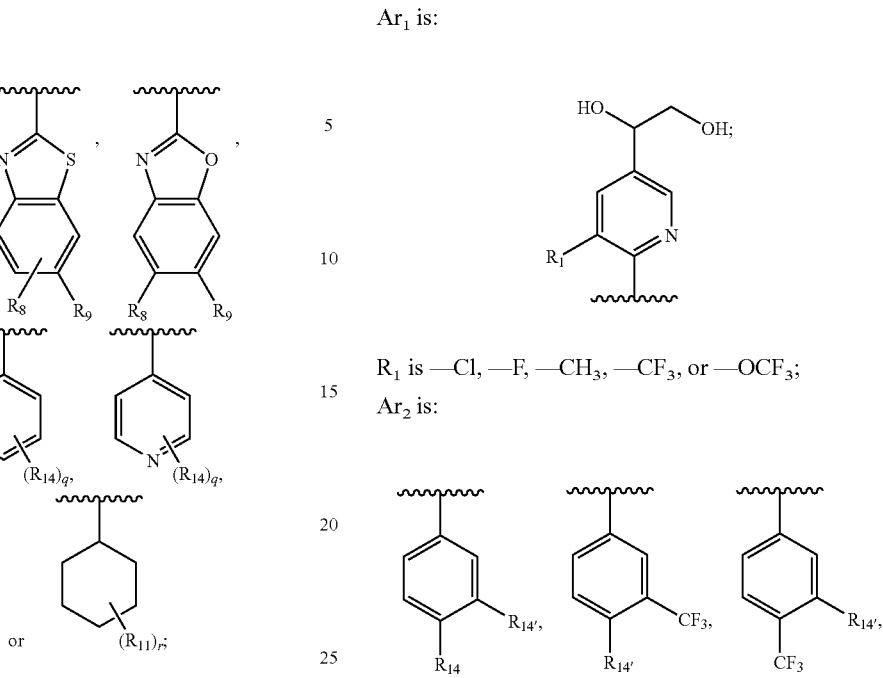

$R_1$ is —Cl, —F, —CH$_3$, —CF$_3$, or —OCF$_3$;

$Ar_2$ is:

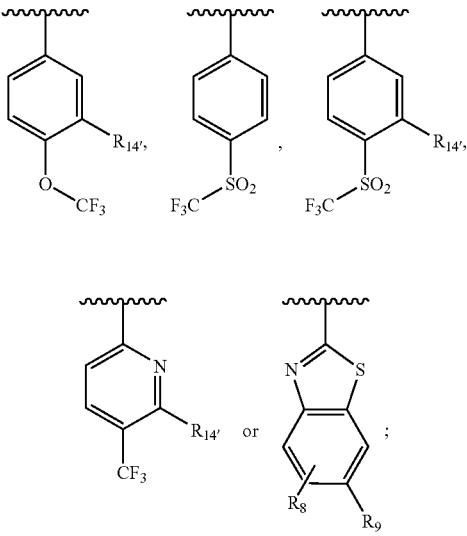

$R_{14}$ is —H, —Cl, —F, —Br, —OCF$_3$, —(C$_1$-C$_6$)alkyl, —S(O)$_2$CF$_3$, —S(O)$_2$(C$_1$-C$_6$)alkyl, —OCH$_3$, —OCH$_2$CH$_3$, or —OCH(CH$_3$)$_2$, and preferably is —CF$_3$, —OCF$_3$, —Cl, or —F;

$R_{14'}$ is —H, —Cl, —F, —Br, —CH$_3$, —CH$_2$CH$_3$, —OCH$_3$, —OCF$_3$, or —OCH$_2$CH$_3$; and each $R_8$ and $R_9$ is independently selected from —H, —Cl, —Br, —F, —CH$_3$, —OCH$_3$, —OCH$_2$CH$_3$, —CF$_3$, —OCF$_3$, iso-propyl, and tert-butyl.

Compounds of formula III are believed to be highly soluble in aqueous solutions at either pH 6.8 or pH 1.2 and are believed to be very potent at the TRPV1 receptor.

Preferred compounds of formula III are compounds of formula IV:

(IV)

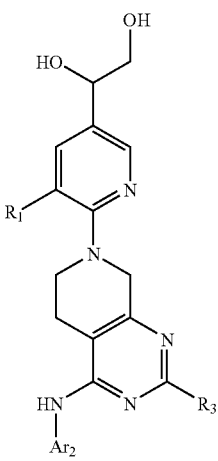

or a pharmaceutically acceptable derivative thereof, where $R_3$ is defined as above for compounds of formula I;

$Ar_2$ is:

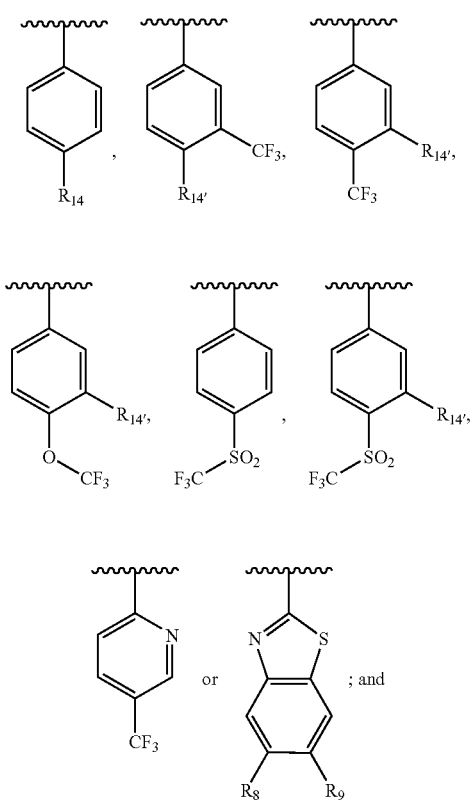

$R_1$ is —Cl, —F, —CH$_3$, —CF$_3$, or —OCF$_3$.

Compounds of formula IV are believed to be highly soluble in aqueous solutions at either pH 6.8 or pH 1.2 and are believed to be very potent at the TRPV1 receptor.

The invention can be understood more fully by reference to the following detailed description and illustrative examples, which are intended to exemplify non-limiting embodiments of the invention.

4. DETAILED DESCRIPTION OF THE INVENTION

The invention includes the following:

(1) A compound of formula I:

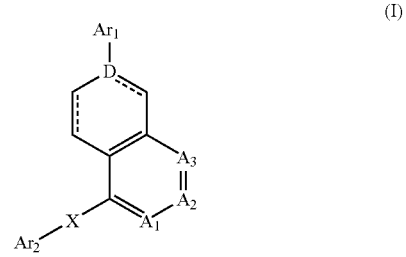

(I)

or a pharmaceutically acceptable derivative thereof, wherein
each dashed line independently denotes the presence or absence of a bond, and wherein $A_1$, $A_2$ and $A_3$ are independently selected from C($R_3$) and N, provided that $A_1$ and $A_2$, or $A_2$ and $A_3$, or $A_1$, $A_2$ and $A_3$ cannot simultaneously be N;

D is N, C or C($R_D$), provided that when D is N or C($R_D$), then the dashed line connected to D is absent and when D is C, then the dashed line connected to D is present and is another bond;

$R_D$ is selected from —H, -halo, —NO$_2$, —CN, —SH, —OH, —C(O)OR$_7$, —C(halo)$_3$, —CH(halo)$_2$, —CH$_2$(halo), and —(C$_1$-C$_6$)alkyl;

X is —O—, —N(R$_{20}$)—, —S—, —S(O)—, or —S(O)$_2$—;

each $R_3$ is independently selected from:

(a) —H, —N$_3$, -halo, —NO$_2$, —CN, —P(O)(OH)$_2$, —S(O)$_2$(OH), —S(O)$_2$(O)—(C$_1$-C$_6$)alkyl, —SH, —OH, —C(O)OR$_7$, —C(halo)$_3$, —CH(halo)$_2$, and —CH$_2$(halo); or (b) —(C$_1$-C$_6$)alkyl, —(C$_1$-C$_6$)alkoxy, —(C$_3$-C$_8$)cycloalkyl, —(C$_2$-C$_6$)alkenyl, —(C$_2$-C$_6$)alkynyl, —(C$_6$-C$_{14}$)aryl, —(C$_1$-C$_6$)alkyl-N(R$_7$)$_2$, —(C$_1$-C$_6$)heteroalkyl, -(5- to 10-membered)heterocycle, -(5- to 10-membered)heteroaryl, —(C$_6$-C$_{14}$)bicycloalkyl, —(C$_1$-C$_6$)thioalkoxy, —(C$_1$-C$_6$)alkyl-(C$_1$-C$_6$)alkoxy, —(C$_1$-C$_6$)alkyl-O—(C$_6$-C$_{14}$)aryl, —(C$_1$-C$_6$)alkyl-R$_7$, —(C$_1$-C$_6$)alkyl-O—(C$_3$-C$_8$)cycloalkyl, —(C$_1$-C$_6$)alkyl-(3- to 7-membered)heterocycle, —(C$_1$-C$_6$)alkyl-(5- to 10-membered)heteroaryl, —(C$_1$-C$_6$)alkyl-N(R$_7$)$_2$, —N(R$_7$)$_2$, —N(R$_7$)—(C$_1$-C$_6$)alkyl-R$_{14}$, —S(O)—(C$_1$-C$_6$)alkyl, —O—(C$_1$-C$_6$)alkyl-R$_{14}$, —O—(C$_1$-C$_6$)alkyl-S(O)$_2$—R$_{14}$, —O—(C$_3$-C$_8$)cycloalkyl, —OR$_{14}$, —SR$_{14}$, —O—(C$_1$-C$_6$)alkyl-O—R$_{14}$, —O—(C$_1$-C$_6$)alkyl-C(O)—N(R$_7$)—(C$_1$-C$_6$)alkyl-OR$_7$, —O—(C$_1$-C$_6$)alkyl-C(O)—R$_{14}$, —O—(C$_1$-C$_6$)alkyl-C(O)—N(R$_7$)$_2$, —C(O)R$_{14}$, —C(O)—(C$_1$-C$_6$)alkyl, —C(O)-(3- to 7-membered)heterocycle, —C(O)-(5- to 10-membered)heteroaryl, —C(O)O—(C$_1$-C$_6$)alkyl, —C(O)N(R$_7$)—(C$_1$-C$_6$)alkyl-(3- to 7-membered)heterocycle, —C(O)N(R$_7$)—(C$_1$-C$_6$)alkyl-(5- to 10-membered)heteroaryl, —C(O)N(R$_7$)$_2$, —OC(O)N(R$_7$)$_2$, —C(O)N(R$_7$)—(C$_1$-C$_6$)alkyl-N(R$_7$)$_2$, —C(O)N(R$_7$)—(C$_1$-C$_6$)alkyl-R$_7$, —S(O)$_2$—(C$_1$-C$_6$)alkyl, and —S(O)$_2$—N(R$_7$)$_2$, each of which can be unsubstituted or substituted with 1, 2, 3 or 4 independently selected R$_{14}$;

Ar₁ is:

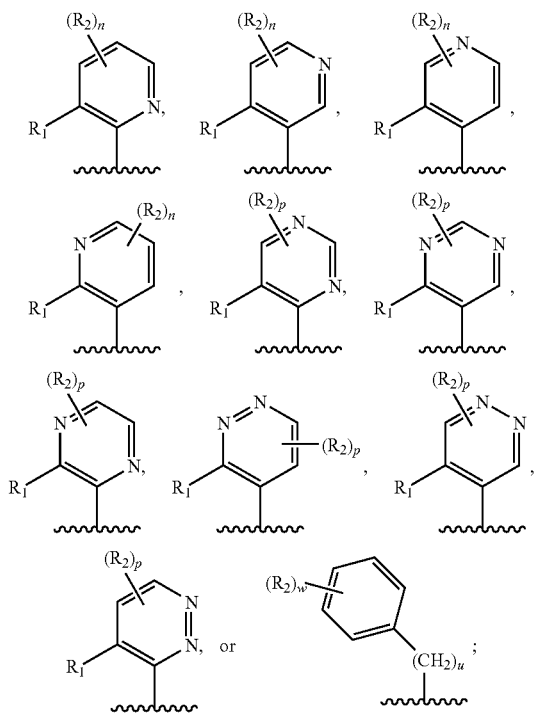

Ar₂ is:

(a) -(3- to 7-membered)heterocycle or -(7- to 10-membered)bicycloheterocycle, each of which can be unsubstituted or substituted with 1, 2, 3, or 4 independently selected R₃ groups; or (b)

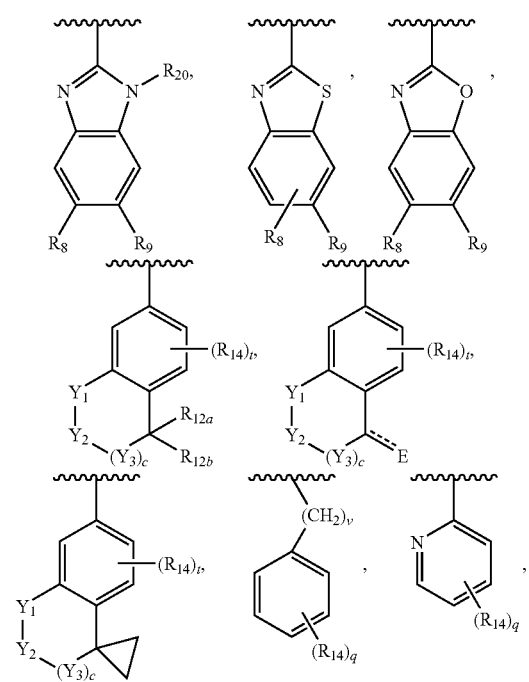

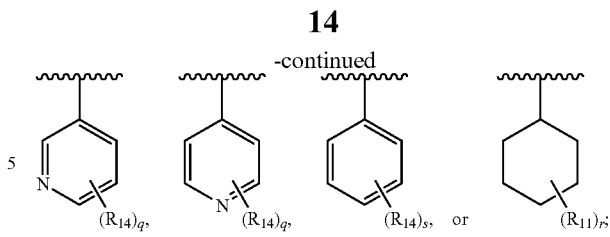

c is the integer 0, 1, or 2;

$Y_1$, $Y_2$, and $Y_3$ are each independently selected from C, N, and O, wherein no more than one of $Y_1$, $Y_2$, and $Y_3$ can be O, and for each $Y_1$, $Y_2$, or $Y_3$ that is N, the N is bonded to one $R_{21}$ group, and for each $Y_1$, $Y_2$, or $Y_3$ that is C, the C is bonded to two $R_{20}$ groups, provided that there are no more than a total of two ($C_1$-$C_6$)alkyl groups substituted on all of $Y_1$, $Y_2$, and $Y_3$;

E is =O, =S, =CH($C_1$-$C_6$)alkyl, =CH($C_2$-$C_6$)alkenyl, —NH($C_1$-$C_6$)alkyl, or =N—$OR_{20}$;

$R_1$ is —H, -halo, —($C_1$-$C_4$)alkyl, —$NO_2$, —CN, —OH, —$OCH_3$, —$NH_2$, —C(halo)₃, —CH(halo)₂, —CH₂(halo), —OC(halo)₃, —OCH(halo)₂, —OCH₂(halo), or —S(O)₂—($C_1$-$C_6$)alkyl;

each $R_2$ is independently selected from:

(a) -halo, —OH, —O($C_1$-$C_4$)alkyl, —CN, —$NO_2$, —$NH_2$, —($C_1$-$C_{10}$)alkyl, —($C_2$-$C_{10}$)alkenyl, —($C_2$-$C_{10}$)alkynyl, and -phenyl; or (b) a group of formula Q, wherein Q is:

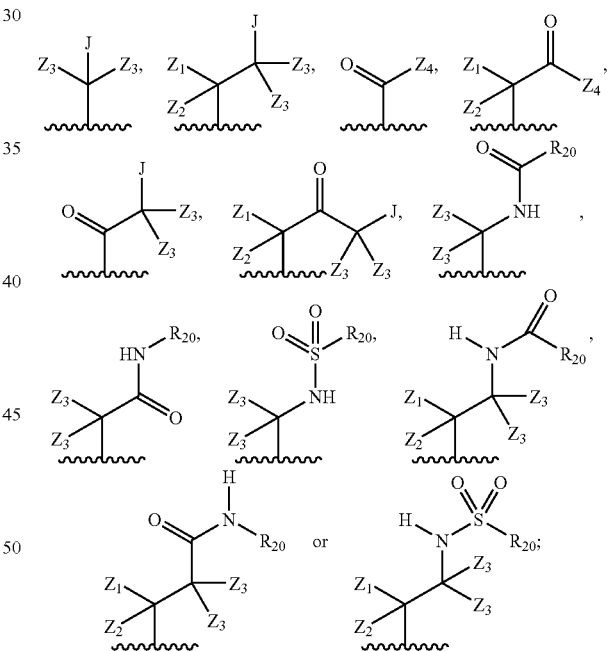

each $Z_1$ is independently selected from —H, —$OR_7$, —$SR_7$, —$CH_2OR_7$, —$CH_2SR_7$, —$CH_2N(R_{20})_2$, and -halo;

each $Z_2$ is independently selected from —H, —($C_1$-$C_6$)alkyl, —($C_2$-$C_6$)alkenyl, —($C_2$-$C_6$)alkynyl, —$CH_2OR_7$, -phenyl, and -halo;

each $Z_3$ is independently selected from —H, —($C_1$-$C_6$)alkyl, —($C_2$-$C_6$)alkenyl, —($C_2$-$C_6$)alkynyl, and -phenyl;

each $Z_4$ is independently selected from —H, —OH, —$OR_{20}$, —($C_1$-$C_6$)alkyl, and —$N(R_{20})_2$;

each J is independently selected from —$OR_{20}$, —$SR_{20}$, —$N(R_{20})_2$, and —CN;

provided that at least one $R_2$ group is a group of formula Q;

each $R_7$ is independently selected from —H, —OH, —($C_1$-$C_6$)alkyl, —($C_1$-$C_6$)alkoxy, —($C_1$-$C_6$)alkyl-($C_6$-$C_{14}$)aryl, —O—($C_6$-$C_{14}$)aryl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, —($C_1$-$C_6$)alkyl-($C_1$-$C_6$)alkoxy, —($C_1$-$C_6$)haloalkyl, —($C_1$-$C_6$)hydroxyalkyl, —($C_1$-$C_6$)alkoxy($C_1$-$C_6$)alkyl, —($C_1$-$C_6$)alkyl-N($R_{20}$)$_2$, —C(O)N($R_{20}$)$_2$, -(3- to 7-membered)heterocycle, -(7- to 10-membered) bicycloheterocycle, —($C_6$-$C_{14}$)bicycloalkyl, and —S(O)$_2$—($C_1$-$C_6$)alkyl;

each $R_8$ and $R_9$ is independently selected from:
(a) —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, and -phenyl, each of which is unsubstituted or substituted with 1 or 2 —OH groups; or
(b) —H, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —SC(halo)$_3$, —SCH(halo)$_2$, —SCH$_2$(halo), —CN, —O—CN, —OH, -halo, —N$_3$, —NO$_2$, —CH=NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, and —S(O)$_2$R$_7$;

each $R_{11}$ is independently selected from —CN, —OH, —($C_1$-$C_6$)alkyl, —($C_2$-$C_6$)alkenyl, -halo, —N$_3$, —NO$_2$, —N(R$_7$)$_2$, —CH=NR$_7$, —NR$_7$OH, —OR$_7$, —C(O)R$_7$, —C(O)OR$_7$, —OC(O)R$_7$, and —OC(O)OR$_7$;

$R_{12a}$ and $R_{12b}$ are each independently selected from —H and —($C_1$-$C_6$)alkyl;

each $R_{14}$ is independently selected from —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_1$-$C_6$)alkoxy, —($C_1$-$C_6$)alkoxy-($C_1$-$C_6$)alkyl, -phenyl, —C(halo)$_3$, —CH(halo)$_2$, —CH$_2$(halo), -(3- to 7-membered)heterocycle, -(5- to 10-membered)heteroaryl, —($C_1$-$C_6$)haloalkyl, —($C_2$-$C_6$)haloalkenyl, —($C_2$-$C_6$)haloalkynyl, —($C_2$-$C_6$)hydroxyalkenyl, —($C_2$-$C_6$)hydroxyalkynyl, —($C_1$-$C_6$)alkoxy($C_2$-$C_6$)alkyl, —($C_1$-$C_6$)alkoxy-($C_2$-$C_6$)alkenyl, —($C_1$-$C_6$)alkoxy($C_2$-$C_6$)alkynyl, —($C_1$-$C_6$)alkoxy-($C_3$-$C_8$)cycloalkyl, —CN, —OH, -halo, —OC(halo)$_3$, —N$_3$, —NO$_2$, —CH=NR$_7$, —N(R$_7$)$_2$, —NR$_7$OH, —OR$_7$, —SR$_7$, —O(CH$_2$)$_b$OR$_7$, —O(CH$_2$)$_b$SR$_7$, —O(CH$_2$)$_b$N(R$_7$)$_2$, —N(R$_7$)(CH$_2$)$_b$OR$_7$, —N(R$_7$)(CH$_2$)$_b$SR$_7$, —N(R$_7$)(CH$_2$)$_b$N(R$_7$)$_2$, —N(R$_7$)C(O)R$_7$, —N(R$_7$)—S(O)$_2$—($C_1$-$C_6$)alkyl, —C(O)—N(R$_7$)$_2$, —C(O)R$_7$, —C(O)OR$_7$, —OC(O)R$_7$, —OC(O)OR$_7$, —S(O)R$_7$, —S(O)$_2$R$_7$, —S(O)$_2$N(R$_7$)$_2$, —S(O)$_2$—C(halo)$_3$, —S(O)$_2$-(3- to 7-membered)heterocycle, —C(O)N(R$_7$)$_2$, —($C_1$-$C_5$)alkyl-C=NOR$_7$, —($C_1$-$C_5$)alkyl-C(O)—N(R$_7$)$_2$, —($C_1$-$C_6$)alkyl-NHS(O)$_2$N(R$_7$)$_2$, and —($C_1$-$C_6$)alkyl-C(=NH)—N(R$_7$)$_2$;

each $R_{20}$ is independently selected from —H, —($C_1$-$C_6$)alkyl, and —($C_3$-$C_8$)cycloalkyl;

each $R_{21}$ is independently selected from —H, —($C_1$-$C_6$)alkyl,

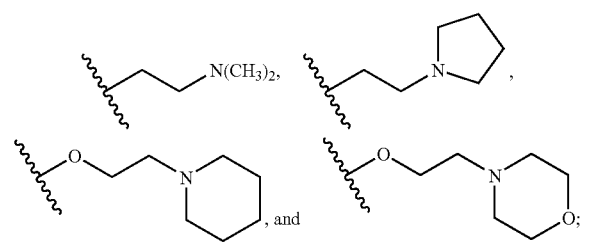

each -halo is independently selected from —F, —Cl, —Br, and —I;

each b is independently selected from the integers 1 and 2;

n is the integer 1, 2, or 3;

p is the integer 1 or 2;

q is the integer 0, 1, 2, 3 or 4;

r is the integer 0, 1, 2, 3, 4, 5, or 6;

s is the integer 0, 1, 2, 3, 4, or 5;

t is the integer 1, 2, or 3;

u is the integer 1, 2, 3 or 4;

v is the integer 1, 2, 3 or 4; and w is the integer 1, 2, 3, 4, or 5;

provided that when $A_1$ and $A_3$ are each N, $A_2$ is C($R_3$), $R_3$ is —H, and $Ar_2$ is substituted phenyl, then Q is not CH$_2$OH.

(2) The compound of (1), wherein X is —O—, —N($R_{20}$)—, or —S(O)$_2$—, and preferably is —N($R_{20}$)—, wherein $R_{20}$ is preferably —H.

(3) The compound of (1) or (2), wherein D is C and preferably the dashed lines are present.

(4) The compound of (1) or (2), wherein D is N and the dashed lines are absent.

(5) The compound of (1) or (2), wherein the dashed line not connected to D is present as part of a double bond and D is N, having the following structure:

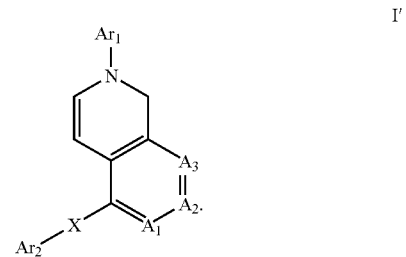

(6) The compound of any one of (1) to (5), wherein $A_1$ and $A_3$ are each N.

(7) The compound of any one of (1) to (6), wherein $A_2$ is C($R_3$).

(8) The compound of (1) or (2), having the following structure:

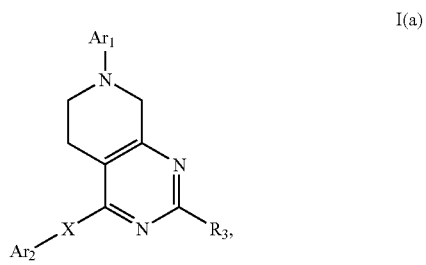

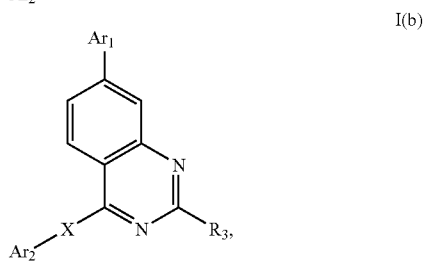

-continued

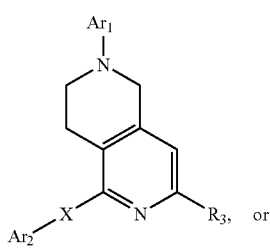
I(c)

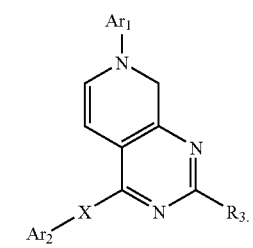
I(d)

(9) The compound of any one of (1) to (8), wherein $Ar_1$ is:

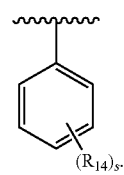

(10) The compound of any one of (1) to (9), wherein $R_1$ is -halo, —C(halo)$_3$, —CH(halo)$_2$, —CH$_2$(halo), or —(C$_1$-C$_6$)alkyl, wherein each -halo is preferably —Cl or —F.

(11) The compound of any one of (1) to (10), wherein the Q-group is:

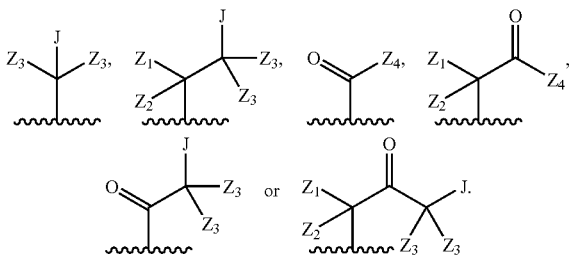

(12) The compound of any one of (1) to (11), wherein n, p, or w is 1, and Q is:

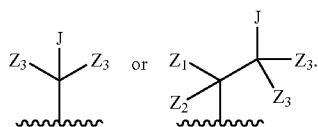

(13) The compound of any one of (1) to (12), wherein J is —OR$_{20}$ or —N(R$_{20}$)$_2$, and preferably is —OR$_{20}$.

(14) The compound of any one of (1) to (13), wherein each $R_{20}$ is independently selected from —H and —(C$_1$-C$_6$)alkyl, and preferably is —H.

(15) The compound of any one of (1) to (14), wherein each $Z_3$ is independently selected from —H and —(C$_1$-C$_6$)alkyl, and preferably is —H.

(16) The compound of any one of (1) to (15), wherein $Z_1$ is —OR$_7$ or —CH$_2$OR$_7$, and preferably is —OR$_7$.

(17) The compound of any one of (1) to (16), wherein $Z_2$ is —H, —(C$_1$-C$_6$)alkyl, or —CH$_2$OR$_7$, and preferably is —H.

(18) The compound of any one of (1) to (17), wherein $Ar_2$ is:

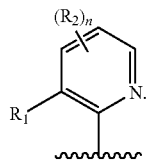

(19) The compound of any one of (1) to (17), wherein $Ar_2$ is:

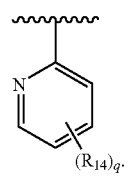

(20) The compound of any one of (1) to (19), wherein each $R_{14}$ is independently selected from -halo, —C(halo)$_3$, —(C$_1$-C$_6$)alkyl, —OC(halo)$_3$, and —S(O$_2$)C(halo)$_3$, and preferably is independently selected from -halo, —C(halo)$_3$, and —OC(halo)$_3$.

(21) The compound of any one of (1) to (20), wherein each -halo is independently selected from —Cl and —F.

(22) The compound of any one of (1) to (21), wherein s or q is 1 or 2.

(23) The compound of any one of (1) to (17), wherein $Ar_2$ is:

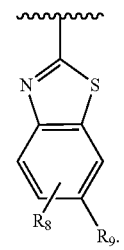

(24) The compound of any one of (1) to (17) and (23), wherein $R_8$ and $R_9$ are independently selected from —H, -halo, and —(C$_1$-C$_6$)alkyl, and preferably $R_8$ and $R_9$ are independently selected from —H and -halo, wherein each -halo is independently selected from —Cl and —F.

(25) A compound of formula II:

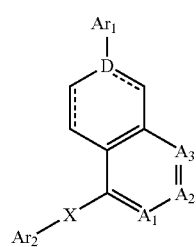
(II)

or a pharmaceutically acceptable derivative thereof, wherein
each dashed line independently denotes the presence or absence of a bond, and wherein $A_1$, $A_2$ and $A_3$ are independently selected from $C(R_3)$ and N, provided that $A_1$ and $A_2$, $A_2$ and $A_3$, or $A_1$, $A_2$ and $A_3$ cannot simultaneously be N;

D is N, C or $C(R_D)$, provided that when D is N or $C(R_D)$, then the dashed line connected to D is absent, and when D is C, then the dashed line connected to D is present and is another bond;

$R_D$ is selected from —H, -halo, —NO$_2$, —CN, —SH, —OH, —C(O)OR$_7$, —C(halo)$_3$, —CH(halo)$_2$, —CH$_2$(halo), and —(C$_1$-C$_6$)alkyl;

X is —O—, —N(R$_{20}$)—, —S—, —S(O)—, or —S(O)$_2$—;

each $R_3$ is independently selected from:
(a) —H, —N$_3$, -halo, —NO$_2$, —CN, —P(O)(OH)$_2$, —S(O)$_2$(OH), —S(O)$_2$(O)—(C$_1$-C$_6$)alkyl, —SH, —OH, —C(O)OR$_7$, —C(halo)$_3$, —CH(halo)$_2$, and —CH$_2$(halo); or
(b) —(C$_1$-C$_6$)alkyl, —(C$_1$-C$_6$)alkoxy, —(C$_3$-C$_8$)cycloalkyl, —(C$_2$-C$_6$)alkenyl, —(C$_2$-C$_6$)alkynyl, —(C$_6$-C$_{14}$)aryl, —(C$_1$-C$_6$)alkyl-N(R$_7$)$_2$, —(C$_1$-C$_6$)heteroalkyl, -(5- to 10-membered)heterocycle, -(5- to 10-membered)heteroaryl, —(C$_6$-C$_{14}$)bicycloalkyl, —(C$_1$-C$_6$)thioalkoxy, —(C$_1$-C$_6$)alkyl-(C$_1$-C$_6$)alkoxy, —(C$_1$-C$_6$)alkyl-O—(C$_6$-C$_{14}$)aryl, —(C$_1$-C$_6$)alkyl-R$_7$, —(C$_1$-C$_6$)alkyl-O—(C$_3$-C$_8$)cycloalkyl, —(C$_1$-C$_6$)alkyl-(3- to 7-membered)heterocycle, —(C$_1$-C$_6$)alkyl-(5- to 10-membered)heteroaryl, —(C$_1$-C$_6$)alkyl-N(R$_7$)$_2$, —N(R$_7$)$_2$, —N(R$_7$)—(C$_1$-C$_6$)alkyl-R$_{14}$, —S(O)—(C$_1$-C$_6$)alkyl, —O—(C$_1$-C$_6$)alkyl-R$_{14}$, —O—(C$_1$-C$_6$)alkyl-S(O)$_2$—R$_{14}$, O—(C$_3$-C$_8$)cycloalkyl, —OR$_{14}$, —SR$_{14}$, —O—(C$_1$-C$_6$)alkyl-O—R$_{14}$, —O—(C$_1$-C$_6$)alkyl-C(O)—N(R$_7$)—(C$_1$-C$_6$)alkyl-OR$_7$, —O—(C$_1$-C$_6$)alkyl-C(O)—R$_{14}$, —O—(C$_1$-C$_6$)alkyl-C(O)—N(R$_7$)$_2$, —C(O)R$_{14}$, —C(O)—(C$_1$-C$_6$)alkyl, —C(O)-(3- to 7-membered)heterocycle, —C(O)-(5- to 10-membered)heteroaryl, —C(O)O—(C$_1$-C$_6$)alkyl, —C(O)N(R$_7$)—(C$_1$-C$_6$)alkyl-(3- to 7-membered)heterocycle, —C(O)N(R$_7$)—(C$_1$-C$_6$)alkyl-(5- to 10-membered)heteroaryl, —C(O)N(R$_7$)$_2$, —OC(O)N(R$_7$)$_2$, —C(O)N(R$_7$)—(C$_1$-C$_6$)alkyl-N(R$_7$)$_2$, —C(O)N(R$_7$)—(C$_1$-C$_6$)alkyl-R$_7$, —S(O)$_2$—(C$_1$-C$_6$)alkyl, and —S(O)$_2$—N(R$_7$)$_2$, each of which can be unsubstituted or substituted with 1, 2, 3 or 4 independently selected R$_{14}$;

Ar$_1$ is:

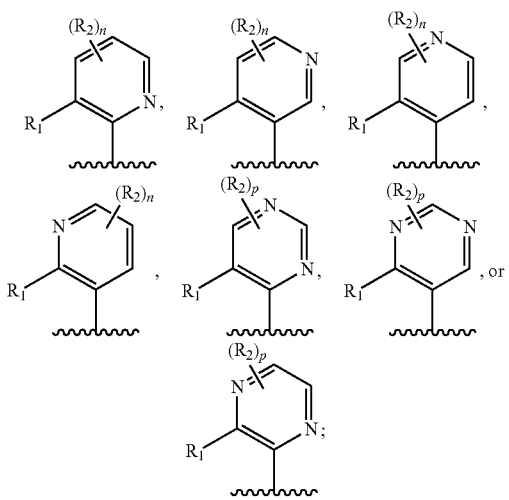

Ar$_2$ is:

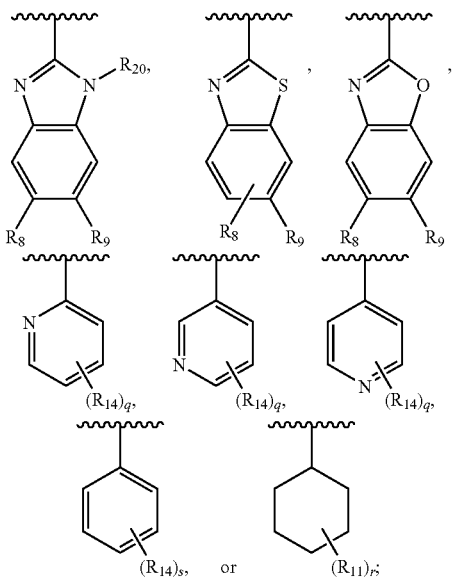

$R_1$ is —H, -halo, —(C$_1$-C$_4$)alkyl, —NO$_2$, —CN, —OH, —OCH$_3$, —NH$_2$, —C(halo)$_3$, —CH(halo)$_2$, —CH$_2$(halo), —OC(halo)$_3$, —OCH(halo)$_2$, —OCH$_2$(halo), or —S(O)$_2$—(C$_1$-C$_6$)alkyl;

each $R_2$ is independently selected from:
(a) -halo, —OH, —O(C$_1$-C$_4$)alkyl, —CN, —NO$_2$, —NH$_2$, —(C$_1$-C$_{10}$)alkyl, —(C$_2$-C$_{10}$)alkenyl, —(C$_2$-C$_{10}$)alkynyl, and -phenyl; or
(b) a group of formula Q, wherein Q is:

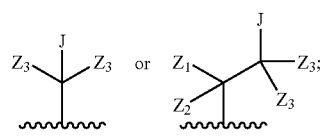

each $Z_1$ is independently selected from —H, —$OR_7$, —$SR_7$, —$CH_2OR_7$, —$CH_2SR_7$, —$CH_2N(R_{20})_2$, and -halo;

each $Z_2$ is independently selected from —H, —($C_1$-$C_6$)alkyl, —($C_2$-$C_6$)alkenyl, —($C_2$-$C_6$)alkynyl, —$CH_2OR_7$, -phenyl, and -halo;

each $Z_3$ is independently selected from —H, —($C_1$-$C_6$)alkyl, —($C_2$-$C_6$)alkenyl, —($C_2$-$C_6$)alkynyl, and -phenyl;

each J is independently selected from —$OR_{20}$, —$SR_{20}$, —$N(R_{20})_2$, and —CN;

provided that at least one $R_2$ group is a group of formula Q;

each $R_7$ is independently selected from —H, —OH, —($C_1$-$C_6$)alkyl, —($C_1$-$C_6$)alkoxy, —($C_1$-$C_6$)alkyl-($C_6$-$C_{14}$)aryl, —O—($C_6$-$C_{14}$)aryl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, —($C_1$-$C_6$)alkyl-($C_1$-$C_6$)alkoxy, —($C_1$-$C_6$)haloalkyl, —($C_1$-$C_6$)hydroxyalkyl, —($C_1$-$C_6$)alkoxy-($C_1$-$C_6$)alkyl, —($C_1$-$C_6$)alkyl-$N(R_{20})_2$, —$C(O)N(R_{20})_2$, -(3- to 7-membered)heterocycle, -(7- to 10-membered)bicycloheterocycle, —($C_6$-$C_{14}$)bicycloalkyl, and —$S(O)_2$—($C_1$-$C_6$)alkyl;

each $R_8$ and $R_9$ is independently selected from:
(a) —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, and -phenyl, each of which is unsubstituted or substituted with 1 or 2 —OH groups; or
(b) —H, —$CH_2C(halo)_3$, —$C(halo)_3$, —$CH(halo)_2$, —$CH_2(halo)$, —$OC(halo)_3$, —$OCH(halo)_2$, —$OCH_2(halo)$, —$SC(halo)_3$, —$SCH(halo)_2$, —$SCH_2(halo)$, —CN, —O—CN, —OH, -halo, —$N_3$, —$NO_2$, —CH=$NR_7$, —$N(R_7)_2$, —$NR_7OH$, —$OR_7$, —$C(O)R_7$, —$C(O)OR_7$, —$OC(O)R_7$, —$OC(O)OR_7$, —$SR_7$, —$S(O)R_7$, and —$S(O)_2R_7$;

each $R_{11}$ is independently selected from —CN, —OH, —($C_1$-$C_6$)alkyl, —($C_2$-$C_6$)alkenyl, -halo, —$N_3$, —$NO_2$, —$N(R_7)_2$, —CH=$NR_7$, —$NR_7OH$, —$OR_7$, —$C(O)R_7$, —$C(O)OR_7$, —$OC(O)R_7$, and —$OC(O)OR_7$;

each $R_{14}$ is independently selected from —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_1$-$C_6$)alkoxy, —($C_1$-$C_6$)alkoxy-($C_1$-$C_6$)alkyl, -phenyl, —$C(halo)_3$, —$CH(halo)_2$, —$CH_2(halo)$, -(3- to 7-membered)heterocycle, -(5- to 10-membered)heteroaryl, —($C_1$-$C_6$)haloalkyl, —($C_2$-$C_6$)haloalkenyl, —($C_2$-$C_6$)haloalkynyl, —($C_2$-$C_6$)hydroxyalkenyl, —($C_2$-$C_6$)hydroxyalkynyl, —($C_1$-$C_6$)alkoxy($C_2$-$C_6$)alkyl, —($C_1$-$C_6$)alkoxy($C_2$-$C_6$)alkenyl, —($C_1$-$C_6$)alkoxy($C_2$-$C_6$)alkynyl, —($C_1$-$C_6$)alkoxy($C_3$-$C_8$)cycloalkyl, —CN, —OH, -halo, —$OC(halo)_3$, —$N_3$, —$NO_2$, —CH=$NR_7$, —$N(R_7)_2$, —$NR_7OH$, —$OR_7$, —$SR_7$, —$O(CH_2)_bOR_7$, —$O(CH_2)_bSR_7$, —$O(CH_2)_bN(R_7)_2$, —$N(R_7)(CH_2)_bOR_7$, —$N(R_7)(CH_2)_bSR_7$, —$N(R_7)(CH_2)_bN(R_7)_2$, —$N(R_7)C(O)R_7$, —$N(R_7)$—$S(O)_2$—($C_1$-$C_6$)alkyl, —C(O)—$N(R_7)_2$, —$C(O)OR_7$, —$C(O)OR_7$, —$OC(O)R_7$, —$OC(O)OR_7$, —$S(O)R_7$, —$S(O)_2R_7$, —$S(O)_2N(R_7)_2$, —$S(O)_2C(halo)_3$, —$S(O)_2$(3- to 7-membered)heterocycle, —$CON(R_7)_2$, —($C_1$-$C_5$)alkyl-C=$NOR_7$, —($C_1$-$C_5$)alkyl-C(O)—$N(R_7)_2$, —($C_1$-$C_6$)alkyl-N(H)$S(O)_2N(R_7)_2$, and —($C_1$-$C_6$)alkyl-C(=NH)—$N(R_7)_2$;

each $R_{20}$ is independently selected from —H, —($C_1$-$C_6$)alkyl, and —($C_3$-$C_8$)cycloalkyl;

each $R_{21}$ is independently selected from —H, —($C_1$-$C_6$)alkyl,

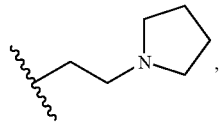

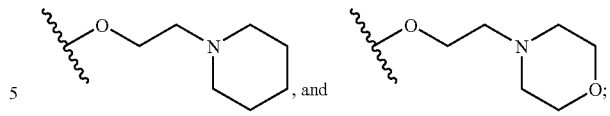

each -halo is independently selected from —F, —Cl, —Br, and —I;

each b is independently selected from the integers 1 and 2;

n is the integer 1, 2, or 3;

p is the integer 1 or 2;

q is the integer 0, 1, 2, 3 or 4;

r is the integer 0, 1, 2, 3, 4, 5, or 6; and s is the integer 0, 1, 2, 3, 4, or 5;

provided that when $A_1$ and $A_3$ are each N, $A_2$ is $C(R_3)$, $R_3$ is —H, and $Ar_2$ is substituted phenyl, then Q is not $CH_2OH$.

(26) The compound of (25), wherein X is —O—, —$N(R_{20})$—, or —$S(O)_2$—, and preferably is —$N(R_{20})$—, wherein $R_{20}$ is preferably —H.

(27) The compound of (25) or (26), wherein D is C and preferably the dashed lines are present.

(28) The compound of (25) or (26), wherein D is N and the dashed lines are absent.

(29) The compound of (25) or (26), wherein the dashed line not connected to D is present as part of a double bond and D is N, having the following structure:

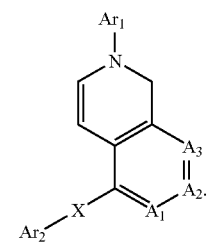

II'

(30) The compound of any one of (25) to (29), wherein $A_1$ and $A_3$ are each N.

(31) The compound of any one of (25) to (30), wherein $A_2$ is $C(R_3)$.

(32) The compound of (25) or (26), having the following structure:

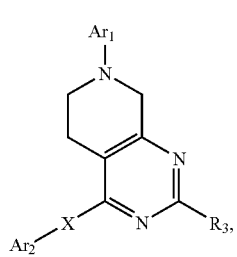

II(a)

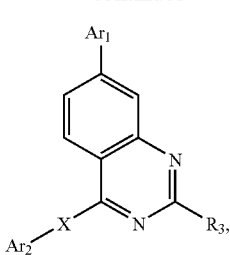

II(b)

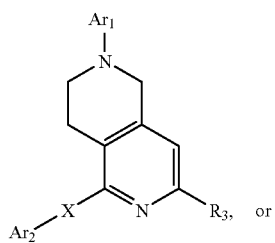

II(c)

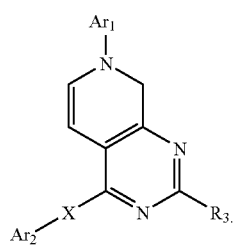

II(d)

(33) The compound of any one of (25) to (32), wherein Ar$_1$ is:

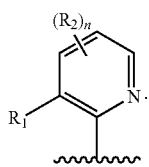

(34) The compound of any one of (25) to (33), wherein R$_1$ is -halo, —C(halo)$_3$, —CH(halo)$_2$, —CH$_2$(halo), or —(C$_1$-C$_6$)alkyl, wherein each -halo is preferably independently selected from —Cl and —F.

(35) The compound of any one of (25) to (34), wherein the Q-group is selected from

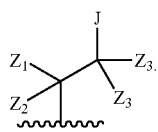

(36) The compound of any one of (25) to (35), wherein J is —OR$_{20}$ or —N(R$_{20}$)$_2$, and preferably is —OR$_{20}$.

(37) The compound of any one of (25) to (36), wherein each R$_{20}$ is independently selected from —H and —(C$_1$-C$_6$)alkyl, and preferably is —H.

(38) The compound of any one of (25) to (37), wherein each Z$_3$ is independently selected from —H and —(C$_1$-C$_6$)alkyl, and preferably is —H.

(39) The compound of any one of (25) to (38), wherein Z$_1$ is —OR$_7$ or —CH$_2$OR$_7$, and preferably is —OR$_7$.

(40) The compound of any one of (25) to (39), wherein Z$_2$ is —H, —(C$_1$-C$_6$)alkyl, or —CH$_2$OR$_7$, and preferably is —H.

(41) The compound of any one of (25) to (40), wherein Ar$_2$ is:

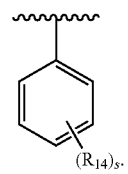

(42) The compound of any one of (25) to (40), wherein Ar$_2$ is:

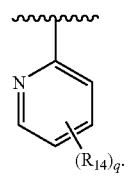

(43) The compound of any one of (25) to (42), wherein each R$_{14}$ is independently selected from -halo, —C(halo)$_3$, —(C$_1$-C$_6$)alkyl, —OR$_7$, —OC(halo)$_3$, and —S(O$_2$)C(halo)$_3$, and preferably is independently selected from -halo, —C(halo)$_3$, and —OC(halo)$_3$.

(44) The compound of any one of (25) to (43), wherein each -halo is independently selected from —Cl and —F.

(45) The compound of any one of (25) to (43), wherein R$_{14}$ is independently selected from —CF$_3$, —OCF$_3$, tert-butyl, and —S(O)$_2$CF$_3$.

(46) The compound of any one of (25) to (45), wherein s or q is 1 or 2.

(47) The compound of any one of (25) to (40), wherein Ar$_2$ is:

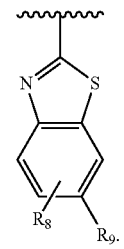

(48) The compound of any one of (25) to (40) and (47), wherein R$_8$ and R$_9$ are independently selected from —H, -halo, and —(C$_1$-C$_6$)alkyl, and preferably R$_8$ and R$_9$ are independently selected from —H and -halo, wherein each -halo is independently selected from —Cl and —F.

(49) A compound of formula III:

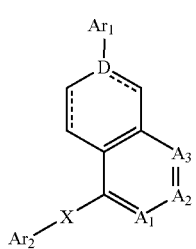

(III)

or a pharmaceutically acceptable derivative thereof, wherein
each dashed line independently denotes the presence or absence of a bond, and wherein $A_1$, $A_2$ and $A_3$ are independently selected from $C(R_3)$ and N, provided that $A_1$ and $A_2$, $A_2$ and $A_3$, or $A_1$, $A_2$ and $A_3$ cannot simultaneously be N;

D is N, C or $C(R_D)$, provided that when D is N or $C(R_D)$, then the dashed line connected to D is absent, and when D is C, then the dashed line connected to D is present and is another bond;

$R_D$ is selected from —H, -halo, —$NO_2$, —CN, —SH, —OH, —C(O)$OR_7$, —C(halo)$_3$, —CH(halo)$_2$, —$CH_2$(halo), and —($C_1$-$C_6$)alkyl;

X is —N($R_{20}$)—;

each $R_3$ is independently selected from:

(a) —H, —$N_3$, -halo, —$NO_2$, —CN, —P(O)(OH)$_2$, —S(O)$_2$(OH), —S(O)$_2$(O)—($C_1$-$C_6$)alkyl, —SH, —OH, —$COOR_7$, —C(halo)$_3$, —CH(halo)$_2$, and —$CH_2$(halo); or (b) —($C_1$-$C_6$)alkyl, —($C_1$-$C_6$)alkoxy, —($C_3$-$C_8$)cycloalkyl, —($C_2$-$C_6$)alkenyl, —($C_2$-$C_6$)alkynyl, —($C_6$-$C_{14}$)aryl, —($C_1$-$C_6$)alkyl-N($R_7$)$_2$, —($C_1$-$C_6$)heteroalkyl, -(3- to 7-membered)heterocycle, -(5- to 10-membered)heteroaryl, —($C_6$-$C_{14}$)bicycloalkyl, —($C_1$-$C_6$)thioalkoxy, —($C_1$-$C_6$)alkyl-($C_1$-$C_6$)alkoxy, —($C_1$-$C_6$)alkyl-O—($C_6$-$C_{14}$)aryl, —($C_1$-$C_6$)alkyl-$R_7$, —($C_1$-$C_6$)alkyl-O—($C_3$-$C_8$)cycloalkyl, —($C_1$-$C_6$)alkyl-(3- to 7-membered)-heterocycle, —($C_1$-$C_6$)alkyl-(5- to 10-membered)heteroaryl, —($C_1$-$C_6$)alkyl-N($R_7$)$_2$, —N($R_7$)$_2$, —N($R_7$)—($C_1$-$C_6$)alkyl-$R_{14}$, —S(O)—($C_1$-$C_6$)alkyl, —O—($C_1$-$C_6$)alkyl-$R_{14}$, —O—($C_1$-$C_6$)alkyl-S(O)$_2$—$R_{14}$, O—($C_3$-$C_8$)cycloalkyl, —$OR_{14}$, —$SR_{14}$, —O—($C_1$-$C_6$)alkyl-O—$R_{14}$, —O—($C_1$-$C_6$)alkyl-C(O)—N($R_7$)—($C_1$-$C_6$)alkyl-$OR_7$, —O—($C_1$-$C_6$)alkyl-C(O)—$R_{14}$, —O—($C_1$-$C_6$)alkyl-C(O)—N($R_7$)$_2$, —C(O)$R_{14}$, —C(O)—($C_1$-$C_6$)alkyl, —C(O)-(3- to 7-membered)heterocycle, —C(O)-(5- to 10-membered)heteroaryl, —C(O)O—($C_1$-$C_6$)alkyl, —C(O)N($R_7$)—($C_1$-$C_6$)alkyl-(3- to 7-membered)heterocycle, —C(O)N($R_7$)—($C_1$-$C_6$)alkyl-(5- to 10-membered)heteroaryl, —C(O)N($R_7$)$_2$, —OC(O)N($R_7$)$_2$, —C(O)N($R_7$)—($C_1$-$C_6$)alkyl-N($R_7$)$_2$, —C(O)N($R_7$)—($C_1$-$C_6$)alkyl-$R_7$, —S(O)$_2$—($C_1$-$C_6$)alkyl, and —S(O)$_2$—N($R_7$)$_2$, each of which can be unsubstituted or substituted with 1, 2, 3 or 4 independently selected $R_{14}$;

$Ar_1$ is:

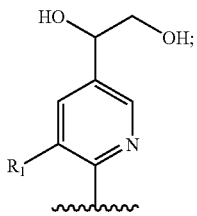

$Ar_2$ is:

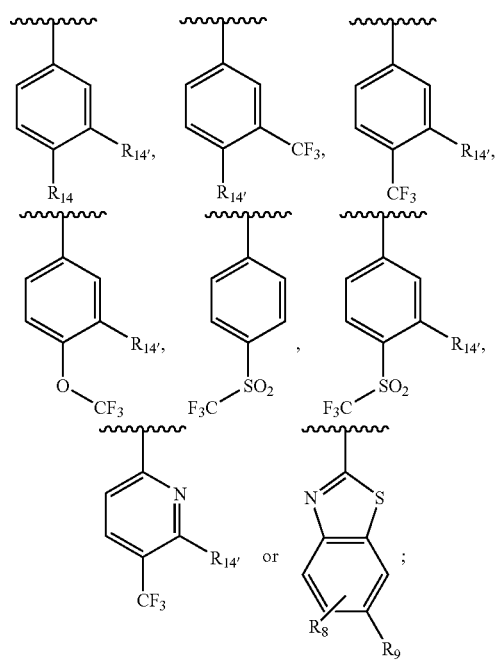

$R_1$ is —Cl, —F, —$CH_3$, —$CF_3$, or —$OCF_3$;

each $R_7$ is independently selected from —H, —OH, —($C_1$-$C_6$)alkyl, —($C_1$-$C_6$)alkoxy, —($C_1$-$C_6$)alkyl-($C_6$-$C_{14}$)aryl, —O—($C_6$-$C_{14}$)aryl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, —($C_1$-$C_6$)alkyl-($C_1$-$C_6$)alkoxy, —($C_1$-$C_6$)haloalkyl, —($C_1$-$C_6$)hydroxyalkyl, —($C_1$-$C_6$)-alkoxy($C_1$-$C_6$)alkyl, —($C_1$-$C_6$)alkyl-N($R_{20}$)$_2$, —C(O)N($R_{20}$)$_2$, -(3- to 7-membered)heterocycle, -(7- to 10-membered)bicycloheterocycle, —($C_6$-$C_{14}$)bicycloalkyl, and —S(O)$_2$—($C_1$-$C_6$)alkyl;

each $R_8$ and $R_9$ is independently selected from:

(a) —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, and -phenyl, each of which is unsubstituted or substituted with 1 or 2 —OH groups; or (b) —H, —$CH_2$C(halo)$_3$, —C(halo)$_3$, —CH(halo)$_2$, —$CH_2$(halo), —OC(halo)$_3$, —OCH(halo)$_2$, —$OCH_2$(halo), —SC(halo)$_3$, —SCH(halo)$_2$, —$SCH_2$(halo), —CN, —O—CN, —OH, -halo, —$N_3$, —$NO_2$, —CH=$NR_7$, —N($R_7$)$_2$, —$NR_7$OH, —$OR_7$, —C(O)$R_7$, —C(O)$OR_7$, —OC(O)$R_7$, —OC(O)$OR_7$, —$SR_7$, —S(O)$R_7$, and —S(O)$_2R_7$;

each $R_{11}$ is independently selected from —CN, —OH, —($C_1$-$C_6$)alkyl, —($C_2$-$C_6$)alkenyl, -halo, —$N_3$, —$NO_2$, —N($R_7$)$_2$, —CH=$NR_7$, —$NR_7$OH, —$OR_7$, —C(O)$R_7$, —C(O)$OR_7$, —OC(O)$R_7$, and —OC(O)$OR_7$;

each $R_{14}$ and $R_{14'}$ is independently selected from —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_1$-$C_6$)alkoxy, —($C_1$-$C_6$)alkoxy-($C_1$-$C_6$)alkyl, -phenyl, —C(halo)$_3$, —CH(halo)$_2$, —CH$_2$(halo), -(3- to 7-membered)heterocycle, -(5- to 10-membered)heteroaryl, —($C_1$-$C_6$)haloalkyl, —($C_2$-$C_6$)haloalkenyl, —($C_2$-$C_6$)haloalkynyl, —($C_2$-$C_6$)hydroxyalkenyl, —($C_2$-$C_6$)hydroxyalkynyl, —($C_1$-$C_6$)alkoxy($C_2$-$C_6$)alkyl, —($C_1$-$C_6$)alkoxy($C_2$-$C_6$)alkenyl, —($C_1$-$C_6$)alkoxy($C_2$-$C_6$)alkynyl, —($C_1$-$C_6$)alkoxy($C_3$-$C_8$)cycloalkyl, —CN, —OH, -halo, —OC(halo)$_3$, —N$_3$, —NO$_2$, —CH=NR$_7$, —N(R$_7$)$_2$, —NR$_7$OH, —OR$_7$, —SR$_7$, —O(CH$_2$)$_b$OR$_7$, —O(CH$_2$)$_b$SR$_7$, —O(CH$_2$)$_b$N(R$_7$)$_2$, —N(R$_7$)(CH$_2$)$_b$OR$_7$, —N(R$_7$)(CH$_2$)$_b$SR$_7$, —N(R$_7$)(CH$_2$)$_b$N(R$_7$)$_2$, —N(R$_7$)C(O)R$_7$, —N(R$_7$—S(O)$_2$—($C_1$-$C_6$)alkyl, —C(O)—N(R$_7$)$_2$, —C(O)R$_7$, —C(O)OR$_7$, —OC(O)R$_7$, —OC(O)OR$_7$, —S(O)R$_7$, —S(O)$_2$R$_7$, —S(O)$_2$N(R$_7$)$_2$, —S(O)$_2$C(halo)$_3$, —S(O)$_2$(3- to 7-membered)heterocycle, —CON(R$_7$)$_2$, —($C_1$-$C_5$)alkyl-C=NOR$_7$, —($C_1$-$C_5$)alkyl-C(O)—N(R$_7$)$_2$, —($C_1$-$C_6$)alkyl-NHS(O)$_2$N(R$_7$)$_2$, and —($C_1$-$C_6$)alkyl-C(=NH)—N(R$_7$)$_2$;

each $R_{20}$ is independently selected from —H, —($C_1$-$C_6$)alkyl, and —($C_3$-$C_8$)cycloalkyl;

each $R_{21}$ is independently selected from —H, —($C_1$-$C_6$)alkyl,

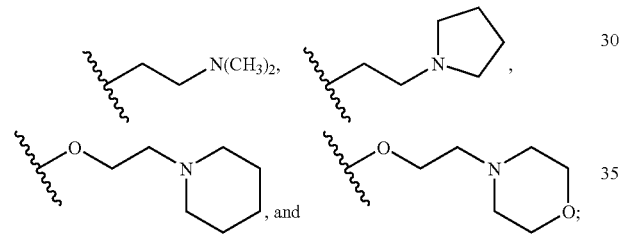

each -halo is independently selected from —F, —Cl, —Br, and —I; and each b is independently selected from the integers 1 and 2.

(50) The compound of (49), wherein each $R_{20}$ is —H.

(51) The compound of (49) or (50), wherein D is C and preferably the dashed lines are present.

(52) The compound of (49) or (50), wherein D is N and the dashed lines are absent.

(53) The compound of (49) or (50), wherein the dashed line not connected to D is present as part of a double bond and D is N, having the following structure:

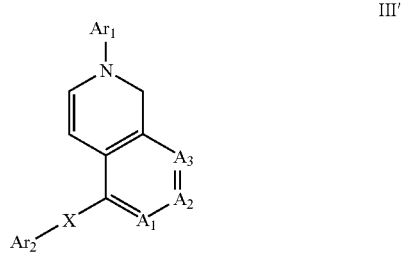

III'

(54) The compound of any one of (49) to (53), wherein $A_1$ and $A_3$ are each N.

(55) The compound of any one of (49) to (54), wherein $A_2$ is C($R_3$).

(56) The compound of (49) or (50), having the following structure:

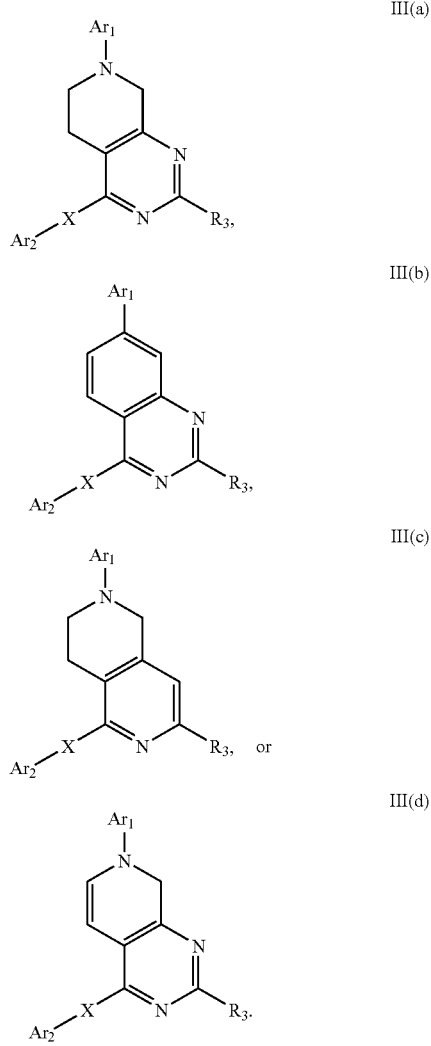

(57) The compound of any one of (49) to (56), wherein $R_1$ is -halo, —C(halo)$_3$, or —($C_1$-$C_6$)alkyl and preferably is —Cl, —F, —CF$_3$ or —CH$_3$.

(58) The compound of any one of (49) to (57), wherein each $R_3$ is independently selected from —H, —($C_1$-$C_6$)alkyl-($C_1$-$C_6$)alkoxy, —N(R$_7$)$_2$, —OR$_7$, —SR$_7$, and —CN and preferably is independently selected from —H, —CH$_2$—O—CH$_3$, —NH$_2$, —SCH$_3$, —OCH$_3$, —OCH$_2$CH$_5$, and —CN.

(59) The compound of any one of (49) to (58), wherein $Ar_2$ is:

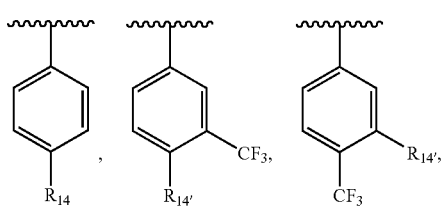

-continued

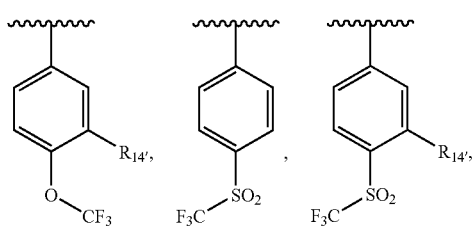

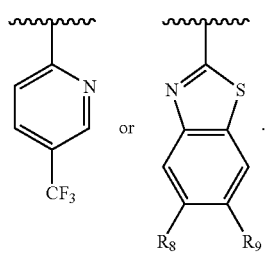

(60) The compound of any one of (49) to (59), wherein Ar$_2$ is:

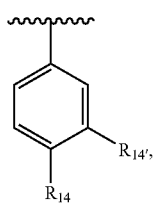

wherein R$_{14}$ is selected from —H, —Cl, —F, —Br, —OCF$_3$, —(C$_1$-C$_6$)alkyl, —S(O)$_2$CF$_3$, —S(O)$_2$(C$_1$-C$_6$)alkyl, —OCH$_3$, —OCH$_2$CH$_3$ and —OCH(CH$_3$)$_2$, and preferably is selected from —CF$_3$, —OCF$_3$, —Cl, and —F; and wherein R$_{14'}$ is selected from —H, —Cl, —F, —Br, —OCF$_3$, —(C$_1$-C$_6$)alkyl, —S(O)$_2$CF$_3$, —S(O)$_2$(C$_1$-C$_6$)alkyl, —OCH$_3$, —OCH$_2$CH$_3$ and —OCH(CH$_3$)$_2$, and preferably is selected from —CF$_3$, —OCF$_3$, —OCH$_3$, —OCH$_2$CH$_3$, —Cl, and —F.

(61) The compound of any one of (49) to (59), wherein Ar$_2$ is:

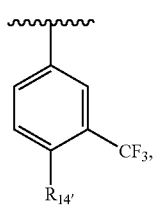

wherein R$_{14'}$ is selected from —H, —Cl, —F, —Br, —OCF$_3$, —(C$_1$-C$_6$)alkyl, —S(O)$_2$CF$_3$, —S(O)$_2$(C$_1$-C$_6$)alkyl, —OCH$_3$, —OCH$_2$CH$_3$ and —OCH(CH$_3$)$_2$, and preferably is selected from —CF$_3$, —OCF$_3$, —OCH$_3$, —OCH$_2$CH$_3$, —Cl, and —F.

(62) The compound of any one of (49) to (59), wherein Ar$_2$ is:

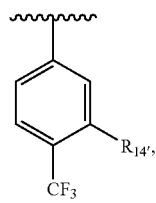

wherein R$_{14'}$ is selected from —H, —Cl, —F, —Br, —OCF$_3$, —(C$_1$-C$_6$)alkyl, —S(O)$_2$CF$_3$, —S(O)$_2$(C$_1$-C$_6$)alkyl, —OCH$_3$, —OCH$_2$CH$_3$ and —OCH(CH$_3$)$_2$, and preferably is selected from —CF$_3$, —OCF$_3$, —OCH$_3$, —OCH$_2$CH$_3$, —Cl, and —F.

(63) The compound of any one of (49) to (59), wherein Ar$_2$ is:

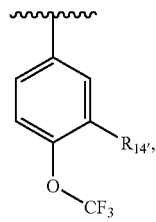

wherein R$_{14'}$ is selected from —H, —Cl, —F, —Br, —OCF$_3$, —(C$_1$-C$_6$)alkyl, —S(O)$_2$CF$_3$, —S(O)$_2$(C$_1$-C$_6$)alkyl, —OCH$_3$, —OCH$_2$CH$_3$ and —OCH(CH$_3$)$_2$, and preferably is selected from —CF$_3$, —OCF$_3$, —OCH$_3$, —OCH$_2$CH$_3$, —Cl, and —F.

(64) The compound of any one of (49) to (59), wherein Ar$_2$ is:

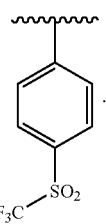

(65) The compound of any one of (49) to (59), wherein Ar$_2$ is:

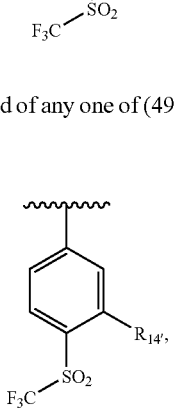

wherein R$_{14'}$ is selected from —H, —Cl, —F, —Br, —OCF$_3$, —(C$_1$-C$_6$)alkyl, —S(O)$_2$CF$_3$, —S(O)$_2$(C$_1$-C$_6$)alkyl, —OCH$_3$, —OCH$_2$CH$_3$ and —OCH(CH$_3$)$_2$, and preferably is selected from —CF$_3$, —OCF$_3$, —OCH$_3$, —OCH$_2$CH$_3$, —Cl, and —F.

(66) The compound of any one of (49) to (59), wherein Ar$_2$ is:

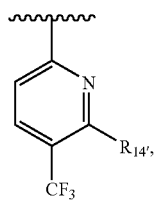

wherein R$_{14'}$ is selected from —H, —Cl, —F, —Br, —OCF$_3$, —(C$_1$-C$_6$)alkyl, —S(O)$_2$CF$_3$, —S(O)$_2$(C$_1$-C$_6$)alkyl, —OCH$_3$, —OCH$_2$CH$_3$ and —OCH(CH$_3$)$_2$, and preferably is selected from —CF$_3$, —OCF$_3$, —OCH$_3$, —OCH$_2$CH$_3$, —Cl, and —F.

(67) The compound of any one of (49) to (59), wherein Ar$_2$ is:

wherein each R$_8$ and R$_9$ is independently selected from —H, —Cl, —Br, —F, —CH$_3$, —OCH$_3$, —OCH$_2$CH$_3$, —CF$_3$, —OCF$_3$, iso-propyl, and tert-butyl.

(68) The compound of any one of (49) to (67), wherein the chiral carbon atom of the Q-group has the (S) configuration:

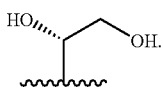

(69) The compound of any one of (49) to (67), wherein the chiral carbon atom of the Q-group has the (R)-configuration:

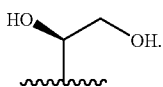

(70) The compound of any one of (49) to (69), wherein A$_2$ is C(R$_3$) and R$_3$ is —(C$_1$-C$_6$)haloalkyl, and preferably is —CH$_2$Cl.

(71) The compound of any one of (49) to (69), wherein A$_2$ is C(R$_3$) and R$_3$ is —(C$_1$-C$_6$)alkoxy substituted with -(3- to 7-membered)heterocycle, and preferably is -methylpiperidinyl.

(72) The compound of any one of (49) to (69), wherein A$_2$ is C(R$_3$) and R$_3$ is —(C$_1$-C$_6$)alkoxy substituted with —(C$_1$-C$_6$)alkyl, and preferably is —CH$_3$OCH$_3$.

(73) The compound of any one of (49) to (69), wherein A$_2$ is C(R$_3$) and R$_3$ is —(C$_1$-C$_6$)alkyl substituted with -(3- to 7-membered)heterocycle, and preferably is —CH$_2$-morpholino.

(74) The compound of any one of (49) to (69), wherein A$_2$ is C(R$_3$) and R$_3$ is —NH$_2$.

(75) The compound of any one of (49) to (69), wherein A$_2$ is C(R$_3$) and R$_3$ is —(C$_1$-C$_6$)thioalkoxy, and preferably is —SCH$_3$.

(76) The compound of any one of (49) to (69), wherein A$_2$ is C(R$_3$) and R$_3$ is —S(O)$_2$—(C$_1$-C$_6$)alkyl, and preferably is —S(O)$_2$CH$_3$.

(77) The compound of any one of (49) to (69), wherein A$_2$ is C(R$_3$) and R$_3$ is —(C$_1$-C$_6$)alkoxy, and preferably is —OCH$_3$.

(78) The compound of any one of (49) to (69), wherein A$_2$ is C(R$_3$) and R$_3$ is —N(R$_7$)$_2$, and preferably is —N(CH$_3$)$_2$.

(79) The compound of any one of (49) to (69), wherein A$_2$ is C(R$_3$) and R$_3$ is —N(R$_7$)$_2$—(C$_1$-C$_6$)alkyl-R$_{14}$ and preferably is —N(H)C$_2$H$_4$N(CH$_3$)$_2$.

(80) The compound of any one of (49) to (69), wherein A$_2$ is C(R$_3$) and R$_3$ is cyano.

(81) A compound of formula IV:

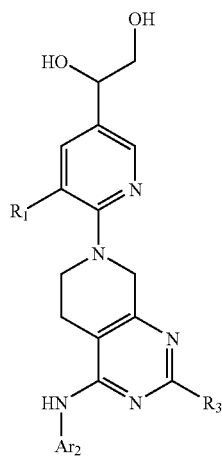

or a pharmaceutically acceptable derivative thereof, wherein R$_3$ is selected from:
(a) —H, —N$_3$, -halo, —NO$_2$, —CN, —P(O)(OH)$_2$, —S(O)$_2$(OH), —S(O)$_2$(O)—(C$_1$-C$_6$)alkyl, —SH, —OH, —COOR$_7$, —C(halo)$_3$, —CH(halo)$_2$, and —CH$_2$(halo); or
(b) —(C$_1$-C$_6$)alkyl, —(C$_1$-C$_6$)alkoxy, —(C$_3$-C$_8$)cycloalkyl, —(C$_2$-C$_6$)alkenyl, —(C$_2$-C$_6$)alkynyl, —(C$_6$-C$_{14}$)aryl, —(C$_1$-C$_6$)alkyl-N(R$_7$)$_2$, —(C$_1$-C$_6$)heteroalkyl, -(3- to 7-membered)heterocycle, -(5- to 10-membered)heteroaryl, —(C$_6$-C$_{14}$)bicycloalkyl, —(C$_1$-C$_6$)thioalkoxy, —(C$_1$-C$_6$)alkyl-(C$_1$-C$_6$)alkoxy, —(C$_1$-C$_6$)alkyl-O—(C$_6$-C$_{14}$)aryl, —(C$_1$-C$_6$)alkyl-R$_7$, —(C$_1$-C$_6$)alkyl-O—(C$_3$-C$_8$)cycloalkyl, —(C$_1$-C$_6$)alkyl-(3- to 7-membered)heterocycle, —(C$_1$-C$_6$)alkyl-(5- to 10-membered)heteroaryl, —(C$_1$-C$_6$)alkyl-N(R$_7$)$_2$, —N(R$_7$)$_2$, —N(R$_7$)—(C$_1$-C$_6$)alkyl-R$_{14}$, —S(O)—(C$_1$-C$_6$)alkyl, —O—(C$_1$-C$_6$)alkyl-R$_{14}$, —O—(C$_1$-C$_6$)alkyl-S(O)$_2$—R$_{14}$, —O—(C$_3$-C$_8$)cycloalkyl, —OR$_{14}$, —SR$_{14}$, —O—(C$_1$-C$_6$)alkyl-O—R$_{14}$, —O—(C$_1$-C$_6$)alkyl-C(O)—N(R$_7$)—(C$_1$-C$_6$)alkyl-OR$_7$, —O—(C$_1$-C$_6$)alkyl-C(O)—R$_{14}$, —O—(C$_1$-C$_6$)

alkyl-C(O)—N(R₇)₂, —C(O)R₁₄, —C(O)—(C₁-C₆)
alkyl, —C(O)-(3- to 7-membered)heterocycle, —C(O)-
(5- to 10-membered)heteroaryl, —C(O)O—(C₁-C₆)
alkyl, —C(O)N(R₇)—(C₁-C₆)alkyl-(3- to 7-membered)
heterocycle, —C(O)N(R₇)—(C₁-C₆)alkyl-(5- to
10-membered)heteroaryl, —C(O)N(R₇)₂, —OC(O)N
(R₇)₂, —C(O)N(R₇)—(C₁-C₆)alkyl-N(R₇)₂, —C(O)N
(R₇)—(C₁-C₆)alkyl-R₇, —S(O)₂—(C₁-C₆)alkyl, and
—S(O)₂—N(R₇)₂, each of which can be unsubstituted
or substituted with 1, 2, 3 or 4 independently selected
R₁₄;

Ar₂ is:

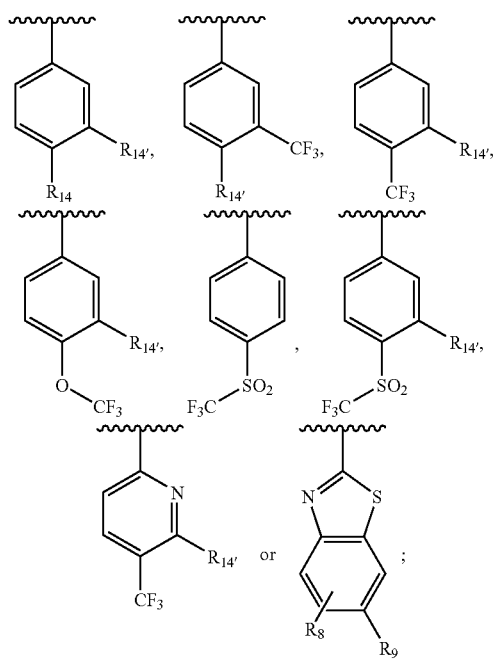

R₁ is —Cl, —F, —CH₃, —CF₃, or —OCF₃;
each R₇ is independently selected from —H, —OH, —(C₁-C₆)alkyl, —(C₁-C₆)alkoxy, —(C₁-C₆)alkyl-(C₆-C₁₄)aryl, O—(C₆-C₁₄)aryl, —(C₂-C₆)alkenyl, —(C₂-C₆)alkynyl, —(C₃-C₈)cycloalkyl, —(C₅-C₈)cycloalkenyl, -phenyl, -benzyl, —(C₁-C₆)alkyl-(C₁-C₆)alkoxy, —(C₁-C₆)haloalkyl, —(C₁-C₆)hydroxyalkyl, —(C₁-C₆)alkoxy(C₁-C₆)alkyl, —(C₁-C₆)alkyl-N(R₂₀)₂, —C(O)N(R₂₀)₂, -(3- to 7-membered)heterocycle, -(7- to 10-membered)bicycloheterocycle, —(C₆-C₁₄)bicycloalkyl, and —S(O)₂—(C₁-C₆)alkyl;
each R₈ and R₉ is independently selected from:
(a) —(C₁-C₆)alkyl, —(C₂-C₆)alkenyl, —(C₂-C₆)alkynyl, —(C₃-C₈)cycloalkyl, —(C₅-C₈)cycloalkenyl, and -phenyl, each of which is unsubstituted or substituted with 1 or 2 —OH groups; or
(b) —H, —CH₂C(halo)₃, —C(halo)₃, —CH(halo)₂, —CH₂(halo), —OC(halo)₃, —OCH(halo)₂, —OCH₂(halo), —SC(halo)₃, —SCH(halo)₂, —SCH₂(halo), —CN, —O—CN, —OH, -halo, —N₃, —NO₂, —CH=NR₇, —N(R₇)₂, —NR₇OH, —OR₇, —C(O)R₇, —C(O)OR₇, —OC(O)R₇, —OC(O)OR₇, —SR₇, —S(O)R₇, and —S(O)₂R₇;
each R₁₁ is independently selected from —CN, —OH, —(C₁-C₆)alkyl, —(C₂-C₆)alkenyl, -halo, —N₃, —NO₂, —N(R₇)₂, —CH=NR₇, —NR₇OH, —OR₇, —C(O)R₇, —C(O)OR₇, —OC(O)R₇, and —OC(O)OR₇;
each R₁₄ and R₁₄' is independently selected from —H, —(C₁-C₆)alkyl, —(C₂-C₆)alkenyl, —(C₂-C₆)alkynyl, —(C₃-C₈)cycloalkyl, —(C₅-C₈)cycloalkenyl, —(C₁-C₆)alkoxy, —(C₁-C₆)alkyl, -phenyl, —C(halo)₃, —CH(halo)₂, —CH₂(halo), -(3- to 7-membered)heterocycle, -(5- to 10-membered)heteroaryl, —(C₁-C₆)haloalkyl, —(C₂-C₆)haloalkenyl, —(C₂-C₆)haloalkynyl, —(C₂-C₆)hydroxyalkenyl, —(C₂-C₆)hydroxyalkynyl, —(C₁-C₆)alkoxy(C₂-C₆)alkyl, —(C₁-C₆)alkoxy(C₂-C₆)alkenyl, —(C₁-C₆)alkoxy(C₂-C₆)alkynyl, —(C₁-C₆)alkoxy(C₃-C₈)cycloalkyl, —CN, —OH, -halo, —OC(halo)₃, —N₃, —NO₂, —CH=NR₇, —N(R₇)₂, —NR₇OH, —OR₇, —SR₇, —O(CH₂)ᵦOR₇, —O(CH₂)ᵦSR₇, —O(CH₂)ᵦN(R₇)₂, —N(R₇)(CH₂)ᵦOR₇, —N(R₇)(CH₂)ᵦSR₇, —N(R₇)(CH₂)ᵦN(R₇)₂, —N(R₇)COR₇, —N(R₇)—S(O)₂—(C₁-C₆)alkyl, —C(O)—N(R₇)₂, —C(O)R₇, —C(O)OR₇, —OC(O)R₇, —OC(O)OR₇, —S(O)R₇, —S(O)₂R₇, —S(O)₂N(R₇)₂, —S(O)₂C(halo)₃, —S(O)₂(3- to 7-membered)heterocycle, —CON(R₇)₂, —(C₁-C₅)alkyl-C=NOR₇, —(C₁-C₅)alkyl-C(O)—N(R₇)₂, —(C₁-C₆)alkyl-N(H)S(O)₂N(R₇)₂, and —(C₁-C₆)alkyl-C(=NH)—N(R₇)₂;
each R₂₀ is independently selected from —H, —(C₁-C₆)alkyl, and —(C₃-C₈)cycloalkyl;
each R₂₁ is independently selected from —H, —(C₁-C₆)alkyl,

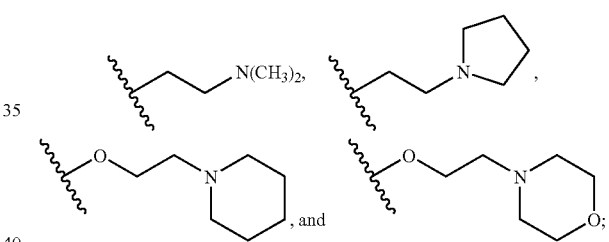

each -halo is independently selected from —F, —Cl, —Br, and —I; and
each b is independently selected from the integers 1 and 2.
(82) The compound of (81), wherein R₁ is —Cl, —F, or —CF₃ and Ar₂ is:

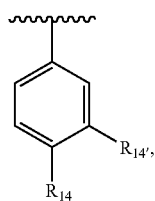

wherein R₁₄ is selected from —H, —Cl, —F, —Br, —OCF₃, —(C₁-C₆)alkyl, —S(O)₂CF₃, —S(O)₂(C₁-C₆)alkyl, —OCH₃, —OCH₂CH₃ and —OCH(CH₃)₂, and preferably is selected from —CF₃, —OCF₃, —Cl, and —F; and wherein R₁₄' is selected from —H, —Cl, —F, —Br, —OCF₃, —(C₁-C₆)alkyl, —S(O)₂CF₃, —S(O)₂(C₁-C₆)alkyl, —OCH₃, —OCH₂CH₃ and —OCH(CH₃)₂, and preferably is selected from —CF₃, —OCF₃, —OCH₃, —OCH₂CH₃, —Cl, and —F.

(83) The compound of (81), wherein $R_1$ is —Cl, —F, or —$CF_3$ and $Ar_2$ is:

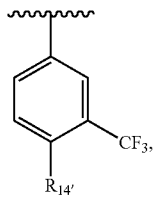

wherein $R_{14'}$ is selected from —H, —Cl, —F, —Br, —$OCF_3$, —($C_1$-$C_6$)alkyl, —$S(O)_2CF_3$, —$S(O)_2(C_1$-$C_6)$alkyl, —$OCH_3$, —$OCH_2CH_3$ and —$OCH(CH_3)_2$, and preferably is selected from —$CF_3$, —$OCF_3$, —$OCH_3$, —$OCH_2CH_3$, —Cl, and —F.

(84) The compound of (81), wherein $R_1$ is —Cl, —F, or —$CF_3$ and $Ar_2$ is:

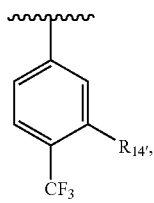

wherein $R_{14'}$ is selected from —H, —Cl, —F, —Br, —$OCF_3$, —($C_1$-$C_6$)alkyl, —$S(O)_2CF_3$, —$S(O)_2(C_1$-$C_6)$alkyl, —$OCH_3$, —$OCH_2CH_3$ and —$OCH(CH_3)_2$, and preferably is selected from —$CF_3$, —$OCF_3$, —$OCH_3$, —$OCH_2CH_3$, —Cl, and —F.

(85) The compound of (81), wherein $R_1$ is —Cl, —F, or —$CF_3$ and $Ar_2$ is:

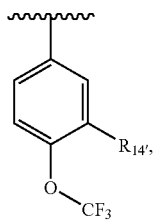

wherein $R_{14'}$ is selected from —H, —Cl, —F, —Br, —$OCF_3$, —($C_1$-$C_6$)alkyl, —$S(O)_2CF_3$, —$S(O)_2(C_1$-$C_6)$alkyl, —$OCH_3$, —$OCH_2CH_3$ and —$OCH(CH_3)_2$, and preferably is selected from —$CF_3$, —$OCF_3$, —$OCH_3$, —$OCH_2CH_3$, —Cl, and —F.

(86) The compound of (81), wherein $R_1$ is —Cl, —F, or —$CF_3$ and $Ar_2$ is:

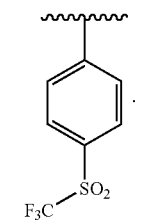

(87) The compound of (81), wherein $R_1$ is —Cl, —F, or —$CF_3$ and $Ar_2$ is:

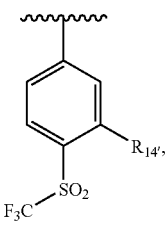

wherein $R_{14'}$ is selected from —H, —Cl, —F, —Br, —$OCF_3$, —($C_1$-$C_6$)alkyl, —$S(O)_2CF_3$, —$S(O)_2(C_1$-$C_6)$alkyl, —$OCH_3$, —$OCH_2CH_3$ and —$OCH(CH_3)_2$, and preferably is selected from —$CF_3$, —$OCF_3$, —$OCH_3$, —$OCH_2CH_3$, —Cl, and —F.

(88) The compound of (81), wherein $R_1$ is —Cl, —F, or —$CF_3$ and $Ar_2$ is:

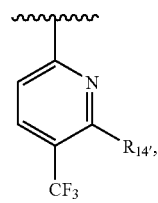

wherein $R_{14'}$ is selected from —H, —Cl, —F, —Br, —$OCF_3$, —($C_1$-$C_6$)alkyl, —$S(O)_2CF_3$, —$S(O)_2(C_1$-$C_6)$alkyl, —$OCH_3$, —$OCH_2CH_3$ and —$OCH(CH_3)_2$, and preferably is selected from —$CF_3$, —$OCF_3$, —$OCH_3$, —$OCH_2CH_3$, —Cl, and —F.

(89) The compound of (81), wherein $R_1$ is —Cl, —F, or —$CF_3$ and $Ar_2$ is:

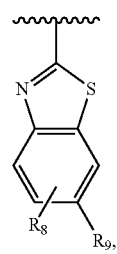

wherein each $R_8$ and $R_9$ is independently selected from —H, —Cl, —Br, —F, —$CH_3$, —$OCH_3$, —$OCH_2CH_3$, —$CF_3$, —$OCF_3$, iso-propyl, and tert-butyl.

(90) The compound of any one of (81) to (89), wherein the chiral carbon atom of the Q-group has the (S)-configuration:

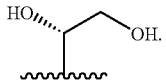

(91) The compound of to any one of (81) to (89), wherein the chiral carbon atom of the Q-group has the (R)-configuration:

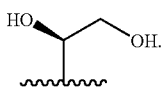

(92) The compound of any one of (1) to (91), wherein the pharmaceutically acceptable derivative is a pharmaceutically acceptable salt.

(93) A composition comprising a compound of any one of (1) to (92) or a pharmaceutically acceptable derivative of the compound of any one of (1) to (91) and a pharmaceutically acceptable carrier or excipient.

(94) A method for treating or preventing pain UI, an ulcer, IBD, or IBS in an animal, comprising administering to an animal in need thereof, an effective amount of a compound of any one of (1) to (92) or a pharmaceutically acceptable derivative of the compound of any one of (1) to (91).

(95) A method of inhibiting TRPV1 function in a cell comprising contacting a cell capable of expressing TRPV1 with an effective amount of a compound of any one of (1) to (92) or a pharmaceutically acceptable derivative of the compound of any one of (1) to (91).

(96) A use of a compound of any one of (1) to (92) or a pharmaceutically acceptable derivative of the compound of any one of (1) to (91) in the production of a medicament for the treatment or prevention of pain, UI, an ulcer, IBD, or IBS in an animal.

(97) A compound of any one of (1) to (92) for use as a medicament.

4.1. Compounds of Formula I

The invention encompasses compounds of formula I:

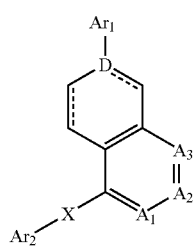

(I)

where the dashed lines, $A_1$, $A_2$, $A_3$, D, X, $Ar_1$ and $Ar_2$ are as defined above for compounds of formula I.

Certain embodiments of a compound of formula I are presented below.

In one embodiment, a compound of formula I is a pharmaceutically acceptable derivative of a compound of formula I.

In another embodiment, a compound of formula I is a compound of formula I where the derivative is a pharmaceutically acceptable salt.

In another embodiment, a compound of formula I is a pharmaceutically acceptable salt of a compound of formula I.

In another embodiment, a compound of formula I is a compound of formula I', i.e., the dashed line not connected to D is present as part of a double bond and D is N:

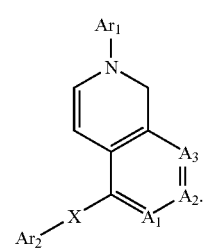

I'

In another embodiment, a compound of formula I is a compound of formula I(a):

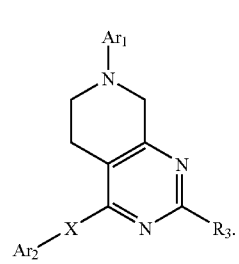

I(a)

In another embodiment, a compound of formula I is a compound of formula I(b):

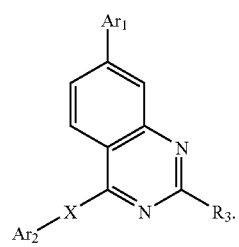

I(b)

In another embodiment, a compound of formula I is a compound of formula I(c):

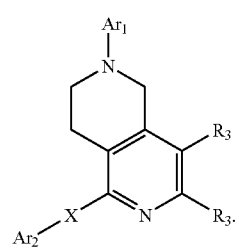

I(c)

In another embodiment, a compound of formula I is a compound of formula I(d):

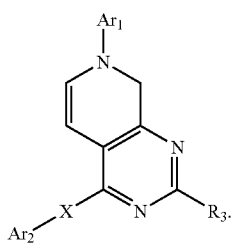

I(d)

In another embodiment, a compound of formula I is a compound of formula I(e):

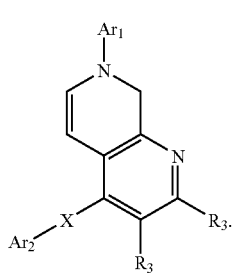

I(e)

In another embodiment, a compound of formula I is a compound of formula I(f):

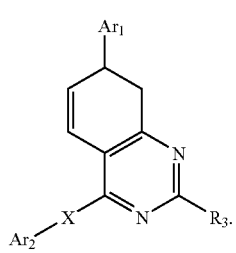

I(f)

In another embodiment, a compound of formula I is a compound of formula I(g):

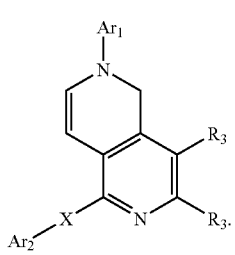

I(g)

In another embodiment, a compound of formula I is a compound of formula I(h):

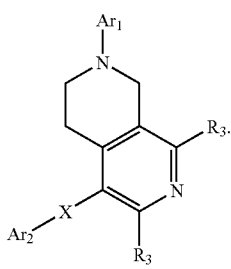

I(h)

In another embodiment, a compound of formula I is a compound of formula I(i):

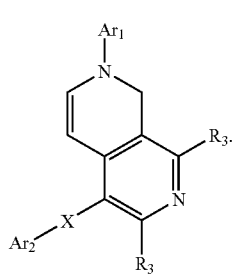

I(i)

In another embodiment, a compound of formula I is a compound of formula I(j):

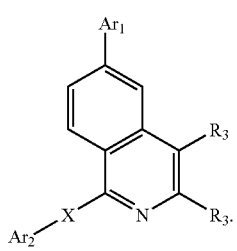

I(j)

In another embodiment, a compound of formula I is a compound of formula I(k):

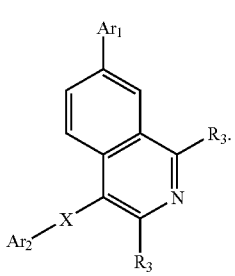

I(k)

In another embodiment, a compound of formula I is a compound of formula I(l):

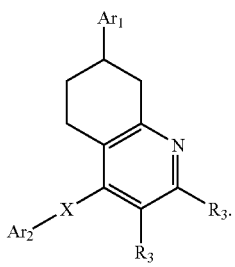

I(l)

In another embodiment, a compound of formula I is a compound of formula I(m):

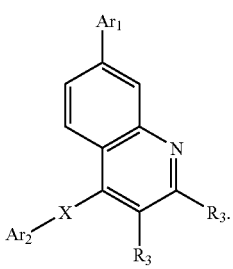

I(m)

In another embodiment, a compound of formula I is a compound of formula I(n):

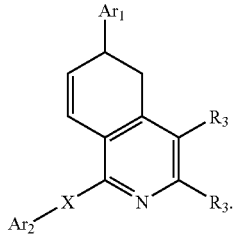

I(n)

In another embodiment, a compound of formula I is a compound of formula I(o):

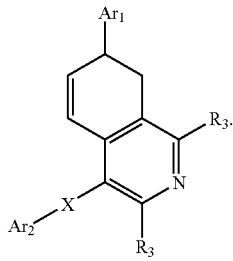

I(o)

In another embodiment, a compound of formula I is a compound of formula I(p):

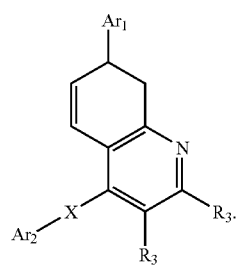

I(p)

In another embodiment, $Ar_1$ is a pyridyl group.
In another embodiment, $Ar_1$ is a pyrimidinyl group.
In another embodiment, $Ar_1$ is a pyrazinyl group.
In another embodiment, $Ar_1$ is a pyridazinyl group.
In another embodiment, $Ar_1$ is a benzyl group.
In another embodiment, $A_1$ is $C(R_3)$.
In another embodiment, $A_1$ is N.
In another embodiment, $A_2$ is $C(R_3)$.
In another embodiment, $A_2$ is N.
In another embodiment, $A_3$ is $C(R_3)$.
In another embodiment, $A_3$ is N.
In another embodiment, D is C.
In another embodiment, D is $C(R_D)$.
In another embodiment, D is N.
In another embodiment, $R_D$ is —H.
In another embodiment, $R_D$ is —F.
In another embodiment, $R_D$ is —Cl.
In another embodiment, $R_D$ is —$(C_1$-$C_6)$alkyl.
In another embodiment, X is —$N(R_{20})$—.
In another embodiment, X is —NH—.
In another embodiment, X is —$N((C_1$-$C_6)$alkyl)-.
In another embodiment, X is —$N((C_3$-$C_8)$cycloalkyl)-.
In another embodiment, X is —O—.
In another embodiment, X is —S—.
In another embodiment, X is —S(O)—.
In another embodiment, X is —$S(O_2)$—.
In another embodiment, $Ar_2$ is a benzoimidazolyl group.
In another embodiment, $Ar_2$ is a benzothiazolyl group.
In another embodiment, $Ar_2$ is a benzooxazolyl group.
In another embodiment, $Ar_2$ is:

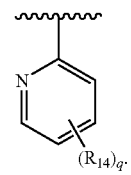

$(R_{14})_q$.

In another embodiment, $Ar_2$ is:

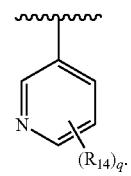

$(R_{14})_q$.

In another embodiment, Ar$_2$ is:

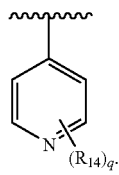

In another embodiment, Ar$_2$ is:

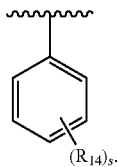

In another embodiment, Ar$_2$ is:

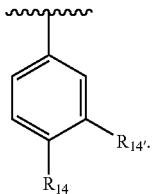

In another embodiment, Ar$_2$ is:

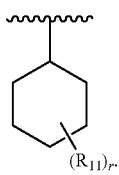

In another embodiment, Ar$_2$ is:

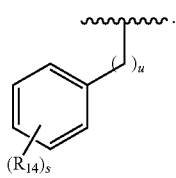

In another embodiment, Ar$_2$ is:

In another embodiment, Ar$_2$ is:

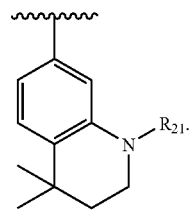

In another embodiment, Ar$_2$ is:

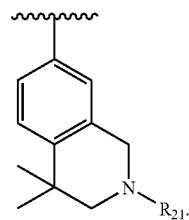

In another embodiment, Ar$_2$ is:

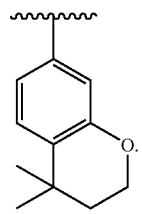 [SMILES: *c1ccc2c(c1)OCCC2(C)C]

In another embodiment, Ar$_2$ is a-(3- to 7-membered)heterocycle.
In another embodiment, Ar$_2$ is a-(7- to 10-membered)bicycloheterocycle.
In another embodiment, n, p, or w is 1.
In another embodiment, n, p, or w is 2.
In another embodiment, n is 3.
In another embodiment, m is 0.
In another embodiment, m is 1.
In another embodiment, m is 2.
In another embodiment, u is 1.
In another embodiment, u is 2.
In another embodiment, v is 1.
In another embodiment, v is 2.
In another embodiment, each R$_3$ is independently —H or —(C$_1$-C$_6$)alkyl.
In another embodiment, each R$_3$ is —H.
In another embodiment, each R$_3$ is -halo.
In another embodiment, each R$_3$ is —CN.
In another embodiment, each R$_3$ is —P(O)(OH)$_2$.
In another embodiment, each R$_3$ is —S(O)$_2$(OH).
In another embodiment, each R$_3$ is —S(O)$_2$(O)—(C$_1$-C$_6$ alkyl).
In another embodiment, each R$_3$ is —OH.
In another embodiment, each R$_3$ is —C(O)OR$_7$.
In another embodiment, each R$_3$ is —C(halo)$_3$.
In another embodiment, each R$_3$ is —CH(halo)$_2$.
In another embodiment, each R$_3$ is —CH$_2$(halo).
In another embodiment, each R$_3$ is —(C$_1$-C$_6$)alkoxy.
In another embodiment, each R$_3$ is —(C$_3$-C$_8$)cycloalkyl.

In another embodiment, each $R_3$ is —$(C_6$-$C_{14})$aryl.
In another embodiment, each $R_3$ is —$(C_1$-$C_6)$alkyl-$N(R_7)_2$.
In another embodiment, each $R_3$ is —$N(R_7)$—$(C_1$-$C_6)$alkyl-$R_{14}$.
In another embodiment, each $R_3$ is —$(C_1$-$C_6)$alkyl-$(C_1$-$C_6)$alkoxy.
In another embodiment, each $R_3$ is —$(C_1$-$C_6)$alkyl-O—$(C_3$-$C_8)$cycloalkyl.
In another embodiment, each $R_3$ is —O—$(C_1$-$C_6)$alkyl-$S(O)_2$—$R_{14}$.
In another embodiment, each $R_3$ is —C(O)-(3- to 7-membered)heterocycle.
In another embodiment, each $R_3$ is —$(C_1$-$C_6)$alkyl-(3- to 7-membered) heterocycle.
In another embodiment, each $R_3$ is —$C(O)N(R_7)$—$(C_1$-$C_6)$alkyl-(3- to 7-membered)heterocycle.
In another embodiment, each $R_3$ is —$(C_1$-$C_6)$alkyl-(5- to 10-membered)heteroaryl.
In another embodiment, each $R_3$ is —$N(R_7)_2$.
In another embodiment, each $R_3$ is —C(O)-(5- to 10-membered)-heteroaryl.
In another embodiment, each $R_3$ is —$S(O)_2$—$(C_1$-$C_6)$alkyl.
In another embodiment, each $R_3$ is —$C(O)N(R_7)$—$(C_1$-$C_6)$alkyl-$N(R_7)_2$.
In another embodiment, each $R_3$ is —$C(O)N(R_7)$—$(C_1$-$C_6)$alkyl-(5- to 10-membered)heteroaryl.
In another embodiment, each $R_3$ is —$S(O)_2$—$N(R_7)_2$.
In another embodiment, each $R_3$ is —$OC(O)N(R_7)_2$.
In another embodiment, each $R_3$ is —$C(O)N(R_7)_2$.
In another embodiment, each $R_3$ is —$C(O)N(R_7)$—$(C_1$-$C_6)$alkyl-$R_7$.
In another embodiment, each $R_3$ is —C(O)—$(C_1$-$C_6)$alkyl.
In another embodiment, each $R_3$ is —C(O)O—$(C_1$-$C_6)$alkyl.
In another embodiment, each $R_3$ is —$S(O)_2$—$(C_1$-$C_6)$alkyl.
In another embodiment, each $R_3$ is —O—$(C_1$-$C_6)$alkyl-$R_{14}$.
In another embodiment, each $R_3$ is —O—$(C_1$-$C_6)$alkyl-O—$R_{14}$.
In another embodiment, each $R_3$ is —O—$(C_1$-$C_6)$alkyl-C(O)—$R_{14}$.
In another embodiment, each $R_3$ is —O—$(C_1$-$C_6)$alkyl-C(O)—$N(R_7)$—$(C_1$-$C_6)$alkyl-$OR_7$.
In another embodiment, each $R_3$ is —$C(O)R_{14}$.
In another embodiment, each $R_3$ is —O—$(C_1$-$C_6)$alkyl-C(O)—$N(R_7)$—$(C_1$-$C_6)$alkyl-$OR_7$.
In another embodiment, each $R_3$ is —O—$(C_1$-$C_6)$alkyl-C(O)—$N(R_7)_2$.
In another embodiment, $R_3$ is —OH.
In another embodiment, $R_3$ is —$NH_2$.
In another embodiment, $R_3$ is —SH.
In another embodiment, $R_3$ is —$(C_1$-$C_6)$haloalkyl.
In another embodiment, $R_3$ is —$(C_1$-$C_6)$alkyl(halo)$_2$.
In another embodiment, $R_3$ is —$(C_1$-$C_6)$alkyl(halo)$_3$.
In another embodiment, $R_3$ is —$C_2H_5Cl$.
In another embodiment, $R_3$ is —$(C_1$-$C_6)$heteroalkyl.
In another embodiment, $R_3$ is —$(C_1$-$C_6)$alkyl-piperidinyl.
In another embodiment, $R_3$ is —$OCF_3$.
In another embodiment, $R_3$ is —$O(C_1$-$C_6)$alkyl.
In another embodiment, $R_3$ is —$S(C_1$-$C_6)$alkyl.
In another embodiment, $R_3$ is —$(C_1$-$C_6)$alkyl-S—$(C_1$-$C_6)$alkyl.
In another embodiment, $R_3$ is -morpholinyl.
In another embodiment, $R_3$ is —$NH(R_7)$—$(C_1$-$C_6)$alkyl.

In another embodiment, $R_3$ is —$NH(R_7)$—$(C_1$-$C_6)$alkyl-morpholinyl.
In another embodiment, $R_3$ is —NH—$(C_1$-$C_6)$alkyl-N$((C_1$-$C_6)$alkyl)$_2$.
In another embodiment, $R_3$ is —$CH_2Cl$.
In another embodiment, $R_3$ is —$OCH_3$.
In another embodiment, $R_3$ is —$OC_2H_5$.
In another embodiment, $R_3$ is —NH—$C_2H_4$-morpholinyl.
In another embodiment, $R_3$ is —$CH_2$—O—$CH_3$.
In another embodiment, $R_3$ is —NH—$C_2H_4$—$N(CH_3)_2$.
In another embodiment, $R_3$ is —$S(O)_2$—$CH_3$.
In another embodiment, $R_3$ is —$CH_2$-piperidyl.
In another embodiment, s or q is 0.
In another embodiment, s or q is 1.
In another embodiment, s or q is 2.
In another embodiment, v is 0.
In another embodiment, v is 0 and X is —O—.
In another embodiment, v is 0 and X is —S—.
In another embodiment, v is 0 and X is —S(O)—.
In another embodiment, v is 0 and X is —$S(O)_2$—.
In another embodiment, v is 0 and X is —$N(R_{20})$—.
In another embodiment, v is 1.
In another embodiment, v is 1 and X is —O—.
In another embodiment, v is 1 and X is —S—.
In another embodiment, v is 1 and X is —S(O)—.
In another embodiment, v is 1 and X is —$S(O)_2$—.
In another embodiment, v is 1 and X is —$N(R_{20})$—.
In another embodiment, $R_1$ is —H.
In another embodiment, $R_1$ is -halo.
In another embodiment, $R_1$ is —Cl.
In another embodiment, $R_1$ is —F.
In another embodiment, $R_1$ is —$CH_2$(halo).
In another embodiment, $R_1$ is —CH(halo)$_2$.
In another embodiment, $R_1$ is —C(halo)$_3$.
In another embodiment, $R_1$ is —$CF_3$.
In another embodiment, $R_1$ is —OC(halo)$_3$.
In another embodiment, $R_1$ is —$OCF_3$.
In another embodiment, $R_1$ is —$CH_3$.
In another embodiment, $R_1$ is —CN.
In another embodiment, $R_1$ is —$NH_2$.
In another embodiment, $R_1$ is —$NO_2$.
In another embodiment, $R_1$ is —$OCH_3$.
In another embodiment, $R_1$ is —OH.
In another embodiment, $R_1$ is —$S(O)_2(C_1$-$C_4$-alkyl).
In another embodiment, $Ar_1$ is a pyridyl group and n is 1.
In another embodiment, $Ar_1$ is a pyrazinyl group and p is 1.
In another embodiment, $Ar_1$ is a pyrimidinyl group and p is 1.
In another embodiment, $Ar_1$ is a pyridazinyl group and p is 1.
In another embodiment, when n and p are 1, then $R_2$ must be Q.
In another embodiment, Q is:

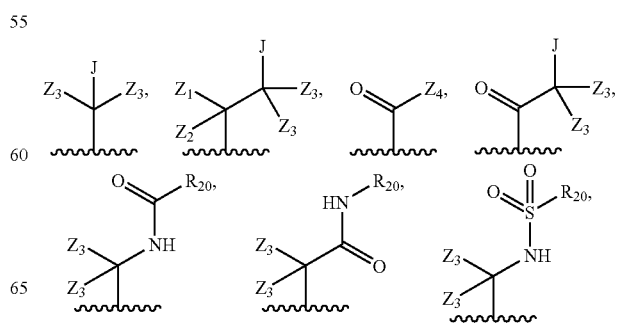

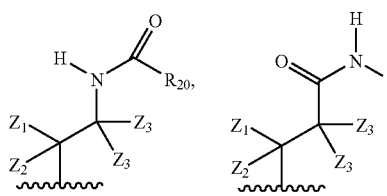 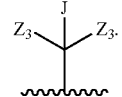

In another embodiment, Q is:

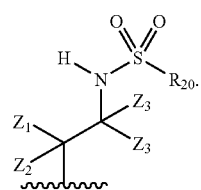 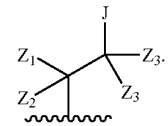

In another embodiment, Q is:

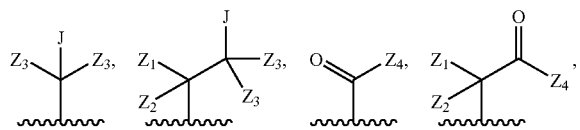 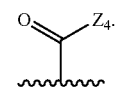

In another embodiment, Q is:

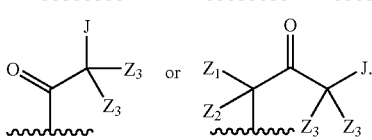 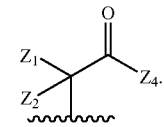

In another embodiment, Q is:

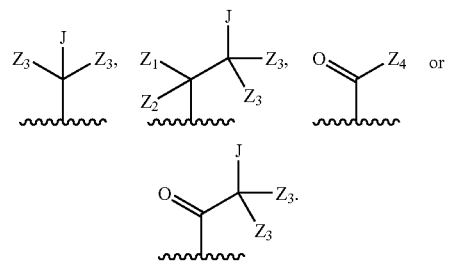 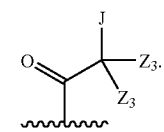

In another embodiment, Q is:

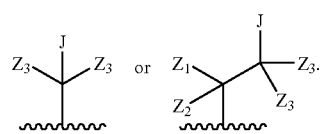

In another embodiment, Q is:

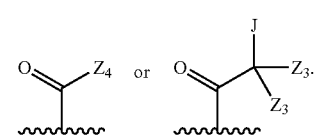

In another embodiment, Q is:

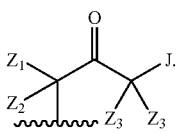

In another embodiment, J is —$OR_{20}$, —$SR_{20}$ or —$N(R_{20})_2$.
In another embodiment, J is —$OR_{20}$.
In another embodiment, J is —OH.
In another embodiment, J is $N(R_{20})_2$.
In another embodiment, J is —CN.
In another embodiment, $Z_1$ is —H.
In another embodiment, $Z_1$ is —OH.
In another embodiment, $Z_1$ is —$OCH_3$.
In another embodiment, $Z_1$ is —$CH_2OH$.
In another embodiment, $Z_2$ is —H, —$(C_1$-$C_6)$alkyl, —$(C_2$-$C_6)$alkenyl, —$(C_2$-$C_6)$alkynyl, -phenyl, or -halo.
In another embodiment, $Z_2$ is —$CH_2OR_7$.
In another embodiment, $Z_2$ is —$CH_2OH$.

In another embodiment, $Z_2$ is —H.
In another embodiment, $Z_2$ is —CH$_3$.
In another embodiment, $Z_3$ is —H.
In another embodiment, $Z_3$ is —CH$_3$.
In another embodiment, $Z_4$ is —H.
In another embodiment, $Z_4$ is —(C$_1$-C$_6$)alkyl.
In another embodiment, $Z_4$ is —N(R$_{20}$)$_2$.
In another embodiment, $Z_4$ is —OR$_{20}$.
In another embodiment, $Z_4$ is —OH.
In another embodiment, Q is:

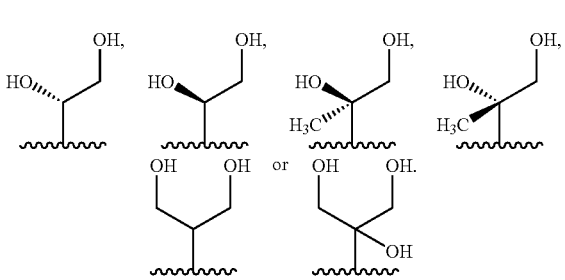

In another embodiment, Q is:

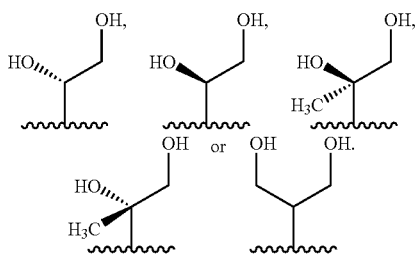

In another embodiment, Q is:

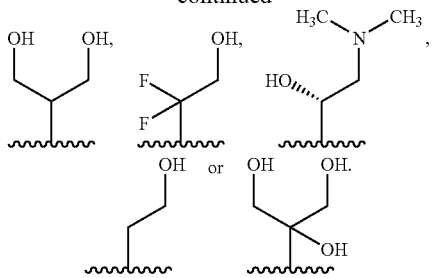

In another embodiment, Q is:

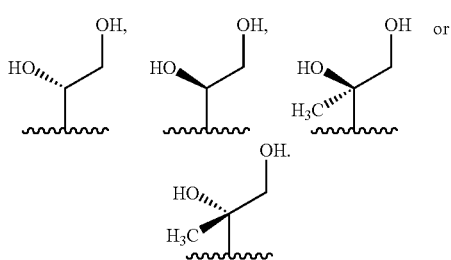

In another embodiment, Q is:

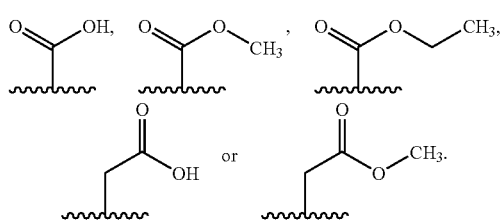

In another embodiment, Q is:

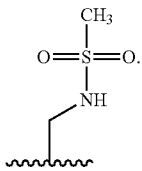

In another embodiment, each $R_{20}$ is independently —H or —$(C_1$-$C_6)$alkyl.

In another embodiment, each $R_{20}$ is independently —H or —$(C_3$-$C_8)$cycloalkyl.

In another embodiment, each $R_{20}$ is independently —$(C_1$-$C_6)$alkyl or —$(C_3$-$C_8)$cycloalkyl.

In another embodiment, each $R_{20}$ is —H.

In another embodiment, each $R_{20}$ is —$(C_1$-$C_6)$alkyl.

In another embodiment, each $R_{20}$ is —$CH_3$.

In another embodiment, each $R_{20}$ is —$(C_3$-$C_8)$cycloalkyl.

In another embodiment, each $R_{20}$ is cyclohexyl.

In another embodiment, $Ar_2$ is a benzothiazolyl, benzoimidazolyl, or benzooxazolyl group; and at least one of $R_8$ and $R_9$ is —H.

In another embodiment, $Ar_2$ is a benzothiazolyl, benzoimidazolyl, or benzooxazolyl group; and at least one of $R_8$ and $R_9$ is not —H.

In another embodiment, $Ar_2$ is a benzothiazolyl, benzoimidazolyl, or benzooxazolyl group; and at least one of $R_8$ and $R_9$ is -halo.

In another embodiment, $Ar_2$ is:

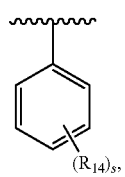

s is 1 and $R_{14}$ is —$(C_1$-$C_6)$alkyl, -halo, —$C(halo)_3$, —$OC(halo)_3$, —$OR_7$, —$N(R_7)_2$, —$S(O)_2R_7$, or —$S(O)_2C(halo)_3$.

In another embodiment, $Ar_2$ is:

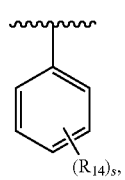

s is 2, and each $R_{14}$ group independently is —$(C_1$-$C_6)$alkyl, -halo, —$C(halo)_3$, —$OC(halo)_3$, —$OR_7$, —$N(R_7)_2$, —$S(O)_2R_7$, or —$S(O)_2C(halo)_3$.

In another embodiment, $Ar_2$ is:

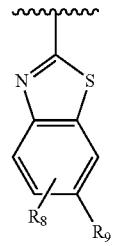

and each $R_8$ and $R_9$ is independently —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, or -phenyl, each of which is unsubstituted or substituted with 1 or 2 —OH groups.

In another embodiment, D is N, n, p, or w is 1, $R_2$ is Q, where Q is:

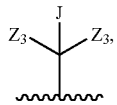

where J is —$OR_{20}$.

In another embodiment, D is N, n, p, or w is 1, $R_2$ is Q, where Q is:

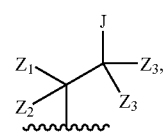

where J is —$OR_{20}$ and $Z_1$ is —$OR_7$.

In another embodiment, D is N, n, p, or w is 1, $R_2$ is Q, where Q is:

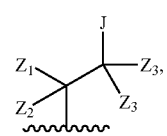

where J is —$OR_{20}$ and $Z_1$ is —$CH_2OR_7$.

In another embodiment, D is N, n, p, or w is 1, $R_2$ is Q, where Q is:

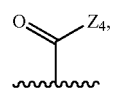

where $Z_4$ is —$OR_{20}$.

In another embodiment, D is N, n, p, or w is 1, $R_2$ is Q, where Q is:

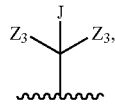

where J is —OH.

In another embodiment, D is N, n, p, or w is 1, $R_2$ is Q, where Q is:

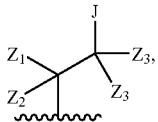

where J is —OH and $Z_1$ is —OH.

In another embodiment, D is N, n, p, or w is 1, $R_2$ is Q, where Q is:

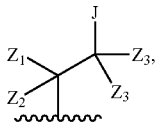

where J is —OH and $Z_1$ is —$CH_2OH$.

In another embodiment, $A_1$, $A_3$ and D are N, n, p, or w is 1, $R_2$ is Q, where Q is:


where J is —OH and $Z_1$ is —OH.

In another embodiment, $A_1$, $A_3$ and D are N, n, p, or w is 1, $R_2$ is Q, where Q is:

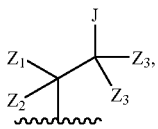

where J is —OH and $Z_1$ is —$CH_2OH$.

In another embodiment, $A_1$, $A_3$ and D are N, $R_1$ is -halo, n, p, or w is 1, $R_2$ is Q, where Q is:

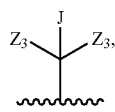

where J is —$OR_{20}$.

In another embodiment, $A_1$, $A_3$ and D are N, $R_1$ is -halo, n, p, or w is 1, $R_2$ is Q, where Q is:

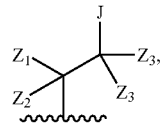

where J is —$OR_{20}$ and $Z_1$ is —$OR_7$.

In another embodiment, $A_1$, $A_3$ and D are N, $R_1$ is -halo, n, p, or w is 1, $R_2$ is Q, where Q is:

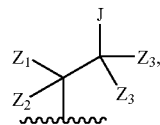

where J is —$OR_{20}$ and $Z_1$ is —$CH_2OR_7$.

In another embodiment, $A_1$, $A_3$ and D are N, $R_1$ is -halo, n, p, or w is 1, $R_2$ is Q, where Q is:

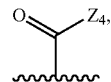

where $Z_4$ is —$OR_{20}$.

In another embodiment, $A_1$, $A_3$ and D are N, $R_1$ is —Cl, n, p, or w is 1, $R_2$ is Q, where Q is:

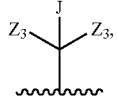

where J is —$OR_{20}$.

In another embodiment, $A_1$, $A_3$ and D are N, $R_1$ is —Cl, n, p, or w is 1, $R_2$ is Q, where Q is:

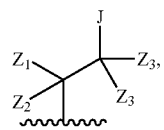

where J is —$OR_{20}$ and $Z_1$ is —$OR_7$.

In another embodiment, $A_1$, $A_3$ and D are N, $R_1$ is —Cl, n, p, or w is 1, $R_2$ is Q, where Q is:

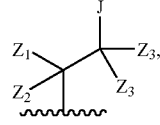

where J is —$OR_{20}$ and $Z_1$ is —$CH_2OR_7$.

In another embodiment, $A_1$, $A_3$ and D are N, $R_1$ is —Cl, n, p, or w is 1, $R_2$ is Q, where Q is:

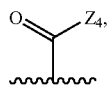

where $Z_4$ is —$OR_{20}$.

In another embodiment, $A_1$, $A_3$ and D are N, $R_1$ is —Cl, n, p, or w is 1, $R_2$ is Q, where Q is:

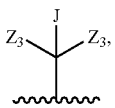

where J is —OH.

In another embodiment, $A_1$, $A_3$ and D are N, $R_1$ is —Cl, n, p, or w is 1, $R_2$ is Q, where Q is:

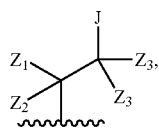

where J is —OH and $Z_1$ is —OH.

In another embodiment, $A_1$, $A_3$ and D are N, $R_1$ is —Cl, n, p, or w is 1, $R_2$ is Q, where Q is:

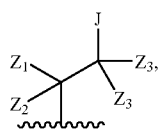

where J is —OH and $Z_1$ is —CH$_2$OH.

In another embodiment, $Ar_1$ is a pyridyl group, where n is 1, and $R_2$ is Q.

In another embodiment, $Ar_1$ is a pyridyl group, where n is 1, $R_2$ is Q, and Q is:

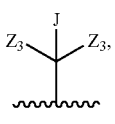

where J is —OH.

In another embodiment, $Ar_1$ is a pyridyl group, where n is 1, $R_2$ is Q, and Q is:

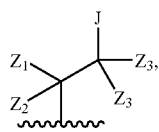

where J is —$OR_{20}$, and $Z_1$ is —$OR_7$.

In another embodiment, $Ar_1$ is a pyridyl group, where n is 1, $R_2$ is Q, and Q is:

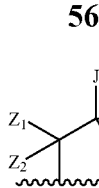

where J is —OH, and $Z_1$ is —OH.

In another embodiment, $Ar_1$ is a pyridyl group, where n is 1, $R_2$ is Q, and Q is:

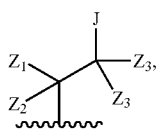

where J is —$OR_{20}$, and $Z_1$ is —$CH_2OR_7$.

In another embodiment, $Ar_1$ is a pyridyl group, where n is 1, $R_2$ is Q, and Q is:

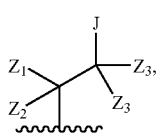

where J is —OH, and $Z_1$ is —CH$_2$OH.

In another embodiment, $Ar_1$ is a pyridyl group, where n is 1, $R_2$ is Q, and Q is:

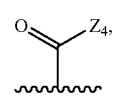

where $Z_4$ is —$OR_{20}$.

In another embodiment, $A_1$, $A_3$ and D are N, $R_1$ is -halo, and $Ar_1$ is a pyridyl group, where n is 1, $R_2$ is Q, and Q is:

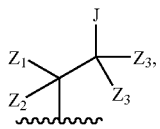

where J is —$OR_{20}$, $Z_1$ is —$OR_7$.

In another embodiment, $A_1$, $A_3$ and D are N, $R_1$ is -halo, and $Ar_1$ is a pyridyl group, where n is 1, $R_2$ is Q, and Q is:

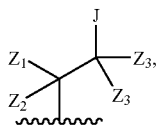

where J is —OH, $Z_1$ is —OH.

In another embodiment, $A_1$, $A_3$ and D are N, $R_1$ is -halo, and $Ar_1$ is a pyridyl group, where n is 1, $R_2$ is Q, and Q is:

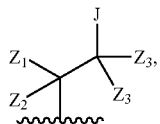

where J is —OR$_{20}$, Z$_1$ is —CH$_2$OR$_7$.

In another embodiment, A$_1$, A$_3$ and D are N, R$_1$ is -halo, and Ar$_1$ is a pyridyl group, where n is 1, R$_2$ is Q, and Q is:

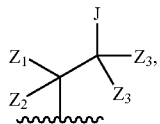

where J is —OH, Z$_1$ is —CH$_2$OH.

In another embodiment, A$_1$, A$_3$ and D are N, R$_1$ is -halo, and Ar$_1$ is a pyridyl group, where n is 1, R$_2$ is Q, and Q is:

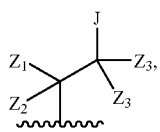

where J is —OH, Z$_1$ is —OH, Ar$_2$ is benzothiazolyl, where at least one of R$_8$ and R$_9$ is not —H.

In another embodiment, A$_1$, A$_3$ and D are N, R$_1$ is -halo, and Ar$_1$ is a pyridyl group, where n is 1, R$_2$ is Q, and Q is:

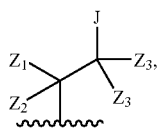

where J is —OH, Z$_1$ is —CH$_2$OH, Ar$_2$ is benzothiazolyl, where at least one of R$_8$ and R$_9$ is not —H.

In another embodiment, A$_1$, A$_3$ and D are N, R$_1$ is -halo, and Ar$_1$ is a pyridyl group, where n is 1, R$_2$ is Q, and Q is:

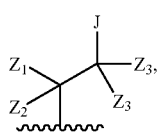

where J is —OH, Z$_1$ is —OH, Ar$_2$ is benzooxazolyl, where at least one of R$_8$ and R$_9$ is not —H.

In another embodiment, A$_1$, A$_3$ and D are N, R$_1$ is -halo, and Ar$_1$ is a pyridyl group, where n is 1, R$_2$ is Q, and Q is:

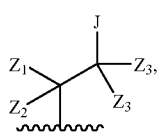

where J is —OH, Z$_1$ is —CH$_2$OH, Ar$_2$ is benzooxazolyl, where at least one of R$_8$ and R$_9$ is not —H.

In another embodiment, A$_1$, A$_3$ and D are N, R$_1$ is -halo, and Ar$_1$ is a pyridyl group, where n is 1, R$_2$ is Q, and Q is:

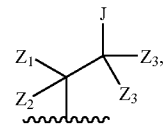

where J is —OH, Z$_1$ is —OH, Ar$_2$ is benzoimidazolyl, where at least one of R$_8$ and R$_9$ is not —H.

In another embodiment, A$_1$, A$_3$ and D are N, R$_1$ is -halo, and Ar$_1$ is a pyridyl group, where n is 1, R$_2$ is Q, and Q is:

where J is —OH, Z$_1$ is —CH$_2$OH, Ar$_2$ is benzoimidazolyl, where at least one of R$_8$ and R$_9$ is not —H.

In another embodiment, A$_1$, A$_3$ and D are N, R$_1$ is -halo, and Ar$_1$ is a pyridyl group, where n is 1, R$_2$ is Q, and Q is:

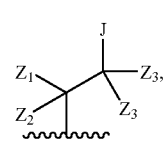

where J is —OH, Z$_1$ is —OH, Ar$_2$ is phenyl, where s is 0 or 1.

In another embodiment, A$_1$, A$_3$ and D are N, R$_1$ is -halo, and Ar$_1$ is a pyridyl group, where n is 1, R$_2$ is Q, and Q is:

where J is —OH, Z$_1$ is —CH$_2$OH, Ar$_2$ is phenyl, where s is 0 or 1.

In another embodiment, A$_1$, A$_3$ and D are N, R$_1$ is -halo, and Ar$_1$ is a pyridyl group, where n is 1, R$_2$ is Q, and Q is:

where J is —OH, Z$_1$ is —OH, Ar$_2$ is phenyl, where s is 2.

In another embodiment, A$_1$, A$_3$ and D are N, R$_1$ is -halo, and Ar$_1$ is a pyridyl group, where n is 1, R$_2$ is Q, and Q is:

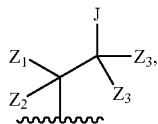

where J is —OH, $Z_1$ is —CH$_2$OH, Ar$_2$ is phenyl, where s is 2.

In another embodiment, D is C, the dashed lines are present as part of double bonds, n, p, or w is 1, $R_2$ is Q, where Q is:

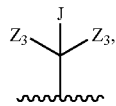

where J is —OR$_{20}$.

In another embodiment, D is C, the dashed lines are present as part of double bonds, n, p, or w is 1, $R_2$ is Q, where Q is:

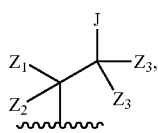

where J is —OR$_{20}$ and $Z_1$ is OR$_7$.

In another embodiment, D is C, the dashed lines are present as part of double bonds, n, p, or w is 1, $R_2$ is Q, where Q is:

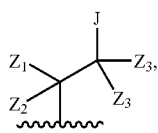

where J is —OR$_{20}$ and $Z_1$ is —CH$_2$OR$_7$.

In another embodiment, D is C, the dashed lines are present as part of double bonds, n, p, or w is 1, $R_2$ is Q, where Q is:

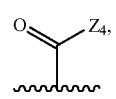

where $Z_4$ is —OR$_{20}$.

In another embodiment, D is C, the dashed lines are present as part of double bonds, n, p, or w is 1, $R_2$ is Q, where Q is:

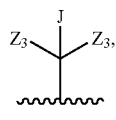

where J is —OH.

In another embodiment, D is C, the dashed lines are present as part of double bonds, n, p, or w is 1, $R_2$ is Q, where Q is:

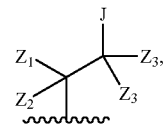

where J is —OH and $Z_1$ is —OH.

In another embodiment, D is C, the dashed lines are present as part of double bonds, n, p, or w is 1, $R_2$ is Q, where Q is:

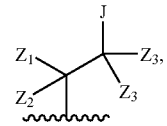

where J is —OH and $Z_1$ is —CH$_2$OH.

In another embodiment, D is C, the dashed lines are present as part of double bonds, $R_1$ is -halo, n, p, or w is 1, $R_2$ is Q, where Q is:

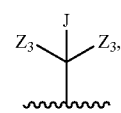

where J is —OH.

In another embodiment, D is C, the dashed lines are present as part of double bonds, $R_1$ is -halo, n, p, or w is 1, $R_2$ is Q, where Q is:

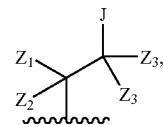

where J is —OH and $Z_1$ is —OH.

In another embodiment, D is C, the dashed line present as part of double bonds, $R_1$ is -halo, n, p, or w is 1, $R_2$ is Q, where Q is:

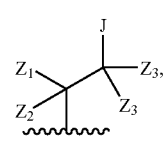

where J is —OH and $Z_1$ is —CH$_2$OH.

In another embodiment, D is C, the dashed line present as part of double bonds, $R_1$ is -halo, and Ar$_1$ is a pyridyl group, where n is 1, $R_2$ is Q, and Q is:

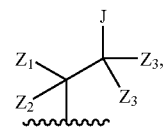

where J is —OH, $Z_1$ is —OH.

In another embodiment, D is C, the dashed lines are present as part of double bonds, $R_1$ is -halo, and $Ar_1$ is a pyridyl group, where n is 1, $R_2$ is Q, and Q is:

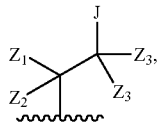

where J is —OH, $Z_1$ is —CH$_2$OH.

In another embodiment, D is C, the dashed lines are present as part of double bonds, $R_1$ is -halo, and $Ar_1$ is a pyridyl group, where n is 1, $R_2$ is Q, and Q is:

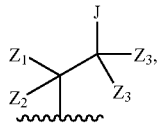

where J is —OH, $Z_1$ is —OH, $Ar_2$ is benzothiazolyl, where at least one of $R_8$ and $R_9$ is not —H.

In another embodiment, D is C, the dashed lines are present as part of double bonds, $R_1$ is -halo, and $Ar_1$ is a pyridyl group, where n is 1, $R_2$ is Q, and Q is:

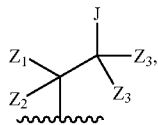

where J is —OH, $Z_1$ is —CH$_2$OH, $Ar_2$ is benzothiazolyl, where at least one of $R_8$ and $R_9$ is not —H.

In another embodiment, D is C, the dashed lines are present as part of double bonds, $R_1$ is -halo, and $Ar_1$ is a pyridyl group, and Q is:

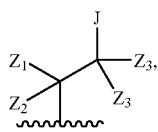

where J is —OH, $Z_1$ is —OH, $Ar_2$ is benzooxazolyl, where at least one of $R_8$ and $R_9$ is not —H.

In another embodiment, D is C, the dashed lines are present as part of double bonds, $R_1$ is -halo, and $Ar_1$ is a pyridyl group, where n is 1, and Q is:

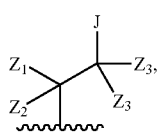

where J is —OH, $Z_1$ is —CH$_2$OH, $Ar_2$ is benzooxazolyl, where at least one of $R_8$ and $R_9$ is not —H.

In another embodiment, D is C, the dashed lines are present as part of double bonds, $R_1$ is -halo, and $Ar_1$ is a pyridyl group, where n is 1, $R_2$ is Q, and Q is:

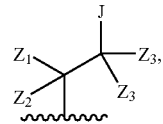

where J is —OH, $Z_1$ is —OH, $Ar_2$ is benzoimidazolyl, where at least one of $R_8$ and $R_9$ is not —H.

In another embodiment, D is C, the dashed lines are present as part of double bonds, $R_1$ is -halo, and $Ar_1$ is a pyridyl group, where n is 1, $R_2$ is Q, and Q is:

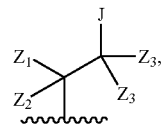

where J is —OH, $Z_1$ is —CH$_2$OH, $Ar_2$ is benzoimidazolyl, where at least one of $R_8$ and $R_9$ is not —H.

In another embodiment, D is C, the dashed lines are present as part of double bonds, $R_1$ is -halo, and $Ar_1$ is a pyridyl group, where n is 1, $R_2$ is Q, and Q is:

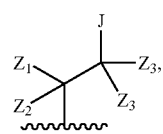

where J is —OH, $Z_1$ is —OH, $Ar_2$ is phenyl, where s is 0 or 1 and $R_{14}$ is —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$, and preferably is —F, —Cl, —CF$_3$, or —OCF$_3$.

In another embodiment, D is C, the dashed lines are present as part of double bonds, $R_1$ is -halo, and $Ar_1$ is a pyridyl group, where n is 1, $R_2$ is Q, and Q is:

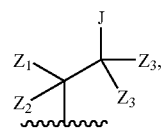

where J is —OH, $Z_1$ is —CH$_2$OH, $Ar_2$ is phenyl, where s is 0 or 1 and $R_{14}$ is —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$, and preferably is —F, —Cl, —CF$_3$, or —OCF$_3$.

In another embodiment, D is C, the dashed lines are present as part of double bonds, $R_1$ is -halo, and $Ar_1$ is a pyridyl group, where n is 1, $R_2$ is Q, and Q is:

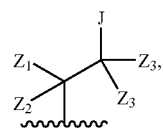

where J is —OH, $Z_1$ is —OH, $Ar_2$ is phenyl, where s is 2, and each $R_{14}$ is independently selected from —(C$_1$-C$_6$)alkyl, -halo, —C(halo)$_3$, —OC(halo)$_3$, —OR$_7$, —N(R$_7$)$_2$, —S(O)$_2$R$_7$, and —S(O)$_2$C(halo)$_3$, and preferably is —F, —Cl, —CF$_3$, or —OCF$_3$.

In another embodiment, D is C, the dashed lines are present as part of double bonds, R$_1$ is -halo, and Ar$_1$ is a pyridyl group, where n is 1, R$_2$ is Q, and Q is:

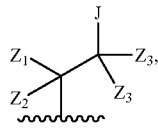

where J is —OH, Z$_1$ is —CH$_2$OH, Ar$_2$ is phenyl, where s is 2, and each R$_{14}$ is independently —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$, and preferably is —F, —Cl, —CF$_3$, or —OCF$_3$.

In another embodiment, D is C, the dashed lines are present as part of double bonds, R$_1$ is -halo, and Ar$_1$ is a pyridyl group, where n is 1, R$_2$ is Q, and Q is:

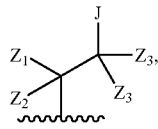

where J is —OH, Z$_1$ is —OH, Ar$_2$ is pyridyl, where q is 0 or 1 and R$_{14}$ is —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$, and preferably is —F, —Cl, —CF$_3$, or —OCF$_3$.

In another embodiment, D is C, the dashed lines are present as part of double bonds, R$_1$ is -halo, and Ar$_1$ is a pyridyl group, where n is 1, R$_2$ is Q, and Q is:

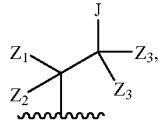

where J is —OH, Z$_1$ is —CH$_2$OH, Ar$_2$ is pyridyl, where q is 0 or 1 and R$_{14}$ is —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$, and preferably is —F, —Cl, —CF$_3$, or —OCF$_3$.

In another embodiment, D is C, the dashed lines are present as part of double bonds, R$_1$ is -halo, and Ar$_1$ is a pyridyl group, where n is 1, R$_2$ is Q, and Q is:

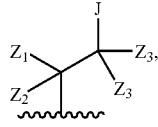

where J is —OH, Z$_1$ is —OH, Ar$_2$ is pyridyl, where q is 2, and each R$_{14}$ is independently selected from —(C$_1$-C$_6$)alkyl, -halo, —C(halo)$_3$, —OC(halo)$_3$, —OR$_7$, —N(R$_7$)$_2$, —S(O)$_2$R$_7$, and —S(O)$_2$C(halo)$_3$, and preferably is —F, —Cl, —CF$_3$, or —OCF$_3$.

In another embodiment, D is C, the dashed lines are present as part of double bonds, R$_1$ is -halo, and Ar$_1$ is a pyridyl group, where n is 1, R$_2$ is Q, and Q is:

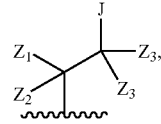

where J is —OH, Z$_1$ is —CH$_2$OH, Ar$_2$ is pyridyl, where q is 2, and each R$_{14}$ is independently —(C$_1$-C$_6$)alkyl, -halo, —C(halo)$_3$, —OC(halo)$_3$, —OR$_7$, —N(R$_7$)$_2$, —S(O)$_2$R$_2$, or —S(O)$_2$C(halo)$_3$, and preferably is —F, —Cl, —CF$_3$, or —OCF$_3$.

In another embodiment, each Z$_3$ is —H, R$_1$ is —Cl, and R$_{20}$ is —H.

In another embodiment, each Z$_3$ is —CH$_3$, R$_1$ is —Cl, and R$_{20}$ is —H.

In another embodiment, one Z$_3$ is —H, the other Z$_3$ is —CH$_3$, R$_1$ is —Cl, and R$_{20}$ is —H.

In another embodiment, each Z$_3$ is —H, R$_1$ is —Cl, and R$_{20}$ is —(C$_1$-C$_6$)alkyl.

In another embodiment, each Z$_3$ is —CH$_3$, R$_1$ is —Cl, and R$_{20}$ is —(C$_1$-C$_6$)alkyl.

In another embodiment, one Z$_3$ is —H, the other Z$_3$ is —CH$_3$, R$_1$ is —Cl, and R$_{20}$ is —(C$_1$-C$_6$)alkyl.

In another embodiment, each Z$_3$ is —H, R$_1$ is —Cl, and R$_{20}$ is —CH$_3$.

In another embodiment, each Z$_3$ is —CH$_3$, R$_1$ is —Cl, and R$_{20}$ is —CH$_3$.

In another embodiment, one Z$_3$ is —H, the other Z$_3$ is —CH$_3$, R$_1$ is —Cl, and R$_{20}$ is —CH$_3$.

In another embodiment, each Z$_3$ is —H, R$_1$ is —Cl, and R$_{20}$ is —CH$_2$CH$_3$.

In another embodiment, each Z$_3$ is —CH$_3$, R$_1$ is —Cl, and R$_{20}$ is —CH$_2$CH$_3$.

In another embodiment, one Z$_3$ is —H, the other Z$_3$ is —CH$_3$, R$_1$ is —Cl, and R$_{20}$ is —CH$_2$CH$_3$.

In another embodiment, each Z$_3$ is —H, R$_1$ is —Cl, and R$_{20}$ is —(C$_3$-C$_8$)cycloalkyl.

In another embodiment, each Z$_3$ is —CH$_3$, R$_1$ is —Cl, and R$_{20}$ is —(C$_3$-C$_8$)cycloalkyl.

In another embodiment, one Z$_3$ is —H, the other Z$_3$ is —CH$_3$, R$_1$ is —Cl, and R$_{20}$ is —(C$_3$-C$_8$)cycloalkyl.

In another embodiment, each Z$_3$ is —H, R$_1$ is —Cl, and R$_{20}$ is -cyclohexyl.

In another embodiment, each Z$_3$ is —CH$_3$, R$_1$ is —Cl, and R$_{20}$ is -cyclohexyl.

In another embodiment, one Z$_3$ is —H, the other Z$_3$ is —CH$_3$, R$_1$ is —Cl, and R$_{20}$ is -cyclohexyl.

In another embodiment, each Z$_3$ is —H, R$_1$ is —Cl, and R$_{20}$ is -cyclopentyl.

In another embodiment, each Z$_3$ is —CH$_3$, R$_1$ is —Cl, and R$_{20}$ is -cyclopentyl.

In another embodiment, one Z$_3$ is —H, the other Z$_3$ is —CH$_3$, R$_1$ is —Cl, and R$_{20}$ is -cyclopentyl.

In another embodiment, each Z$_3$ is —H, R$_1$ is —F, and R$_{20}$ is —H.

In another embodiment, each Z$_3$ is —CH$_3$, R$_1$ is —F, and R$_{20}$ is —H.

In another embodiment, one Z$_3$ is —H, the other Z$_3$ is —CH$_3$, R$_1$ is —F, and R$_{20}$ is —H.

In another embodiment, each Z$_3$ is —H, R$_1$ is —F, and R$_{20}$ is —(C$_1$-C$_6$)alkyl.

In another embodiment, each $Z_3$ is —$CH_3$, $R_1$ is —F, and $R_{20}$ is —($C_1$-$C_6$)alkyl.

In another embodiment, one $Z_3$ is —H, the other $Z_3$ is —$CH_3$, $R_1$ is —F, and $R_{20}$ is —($C_1$-$C_6$)alkyl.

In another embodiment, each $Z_3$ is —H, $R_1$ is —F, and $R_{20}$ is —$CH_3$.

In another embodiment, each $Z_3$ is —$CH_3$, $R_1$ is —F, and $R_{20}$ is —$CH_3$.

In another embodiment, one $Z_3$ is —H, the other $Z_3$ is —$CH_3$, $R_1$ is —F, and $R_{20}$ is —$CH_3$.

In another embodiment, each $Z_3$ is —H, $R_1$ is —F, and $R_{20}$ is —$CH_2CH_3$.

In another embodiment, each $Z_3$ is —$CH_3$, $R_1$ is —F, and $R_{20}$ is —$CH_2CH_3$.

In another embodiment, one $Z_3$ is —H, the other $Z_3$ is —$CH_3$, $R_1$ is —F, and $R_{20}$ is —$CH_2CH_3$.

In another embodiment, each $Z_3$ is —H, $R_1$ is —F, and $R_{20}$ is —($C_3$-$C_8$)cycloalkyl.

In another embodiment, each $Z_3$ is —$CH_3$, $R_1$ is —F, and $R_{20}$ is —($C_3$-$C_8$)cycloalkyl.

In another embodiment, one $Z_3$ is —H, the other $Z_3$ is —$CH_3$, $R_1$ is —F, and $R_{20}$ is —($C_3$-$C_8$)cycloalkyl.

In another embodiment, each $Z_3$ is —H, $R_1$ is —F, and $R_{20}$ is -cyclohexyl.

In another embodiment, each $Z_3$ is —$CH_3$, $R_1$ is —F, and $R_{20}$ is -cyclohexyl.

In another embodiment, one $Z_3$ is —H, the other $Z_3$ is —$CH_3$, $R_1$ is —F, and $R_{20}$ is -cyclohexyl.

In another embodiment, each $Z_3$ is —H, $R_1$ is —F, and $R_{20}$ is -cyclopentyl.

In another embodiment, each $Z_3$ is —$CH_3$, $R_1$ is —F, and $R_{20}$ is -cyclopentyl.

In another embodiment, one $Z_3$ is —H, the other $Z_3$ is —$CH_3$, $R_1$ is —F, and $R_{20}$ is -cyclopentyl.

In another embodiment, each $Z_3$ is —H, $R_1$ is —$CF_3$, and $R_{20}$ is —H.

In another embodiment, each $Z_3$ is —$CH_3$, $R_1$ is —$CF_3$, and $R_{20}$ is —H.

In another embodiment, one $Z_3$ is —H, the other $Z_3$ is —$CH_3$, $R_1$ is —$CF_3$, and $R_{20}$ is —H.

In another embodiment, each $Z_3$ is —H, $R_1$ is —$CF_3$, and $R_{20}$ is —($C_1$-$C_6$)alkyl.

In another embodiment, each $Z_3$ is —$CH_3$, $R_1$ is —$CF_3$, and $R_{20}$ is —($C_1$-$C_6$)alkyl.

In another embodiment, one $Z_3$ is —H, the other $Z_3$ is —$CH_3$, $R_1$ is —$CF_3$, and $R_{20}$ is —($C_1$-$C_6$)alkyl.

In another embodiment, each $Z_3$ is —H, $R_1$ is —$CF_3$, and $R_{20}$ is —$CH_3$.

In another embodiment, each $Z_3$ is —$CH_3$, $R_1$ is —$CF_3$, and $R_{20}$ is —$CH_3$.

In another embodiment, one $Z_3$ is —H, the other $Z_3$ is —$CH_3$, $R_1$ is —$CF_3$, and $R_{20}$ is —$CH_3$.

In another embodiment, each $Z_3$ is —H, $R_1$ is —$CF_3$, and $R_{20}$ is —$CH_2CH_3$.

In another embodiment, each $Z_3$ is —$CH_3$, $R_1$ is —$CF_3$, and $R_{20}$ is —$CH_2CH_3$.

In another embodiment, one $Z_3$ is —H, the other $Z_3$ is —$CH_3$, $R_1$ is —$CF_3$, and $R_{20}$ is —$CH_2CH_3$.

In another embodiment, each $Z_3$ is —H, $R_1$ is —$CF_3$, and $R_{20}$ is —($C_3$-$C_8$)cycloalkyl.

In another embodiment, each $Z_3$ is —$CH_3$, $R_1$ is —$CF_3$, and $R_{20}$ is —($C_3$-$C_8$)cycloalkyl.

In another embodiment, one $Z_3$ is —H, the other $Z_3$ is —$CH_3$, $R_1$ is —$CF_3$, and $R_{20}$ is —($C_3$-$C_8$)cycloalkyl.

In another embodiment, each $Z_3$ is —H, $R_1$ is —$CF_3$, and $R_{20}$ is -cyclohexyl.

In another embodiment, each $Z_3$ is —$CH_3$, $R_1$ is —$CF_3$, and $R_{20}$ is -cyclohexyl.

In another embodiment, one $Z_3$ is —H, the other $Z_3$ is —$CH_3$, $R_1$ is —$CF_3$, and $R_{20}$ is -cyclohexyl.

In another embodiment, each $Z_3$ is —H, $R_1$ is —$CF_3$, and $R_{20}$ is -cyclopentyl.

In another embodiment, each $Z_3$ is —$CH_3$, $R_1$ is —$CF_3$, and $R_{20}$ is -cyclopentyl.

In another embodiment, one $Z_3$ is —H, the other $Z_3$ is —$CH_3$, $R_1$ is —$CF_3$, and $R_{20}$ is -cyclopentyl.

In another embodiment, Q is:

![structure: HO-CH(wavy)-CH2-OH]

where the compound of formula I is racemic.

In another embodiment, Q is:

![two structures showing R and S enantiomers of HO-CH-CH2-OH]

where the % ee of the R enantiomer is greater than 60%.

In another embodiment, Q is:

![two structures showing R and S enantiomers of HO-CH-CH2-OH]

where the % ee of the R enantiomer is greater than 70%.

In another embodiment, Q is:

![two structures showing R and S enantiomers of HO-CH-CH2-OH]

where the % ee of the R enantiomer is greater than 80%.

In another embodiment, Q is:

![two structures showing R and S enantiomers of HO-CH-CH2-OH]

where the % ee of the R enantiomer is greater than 90%.

In another embodiment, Q is:

![two structures showing R and S enantiomers of HO-CH-CH2-OH]

where the % ee of the R enantiomer is greater than 99%.

In another embodiment, Q is:

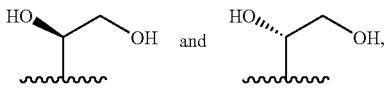

where the % ee of the S enantiomer is greater than 60%.

In another embodiment, Q is:

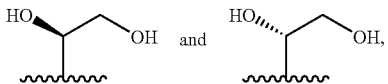

where the % ee of the S enantiomer is greater than 70%.

In another embodiment, Q is:

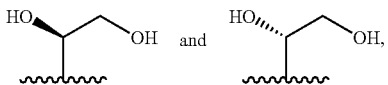

where the % ee of the S enantiomer is greater than 80%.

In another embodiment, Q is:

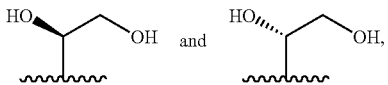

where the % ee of the S enantiomer is greater than 90%.

In another embodiment, Q is:

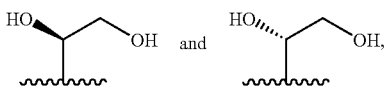

where the % ee of the S enantiomer is greater than 99%.

Aqueous solubility of compounds is often a desirable feature. For example, aqueous solubility of a compound permits that compound to be more easily formulated into a variety of dosage forms that can be administered to an animal. When a compound is not fully soluble in the blood, it can precipitate in the blood, and the animal's exposure to the drug will accordingly not correspond to the administered dose. Aqueous solubility increases the likelihood that a compound will not precipitate in an animal's blood, and increases the ability to predict exposure at the target sight of the compound. Compounds of formula I are believed to be highly soluble in aqueous solution.

4.2. Compounds of Formula II

Preferred compounds of formula I are compounds of formula II:

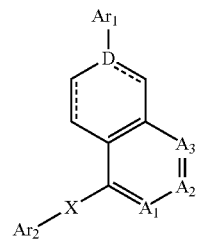

(II)

or a pharmaceutically acceptable derivative thereof, where the dashed lines, $A_1, A_2, A_3, D, X, Ar_1,$ and $Ar_2$ are as defined above for compounds of formula II.

Certain embodiments of a compound of formula II are presented below.

In one embodiment, a compound of formula II is a pharmaceutically acceptable derivative of a compound of formula II.

In another embodiment, a compound of formula II is a compound of formula II where the derivative is a pharmaceutically acceptable salt.

In another embodiment, a compound of formula II is a pharmaceutically acceptable salt of a compound of formula II.

In another embodiment, Q is:

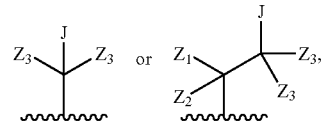

each $Z_1$ is independently selected from —OH, —SH, —N($R_{20}$)$_2$, —CH$_2$OH, —CH$_2$SH, and —CH$_2$N($R_{20}$)$_2$;

each $Z_2$ is independently selected from —H, —CH$_3$, and —CH$_2$OR$_7$;

each $Z_3$ is independently selected from —H and —CH$_3$; and each J is independently selected from —OH, —SH, and —N($R_{20}$)$_2$.

In another embodiment, a compound of formula II is a compound of formula II', i.e., the dashed line not connected to D is present as part of a double bond and D is N:

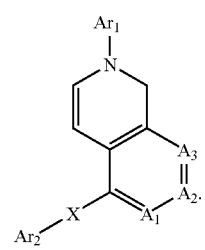

II'

In another embodiment, a compound of formula II is a compound of formula II(a):

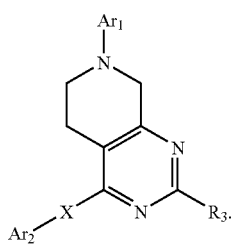

In another embodiment, a compound of formula II is a compound of formula II(b):

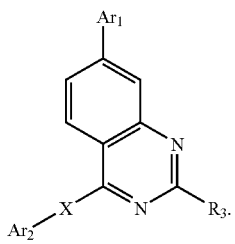

In another embodiment, a compound of formula II is a compound of formula II(c):

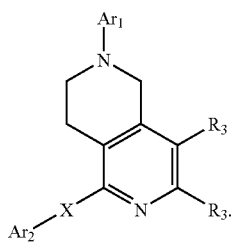

In another embodiment, a compound of formula II is a compound of formula II(d):

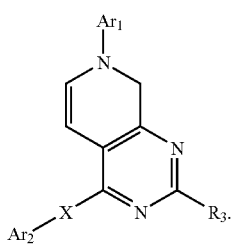

In another embodiment, Ar$_1$ is a pyridyl group.
In another embodiment, Ar$_1$ is a pyrimidinyl group.
In another embodiment, Ar$_1$ is a pyrazinyl group.
In another embodiment, Ar$_1$ is a pyridazinyl group.
In another embodiment, A$_1$ is C(R$_3$).
In another embodiment, A$_1$ is N.
In another embodiment, A$_2$ is C(R$_3$).
In another embodiment, A$_2$ is N.
In another embodiment, A$_3$ is C(R$_3$).
In another embodiment, A$_3$ is N.
In another embodiment, D is C.
In another embodiment, D is N.
In another embodiment, D is C(R$_D$).
In another embodiment, R$_D$ is —H.
In another embodiment, R$_D$ is —F.
In another embodiment, R$_D$ is —Cl.
In another embodiment, R$_D$ is —(C$_1$-C$_6$)alkyl.
In another embodiment, X is —N(R$_{20}$)—.
In another embodiment, X is —NH—.
In another embodiment, X is —N((C$_1$-C$_6$)alkyl)-.
In another embodiment, X is —N((C$_3$-C$_8$)cycloalkyl)-.
In another embodiment, X is —O—.
In another embodiment, X is —S—.
In another embodiment, X is —S(O)—.
In another embodiment, X is —S(O$_2$)—.
In another embodiment, Ar$_2$ is a benzoimidazolyl group.
In another embodiment, Ar$_2$ is a benzothiazolyl group.
In another embodiment, Ar$_2$ is a benzooxazolyl group.
In another embodiment, Ar$_2$ is:

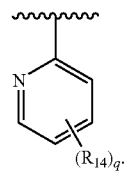

In another embodiment, Ar$_2$ is:

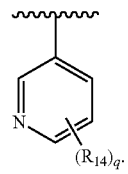

In another embodiment, Ar$_2$ is:

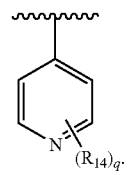

In another embodiment, Ar$_2$ is:

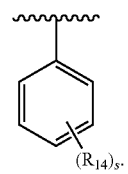

In another embodiment, Ar$_2$ is:

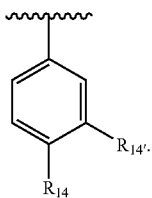

In another embodiment, Ar$_2$ is:

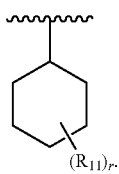

In another embodiment, Ar$_2$ is:

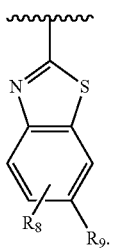

In another embodiment, n or p is 1.
In another embodiment, n or p is 2.
In another embodiment, n is 3.
In another embodiment, each R$_3$ is independently —H or —(C$_1$-C$_6$)alkyl.
In another embodiment, each R$_3$ is —H.
In another embodiment, each R$_3$ is -halo.
In another embodiment, each R$_3$ is —CN.
In another embodiment, each R$_3$ is —P(O)(OH)$_2$.
In another embodiment, each R$_3$ is —S(O)$_2$(OH).
In another embodiment, each R$_3$ is —S(O)$_2$(O)—(C$_1$-C$_6$)alkyl).
In another embodiment, each R$_3$ is —OH.
In another embodiment, each R$_3$ is —C(O)OR$_7$.
In another embodiment, each R$_3$ is —C(halo)$_3$.
In another embodiment, each R$_3$ is —CH(halo)$_2$.
In another embodiment, each R$_3$ is —CH$_2$(halo).
In another embodiment, each R$_3$ is —(C$_1$-C$_6$)alkoxy.
In another embodiment, each R$_3$ is —(C$_3$-C$_8$)cycloalkyl.
In another embodiment, each R$_3$ is —(C$_6$-C$_{14}$)aryl.
In another embodiment, each R$_3$ is —(C$_1$-C$_6$)alkyl-N(R$_7$)$_2$.
In another embodiment, each R$_3$ is —N(R$_7$)—(C$_1$-C$_6$)alkyl-R$_{14}$.
In another embodiment, each R$_3$ is —(C$_1$-C$_6$)alkyl-(C$_1$-C$_6$)alkoxy.
In another embodiment, each R$_3$ is —(C$_1$-C$_6$)alkyl-O—(C$_3$-C$_8$)cycloalkyl.
In another embodiment, each R$_3$ is —(C$_1$-C$_6$)alkyl-N(R$_7$)$_2$.

In another embodiment, each R$_3$ is —O—(C$_1$-C$_6$)alkyl-S(O)$_2$—R$_{14}$.
In another embodiment, each R$_3$ is —C(O)-(3- to 7-membered)heterocycle.
In another embodiment, each R$_3$ is —(C$_1$-C$_6$)alkyl-(3- to 7-membered)heterocycle.
In another embodiment, each R$_3$ is —C(O)N(R$_7$)—(C$_1$-C$_6$)alkyl-(3- to 7-membered)-heterocycle.
In another embodiment, each R$_3$ is —(C$_1$-C$_6$)alkyl-(5- to 10-membered)heteroaryl.
In another embodiment, each R$_3$ is —N(R$_7$)$_2$.
In another embodiment, each R$_3$ is —C(O)-(5- to 10-membered)heteroaryl.
In another embodiment, each R$_3$ is —S(O)$_2$—(C$_1$-C$_6$)alkyl.
In another embodiment, each R$_3$ is —C(O)N(R$_7$)—(C$_1$-C$_6$)alkyl-N(R$_7$)$_2$.
In another embodiment, each R$_3$ is —C(O)N(R$_7$)—(C$_1$-C$_6$)alkyl-(5- to 10-membered)heteroaryl.
In another embodiment, each R$_3$ is —S(O)$_2$—N(R$_7$)$_2$.
In another embodiment, each R$_3$ is —OC(O)N(R$_7$)$_2$.
In another embodiment, each R$_3$ is —C(O)N(R$_7$)$_2$.
In another embodiment, each R$_3$ is —C(O)N(R$_7$)—(C$_1$-C$_6$)alkyl-R$_7$.
In another embodiment, each R$_3$ is —C(O)—(C$_1$-C$_6$)alkyl.
In another embodiment, each R$_3$ is —C(O)O—(C$_1$-C$_6$)alkyl.
In another embodiment, each R$_3$ is —S(O)$_2$—(C$_1$-C$_6$)alkyl.
In another embodiment, each R$_3$ is —O—(C$_1$-C$_6$)alkyl-R$_{14}$.
In another embodiment, each R$_3$ is —O—(C$_1$-C$_6$)alkyl-O—R$_{14}$.
In another embodiment, each R$_3$ is —O—(C$_1$-C$_6$)alkyl-C(O)—R$_{14}$.
In another embodiment, each R$_3$ is —O—(C$_1$-C$_6$)alkyl-C(O)—N(R$_7$)—(C$_1$-C$_6$)alkyl-OR$_7$.
In another embodiment, each R$_3$ is —C(O)R$_{14}$.
In another embodiment, each R$_3$ is —O—(C$_1$-C$_6$)alkyl-C(O)—N(R$_7$)—(C$_1$-C$_6$)alkyl-OR$_7$.
In another embodiment, each R$_3$ is —O—(C$_1$-C$_6$)alkyl-C(O)—N(R$_7$)$_2$.
In another embodiment, R$_3$ is —OH.
In another embodiment, R$_3$ is —NH$_2$.
In another embodiment, R$_3$ is —SH.
In another embodiment, R$_3$ is —(C$_1$-C$_6$)haloalkyl.
In another embodiment, R$_3$ is —(C$_1$-C$_6$)alkyl(halo)$_2$.
In another embodiment, R$_3$ is —(C$_1$-C$_6$)alkyl(halo)$_3$.
In another embodiment, R$_3$ is —C$_2$H$_5$Cl.
In another embodiment, R$_3$ is —(C$_1$-C$_6$)heteroalkyl.
In another embodiment, R$_3$ is —(C$_1$-C$_6$)alkyl-piperidinyl.
In another embodiment, R$_3$ is —OCF$_3$.
In another embodiment, R$_3$ is —O(C$_1$-C$_6$)alkyl.
In another embodiment, R$_3$ is —(C$_1$-C$_6$)alkyl-O—(C$_1$-C$_6$)alkyl.
In another embodiment, R$_3$ is —S(C$_1$-C$_6$)alkyl.
In another embodiment, R$_3$ is —(C$_1$-C$_6$)alkyl-S—(C$_1$-C$_6$)alkyl.
In another embodiment, R$_3$ is —S(O)$_2$(C$_1$-C$_6$)alkyl.
In another embodiment, R$_3$ is -morpholinyl.
In another embodiment, R$_3$ is —NH—(C$_1$-C$_6$)alkyl.
In another embodiment, R$_3$ is —NH—(C$_1$-C$_6$)alkyl-morpholinyl.
In another embodiment, R$_3$ is —N((C$_1$-C$_6$)alkyl)$_2$.
In another embodiment, R$_3$ is —NH—(C$_1$-C$_6$)alkyl-N((C$_1$-C$_6$)alkyl)$_2$.
In another embodiment, R$_3$ is —CN.

In another embodiment, $R_3$ is —H.
In another embodiment, $R_3$ is -halo.
In another embodiment, $R_3$ is —$CH_2Cl$.
In another embodiment, $R_3$ is —$OCH_3$.
In another embodiment, $R_3$ is —$OC_2H_5$.
In another embodiment, $R_3$ is —$(C_1$-$C_6)$thioalkoxy.
In another embodiment, $R_3$ is S—$CH_3$.
In another embodiment, $R_3$ is —$CH_2$—O—$CH_3$.
In another embodiment, $R_3$ is —$CH_2$-piperidyl.
In another embodiment, $R_3$ is —$S(O)_2$—$CH_3$.
In another embodiment, $R_3$ is —NH—$C_2H_4$-morpholinyl.
In another embodiment, $R_3$ is —NH—$C_2H_4$—$N(CH_3)_2$.
In another embodiment, $R_3$ is -halo.
In another embodiment, s or q is 0.
In another embodiment, s or q is 1.
In another embodiment, s or q is 2.
In another embodiment, $R_1$ is —H.
In another embodiment, $R_1$ is -halo.
In another embodiment, $R_1$ is —Cl.
In another embodiment, $R_1$ is —F.
In another embodiment, $R_1$ is —$CH_3$.
In another embodiment, $R_1$ is —$NO_2$.
In another embodiment, $R_1$ is —CN.
In another embodiment, $R_1$ is —OH.
In another embodiment, $R_1$ is —$OCH_3$.
In another embodiment, $R_1$ is —$NH_2$.
In another embodiment, $R_1$ is —$C(halo)_3$.
In another embodiment, $R_1$ is $CF_3$.
In another embodiment, $R_1$ is —$CH(halo)_2$.
In another embodiment, $R_1$ is —$CH_2(halo)$.
In another embodiment, $R_1$ is —$S(O)_2(C_1$-$C_4$-alkyl).
In another embodiment, $Ar_1$ is a pyridyl group and n is 1.
In another embodiment, $Ar_1$ is a pyrazinyl group and p is 1.
In another embodiment, $Ar_1$ is a pyrimidinyl group and p is 1.
In another embodiment, $Ar_1$ is a pyridazinyl group and p is 1.
In another embodiment, Q is:

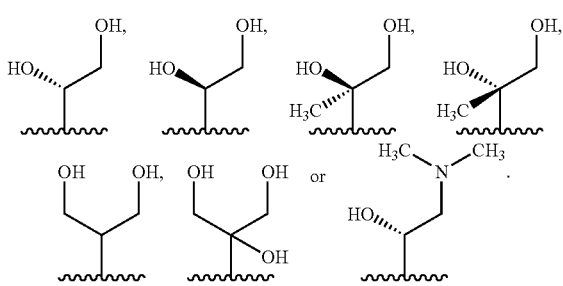

In another embodiment, J is —$N(R_{20})_2$.
In another embodiment, J is —OH.
In another embodiment, $Z_1$ is —OH.
In another embodiment, $Z_1$ is —$CH_2OH$.
In another embodiment, $Z_2$ is —$CH_2OR_7$.
In another embodiment, $Z_2$ is —$CH_2OH$.
In another embodiment, $Z_2$ is —H or —$CH_3$.
In another embodiment, $Z_2$ is —H.
In another embodiment, $Z_2$ is —$CH_3$.
In another embodiment, $Z_3$ is —H.
In another embodiment, $Z_3$ is —$CH_3$.
In another embodiment, each $R_{20}$ is independently —H or —$(C_1$-$C_6)$alkyl.
In another embodiment, each $R_{20}$ is independently —H or —$(C_3$-$C_8)$cycloalkyl.
In another embodiment, each $R_{20}$ is independently —$(C_1$-$C_6)$alkyl or —$(C_3$-$C_8)$cycloalkyl.
In another embodiment, each $R_{20}$ is —H.
In another embodiment, each $R_{20}$ is —$(C_1$-$C_6)$alkyl.
In another embodiment, each $R_{20}$ is —$CH_3$.
In another embodiment, each $R_{20}$ is —$(C_3$-$C_8)$cycloalkyl.
In another embodiment, each $R_{20}$ is cyclohexyl.
In another embodiment, $Ar_2$ is a benzothiazolyl, benzoimidazolyl, or benzooxazolyl group; and at least one of $R_8$ and $R_9$ is —H.
In another embodiment, $Ar_2$ is a benzothiazolyl, benzoimidazolyl, or benzooxazolyl group; and at least one of $R_8$ and $R_9$ is not —H.
In another embodiment, $Ar_2$ is a benzothiazolyl, benzoimidazolyl, or benzooxazolyl group; and at least one of $R_8$ and $R_9$ is -halo.
In another embodiment, $Ar_2$ is:

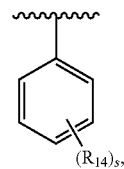

s is 1 and $R_{14}$ is —$(C_1$-$C_6)$alkyl, -halo, —$C(halo)_3$, —$OC(halo)_3$, —$OR_7$, —$N(R_7)_2$, —$S(O)_2R_7$, or —$S(O)_2C(halo)_3$.
In another embodiment, $Ar_2$ is:

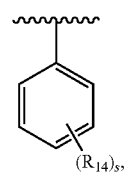

s is 2, and each $R_{14}$ group independently is —$(C_1$-$C_6)$alkyl, -halo, —$C(halo)_3$, —$OC(halo)_3$, —$OR_7$, —$N(R_7)_2$, —$S(O)_2R_7$, or —$S(O)_2C(halo)_3$.
In another embodiment, $Ar_2$ is:

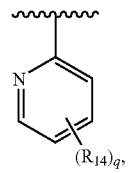

q is 2, and each $R_{14}$ group independently is —$(C_1$-$C_6)$alkyl, -halo, —$C(halo)_3$, —$OC(halo)_3$, —$OR_7$, —$N(R_7)_2$, —$S(O)_2R_7$, or —$S(O)_2C(halo)_3$.
In another embodiment, $Ar_2$ is:

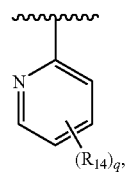

q is 1, and $R_{14}$ group independently is —($C_1$-$C_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, Ar$_2$ is:

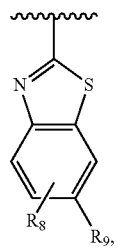

each $R_8$ and $R_9$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, or -phenyl, each of which is unsubstituted or substituted with 1 or 2 —OH groups;

In another embodiment, J is —OH, and $Z_1$ is —OH.
In another embodiment, J is —OH and $Z_1$ is —CH$_2$OH.
In another embodiment, J is —OH, $Z_1$ is —OH, $Z_2$ is —H, and $Z_3$ is —H.
In another embodiment, J is —OH, $Z_1$ is —CH$_2$OH, $Z_2$ is —H, and $Z_3$ is —H.
In another embodiment, D is N, J is —OH, $Z_1$ is —OH, $Z_2$ is —H, and $Z_3$ is —H.
In another embodiment, D is N, J is —OH, $Z_1$ is —CH$_2$OH, $Z_2$ is —H, and $Z_3$ is —H.
In another embodiment, D is N, J is —OH, $Z_1$ is —OH, $Z_2$ is —H, and $Z_3$ is —H.
In another embodiment, D is N, J is —OH, $Z_1$ is —CH$_2$OH, $Z_2$ is —H, and $Z_3$ is —H.
In another embodiment, D is N, $R_1$ is -halo, J is —OH, $Z_1$ is —OH, $Z_2$ is —H, and $Z_3$ is —H.
In another embodiment, D is N, $R_1$ is -halo, J is —OH, $Z_1$ is —CH$_2$OH, $Z_2$ is —H, and $Z_3$ is —H.
In another embodiment, D is N, $R_1$ is —F, J is —OH, $Z_1$ is —OH, $Z_2$ is —H, and $Z_3$ is —H.
In another embodiment, D is N, $R_1$ is —F, J is —OH, $Z_1$ is —CH$_2$OH, $Z_2$ is —H, and $Z_3$ is —H.
In another embodiment, Ar$_1$ is:

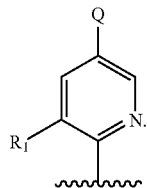

In another embodiment, D is N, $R_1$ is -halo, Ar$_1$ is:

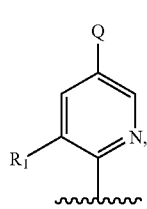

J is —OH, $Z_1$ is —OH, $Z_2$ is —H, and $Z_3$ is —H.

In another embodiment, D is N, $R_1$ is -halo, Ar$_1$ is:

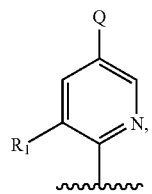

J is —OH, $Z_1$ is —CH$_2$OH, $Z_2$ is —H, and $Z_3$ is —H.
In another embodiment, D is N, $R_1$ is -halo, Ar$_1$ is:

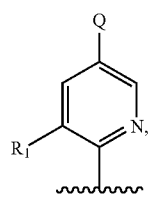

J is —OH, $Z_1$ is —OH, $Z_2$ is —H, $Z_3$ is —H, Ar$_2$ is benzooxazolyl, where at least one of $R_8$ and $R_9$ is not —H.
In another embodiment, D is N, $R_1$ is -halo, Ar$_1$ is:

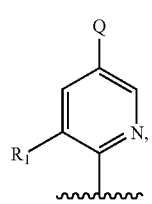

J is —OH, $Z_1$ is —CH$_2$OH, $Z_2$ is —H, $Z_3$ is —H, Ar$_2$ is benzooxazolyl, where at least one of $R_8$ and $R_9$ is not —H.
In another embodiment, D is N, $R_1$ is -halo, Ar$_1$ is:

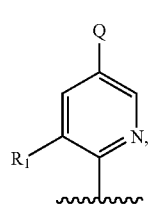

J is —OH, $Z_1$ is —OH, $Z_2$ is —H, $Z_3$ is —H, Ar$_2$ is benzothiazolyl, where at least one of $R_8$ and $R_9$ is not —H.
In another embodiment, D is N, $R_1$ is -halo, Ar$_1$ is:

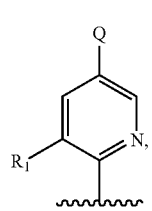

J is —OH, $Z_1$ is —CH$_2$OH, $Z_2$ is —H, $Z_3$ is —H, Ar$_2$ is benzothiazolyl, where at least one of $R_8$ and $R_9$ is not —H.

In another embodiment, D is N, R$_1$ is -halo, Ar$_1$ is:

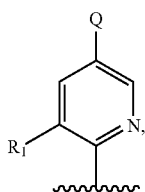

J is —OH, Z$_1$ is —OH, Z$_2$ is —H, Z$_3$ is —H, Ar$_2$ is benzoimidazolyl, where at least one of R$_8$ and R$_9$ is not —H.

In another embodiment, D is N, R$_1$ is -halo, Ar$_1$ is:

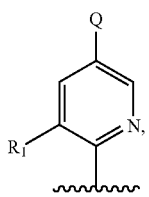

J is —OH, Z$_1$ is —CH$_2$OH, Z$_2$ is —H, Z$_3$ is —H, Ar$_2$ is benzoimidazolyl, where at least one of R$_8$ and R$_9$ is not —H.

In another embodiment, D is N, R$_1$ is -halo, Ar$_1$ is:

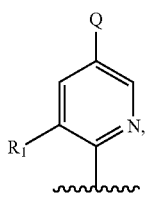

J is —OH, Z$_1$ is —OH, Z$_2$ is —H, Z$_3$ is —H, Ar$_2$ is phenyl, where s is 1.

In another embodiment, D is N, R$_1$ is -halo, Ar$_1$ is:

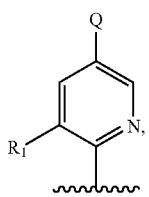

J is —OH, Z$_1$ is —CH$_2$OH, Z$_2$ is —H, Z$_3$ is —H, Ar$_2$ is phenyl, where s is 2.

In another embodiment, D is N, R$_1$ is -halo, Ar$_1$ is:

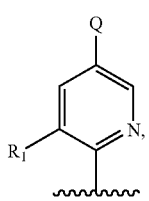

J is —OH, Z$_1$ is —OH, Z$_2$ is —H, Z$_3$ is —H, Ar$_2$ is pyridyl, where q is 1.

In another embodiment, D is N, R$_1$ is -halo, Ar$_1$ is:

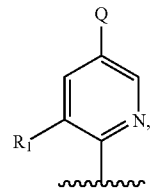

J is —OH, Z$_1$ is —CH$_2$OH, Z$_2$ is —H, Z$_3$ is —H, Ar$_2$ is pyridyl, where q is 2.

In another embodiment, D is C, the dashed lines are present as part of double bonds, R$_1$ is -halo, Ar$_1$ is:

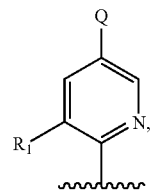

J is —OH, Z$_1$ is —OH, Z$_2$ is —H, and Z$_3$ is —H.

In another embodiment, D is C, the dashed lines are present as part of double bonds, R$_1$ is -halo, Ar$_1$ is:

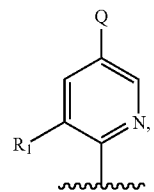

J is —OH, Z$_1$ is —CH$_2$OH, Z$_2$ is —H, and Z$_3$ is —H.

In another embodiment, D is C, the dashed lines are present as part of double bonds, R$_1$ is -halo, Ar$_1$ is:

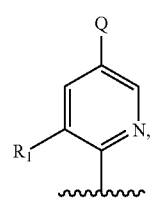

J is —OH, Z$_1$ is —OH, Z$_2$ is —H, Z$_3$ is —H, Ar$_2$ is benzooxazolyl, where at least one of R$_8$ and R$_9$ is not —H.

In another embodiment, D is C, the dashed lines are present as part of double bonds, R$_1$ is -halo, Ar$_1$ is:

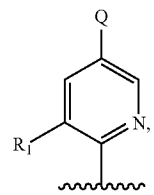

J is —OH, Z$_1$ is —CH$_2$OH, Z$_2$ is —H, Z$_3$ is —H, Ar$_2$ is benzooxazolyl, where at least one of R$_8$ and R$_9$ is not —H.

In another embodiment, D is C, the dashed lines are present as part of double bonds, $R_1$ is -halo, $Ar_1$ is:

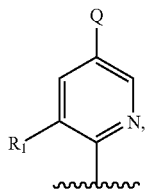

J is —OH, $Z_1$ is —OH, $Z_2$ is —H, $Z_3$ is —H, $Ar_2$ is benzothiazolyl, where at least one of $R_8$ and $R_9$ is not —H.

In another embodiment, D is C, the dashed lines are present as part of double bonds, $R_1$ is -halo, $Ar_1$ is:

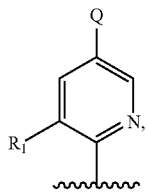

J is —OH, $Z_1$ is —CH$_2$OH, $Z_2$ is —H, $Z_3$ is —H, $Ar_2$ is benzothiazolyl, where at least one of $R_8$ and $R_9$ is not —H.

In another embodiment, D is C, the dashed lines are present as part of double bonds, $R_1$ is -halo, $Ar_1$ is:

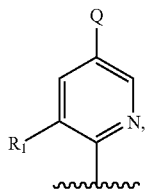

J is —OH, $Z_1$ is —OH, $Z_2$ is —H, $Z_3$ is —H, $Ar_2$ is benzoimidazolyl, where at least one of $R_8$ and $R_9$ is not —H.

In another embodiment, D is C, the dashed lines are present as part of double bonds, $R_1$ is -halo, $Ar_1$ is:

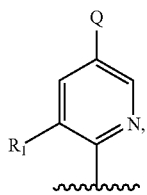

J is —OH, $Z_1$ is —CH$_2$OH, $Z_2$ is —H, $Z_3$ is —H, $Ar_2$ is benzoimidazolyl, where at least one of $R_8$ and $R_9$ is not —H.

In another embodiment, D is C, the dashed lines are present as part of double bonds, $R_1$ is -halo, $Ar_1$ is:

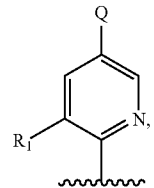

J is —OH, $Z_1$ is —OH, $Z_2$ is —H, $Z_3$ is —H, $Ar_2$ is phenyl, where s is 1.

In another embodiment, D is C, the dashed lines are present as part of double bonds, $R_1$ is -halo, $Ar_1$ is:

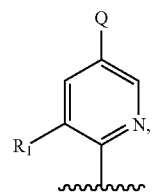

J is —OH, $Z_1$ is —OH, $Z_2$ is —H, $Z_3$ is —H, $Ar_2$ is phenyl, where s is 2.

In another embodiment, D is C, the dashed lines are present as part of double bonds, $R_1$ is -halo, $Ar_1$ is:

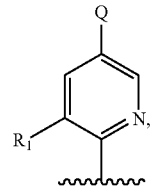

J is —OH, $Z_1$ is —CH$_2$OH, $Z_2$ is —H, $Z_3$ is —H, $Ar_2$ is phenyl, where s is 1.

In another embodiment, D is C, the dashed lines are present as part of double bonds, $R_1$ is -halo, $Ar_1$ is:

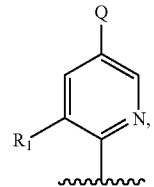

J is —OH, $Z_1$ is —CH$_2$OH, $Z_2$ is —H, $Z_3$ is —H, $Ar_2$ is phenyl, where s is 2.

In another embodiment, D is C, the dashed lines are present as part of double bonds, $R_1$ is -halo, $Ar_1$ is:

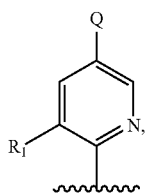

J is —OH, $Z_1$ is —OH, $Z_2$ is —H, $Z_3$ is —H, $Ar_2$ is phenyl, where s is 1, and $R_{14}$ is —$(C_1$-$C_6)$alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, D is C, the dashed lines are present as part of double bonds, $R_1$ is -halo, $Ar_1$ is:

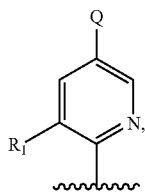

J is —OH, $Z_1$ is —CH$_2$OH, $Z_2$ is —H, $Z_3$ is —H, $Ar_2$ is phenyl, where s is 1, and $R_{14}$ is —$(C_1$-$C_6)$alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, D is C, the dashed lines are present as part of double bonds, $R_1$ is -halo, $Ar_1$ is:

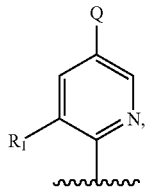

J is —OH, $Z_1$ is —OH, $Z_2$ is —H, $Z_3$ is —H, $Ar_2$ is phenyl, where s is 2, and each $R_{14}$ is independently —$(C_1$-$C_6)$alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, D is C, the dashed lines are present as part of double bonds, $R_1$ is -halo, $Ar_1$ is:

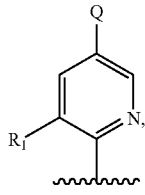

J is —OH, $Z_1$ is —CH$_2$OH, $Z_2$ is —H, $Z_3$ is —H, $Ar_2$ is phenyl, where s is 2, and each $R_{14}$ is independently —$(C_1$-$C_6)$alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, D is C, the dashed lines are present as part of double bonds, $R_1$ is -halo, $Ar_1$ is:

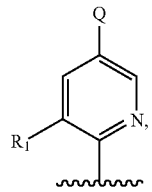

J is —OH, $Z_1$ is —OH, $Z_2$ is —H, $Z_3$ is —H, $Ar_2$ is pyridyl, where q is 1.

In another embodiment, D is C, the dashed lines are present as part of double bonds, $R_1$ is -halo, $Ar_1$ is:

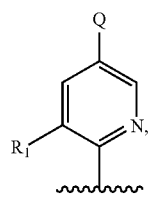

J is —OH, $Z_1$ is —OH, $Z_2$ is —H, $Z_3$ is —H, $Ar_2$ is pyridyl, where q is 2.

In another embodiment, D is C, the dashed lines are present as part of double bonds, $R_1$ is -halo, $Ar_1$ is:

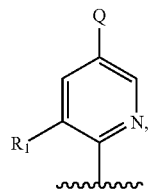

J is —OH, $Z_1$ is —CH$_2$OH, $Z_2$ is —H, $Z_3$ is —H, $Ar_2$ is pyridyl, where q is 1.

In another embodiment, D is C, the dashed lines are present as part of double bonds, $R_1$ is -halo, $Ar_1$ is:

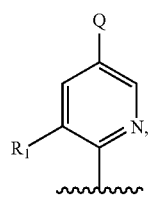

J is —OH, $Z_1$ is —CH$_2$OH, $Z_2$ is —H, $Z_3$ is —H, $Ar_2$ is pyridyl, where q is 2.

In another embodiment, D is C, the dashed lines are present as part of double bonds, $R_1$ is -halo, $Ar_1$ is:

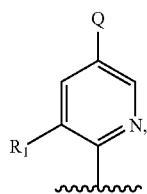

J is —OH, $Z_1$ is —OH, $Z_2$ is —H, $Z_3$ is —H, $Ar_2$ is pyridyl, where q is 1, and $R_{14}$ is —$(C_1-C_6)$alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, D is C, the dashed lines are present as part of double bonds, $R_1$ is -halo, $Ar_1$ is:

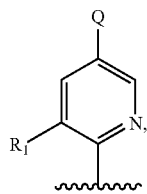

J is —OH, $Z_1$ is —CH$_2$OH, $Z_2$ is —H, $Z_3$ is —H, $Ar_2$ is pyridyl, where q is 1, and $R_{14}$ is —$(C_1-C_6)$alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, D is C, the dashed lines are present as part of double bonds, $R_1$ is -halo, $Ar_1$ is:

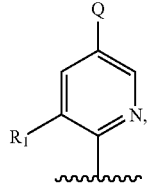

J is —OH, $Z_1$ is —OH, $Z_2$ is —H, $Z_3$ is —H, $Ar_2$ is pyridyl, where q is 2, and each $R_{14}$ is independently —$(C_1-C_6)$alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, D is C, the dashed lines are present as part of double bonds, $R_1$ is -halo, $Ar_1$ is:

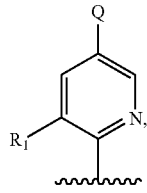

J is —OH, $Z_1$ is —CH$_2$OH, $Z_2$ is —H, $Z_3$ is —H, $Ar_2$ is pyridyl, where q is 2, and each $R_{14}$ is independently —$(C_1-C_6)$alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, Q is:

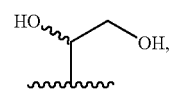

where the compound of formula II is racemic.

In another embodiment, Q is:

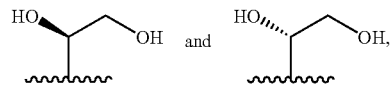

where the % ee of the R enantiomer is greater than 60%.

In another embodiment, Q is:

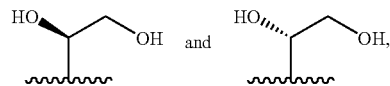

where the % ee of the R enantiomer is greater than 70%.

In another embodiment, Q is:

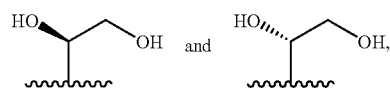

where the % ee of the R enantiomer is greater than 80%.

In another embodiment, Q is:

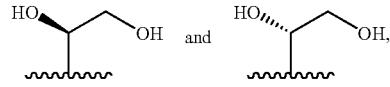

where the % ee of the R enantiomer is greater than 90%.

In another embodiment, Q is:

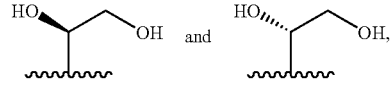

where the % ee of the R enantiomer is greater than 99%.

In another embodiment, Q is:

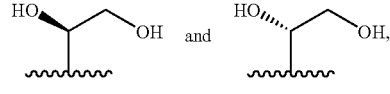

where the % ee of the S enantiomer is greater than 60%.

In another embodiment, Q is:

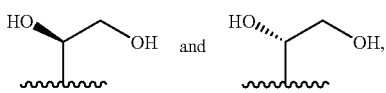 and where the % ee of the S enantiomer is greater than 70%.

In another embodiment, Q is:

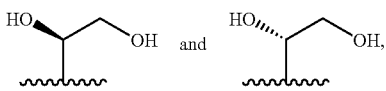 and where the % ee of the S enantiomer is greater than 80%.

In another embodiment, Q is:

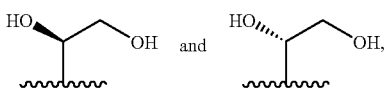 and where the % ee of the S enantiomer is greater than 90%.

In another embodiment, Q is:

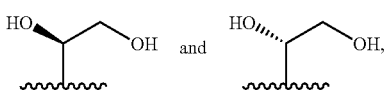 and where the % ee of the S enantiomer is greater than 99%.

In another embodiment, Q is:

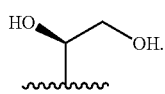

In another embodiment, Q is:

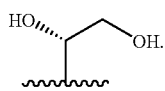

4.3. Compounds of Formula III

Preferred compounds of formula II are compounds of formula III:

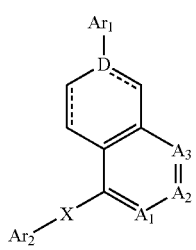

or a pharmaceutically acceptable derivative thereof, where the dashed lines, $A_1$, $A_2$, $A_3$, D, and X are as defined above for compounds of formula I;

$Ar_1$ is:

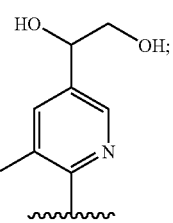

$R_1$ is —Cl, —F, —CH$_3$, —OCF$_3$ or —CF$_3$;

$Ar_2$ is:

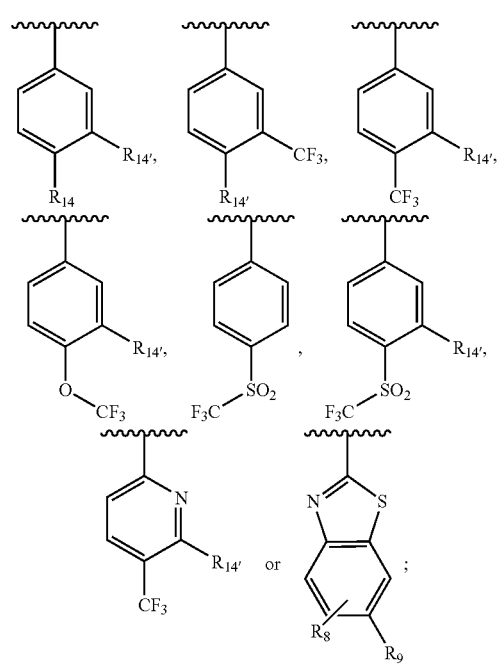

$R_{14}$ is —H, —Cl, —F, —Br, —OCF$_3$, —(C$_1$-C$_6$)alkyl, —S(O)$_2$CF$_3$, —S(O)$_2$(C$_1$-C$_6$)alkyl, —OCH$_3$, —OCH$_2$CH$_3$, or —OCH(CH$_3$)$_2$, and preferably is —CF$_3$, —OCF$_3$, —Cl, or —F;

$R_{14'}$ is —H, —Cl, —F, Br, —CH$_3$, —CH$_2$CH$_3$, —OCH$_3$, —OCF$_3$, or —OCH$_2$CH$_3$; and each $R_8$ and $R_9$ is independently selected from —H, —Cl, —Br, —F, —CH$_3$, —OCH$_3$, —OCH$_2$CH$_3$, —CF$_3$, —OCF$_3$, iso-propyl, and tert-butyl.

Certain embodiments of formula III are presented below.

In one embodiment, a compound of formula III is a pharmaceutically acceptable derivative of a compound of formula III.

In another embodiment, a compound of formula III is a compound of formula III where the derivative is a pharmaceutically acceptable salt.

In another embodiment, a compound of formula III is a pharmaceutically acceptable salt of a compound of formula III.

In another embodiment, Ar₁ is:

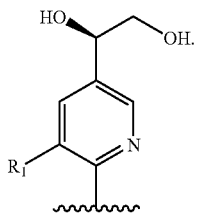

In a preferred embodiment, Ar₁ is:

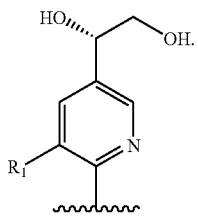

In another embodiment, a compound of formula III is a compound of formula III', i.e., the dashed line not connected to D is present as part of a double bond and D is N

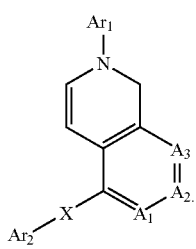

In another embodiment, a compound of formula III is a compound of formula III(a):

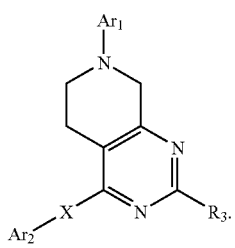

In another embodiment, a compound of formula III is a compound of formula III(b):

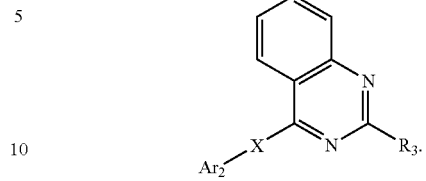

In another embodiment, a compound of formula III is a compound of formula III(c):

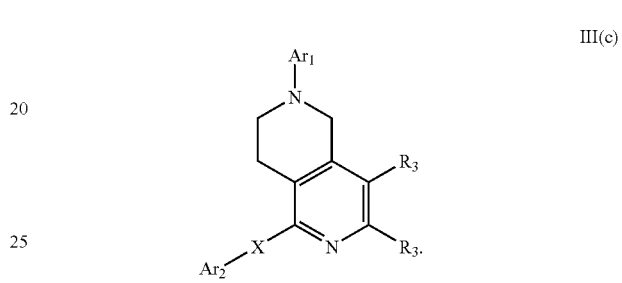

In another embodiment, a compound of formula III is a compound of formula III(d):

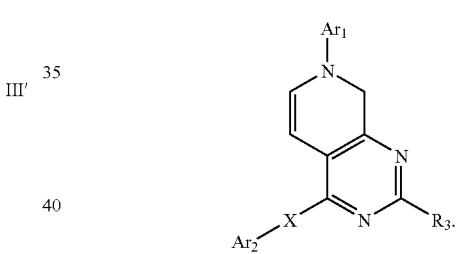

In another embodiment, X is —NH—.
In another embodiment, X is —N(($C_1$-$C_6$)alkyl)-.
In another embodiment, X is —N(($C_3$-$C_8$)cycloalkyl)-.
In another embodiment, $A_2$ is C($R_3$).
In another embodiment, the dashed lines denote the presence of double bonds.
In another embodiment, $A_1$, $A_3$ and D are N.
In another embodiment, $R_1$ is —Cl, —F, —OCF₃, —CF₃ or CH₃.
In another embodiment, each $R_{20}$ is independently —H or —($C_1$-$C_6$)alkyl.
In another embodiment, each $R_{20}$ is independently —H or —($C_3$-$C_8$)cycloalkyl.
In another embodiment, each $R_{20}$ is independently —($C_1$-$C_6$)alkyl or —($C_3$-$C_8$)cycloalkyl.
In another embodiment, each $R_{20}$ is —H.
In another embodiment, each $R_{20}$ is —($C_1$-$C_6$)alkyl.
In another embodiment, each $R_{20}$ is —CH₃.
In another embodiment, each $R_{20}$ is —($C_3$-$C_8$)cycloalkyl.
In another embodiment, each $R_{20}$ is cyclohexyl.

In another embodiment, Ar$_2$ is:

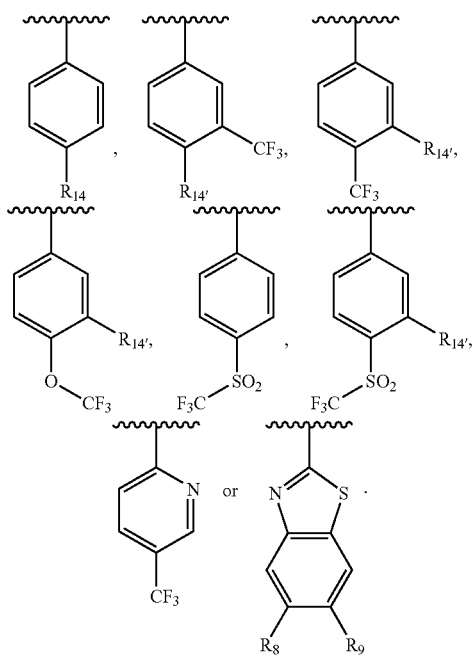

In another embodiment, each R$_3$ is independently —H or —(C$_1$-C$_6$)alkyl.
In another embodiment, each R$_3$ is —H.
In another embodiment, each R$_3$ is -halo.
In another embodiment, each R$_3$ is —CN.
In another embodiment, each R$_3$ is —S(O)$_2$(OH).
In another embodiment, each R$_3$ is —C(O)OR$_7$.
In another embodiment, each R$_3$ is —C(halo)$_3$.
In another embodiment, each R$_3$ is —(C$_1$-C$_6$)alkoxy.
In another embodiment, each R$_3$ is —(C$_1$-C$_6$)thioalkoxy.
In another embodiment, each R$_3$ is —(C$_6$-C$_{14}$)aryl.
In another embodiment, each R$_3$ is —C(O)—(3- to 7-membered)heterocycle.
In another embodiment, each R$_3$ is —(C$_1$-C$_6$)alkyl-(3- to 7-membered)heterocycle.
In another embodiment, each R$_3$ is —(C$_1$-C$_6$)alkyl-(5- to 10-membered)-heteroaryl.
In another embodiment, each R$_3$ is —N(R$_7$)$_2$.
In another embodiment, each R$_3$ is —C(O)-(5- to 10-membered)-heteroaryl.
In another embodiment, each R$_3$ is —S(O)$_2$—(C$_1$-C$_6$)alkyl.
In another embodiment, each R$_3$ is —S(O)$_2$—N(R$_7$)$_2$.
In another embodiment, each R$_3$ is —OC(O)N(R$_7$)$_2$.
In another embodiment, each R$_3$ is —C(O)N(R$_7$)$_2$.
In another embodiment, each R$_3$ is —C(O)—(C$_1$-C$_6$)alkyl.
In another embodiment, each R$_3$ is —C(O)O—(C$_1$-C$_6$)alkyl.
In another embodiment, each R$_3$ is —S(O)$_2$—(C$_1$-C$_6$)alkyl.
In another embodiment, each R$_3$ is —C(O)R$_{14}$.
In another embodiment, R$_3$ is —NH$_2$.
In another embodiment, R$_3$ is —C$_2$H$_5$Cl.
In another embodiment, R$_3$ is —(C$_1$-C$_6$)heteroalkyl.
In another embodiment, R$_3$ is —(C$_1$-C$_6$)alkyl-piperidinyl.
In another embodiment, R$_3$ is —OCF$_3$.
In another embodiment, R$_3$ is —O(C$_1$-C$_6$)alkyl.
In another embodiment, R$_3$ is —(C$_1$-C$_6$)alkyl-O—(C$_1$-C$_6$)alkyl.
In another embodiment, R$_3$ is —S(C$_1$-C$_6$)alkyl.
In another embodiment, R$_3$ is —S(O)$_2$(C$_1$-C$_6$)alkyl.
In another embodiment, R$_3$ is -morpholinyl.
In another embodiment, R$_3$ is —OCH$_3$.
In another embodiment, R$_3$ is —OC$_2$H$_5$.
In another embodiment, R$_3$ is —(C$_1$-C$_6$)alkyl-N(R$_7$)$_2$.
In another embodiment, R$_3$ is S—CH$_3$.
In another embodiment, R$_3$ is —(C$_1$-C$_6$)alkyl-(C$_1$-C$_6$)alkoxy.
In another embodiment, R$_3$ is —CH$_2$—O—CH$_3$.
In another embodiment, R$_3$ is —CH$_2$-piperidyl.
In another embodiment, R$_3$ is —S(O)$_2$—CH$_3$.
In another embodiment, R$_3$ is —OH.
In another embodiment, each R$_3$ is —N(R$_7$)—(C$_1$-C$_6$)alkyl-R$_{14}$.
In another embodiment, R$_3$ is —NH—C$_2$H$_4$-morpholinyl.
In another embodiment, R$_3$ is —NH—C$_2$H$_4$N(CH$_3$)$_2$.
In another embodiment, R$_3$ is —SH.
In another embodiment, Ar$_1$ is:

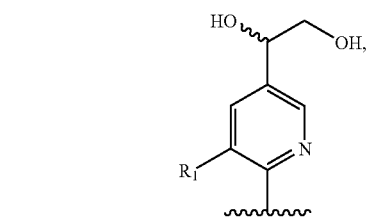

where the compound of formula III is racemic.
In another embodiment, Ar$_1$ is:

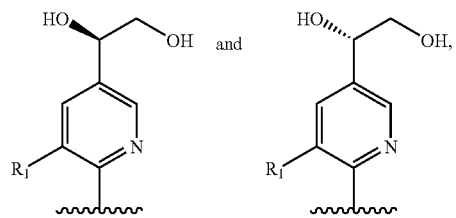

where the % ee of the R enantiomer is greater than 60%.
In another embodiment, Ar$_1$ is:

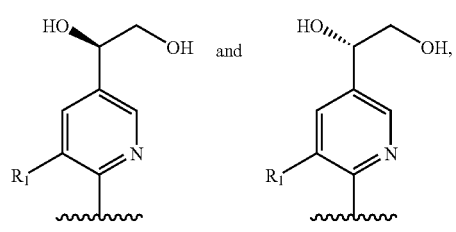

where the % ee of the R enantiomer is greater than 70%.

In another embodiment, Ar$_1$ is:

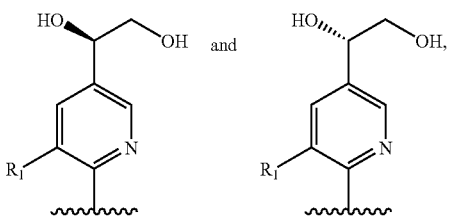

where the % ee of the R enantiomer is greater than 80%.
In another embodiment, Ar$_1$ is:

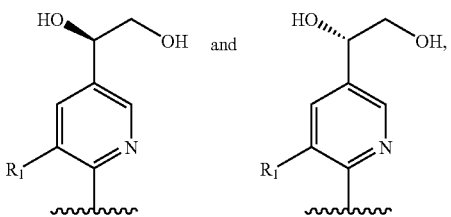

where the % ee of the R enantiomer is greater than 90%.
In another embodiment, Ar$_1$ is:

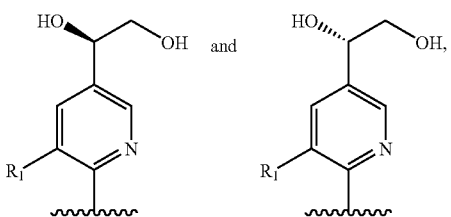

where the % ee of the R enantiomer is greater than 99%.
In another embodiment, Ar$_1$ is:

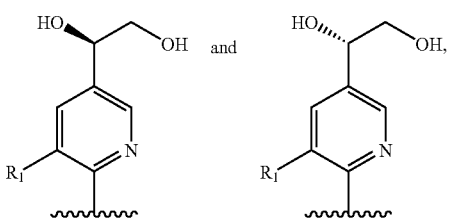

where the % ee of the S enantiomer is greater than 60%.
In another embodiment, Ar$_1$ is:

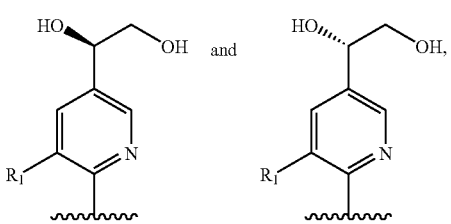

where the % ee of the S enantiomer is greater than 70%.

In another embodiment, Ar$_1$ is:

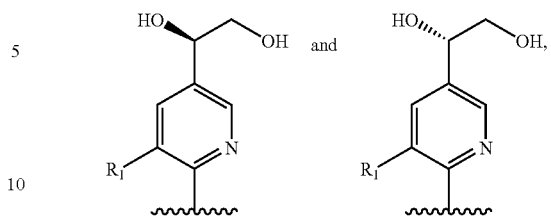

where the % ee of the S enantiomer is greater than 80%.
In another embodiment, Ar$_1$ is:

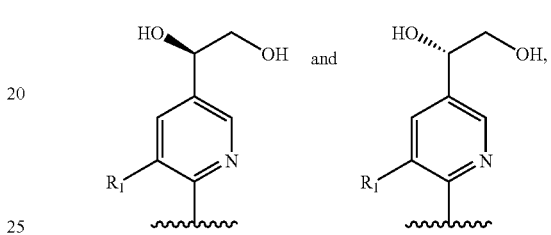

where the % ee of the S enantiomer is greater than 90%.
In another embodiment, Ar$_1$ is:

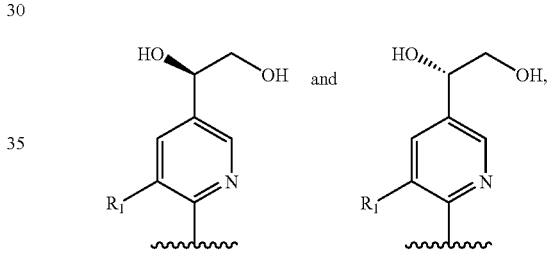

where the % ee of the S enantiomer is greater than 99%.
In another embodiment, Ar$_1$ is:

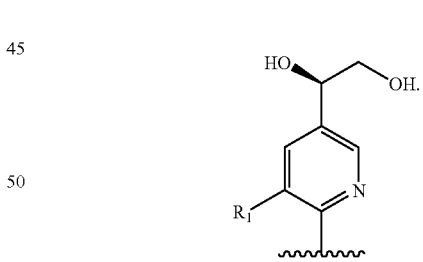

In another embodiment, Ar$_1$ is:

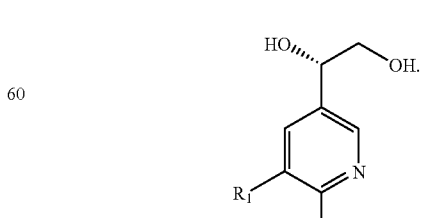

In another embodiment, the compound of formula III is a compound of formula III(a1) to III(d1):
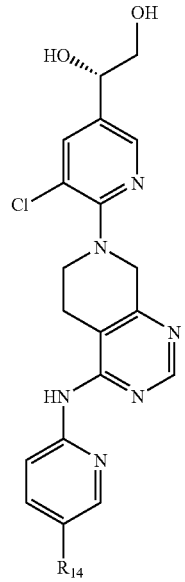
III(a1)
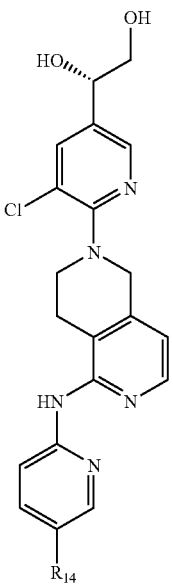
III(c1)
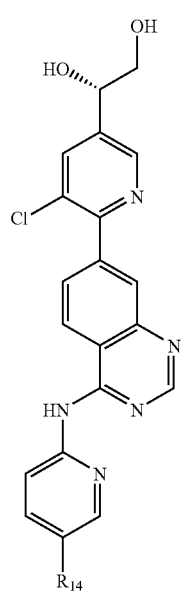
III(b1)
III(d1)
or a pharmaceutically acceptable derivative thereof, where $R_{14}$ is as defined above for the compounds of formula I.
In another embodiment, the compound of formula III is a compound of formula III(a2) to III(d2):

III(a2)
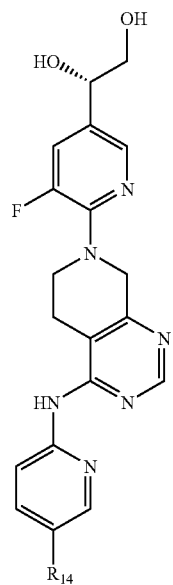
III(c2)
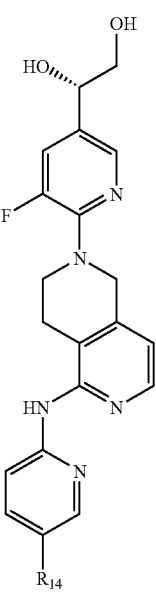
III(b2)
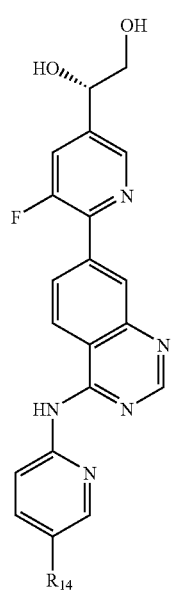
III(d2)
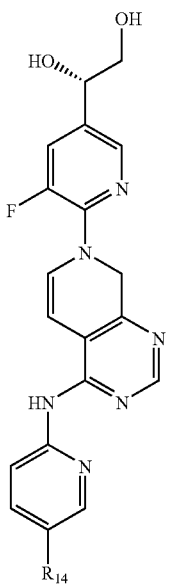
or a pharmaceutically acceptable derivative thereof, where $R_{14}$ is as defined above for the compounds of formula I.
In another embodiment, the compound of formula III is a compound of formula III(a3) to III(d3):

III(a3)
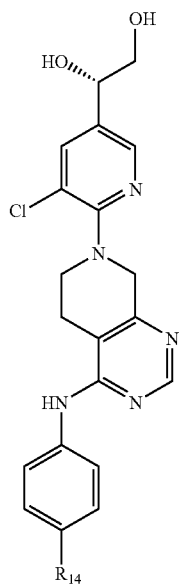
III(c3)
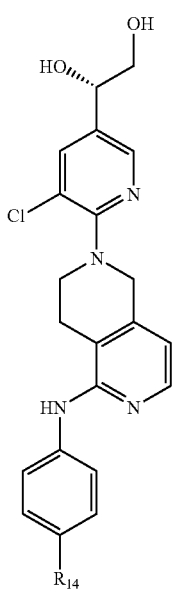
III(b3)
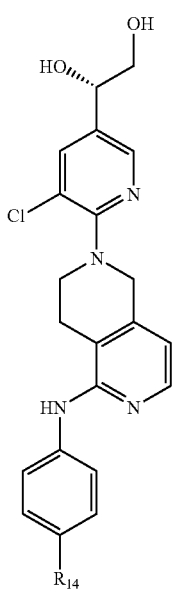
III(d3)
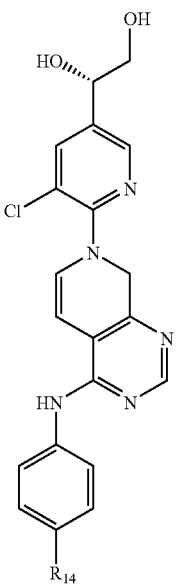
or a pharmaceutically acceptable derivative thereof, where $R_{14}$ is as defined above for the compounds of formula I.
In another embodiment, the compound of formula III is a compound of formula III(a4) to III(d4):

III(a4)
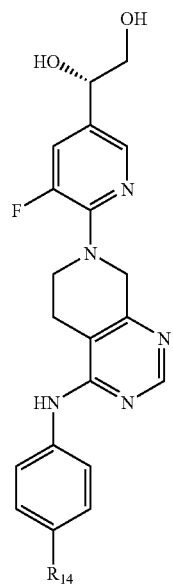
III(c4)
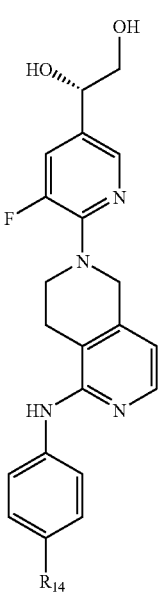
III(b4)
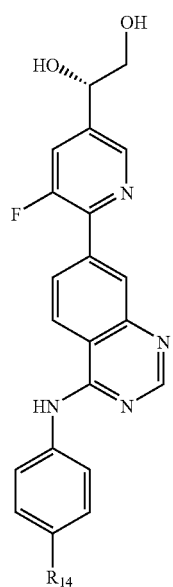
III(d4)
or a pharmaceutically acceptable derivative thereof, where $R_{14}$ is as defined above for the compounds of formula I.
In another embodiment, the compound of formula III is a compound of formula III(a5) to III(d5):

III(a5)
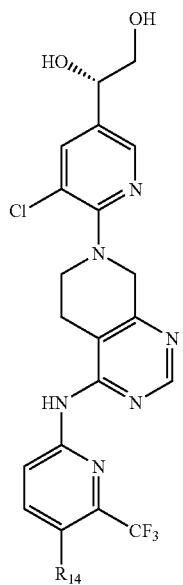
III(c5)
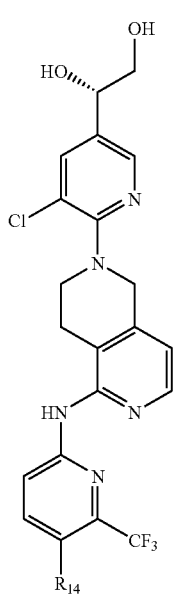
III(b5)
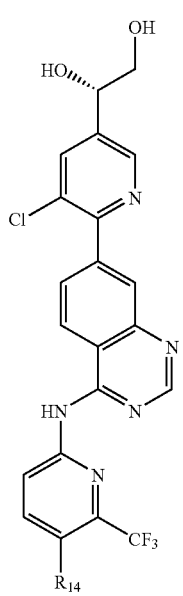
III(d5)
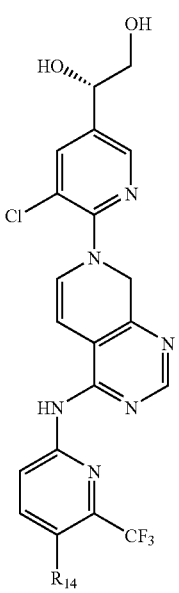
or a pharmaceutically acceptable derivative thereof, where $R_{14}$ is as defined above for the compounds of formula I.
In another embodiment, the compound of formula III is a compound of formula III(a6) to III(d6):

III(a6)
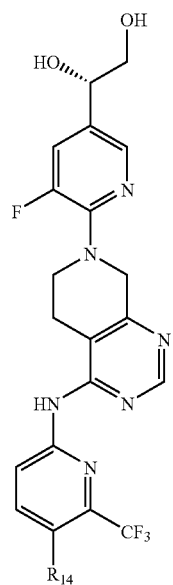
III(c6)
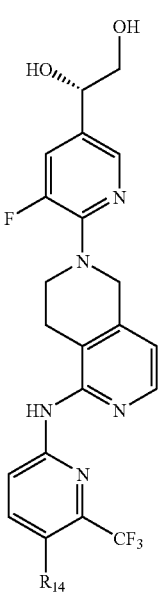
III(b6)
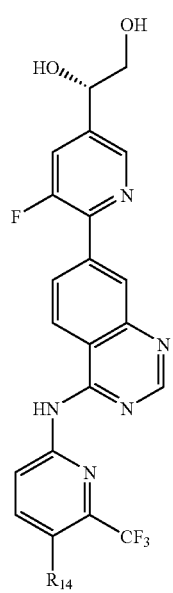
III(d6)
or a pharmaceutically acceptable derivative thereof, where $R_{14}$ is as defined above for the compounds of formula I.
In another embodiment, the compound of formula III is a compound of formula III(a7) to III(d7):

or a pharmaceutically acceptable derivative thereof, where R$_{14}$ is as defined above for the compounds of formula I.

In another embodiment, the compound of formula III is a compound of formula III(a8) to III(d8):

III(a8)
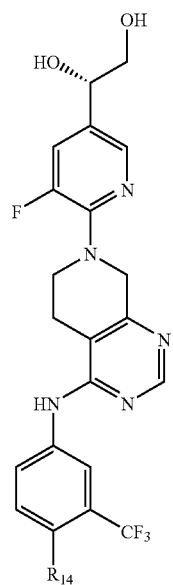
III(c8)
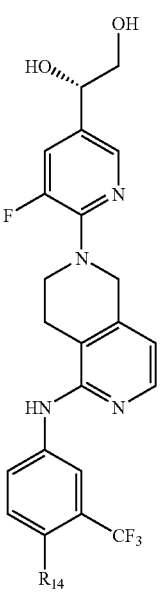
III(b8)
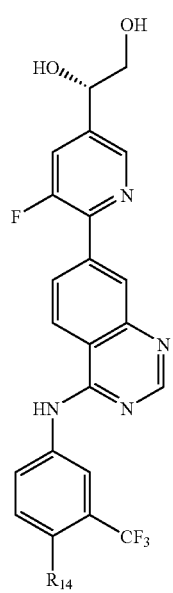
III(d8)
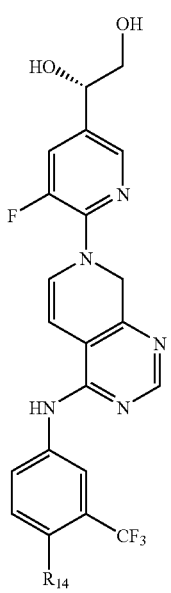
or a pharmaceutically acceptable derivative thereof, where R$_{14}$ is as defined above for the compounds of formula I.
In another embodiment, the compound of formula III is a compound of formula III(a9) to III(d9):

III(a9)
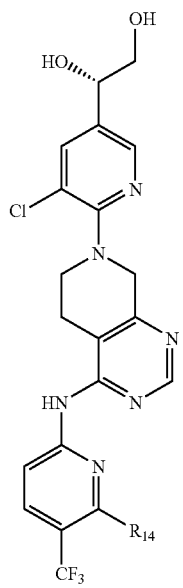
III(b9)
III(c9)
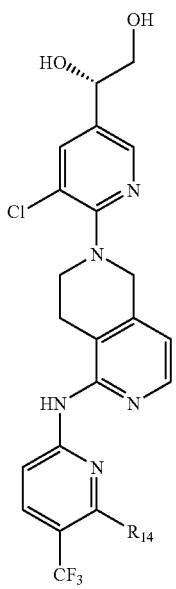
III(d9)
or a pharmaceutically acceptable derivative thereof, where $R_{14}$ is as defined above for the compounds of formula I.
In another embodiment, the compound of formula III is a compound of formula III(a10) to III(d10):

111
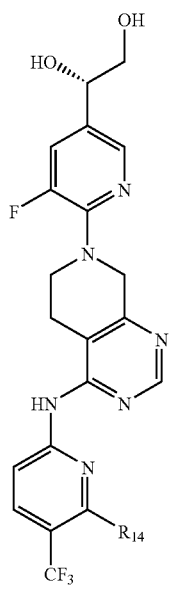
III(a10)
112
-continued
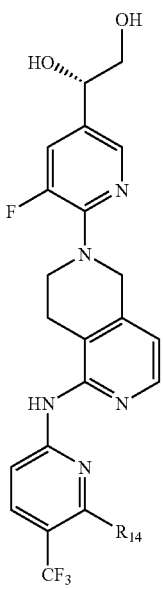
III(c10)
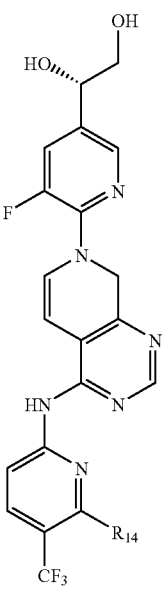
III(b10)
III(d10)
or a pharmaceutically acceptable derivative thereof, where $R_{14}$ is as defined above for the compounds of formula I.
In another embodiment, the compound of formula III is a compound of formula III(a11) to III(d11):

III(a11)
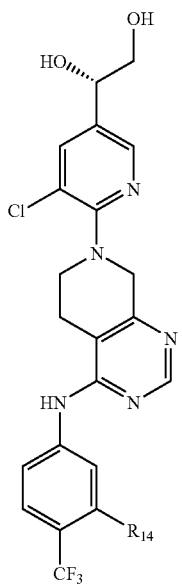
III(c11)
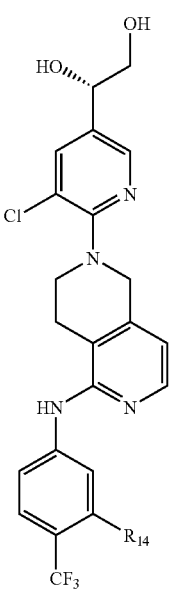
III(b11)
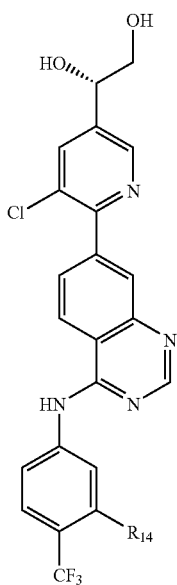
III(d11)
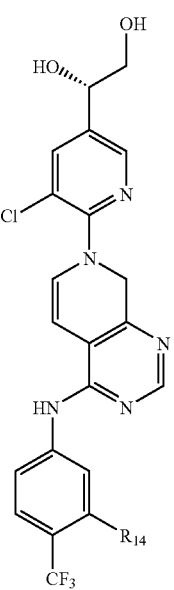
or a pharmaceutically acceptable derivative thereof, where $R_{14}$ is as defined above for the compounds of formula I.
In another embodiment, the compound of formula III is a compound of formula III(a12) to III(d12):

III(a12)
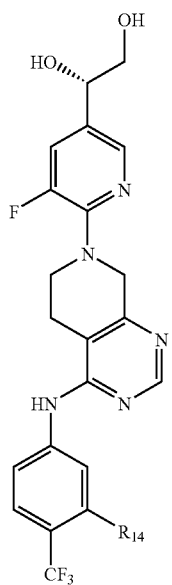
III(b12)
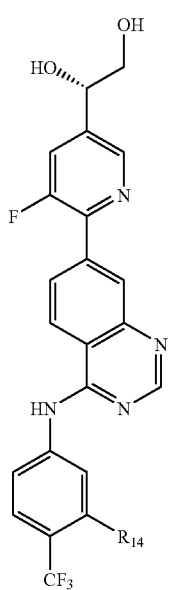
III(c12)
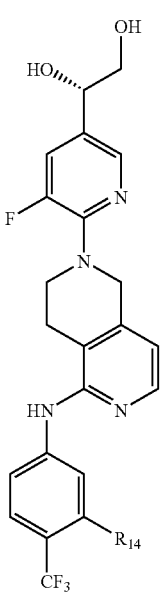
III(d12)
or a pharmaceutically acceptable derivative thereof, where $R_{14}$ is as defined above for the compounds of formula I.
In another embodiment, the compound of formula III is a compound of formula III(a13) to III(d13):

III(a13)
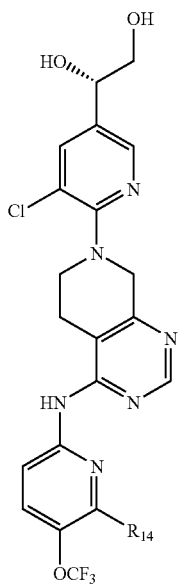
III(c13)
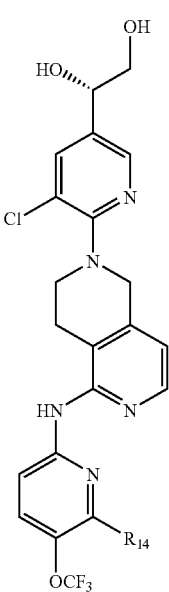
III(b13)
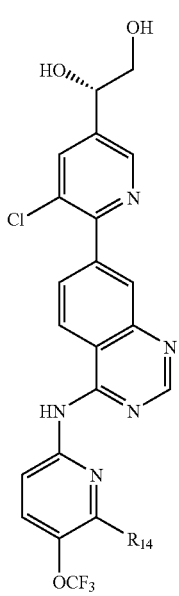
III(d13)
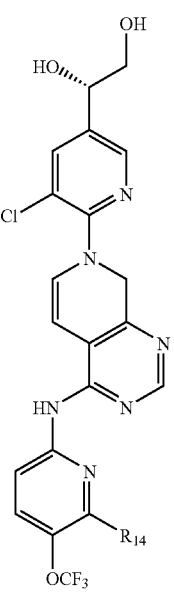
or a pharmaceutically acceptable derivative thereof, where R$_{14}$ is as defined above for the compounds of formula I.
In another embodiment, the compound of formula III is a compound of formula III(a14) to III(d14):

III(a14)
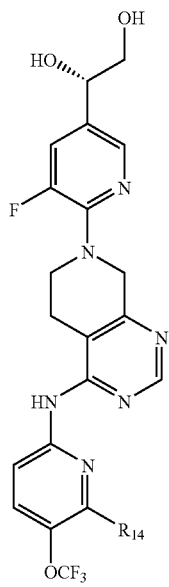
III(b14)
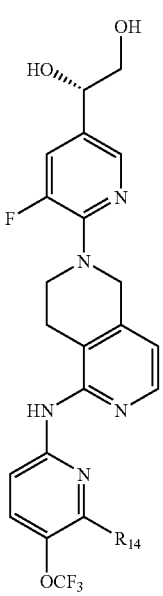
III(c14)
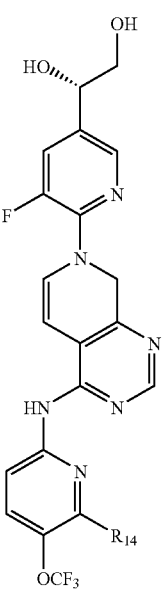
III(d14)
or a pharmaceutically acceptable derivative thereof, where $R_{14}$ is as defined above for the compounds of formula I.
In another embodiment, the compound of formula III is a compound of formula III(a15) to III(d15):

III(a15)
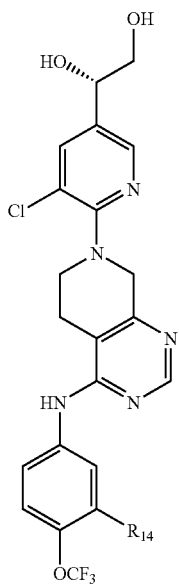
III(b15)
III(c15)
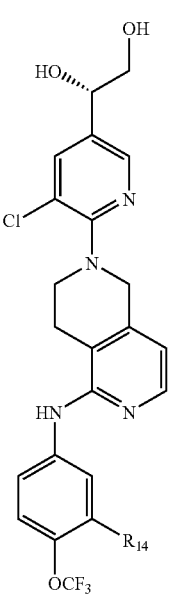
III(d15)
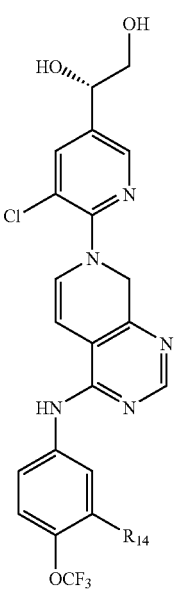
or a pharmaceutically acceptable derivative thereof, where $R_{14}$ is as defined above for the compounds of formula I.
In another embodiment, the compound of formula III is a compound of formula III(a16) to III(d16):

123                                                                                 124
                                                                                    -continued
III(a16)                                                                            III(c16)
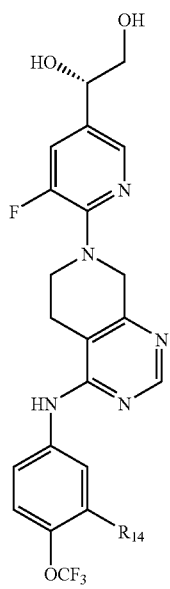                                                                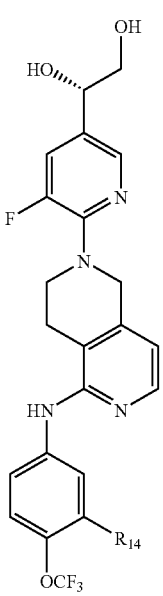
III(b16)                                                                            III(d16)
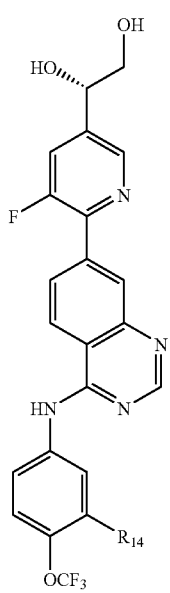
or a pharmaceutically acceptable derivative thereof, where $R_{14}$ is as defined above for the compounds of formula I.
Illustrative compounds of formula III are listed below in Tables 1-47.

TABLE 1

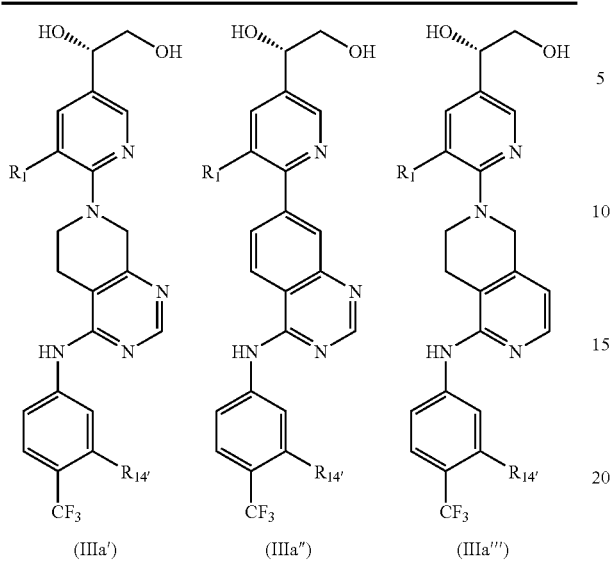

(IIIa′)  (IIIa″)  (IIIa‴)

and pharmaceutically acceptable derivatives thereof, where:

| Compound | $R_1$ | $R_{14'}$ |
|---|---|---|
| AAA (a′, a″, or a‴) | —Cl | —Cl |
| AAB (a′, a″, or a‴) | —Cl | —F |
| AAC (a′, a″, or a‴) | —Cl | —OCH$_3$ |
| AAD (a′, a″, or a‴) | —Cl | —OCH$_2$CH$_3$ |
| AAE (a′, a″, or a‴) | —F | —Cl |
| AAF (a′, a″, or a‴) | —F | —F |
| AAG (a′, a″, or a‴) | —F | —OCH$_3$ |
| AAH (a′, a″, or a‴) | —F | —OCH$_2$CH$_3$ |
| AAI (a′, a″, or a‴) | —CF$_3$ | —Cl |
| AAJ (a′, a″, or a‴) | —CF$_3$ | —F |
| AAK (a′, a″, or a‴) | —CF$_3$ | —OCH$_3$ |
| AAL (a′, a″, or a‴) | —CF$_3$ | —OCH$_2$CH$_3$ |

TABLE 2

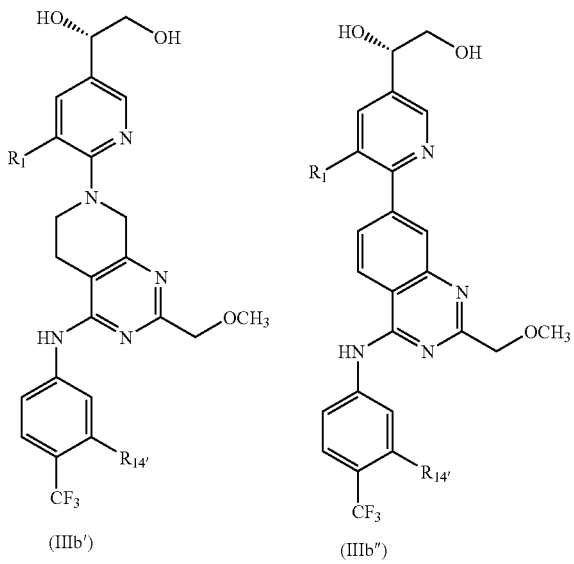

(IIIb′)  (IIIb″)

TABLE 2-continued

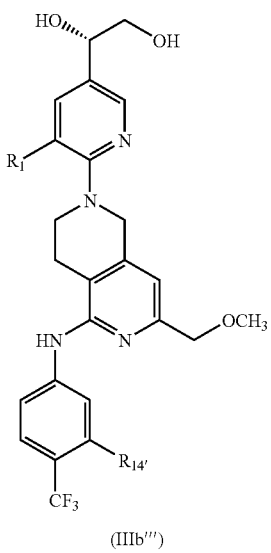

(IIIb‴)

and pharmaceutically acceptable derivatives thereof, where:

| Compound | $R_1$ | $R_{14'}$ |
|---|---|---|
| AAM (b′, b″, or b‴) | —Cl | —Cl |
| AAN (b′, b″, or b‴) | —Cl | —F |
| AAO (b′, b″, or b‴) | —Cl | —OCH$_3$ |
| AAP (b′, b″, or b‴) | —Cl | —OCH$_2$CH$_3$ |
| AAQ (b′, b″, or b‴) | —F | —Cl |
| AAR (b′, b″, or b‴) | —F | —F |
| AAS (b′, b″, or b‴) | —F | —OCH$_3$ |
| AAT (b′, b″, or b‴) | —F | —OCH$_2$CH$_3$ |
| AAU (b′, b″, or b‴) | —CF$_3$ | —Cl |
| AAV (b′, b″, or b‴) | —CF$_3$ | —F |
| AAW (b′, b″, or b‴) | —CF$_3$ | —OCH$_3$ |
| AAX (b′, b″, or b‴) | —CF$_3$ | —OCH$_2$CH$_3$ |

TABLE 3

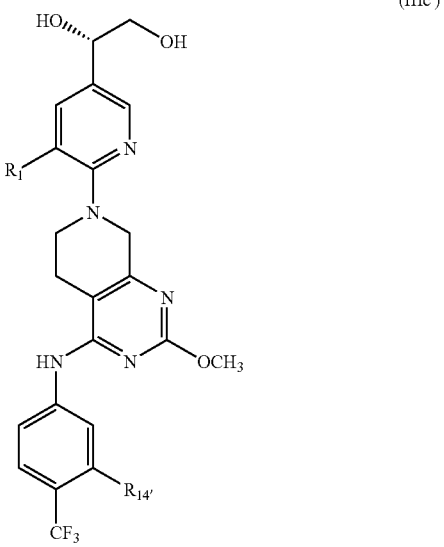

(IIIc′)

TABLE 3-continued

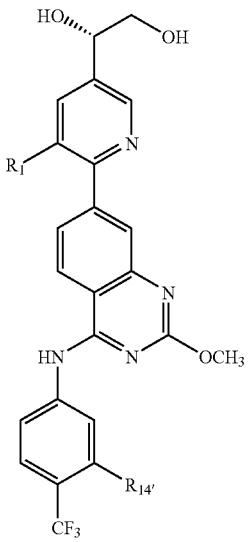
(IIIc'')

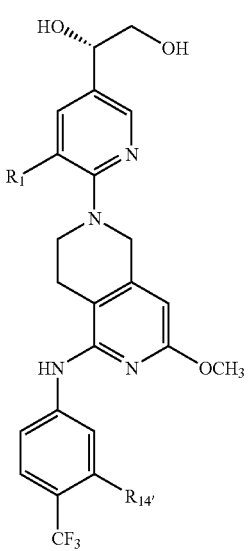
(IIIc''')

and pharmaceutically acceptable derivatives thereof, where:

| Compound | $R_1$ | $R_{14'}$ |
|---|---|---|
| AAY (c', c'', or c''') | —Cl | —Cl |
| AAZ (c', c'', or c''') | —Cl | —F |
| ABA (c', c'', or c''') | —Cl | —OCH$_3$ |
| ABB (c', c'', or c''') | —Cl | —OCH$_2$CH$_3$ |
| ABC (c', c'', or c''') | —F | —Cl |
| ABD (c', c'', or c''') | —F | —F |
| ABE (c', c'', or c''') | —F | —OCH$_3$ |
| ABF (c', c'', or c''') | —F | —OCH$_2$CH$_3$ |
| ABG (c', c'', or c''') | —CF$_3$ | —Cl |
| ABH (c', c'', or c''') | —CF$_3$ | —F |
| ABI (c', c'', or c''') | —CF$_3$ | —OCH$_3$ |
| ABJ (c', c'', or c''') | —CF$_3$ | —OCH$_2$CH$_3$ |

TABLE 4

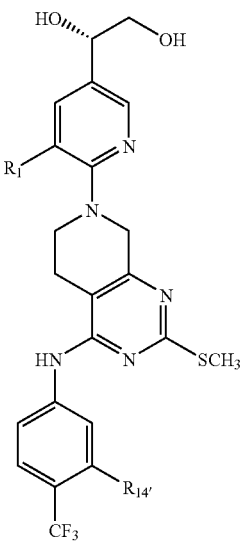
(IIId')

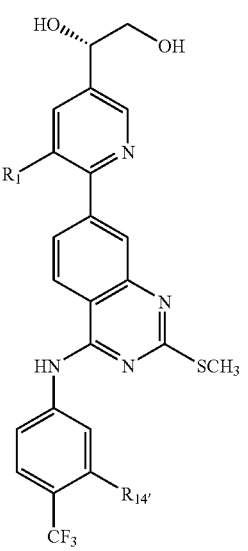
(IIId'')

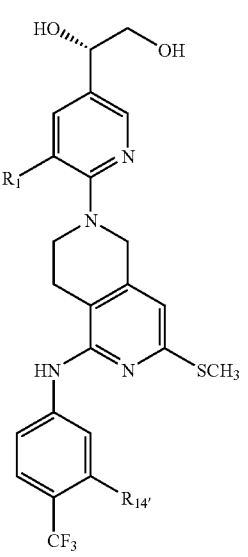
(IIId''')

TABLE 4-continued and pharmaceutically acceptable derivatives thereof, where:

| Compound | $R_1$ | $R_{14'}$ |
|---|---|---|
| ABK (d', d'', or d''') | —Cl | —Cl |
| ABL (d', d'', or d''') | —Cl | —F |
| ABM (d', d'', or d''') | —Cl | —OCH$_3$ |
| ABN (d', d'', or d''') | —Cl | —OCH$_2$CH$_3$ |
| ABO (d', d'', or d''') | —F | —Cl |
| ABP (d', d'', or d''') | —F | —F |
| ABQ (d', d'', or d''') | —F | —OCH$_3$ |
| ABR (d', d'', or d''') | —F | —OCH$_2$CH$_3$ |
| ABS (d', d'', or d''') | —CF$_3$ | —Cl |
| ABT (d', d'', or d''') | —CF$_3$ | —F |
| ABU (d', d'', or d''') | —CF$_3$ | —OCH$_3$ |
| ABV (d', d'', or d''') | —CF$_3$ | —OCH$_2$CH$_3$ |

TABLE 5

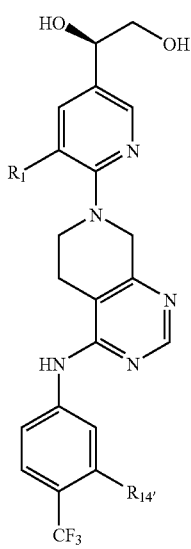

(IIIe')

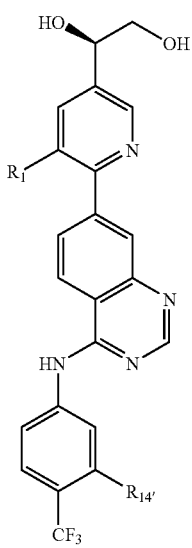

(IIIe'')

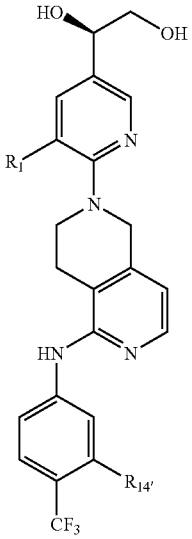

(IIIe''')

and pharmaceutically acceptable derivatives thereof, where:

| Compound | $R_1$ | $R_{14'}$ |
|---|---|---|
| ABW (e', e'', or e''') | —Cl | —Cl |
| ABX (e', e'', or e''') | —Cl | —F |
| ABY (e', e'', or e''') | —Cl | —OCH$_3$ |
| ABZ (e', e'', or e''') | —Cl | —OCH$_2$CH$_3$ |
| ACA (e', e'', or e''') | —F | —Cl |
| ACB (e', e'', or e''') | —F | —F |
| ACC (e', e'', or e''') | —F | —OCH$_3$ |
| ACD (e', e'', or e''') | —F | —OCH$_2$CH$_3$ |
| ACE (e', e'', or e''') | —CF$_3$ | —Cl |
| ACF (e', e'', or e''') | —CF$_3$ | —F |
| ACG (e', e'', or e''') | —CF$_3$ | —OCH$_3$ |
| ACH (e', e'', or e''') | —CF$_3$ | —OCH$_2$CH$_3$ |

TABLE 6

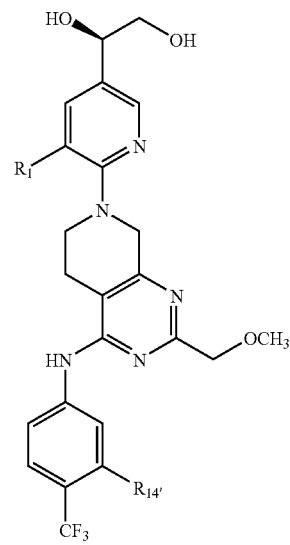

(IIIf')

TABLE 6-continued

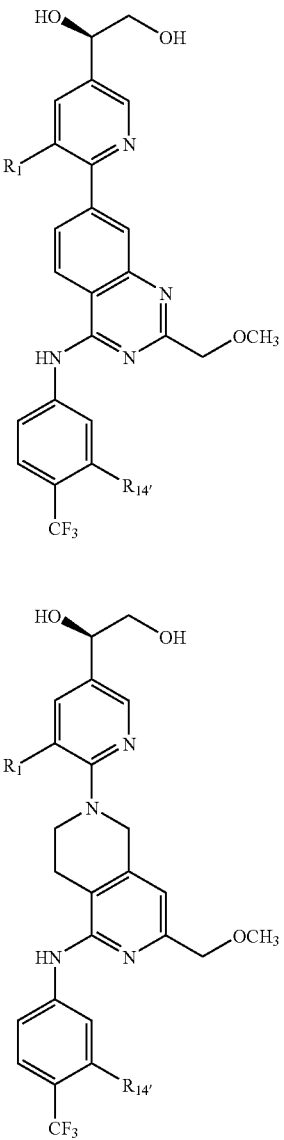

(IIIf'')

(IIIf''')

and pharmaceutically acceptable derivatives thereof, where:

| Compound | R₁ | R₁₄' |
|---|---|---|
| ACI (f, f', or f''') | —Cl | —Cl |
| ACJ (f, f', or f''') | —Cl | —F |
| ACK (f, f', or f''') | —Cl | —OCH₃ |
| ACL (f, f', or f''') | —Cl | —OCH₂CH₃ |
| ACM (f, f', or f''') | —F | —Cl |
| ACN (f, f', or f''') | —F | —F |
| ACO (f, f', or f''') | —F | —OCH₃ |
| ACP (f, f', or f''') | —F | —OCH₂CH₃ |
| ACQ (f, f', or f''') | —CF₃ | —Cl |
| ACR (f, f', or f''') | —CF₃ | —F |
| ACS (f, f', or f''') | —CF₃ | —OCH₃ |
| ACT (f, f', or f''') | —CF₃ | —OCH₂CH₃ |

TABLE 7

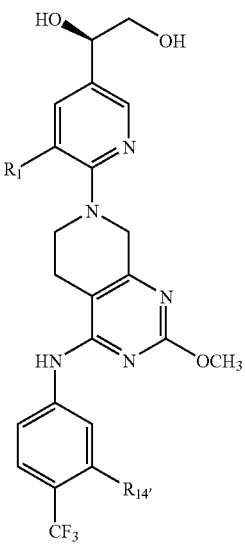

(IIIg')

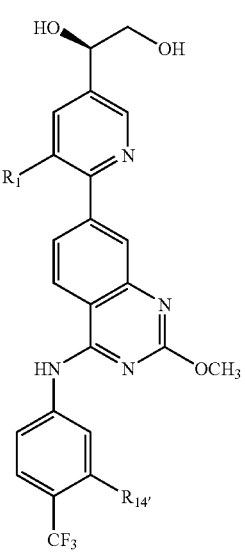

(IIIg'')

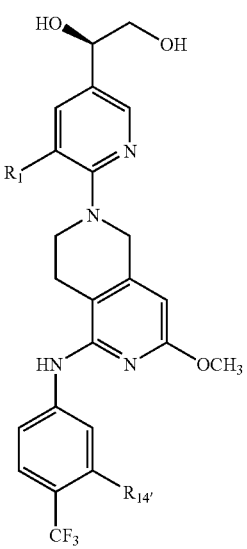

(IIIg''')

TABLE 7-continued and pharmaceutically acceptable derivatives thereof, where:

| Compound | $R_1$ | $R_{14'}$ |
|---|---|---|
| ACU (g', g'', or g''') | —Cl | —Cl |
| ACV (g', g'', or g''') | —Cl | —F |
| ACW (g', g'', or g''') | —Cl | —OCH₃ |
| ACX (g', g'', or g''') | —Cl | —OCH₂CH₃ |
| ACY (g', g'', or g''') | —F | —Cl |
| ACZ (g', g'', or g''') | —F | —F |
| ADA (g', g'', or g''') | —F | OCH₃ |
| ADB (g', g'', or g''') | —F | —OCH₂CH₃ |
| ADC (g', g'', or g''') | —CF₃ | —Cl |
| ADD (g', g'', or g''') | —CF₃ | —F |
| ADE (g', g'', or g''') | —CF₃ | —OCH₃ |
| ADF (g', g'', or g''') | —CF₃ | —OCH₂CH₃ |

TABLE 8

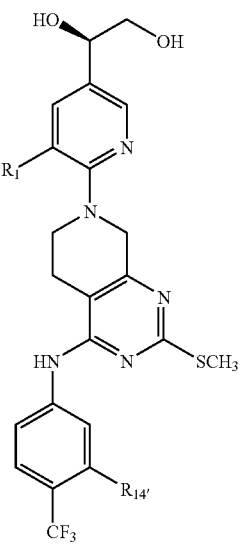

(IIIh')

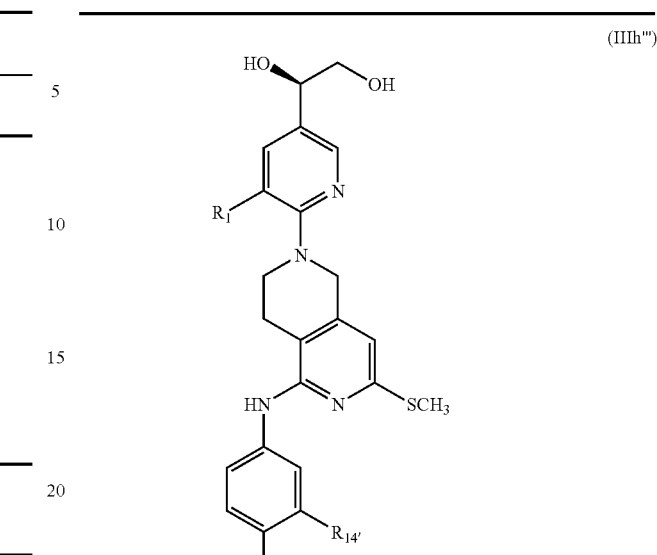

(IIIh'')

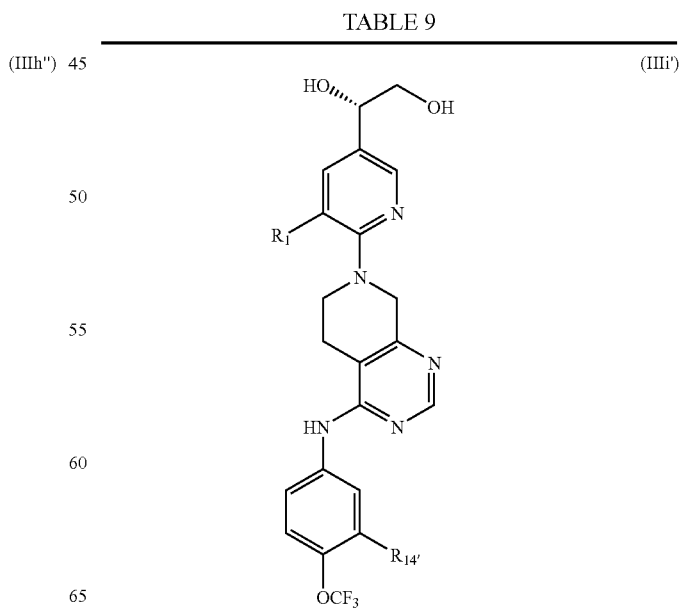

(IIIh''')

and pharmaceutically acceptable derivatives thereof, where:

| Compound | $R_1$ | $R_{14'}$ |
|---|---|---|
| ADG (h', h'', or h''') | —Cl | —Cl |
| ADH (h', h'', or h''') | —Cl | —F |
| ADI (h', h'', or h''') | —Cl | —OCH₃ |
| ADJ (h', h'', or h''') | —Cl | —OCH₂CH₃ |
| ADK (h', h'', or h''') | —F | —Cl |
| ADL (h', h'', or h''') | —F | —F |
| ADM (h', h'', or h''') | —F | —OCH₃ |
| AND (h', h'', or h''') | —F | —OCH₂CH₃ |
| ADO (h', h'', or h''') | —CF₃ | —Cl |
| ADP (h', h'', or h''') | —CF₃ | —F |
| ADQ (h', h'', or h''') | —CF₃ | —OCH₃ |
| ADR (h', h'', or h''') | —CF₃ | —OCH₂CH₃ |

TABLE 9

(IIIi')

TABLE 9-continued
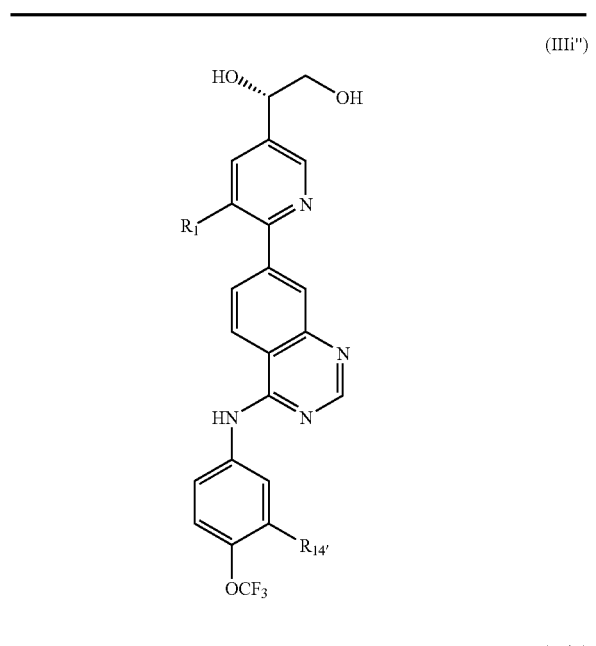
(IIIi''')
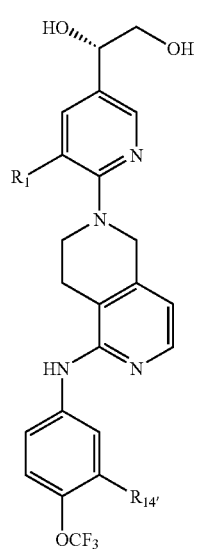
(IIIi'''')
and pharmaceutically acceptable derivatives thereof, where:
| Compound | R₁ | R₁₄' |
|---|---|---|
| BAA (i', i'', or i''') | —Cl | —CH₃ |
| BAB (i', i'', or i''') | —Cl | —CH₂CH₃ |
| BAC (i', i'', or i''') | —Cl | —Cl |
| BAD (i', i'', or i''') | —F | —CH₃ |
| BAE (i', i'', or i''') | —F | —CH₂CH₃ |
| BAF (i', i'', or i''') | —F | —Cl |
| BAG (i', i'', or i''') | —CF₃ | —CH₃ |
| BAH (i', i'', or i''') | —CF₃ | —CH₂CH₃ |
| BAI (i', i'', or i''') | —CF₃ | —Cl |
TABLE 10
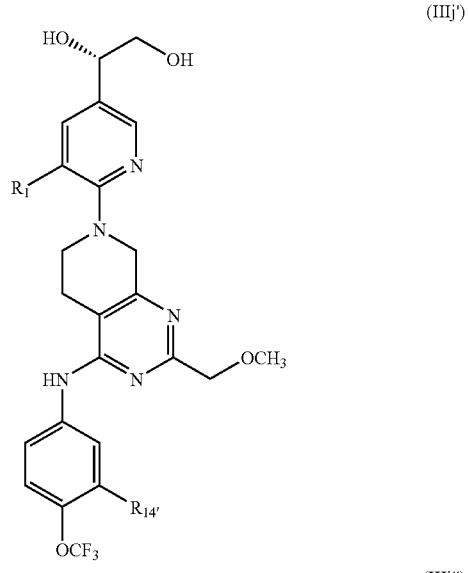
(IIIj')
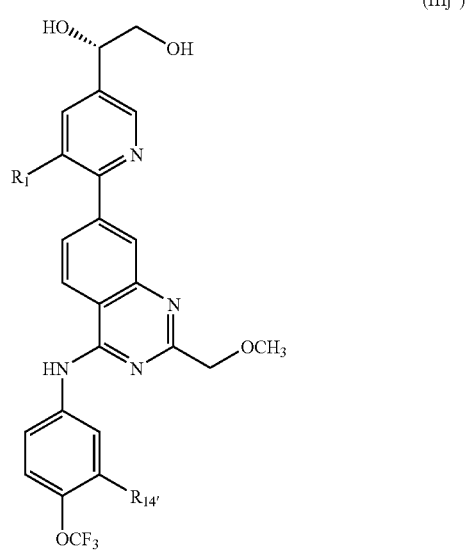
(IIIj'')
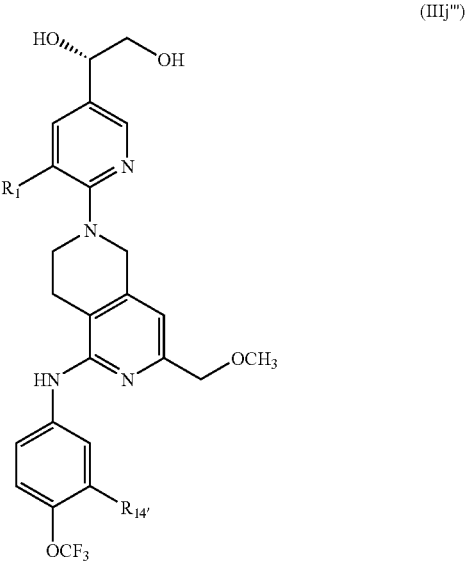
(IIIj''')

TABLE 10-continued and pharmaceutically acceptable derivatives thereof, where:

| Compound | $R_1$ | $R_{14'}$ |
|---|---|---|
| BAJ (j', j", or j''') | —Cl | —CH$_3$ |
| BAK (j', j", or j''') | —Cl | —CH$_2$CH$_3$ |
| BAL (j', j", or j''') | —Cl | —Cl |
| BAM (j', j", or j''') | —F | —CH$_3$ |
| BAN (j', j", or j''') | —F | —CH$_2$CH$_3$ |
| BAO (j', j", or j''') | —F | —Cl |
| BAP (j', j", or j''') | —CF$_3$ | —CH$_3$ |
| BAQ (j', j", or j''') | —CF$_3$ | —CH$_2$CH$_3$ |
| BAR (j', j", or j''') | —CF$_3$ | —Cl |

TABLE 11

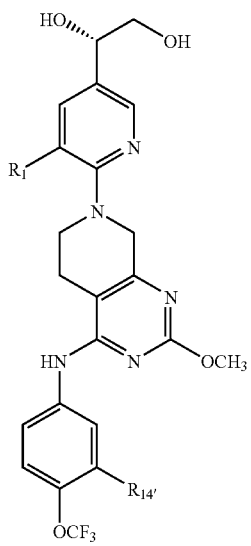

(IIIk')

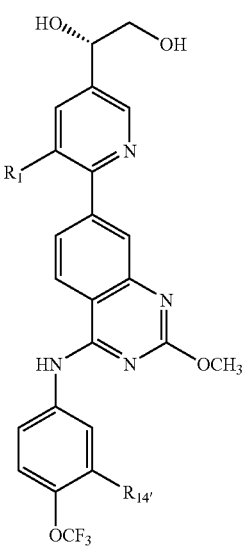

(IIIk")

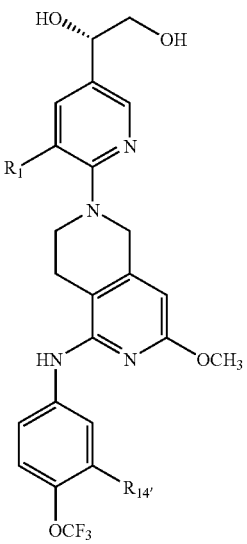

(IIIk''')

and pharmaceutically acceptable derivatives thereof, where:

| Compound | $R_1$ | $R_{14'}$ |
|---|---|---|
| BAS (k', k", or k''') | —Cl | —CH$_3$ |
| BAT (k', k", or k''') | —Cl | —CH$_2$CH$_3$ |
| BAU (k', k", or k''') | —Cl | —Cl |
| BAV (k', k", or k''') | —F | —CH$_3$ |
| BAW (k', k", or k''') | —F | —CH$_2$CH$_3$ |
| BAX (k', k", or k''') | —F | —Cl |
| BAY (k', k", or k''') | —CF$_3$ | —CH$_3$ |
| BAZ (k', k", or k''') | —CF$_3$ | —CH$_2$CH$_3$ |
| BBA (k', k", or k''') | —CF$_3$ | —Cl |

TABLE 12

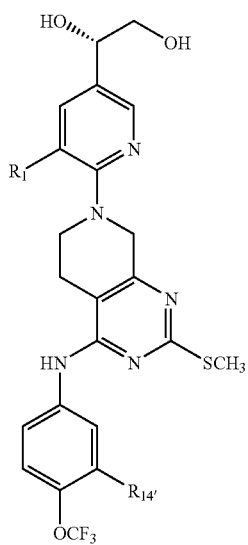

(IIIl')

TABLE 12-continued
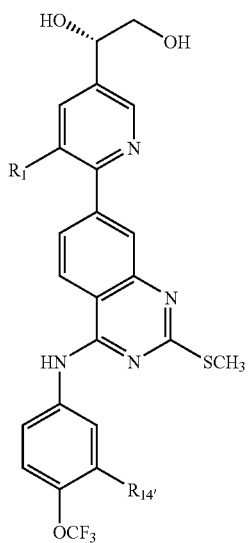
(IIIl'')
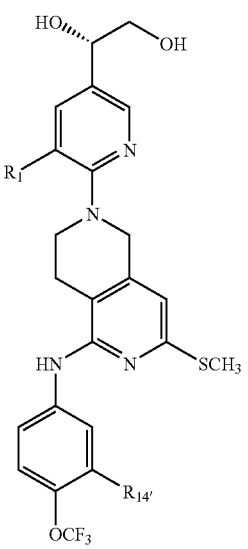
(IIIl''')
and pharmaceutically acceptable derivatives thereof, where:
| Compound | R₁ | R₁₄' |
|---|---|---|
| BBB (l', l'', or l''') | —Cl | —CH₃ |
| BBC (l', l'', or l''') | —Cl | —CH₂CH₃ |
| BBD (l', l'', or l''') | —Cl | Cl |
| BBE (l', l'', or l''') | —F | —CH₃ |
| BBF (l', l'', or l''') | —F | —CH₂CH₃ |
| BBG (l', l'', or l''') | —F | —Cl |
| BBH (l', l'', or l''') | —CF₃ | —CH₃ |
| BBI (l', l'', or l''') | —CF₃ | —CH₂CH₃ |
| BBJ (l', l'', or l''') | —CF₃ | —Cl |
TABLE 13
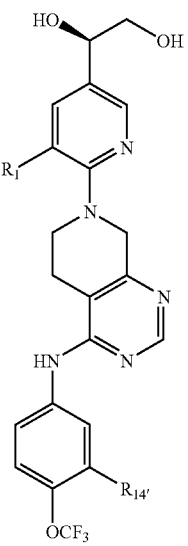
(IIIm')
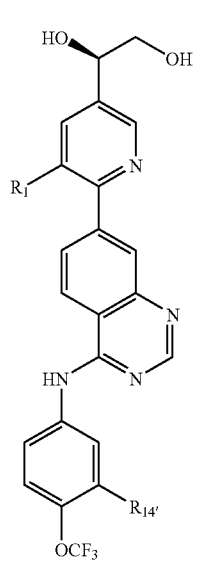
(IIIm'')
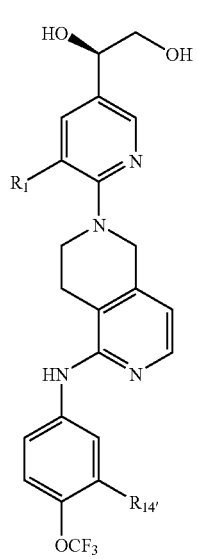
(IIIm''')

TABLE 13-continued and pharmaceutically acceptable derivatives thereof, where:

| Compound | $R_1$ | $R_{14'}$ |
|---|---|---|
| BBK (m', m", or m''') | —Cl | —$CH_3$ |
| BBL (m', m", or m''') | —Cl | —$CH_2CH_3$ |
| BBM (m', m", or m''') | —Cl | —Cl |
| BBN (m', m", or m''') | —F | —$CH_3$ |
| BBO (m', m", or m''') | —F | —$CH_2CH_3$ |
| BBP (m', m", or m''') | —F | —Cl |
| BBQ (m', m", or m''') | —$CF_3$ | —$CH_3$ |
| BBR (m', m", or m''') | —$CF_3$ | —$CH_2CH_3$ |
| BBS (m', m", or m''') | —$CF_3$ | —Cl |

TABLE 14

(IIIn')

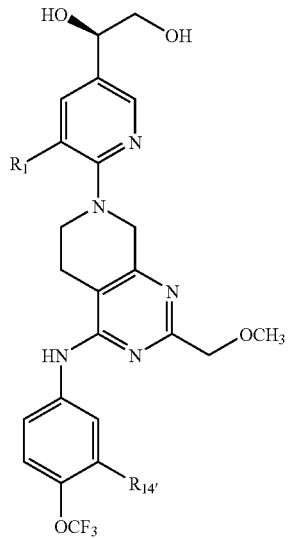

(IIIn")

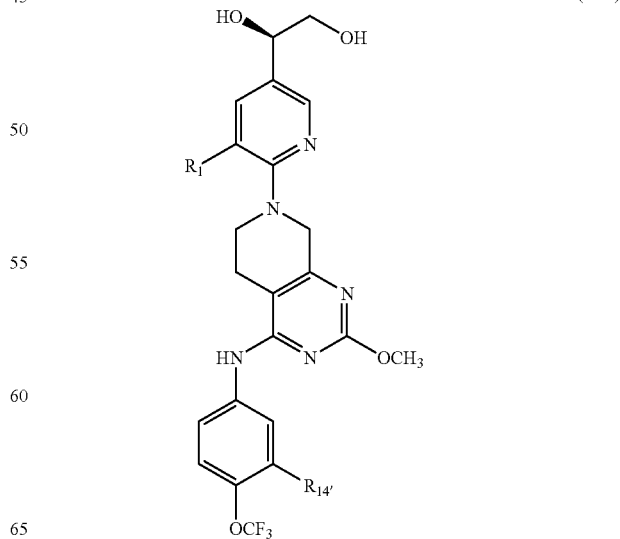

TABLE 14-continued (IIIn''')

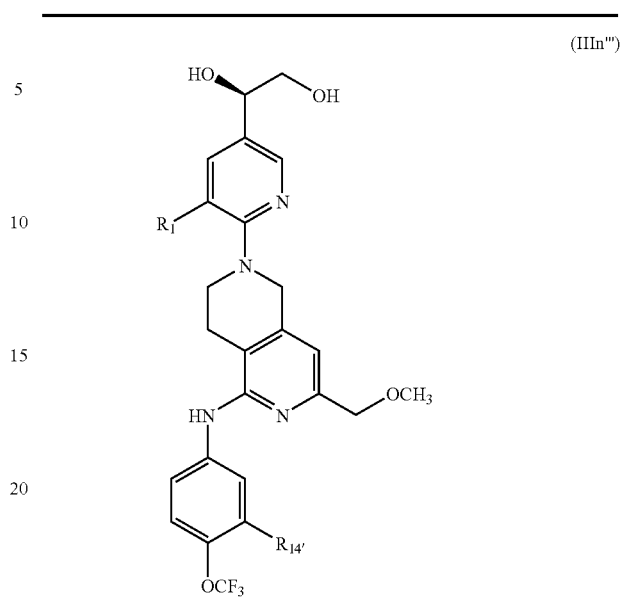

and pharmaceutically acceptable derivatives thereof, where:

| Compound | $R_1$ | $R_{14'}$ |
|---|---|---|
| BBT (n', n", or n''') | —Cl | —$CH_3$ |
| BBU (n', n", or n''') | —Cl | —$CH_2CH_3$ |
| BBV (n', n", or n''') | —Cl | —Cl |
| BBW (n', n", or n''') | —F | —$CH_3$ |
| BBX (n', n", or n''') | —F | —$CH_2CH_3$ |
| BBY (n', n", or n''') | —F | —Cl |
| BBZ (n', n", or n''') | —$CF_3$ | —$CH_3$ |
| BCA (n', n", or n''') | —$CF_3$ | —$CH_2CH_3$ |
| BCB (n', n", or n''') | —$CF_3$ | —Cl |

TABLE 15

(IIIo')

TABLE 15-continued
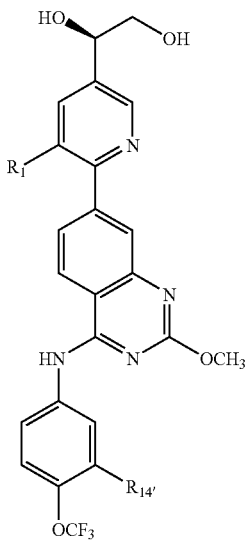
(IIIo")
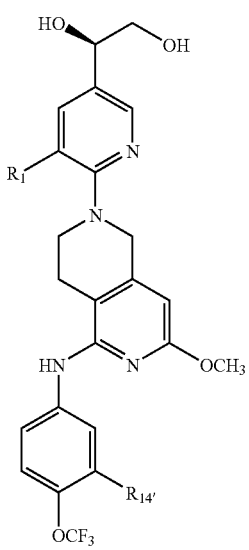
(IIIo''')
and pharmaceutically acceptable derivatives thereof, where:
| Compound | R₁ | R₁₄' |
|---|---|---|
| BCC (o', o'', or o''') | —Cl | —CH₃ |
| BCD (o', o'', or o''') | —Cl | —CH₂CH₃ |
| BCE (o', o'', or o''') | —Cl | —Cl |
| BCF (o', o'', or o''') | —F | —CH₃ |
| BCG (o', o'', or o''') | —F | —CH₂CH₃ |
| BCH (o', o'', or o''') | —F | —Cl |
| BCI (o', o'', or o''') | —CF₃ | —CH₃ |
| BCJ (o', o'', or o''') | —CF₃ | —CH₂CH₃ |
| BCK (o', o'', or o''') | —CF₃ | —Cl |
TABLE 16
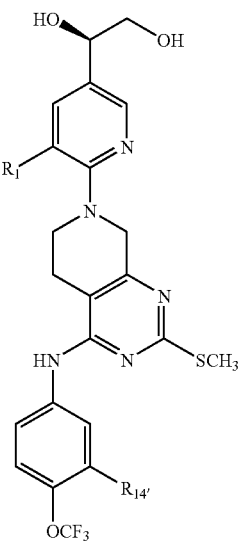
(IIIp')
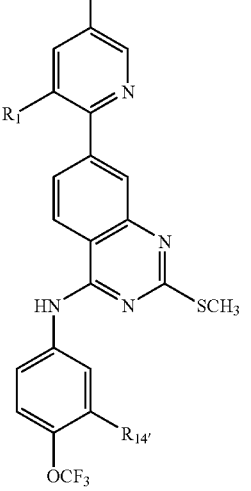
(IIIp'')
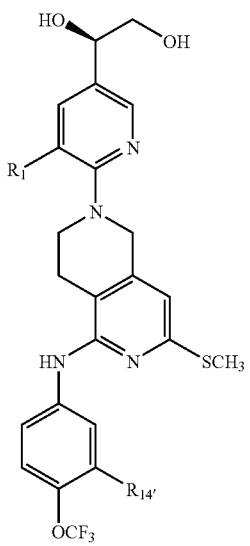
(IIIp''')

TABLE 16-continued and pharmaceutically acceptable derivatives thereof, where:

| Compound | $R_1$ | $R_{14'}$ |
|---|---|---|
| BCL (p', p", or p''') | —Cl | —$CH_3$ |
| BCM (p', p", or p''') | —Cl | —$CH_2CH_3$ |
| BCN (p', p", or p''') | —Cl | —Cl |
| BCO (p', p", or p''') | —F | —$CH_3$ |
| BCP (p', p", or p''') | —F | —$CH_2CH_3$ |
| BCQ (p', p", or p''') | —F | —Cl |
| BCR (p', p", or p''') | —$CF_3$ | —$CH_3$ |
| BCS (p', p", or p''') | —$CF_3$ | —$CH_2CH_3$ |
| BCT (p', p", or p''') | —$CF_3$ | —Cl |

TABLE 17

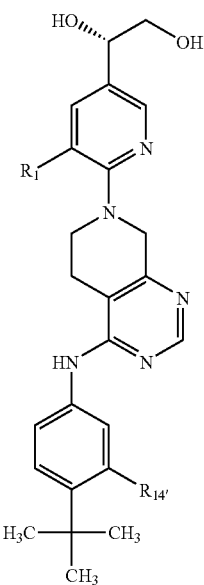

(IIIq')

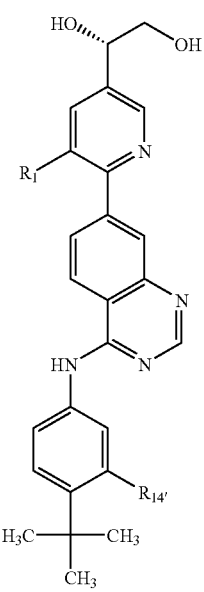

(IIIq")

TABLE 17-continued

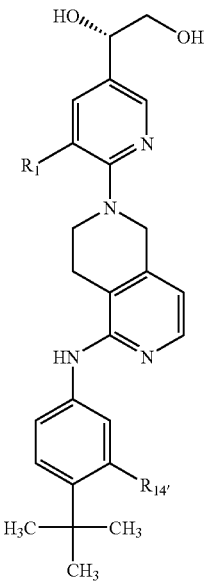

(IIIq''')

and pharmaceutically acceptable derivatives thereof, where:

| Compound | $R_1$ | $R_{14'}$ |
|---|---|---|
| CAA (q', q", or q''') | —Cl | —$CH_3$ |
| CAB (q', q", or q''') | —Cl | —$CH_2CH_3$ |
| CAC (q', q", or q''') | —Cl | —Cl |
| CAD (q', q", or q''') | —F | —$CH_3$ |
| CAE (q', q", or q''') | —F | —$CH_2CH_3$ |
| CAF (q', q", or q''') | —F | —Cl |
| CAG (q', q", or q''') | —$CF_3$ | —$CH_3$ |
| CAH (q', q", or q''') | —$CF_3$ | —$CH_2CH_3$ |
| CAI (q', q", or q''') | —$CF_3$ | —Cl |

TABLE 18

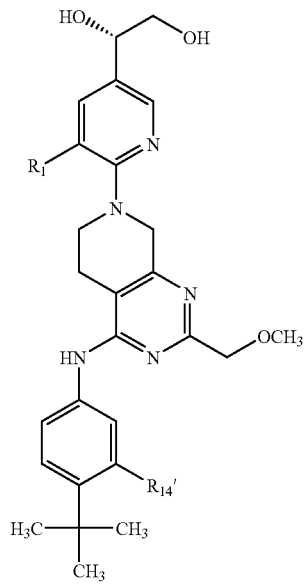

(IIIr')

TABLE 18-continued

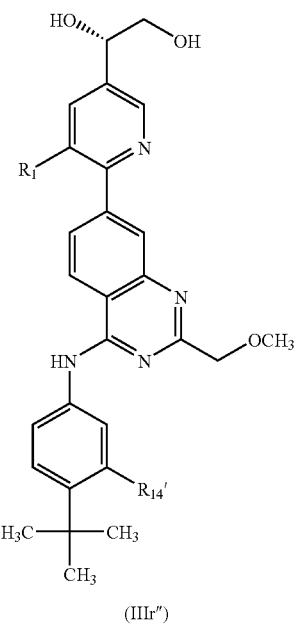

(IIIr″)

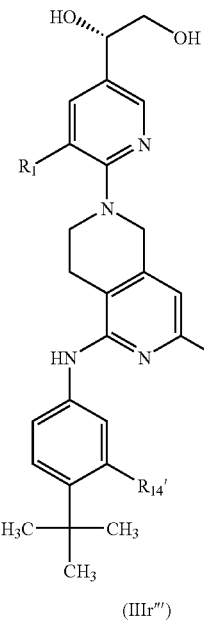

(IIIr‴)

and pharmaceutically acceptable derivatives thereof, where:

| Compound | $R_1$ | $R_{14'}$ |
|---|---|---|
| CAJ (r', r'', or r''') | —Cl | —CH₃ |
| CAK (r', r'', or r''') | —Cl | —CH₂CH₃ |
| CAL (r', r'', or r''') | —Cl | —Cl |
| CAM (r', r'', or r''') | —F | —CH₃ |
| CAN (r', r'', or r''') | —F | —CH₂CH₃ |
| CAO (r', r'', or r''') | —F | —Cl |
| CAP (r', r'', or r''') | —CF₃ | —CH₃ |
| CAQ (r', r'', or r''') | —CF₃ | —CH₂CH₃ |
| CAR ((r', r'', or r''') | —CF₃ | —Cl |

TABLE 19

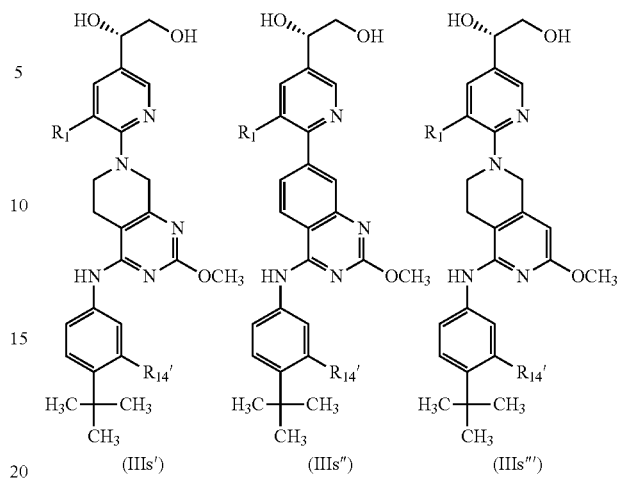

(IIIs')    (IIIs″)    (IIIs‴)

and pharmaceutically acceptable derivatives thereof, where:

| Compound | $R_1$ | $R_{14'}$ |
|---|---|---|
| CAS (s', s'', or s''') | —Cl | —CH₃ |
| CAT (s', s'', or s''') | —Cl | —CH₂CH₃ |
| CAU (s', s'', or s''') | —Cl | —Cl |
| CAV (s', s'', or s''') | —F | —CH₃ |
| CAQ (s', s'', or s''') | —F | —CH₂CH₃ |
| CAX (s', s'', or s''') | —F | —Cl |
| CAY (s', s'', or s''') | —CF₃ | —CH₃ |
| CAZ (s', s'', or s''') | —CF₃ | —CH₂CH₃ |
| CBA ((s', s'', or s''') | —CF₃ | —Cl |

TABLE 20

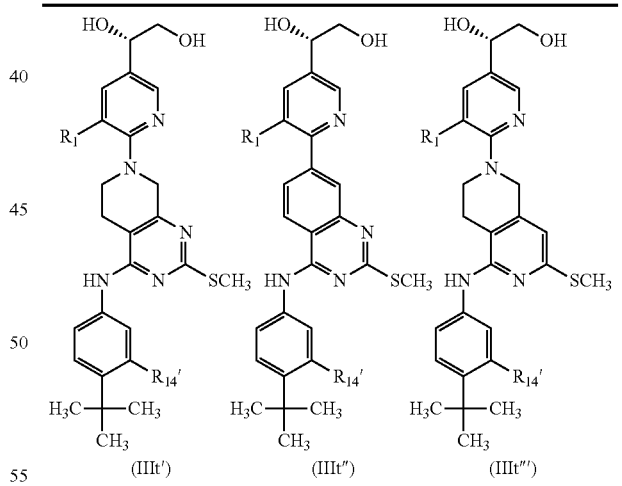

(IIIt')    (IIIt″)    (IIIt‴)

and pharmaceutically acceptable derivatives thereof, where:

| Compound | $R_1$ | $R_{14'}$ |
|---|---|---|
| CBB (t', t'', or t''') | —Cl | —CH₃ |
| CBC (t', t'', or t''') | —Cl | —CH₂CH₃ |
| CBD (t', t'', or t''') | —Cl | —Cl |
| CBE (t', t'', or t''') | —F | —CH₃ |
| CBF (t', t'', or t''') | —F | —CH₂CH₃ |
| CBG (t', t'', or t''') | —F | —Cl |
| CBH (t', t'', or t''') | —CF₃ | —CH₃ |
| CBI (t', t'', or t''') | —CF₃ | —CH₂CH₃ |
| CBJ ((t', t'', or t''') | —CF₃ | —Cl |

TABLE 21

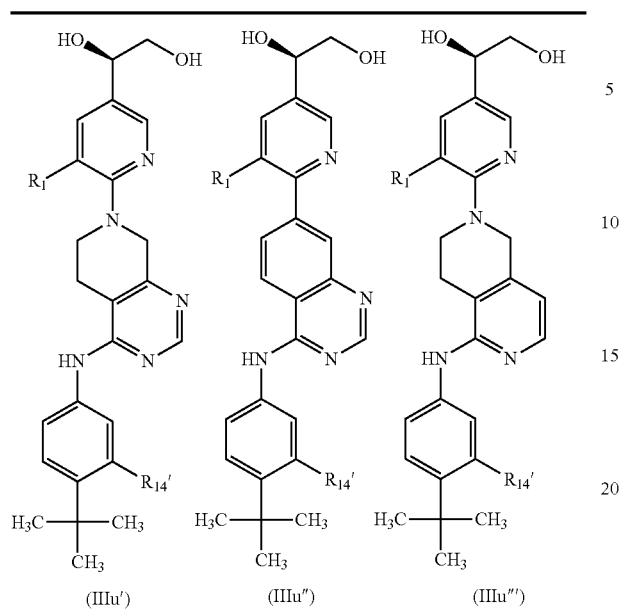

(IIIu') (IIIu'') (IIIu''')

and pharmaceutically acceptable derivatives thereof, where:

| Compound | $R_1$ | $R_{14'}$ |
|---|---|---|
| CBK (u', u'', or u''') | —Cl | —CH$_3$ |
| CBL (u', u'', or u''') | —Cl | —CH$_2$CH$_3$ |
| CBM (u', u'', or u''') | —Cl | —Cl |
| CBN (u', u'', or u''') | —F | —CH$_3$ |
| CBO (u', u'', or u''') | —F | —CH$_2$CH$_3$ |
| CBP (u', u'', or u''') | —F | —Cl |
| CBQ (u', u'', or u''') | —CF$_3$ | —CH$_3$ |
| CBR (u', u'', or u''') | —CF$_3$ | —CH$_2$CH$_3$ |
| CBS ((u', u'', or u''') | —CF$_3$ | —Cl |

TABLE 22

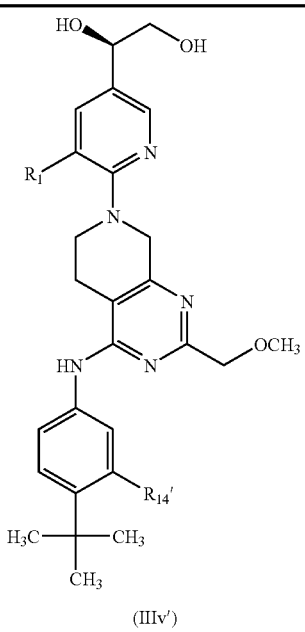

(IIIv')

TABLE 22-continued

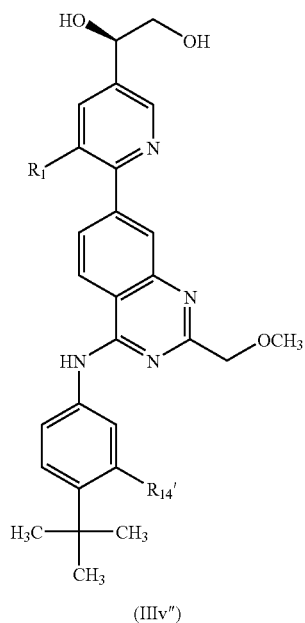

(IIIv'')

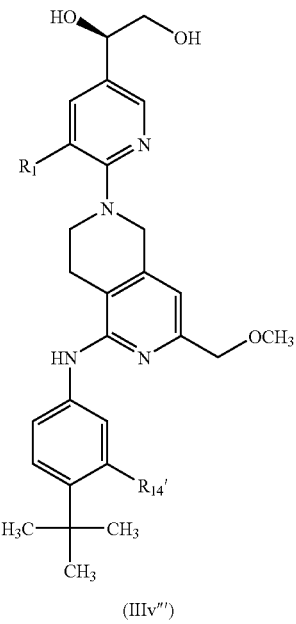

(IIIv''')

and pharmaceutically acceptable derivatives thereof, where:

| Compound | $R_1$ | $R_{14'}$ |
|---|---|---|
| CBT (v', v'', or v''') | —Cl | —CH$_3$ |
| CBU (v', v'', or v''') | —Cl | —CH$_2$CH$_3$ |
| CBV (v', v'', or v''') | —Cl | —Cl |
| CBW (v', v'', or v''') | —F | —CH$_3$ |
| CBX (v', v'', or v''') | —F | —CH$_2$CH$_3$ |
| CBY (v', v'', or v''') | —F | —Cl |
| CBZ (v', v'', or v''') | —CF$_3$ | —CH$_3$ |
| CCA (v', v'', or v''') | —CF$_3$ | —CH$_2$CH$_3$ |
| CCB ((v', v'', or v''') | —CF$_3$ | —Cl |

TABLE 23

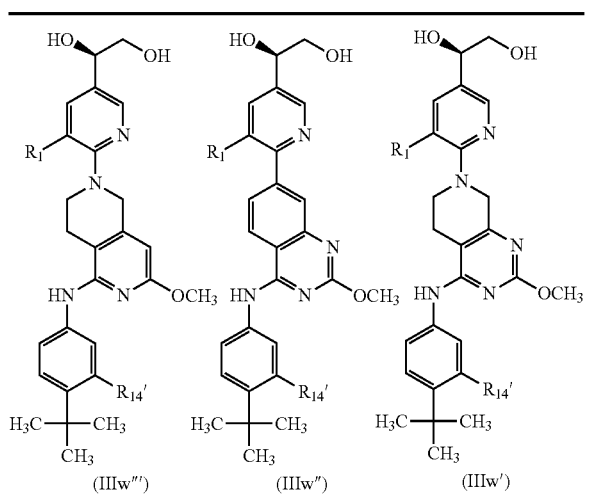

(IIIw‴)  (IIIw″)  (IIIw′)

and pharmaceutically acceptable derivatives thereof, where:

| Compound | $R_1$ | $R_{14'}$ |
|---|---|---|
| CCC (w', w", or w‴) | —Cl | —CH$_3$ |
| CCD (w', w", or w‴) | —Cl | —CH$_2$CH$_3$ |
| CCE (w', w", or w‴) | —Cl | —Cl |
| CCF (w', w", or w‴) | —F | —CH$_3$ |
| CCG (w', w", or w‴) | —F | —CH$_2$CH$_3$ |
| CCH (w', w", or w‴) | —F | —Cl |
| CCI (w', w", or w‴) | —CF$_3$ | —CH$_3$ |
| CCJ (w', w", or w‴) | —CF$_3$ | —CH$_2$CH$_3$ |
| CCK (w', w", or w‴) | —CF$_3$ | —Cl |

TABLE 24

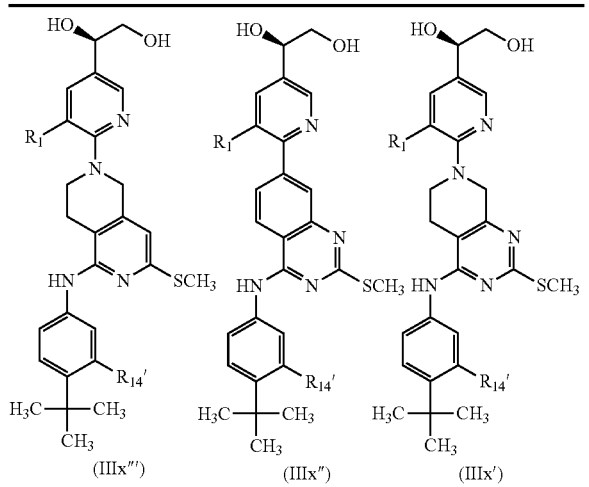

(IIIx‴)  (IIIx″)  (IIIx′)

and pharmaceutically acceptable derivatives thereof, where:

| Compound | $R_1$ | $R_{14'}$ |
|---|---|---|
| CCL (x', x", or x‴) | —Cl | —CH$_3$ |
| CCM (x', x", or x‴) | —Cl | —CH$_2$CH$_3$ |
| CCN (x', x", or x‴) | —Cl | —Cl |
| CCO (x', x", or x‴) | —F | —CH$_3$ |
| CCP (x', x", or x‴) | —F | —CH$_2$CH$_3$ |
| CCQ (x', x", or x‴) | —F | —Cl |
| CCR (x', x", or x‴) | —CF$_3$ | —CH$_3$ |
| CCS (x', x", or x‴) | —CF$_3$ | —CH$_2$CH$_3$ |
| CCT (x', x", or x‴) | —CF$_3$ | —Cl |

TABLE 25

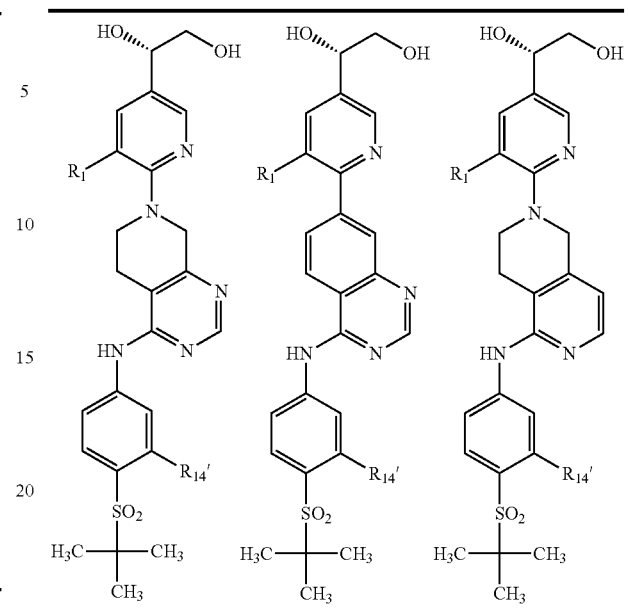

(IIIy′)  (IIIy″)  (IIIy‴)

and pharmaceutically acceptable derivatives thereof, where:

| Compound | $R_1$ | $R_{14'}$ |
|---|---|---|
| DAA (y', y", or y‴) | —Cl | —CH$_3$ |
| DAB (y', y", or y‴) | —Cl | —CH$_2$CH$_3$ |
| DAC (y', y", or y‴) | —Cl | —Cl |
| DAD (y', y", or y‴) | —F | —CH$_3$ |
| DAE (y', y", or y‴) | —F | —CH$_2$CH$_3$ |
| DAF (y', y", or y‴) | —F | —Cl |
| DAG ((y', y", or y‴) | —CF$_3$ | —CH$_3$ |
| DAH (y', y", or y‴) | —CF$_3$ | —CH$_2$CH$_3$ |
| DAI (y', y", or y‴) | —CF$_3$ | —Cl |

TABLE 26

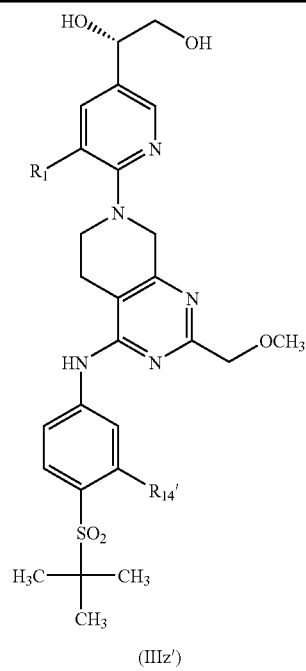

(IIIz′)

TABLE 26-continued

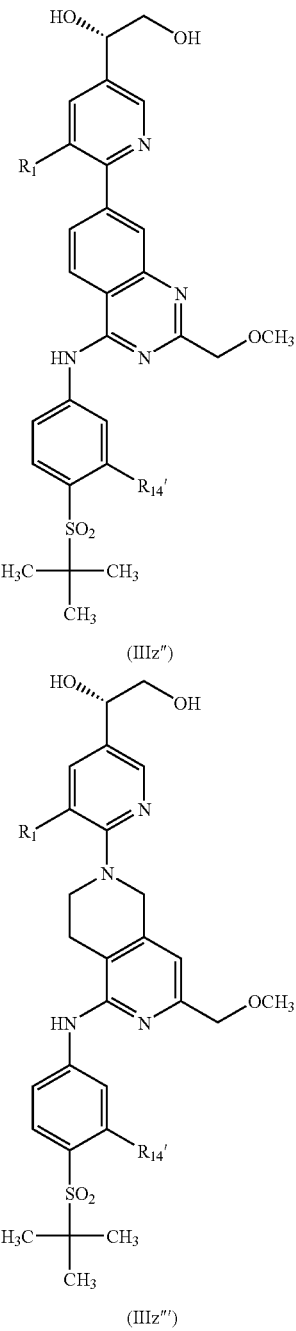

and pharmaceutically acceptable derivatives thereof, where:

| Compound | $R_1$ | $R_{14'}$ |
|---|---|---|
| DAJ (z', z", or z''') | —Cl | —CH$_3$ |
| DAK (z', z", or z''') | —Cl | —CH$_2$CH$_3$ |
| DAL (z', z", or z''') | —Cl | —Cl |
| DAM (z', z", or z''') | —F | —CH$_3$ |
| DAN (z', z", or z''') | —F | —CH$_2$CH$_3$ |
| DAG (z', z", or z''') | —F | —Cl |
| DAP ((z', z", or z''') | —CF$_3$ | —CH$_3$ |
| DAQ (z', z", or z''') | —CF$_3$ | —CH$_2$CH$_3$ |
| DAIR (z', z", or z''') | —CF$_3$ | —Cl |

TABLE 27

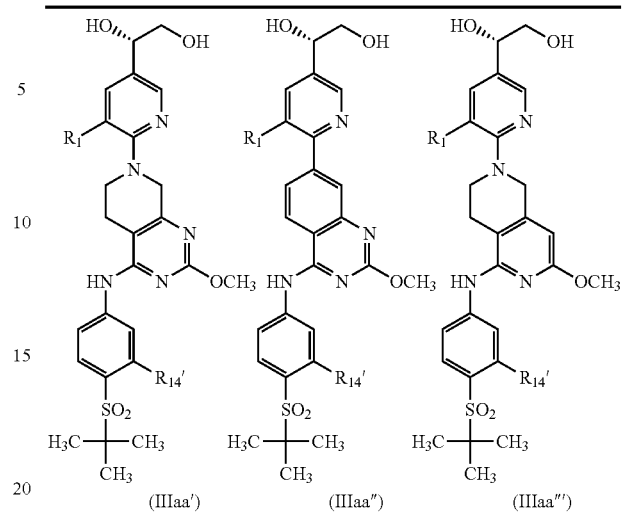

and pharmaceutically acceptable derivatives thereof, where:

| Compound | $R_1$ | $R_{14'}$ |
|---|---|---|
| DAS (aa', aa", or aa''') | —Cl | —CH$_3$ |
| DAT (aa', aa", or aa''') | —Cl | —CH$_2$CH$_3$ |
| DAU (aa', aa", or aa''') | —Cl | —Cl |
| DAV (aa', aa", or aa''') | —F | —CH$_3$ |
| DAW (aa', aa", or aa''') | —F | —CH$_2$CH$_3$ |
| DAX (aa', aa", or aa''') | —F | —Cl |
| DAY ((aa', aa", or aa''') | —CF$_3$ | —CH$_3$ |
| DAZ (aa', aa", or aa''') | —CF$_3$ | —CH$_2$CH$_3$ |
| DBA (aa', aa", or aa''') | —CF$_3$ | —Cl |

TABLE 28

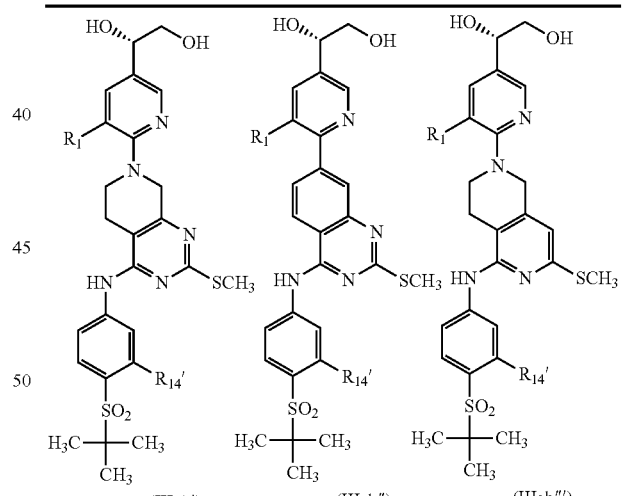

and pharmaceutically acceptable derivatives thereof, where:

| Compound | $R_1$ | $R_{14'}$ |
|---|---|---|
| DBB (ab', ab", or ab''') | —Cl | —CH$_3$ |
| DBC (ab', ab", or ab''') | —Cl | —CH$_2$CH$_3$ |
| DBD (ab', ab", or ab''') | —Cl | —Cl |
| DBE (ab', ab", or ab''') | —F | —CH$_3$ |
| DBF (ab', ab", or ab''') | —F | —CH$_2$CH$_3$ |
| DBG (ab', ab", or ab''') | —F | —Cl |
| DBH ((ab', ab", or ab''') | —CF$_3$ | —CH$_3$ |
| DBI (ab', ab", or ab''') | —CF$_3$ | —CH$_2$CH$_3$ |
| DBJ (ab', ab", or ab''') | —CF$_3$ | —Cl |

TABLE 29

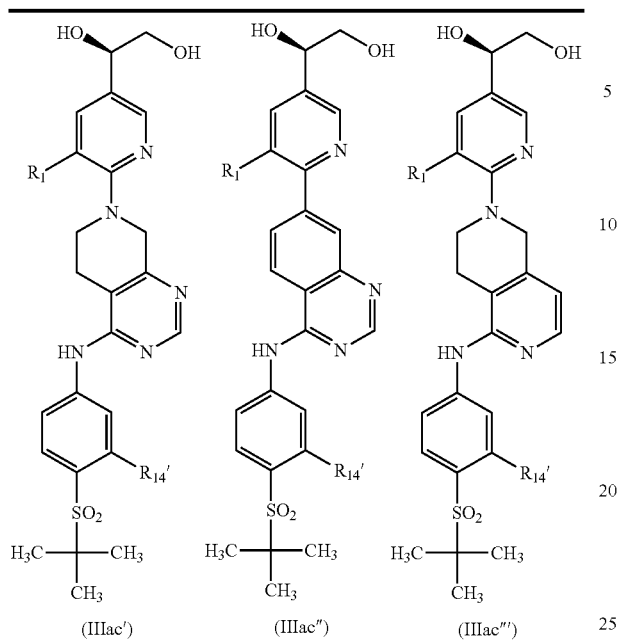

(IIIac') (IIIac'') (IIIac''')

and pharmaceutically acceptable derivatives thereof, where:

| Compound | R₁ | R₁₄' |
|---|---|---|
| DBK (ac', ac'', or ac''') | —Cl | —CH₃ |
| DBL (ac', ac'', or ac''') | —Cl | —CH₂CH₃ |
| DBM (ac', ac'', or ac''') | —Cl | —Cl |
| DBN (ac', ac'', or ac''') | —F | —CH₃ |
| DBO (ac', ac'', or ac''') | —F | —CH₂CH₃ |
| DBP (ac', ac'', or ac''') | —F | —Cl |
| DBQ ((ac', ac'', or ac''') | —CF₃ | —CH₃ |
| DBR (ac', ac'', or ac''') | —CF₃ | —CH₂CH₃ |
| DBS (ac', ac'', or ac''') | —CF₃ | —Cl |

TABLE 30

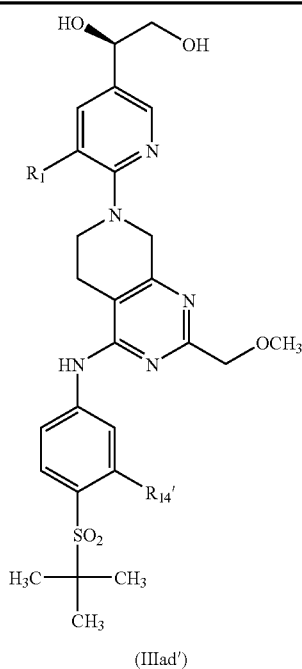

(IIIad')

TABLE 30-continued

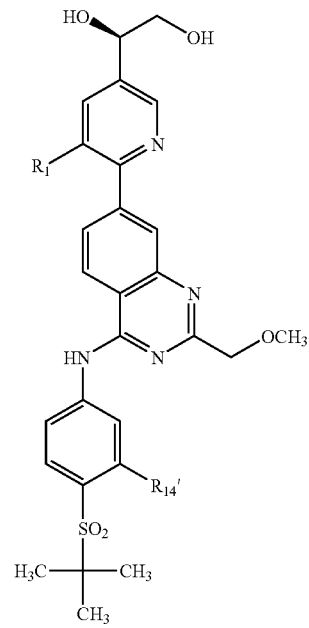

(IIIad'')

(IIIad''')

and pharmaceutically acceptable derivatives thereof, where:

| Compound | R₁ | R₁₄' |
|---|---|---|
| DBT (ad', ad'', or ad''') | —Cl | —CH₃ |
| DBU (ad', ad'', or ad''') | —Cl | —CH₂CH₃ |
| DBV (ad', ad'', or ad''') | —Cl | —Cl |
| DBW (ad', ad'', or ad''') | —F | —CH₃ |
| DBX (ad', ad'', or ad''') | —F | —CH₂CH₃ |
| DBY (ad', ad'', or ad''') | —F | —Cl |
| DBZ ((ad', ad'', or ad''') | —CF₃ | —CH₃ |
| DCA (ad', ad'', or ad''') | —CF₃ | —CH₂CH₃ |
| DCB (ad', ad'', or ad''') | —CF₃ | —Cl |

TABLE 31

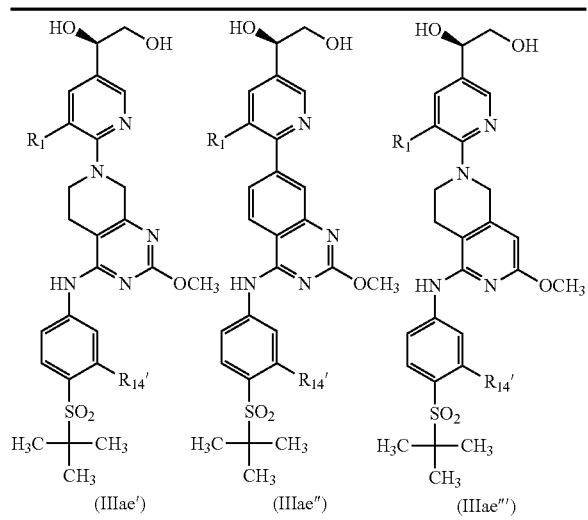

(IIIae′)  (IIIae″)  (IIIae‴)

and pharmaceutically acceptable derivatives thereof, where:

| Compound | $R_1$ | $R_{14'}$ |
|---|---|---|
| DCC (ae′, ae″, or ae‴) | —Cl | —CH$_3$ |
| DCD (ae′, ae″, or ae‴) | —Cl | —CH$_2$CH$_3$ |
| DCE (ae′, ae″, or ae‴) | —Cl | —Cl |
| DCF (ae′, ae″, or ae‴) | —F | —CH$_3$ |
| DCG (ae′, ae″, or ae‴) | —F | —CH$_2$CH$_3$ |
| DCH (ae′, ae″, or ae‴) | —F | —Cl |
| DCI ((ae′, ae″, or ae‴) | —CF$_3$ | —CH$_3$ |
| DCJ (ae′, ae″, or ae‴) | —CF$_3$ | —CH$_2$CH$_3$ |
| DCK (ae′, ae″, or ae‴) | —CF$_3$ | —Cl |

TABLE 32

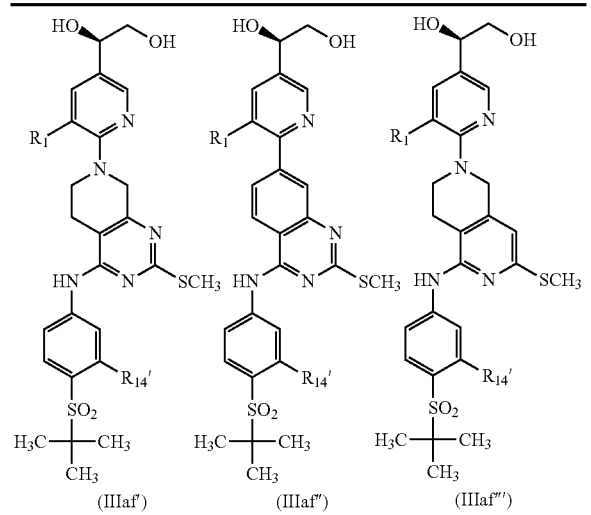

(IIIaf′)  (IIIaf″)  (IIIaf‴)

and pharmaceutically acceptable derivatives thereof, where:

| Compound | $R_1$ | $R_{14'}$ |
|---|---|---|
| DCL (af′, af″, or af‴) | —Cl | —CH$_3$ |
| DCM (af′, af″, or af‴) | —Cl | —CH$_2$CH$_3$ |
| DCN (af′, af″, or af‴) | —Cl | —Cl |
| DCO (af′, af″, or af‴) | —F | —CH$_3$ |
| DCP (af′, af″, or af‴) | —F | —CH$_2$CH$_3$ |
| DCQ (af′, af″, or af‴) | —F | —Cl |
| DCR (af′, af″, or af‴) | —CF$_3$ | —CH$_3$ |
| DCS (af′, af″, or af‴) | —CF$_3$ | —CH$_2$CH$_3$ |
| DCT (af′, af″, or af‴) | —CF$_3$ | —Cl |

TABLE 33

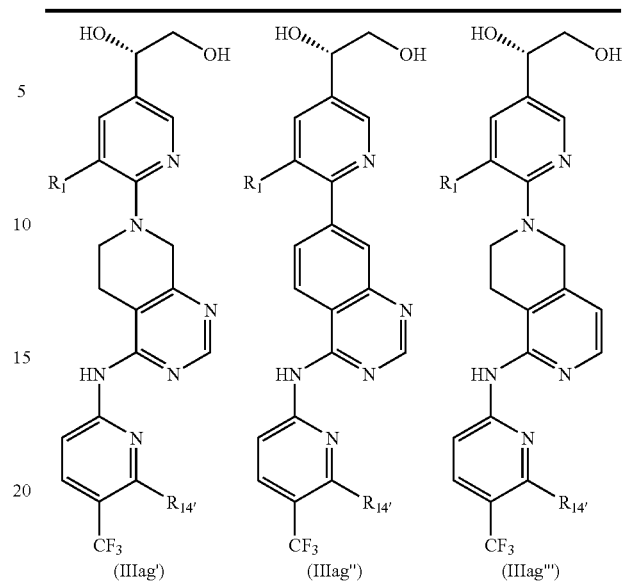

(IIIag′)  (IIIag″)  (IIIag‴)

and pharmaceutically acceptable derivatives thereof, where:

| Compound | $R_1$ | $R_{14'}$ |
|---|---|---|
| EAA (ag′, ag″, or ag‴) | —Cl | —Cl |
| EAB (ag′, ag″, or ag‴) | —Cl | —F |
| EAC (ag′, ag″, or ag‴) | —Cl | —Br |
| EAD (ag′, ag″, or ag‴) | —Cl | —OCH$_3$ |
| EAE (ag′, ag″, or ag‴) | —Cl | —OCH$_2$CH$_3$ |
| EAF (ag′, ag″, or ag‴) | —F | —Cl |
| EAG (ag′, ag″, or ag‴) | —F | —F |
| EAH (ag′, ag″, or ag‴) | —F | —Br |
| EAI (ag′, ag″, or ag‴) | —F | —OCH$_3$ |
| EAJ (ag′, ag″, or ag‴) | —F | —OCH$_2$CH$_3$ |
| EAK (ag′, ag″, or ag‴) | —CF$_3$ | —Cl |
| EAL (ag′, ag″, or ag‴) | —CF$_3$ | —F |
| EAM (ag′, ag″, or ag‴) | —CF$_3$ | —Br |
| EAN (ag′, ag″, or ag‴) | —CF$_3$ | —OCH$_3$ |
| EAO (ag′, ag″, or ag‴) | —CF$_3$ | —OCH$_2$CH$_3$ |

TABLE 34

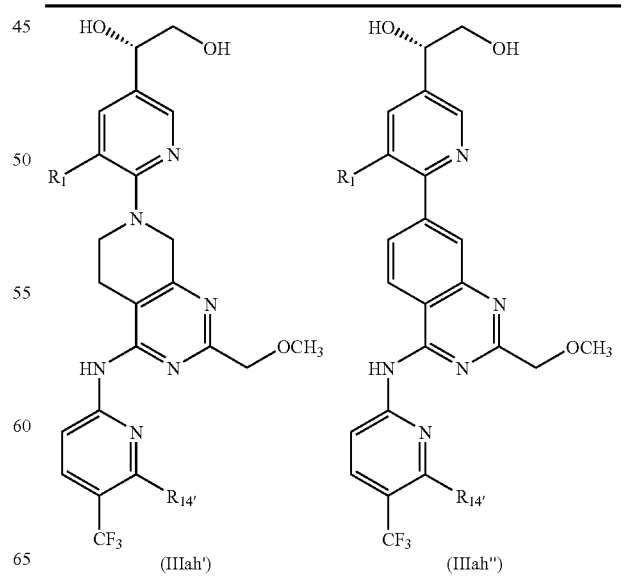

(IIIah′)  (IIIah″)

TABLE 34-continued

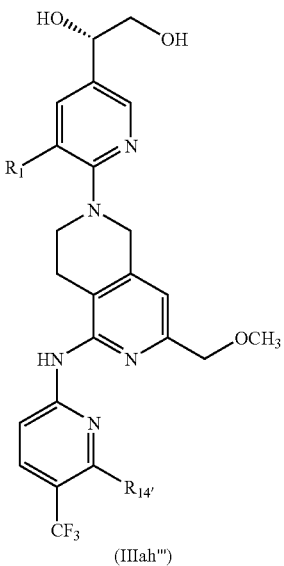

(IIIah''')

and pharmaceutically acceptable derivatives thereof, where:

| Compound | R₁ | R₁₄' |
|---|---|---|
| EAP (ah', ah'', or ah''') | —Cl | —Cl |
| EAQ (ah', ah'', or ah''') | —Cl | —F |
| EAR (ah', ah'', or ah''') | —Cl | —Br |
| EAS (ah', ah'', or ah''') | —Cl | —OCH₃ |
| EAT (ah', ah'', or ah''') | —Cl | —OCH₂CH₃ |
| EAU (ah', ah'', or ah''') | —F | —Cl |
| EAV (ah', ah'', or ah''') | —F | —F |
| EAW (ah', ah'', or ah''') | —F | —Br |
| EAX (ah', ah'', or ah''') | —F | —OCH₃ |
| EAY (ah', ah'', or ah''') | —F | —OCH₂CH₃ |
| EAZ (ah', ah'', or ah''') | —CF₃ | —Cl |
| EBA (ah', ah'', or ah''') | —CF₃ | —F |
| EBB (ah', ah'', or ah''') | —CF₃ | —Br |
| EBC (ah', ah'', or ah''') | —CF₃ | —OCH₃ |
| EBD (ah', ah'', or ah''') | —CF₃ | —OCH₂CH₃ |

TABLE 35

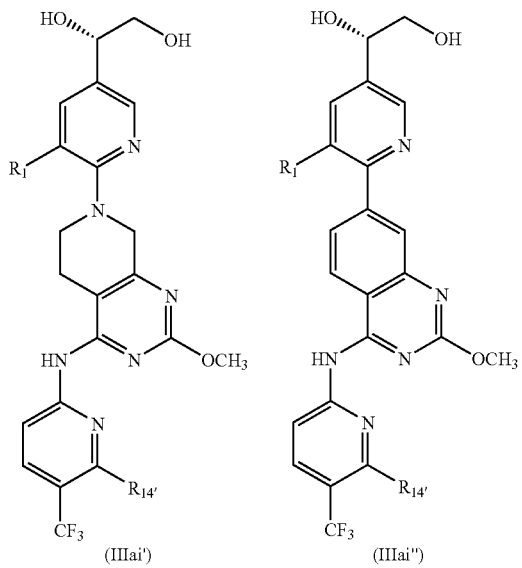

(IIIai')  (IIIai'')

TABLE 35-continued

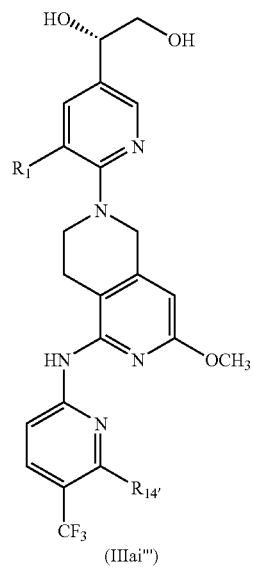

(IIIai''')

and pharmaceutically acceptable derivatives thereof, where:

| Compound | R₁ | R₁₄' |
|---|---|---|
| EBE (ai', ai'', or ai''') | —Cl | —Cl |
| EBF (ai', ai'', or ai''') | —Cl | —F |
| EBG (ai', ai'', or ai''') | —Cl | —Br |
| EBH (ai', ai'', or ai''') | —Cl | —OCH₃ |
| EBI (ai', ai'', or ai''') | —Cl | —OCH₂CH₃ |
| EBJ (ai', ai'', or ai''') | —F | —Cl |
| EBK (ai', ai'', or ai''') | —F | —F |
| EBL (ai', ai'', or ai''') | —F | —Br |
| EBM (ai', ai'', or ai''') | —F | —OCH₃ |
| EBN (ai', ai'', or ai''') | —F | —OCH₂CH₃ |
| EBO (ai', ai'', or ai''') | —CF₃ | —Cl |
| EBP (ai', ai'', or ai''') | —CF₃ | —F |
| EBQ (ai', ai'', or ai''') | —CF₃ | —Br |
| EBR (ai', ai'', or ai''') | —CF₃ | —OCH₃ |
| EBS (ai', ai'', or ai''') | —CF₃ | —OCH₂CH₃ |

TABLE 36

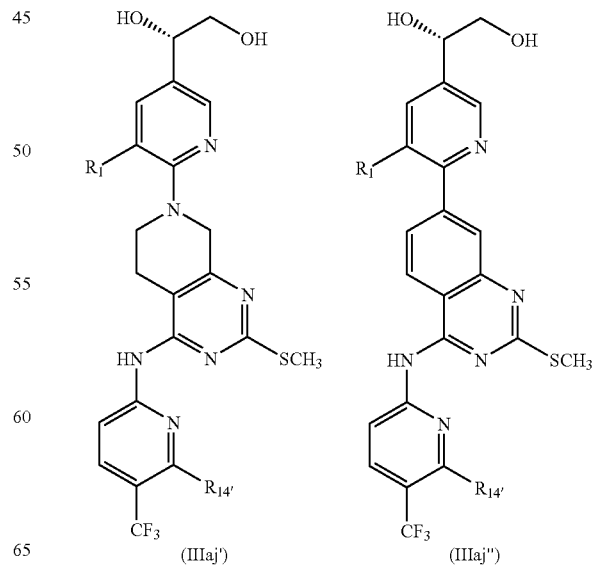

(IIIaj')  (IIIaj'')

TABLE 36-continued

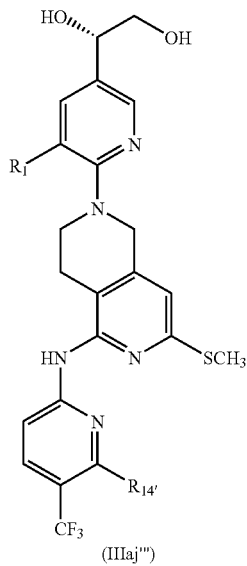

(IIIaj''')

and pharmaceutically acceptable derivatives thereof, where:

| Compound | $R_1$ | $R_{14'}$ |
|---|---|---|
| EBT (aj', aj'', or aj''') | —Cl | —Cl |
| EBU (aj', aj'', or aj''') | —Cl | —F |
| EBV (aj', aj'', or aj''') | —Cl | —Br |
| EBW (aj', aj'', or aj''') | —Cl | —OCH$_3$ |
| EBX (aj', aj'', or aj''') | —Cl | —OCH$_2$CH$_3$ |
| EBY (aj', aj'', or aj''') | —F | —Cl |
| EBZ (aj', aj'', or aj''') | —F | —F |
| ECA (aj', aj'', or aj''') | —F | —Br |
| ECB (aj', aj'', or aj''') | —F | —OCH$_3$ |
| ECC (aj', aj'', or aj''') | —F | —OCH$_2$CH$_3$ |
| ECD (aj', aj'', or aj''') | —CF$_3$ | —Cl |
| ECE (aj', aj'', or aj''') | —CF$_3$ | —F |
| ECF (aj', aj'', or aj''') | —CF$_3$ | —Br |
| ECG (aj', aj'', or aj''') | —CF$_3$ | —OCH$_3$ |
| ECH (aj', aj'', or aj''') | —CF$_3$ | —OCH$_2$CH$_3$ |

TABLE 37

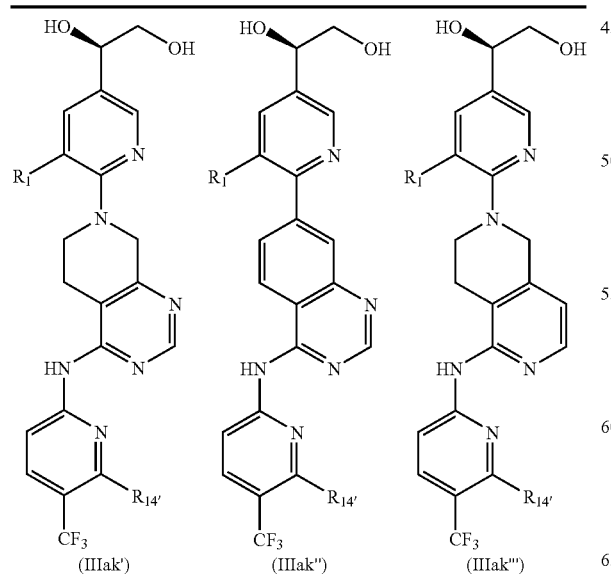

(IIIak')  (IIIak'')  (IIIak''')

TABLE 37-continued and pharmaceutically acceptable derivatives thereof, where:

| Compound | $R_1$ | $R_{14'}$ |
|---|---|---|
| ECI (ak', ak'', or ak''') | —Cl | —Cl |
| ECJ (ak', ak'', or ak''') | —Cl | —F |
| ECK (ak', ak'', or ak''') | —Cl | —Br |
| ECL (ak', ak'', or ak''') | —Cl | —OCH$_3$ |
| ECM (ak', ak'', or ak''') | —Cl | —OCH$_2$CH$_3$ |
| ECN (ak', ak'', or ak''') | —F | —Cl |
| ECO (ak', ak'', or ak''') | —F | —F |
| ECP (ak', ak'', or ak''') | —F | —Br |
| ECQ (ak', ak'', or ak''') | —F | —OCH$_3$ |
| ECR (ak', ak'', or ak''') | —F | —OCH$_2$CH$_3$ |
| ECS (ak', ak'', or ak''') | —CF$_3$ | —Cl |
| ECT (ak', ak'', or ak''') | —CF$_3$ | —F |
| ECU (ak', ak'', or ak''') | —CF$_3$ | —Br |
| ECV (ak', ak'', or ak''') | —CF$_3$ | —OCH$_3$ |
| ECW (ak', ak'', or ak''') | —CF$_3$ | —OCH$_2$CH$_3$ |

TABLE 38

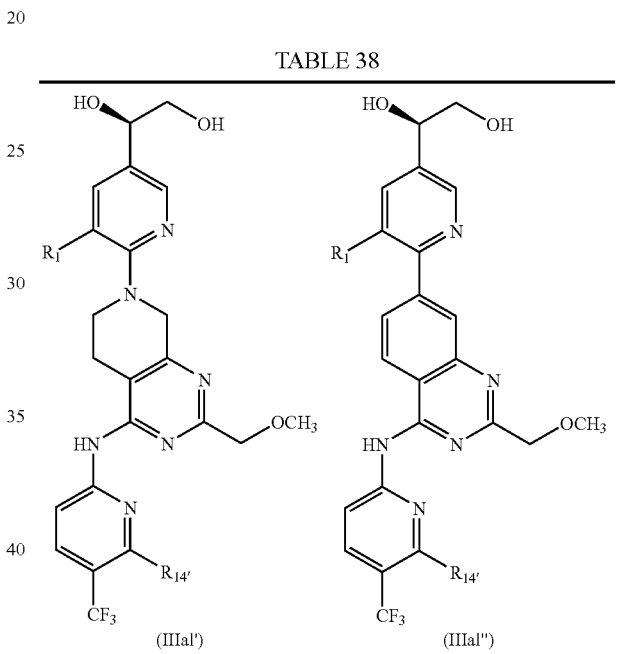

(IIIal')  (IIIal'')

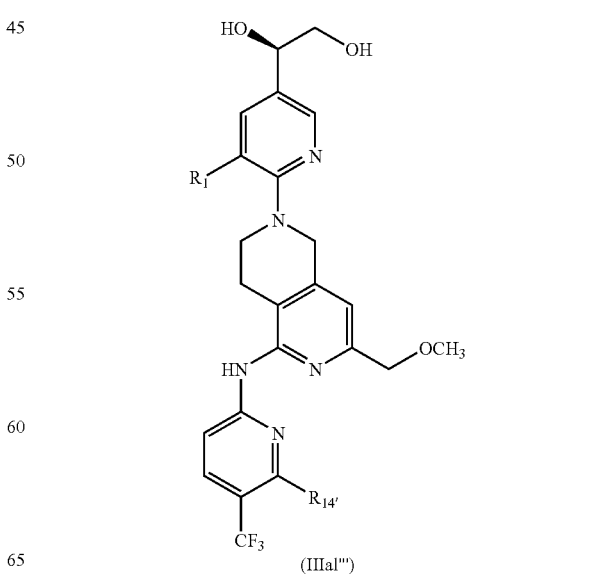

(IIIal''')

TABLE 38-continued and pharmaceutically acceptable derivatives thereof, where:

| Compound | $R_1$ | $R_{14'}$ |
|---|---|---|
| ECX (al', al", or al''') | —Cl | —Cl |
| ECY (al', al", or al''') | —Cl | —F |
| ECZ (al', al", or al''') | —Cl | —Br |
| EDA (al', al", or al''') | —Cl | —OCH$_3$ |
| EDB (al', al", or al''') | —Cl | —OCH$_2$CH$_3$ |
| EDC (al', al", or al''') | —F | —Cl |
| EDD (al', al", or al''') | —F | —F |
| EDE (al', al", or al''') | —F | —Br |
| EDF (al', al", or al''') | —F | —OCH$_3$ |
| EDG (al', al", or al''') | —F | —OCH$_2$CH$_3$ |
| EDH (al', al", or al''') | —CF$_3$ | —Cl |
| EDI (al', al", or al''') | —CF$_3$ | —F |
| EDJ (al', al", or al''') | —CF$_3$ | —Br |
| EDK (al', al", or al''') | —CF$_3$ | —OCH$_3$ |
| EDL (al', al", or al''') | —CF$_3$ | —OCH$_2$CH$_3$ |

TABLE 39-continued and pharmaceutically acceptable derivatives thereof, where:

| Compound | $R_1$ | $R_{14'}$ |
|---|---|---|
| EDM (am', am", or am''') | —Cl | —Cl |
| EDN (am', am", or am''') | —Cl | —F |
| EDO (am', am", or am''') | —Cl | —Br |
| EDP (am', am", or am''') | —Cl | —OCH$_3$ |
| EDQ (am', am", or am''') | —Cl | —OCH$_2$CH$_3$ |
| EDR (am', am", or am''') | —F | —Cl |
| EDS (am', am", or am''') | —F | —F |
| EDT (am', am", or am''') | —F | —Br |
| EDU (am', am", or am''') | —F | —OCH$_3$ |
| EDV (am', am", or am''') | —F | —OCH$_2$CH$_3$ |
| EDW (am', am", or am''') | —CF$_3$ | —Cl |
| EDX (am', am", or am''') | —CF$_3$ | —F |
| EDY (am', am", or am''') | —CF$_3$ | —Br |
| EDZ (am', am", or am''') | —CF$_3$ | —OCH$_3$ |
| EEA (am', am", or am''') | —CF$_3$ | —OCH$_2$CH$_3$ |

TABLE 39

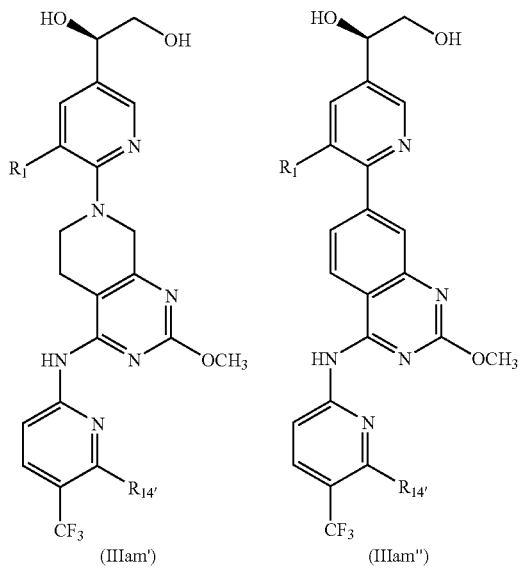

(IIIam')   (IIIam")

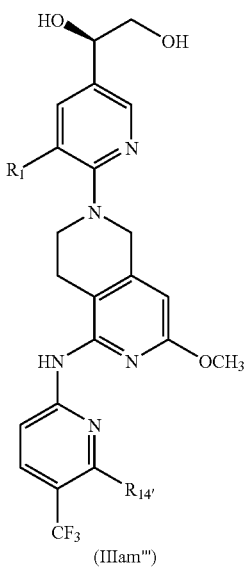

(IIIam''')

TABLE 40

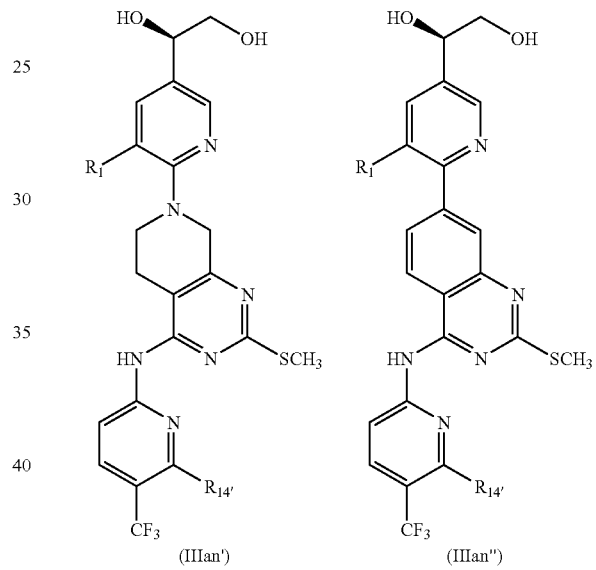

(IIIan')   (IIIan")

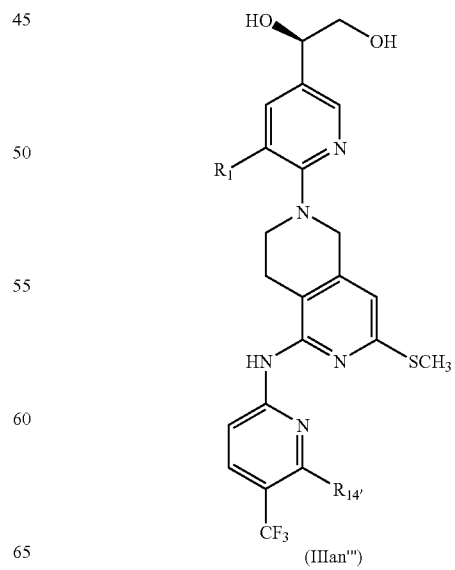

(IIIan''')

TABLE 40-continued and pharmaceutically acceptable derivatives thereof, where:

| Compound | $R_1$ | $R_{14'}$ |
|---|---|---|
| EEB (an', an'', or an''') | —Cl | —Cl |
| EEC (an', an'', or an''') | —Cl | —F |
| EED (an', an'', or an''') | —Cl | —Br |
| EEE (an', an'', or an''') | —Cl | —OCH$_3$ |
| EEF (an', an'', or an''') | —Cl | —OCH$_2$CH$_3$ |
| EEG (an', an'', or an''') | —F | —Cl |
| EEH (an', an'', or an''') | —F | —F |
| EEI (an', an'', or an''') | —F | —Br |
| EEJ (an', an'', or an''') | —F | —OCH$_3$ |
| EEK (an', an'', or an''') | —F | —OCH$_2$CH$_3$ |
| EEL (an', an'', or an''') | —CF$_3$ | —Cl |
| EEM (an', an'', or an''') | —CF$_3$ | —F |
| EEN (an', an'', or an''') | —CF$_3$ | —Br |
| EEO (an', an'', or an''') | —CF$_3$ | —OCH$_3$ |
| EEP (an', an'', or an''') | —CF$_3$ | —OCH$_2$CH$_3$ |

In other embodiments, substituent $R_{14'}$ of Tables 1-40 can be H.

TABLE 41

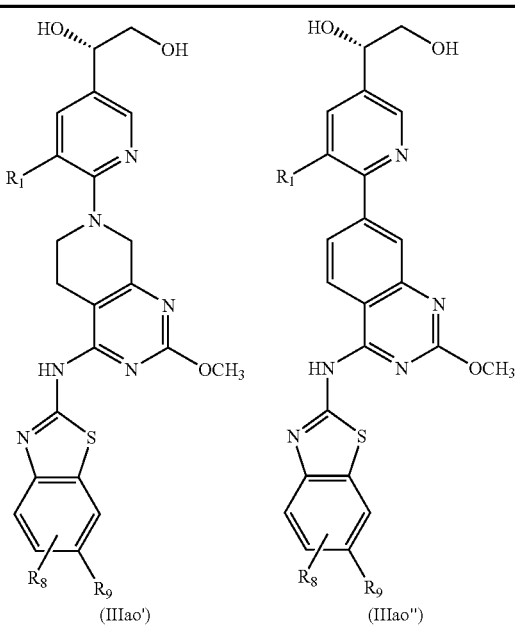

(IIIao')        (IIIao'')

TABLE 41-continued

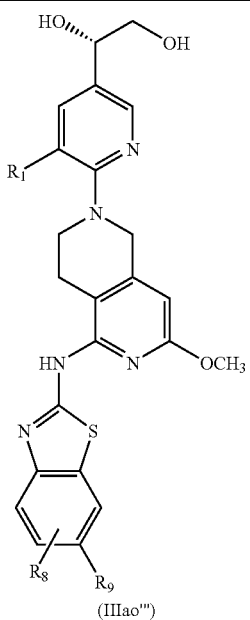

(IIIao''')

and pharmaceutically acceptable derivatives thereof, where:

| Compound | $R_1$ | $R_9$ |
|---|---|---|
| FAA (ao', ao'', or ao''') | —Cl | —Cl |
| FAB (ao', ao'', or ao''') | —Cl | —F |
| FAC (ao', ao'', or ao''') | —Cl | —CH$_3$ |
| FAD (ao', ao'', or ao''') | —F | —Cl |
| FAE (ao', ao'', or ao''') | —F | —F |
| FAF (ao', ao'', or ao''') | —F | —CH$_3$ |
| FAG (ao', ao'', or ao''') | —CF$_3$ | —Cl |
| FAH (ao', ao'', or ao''') | —CF$_3$ | —F |
| FAI (ao', ao'', or ao''') | —CF$_3$ | —CH$_3$ | and $R_8$ is —H.

TABLE 42

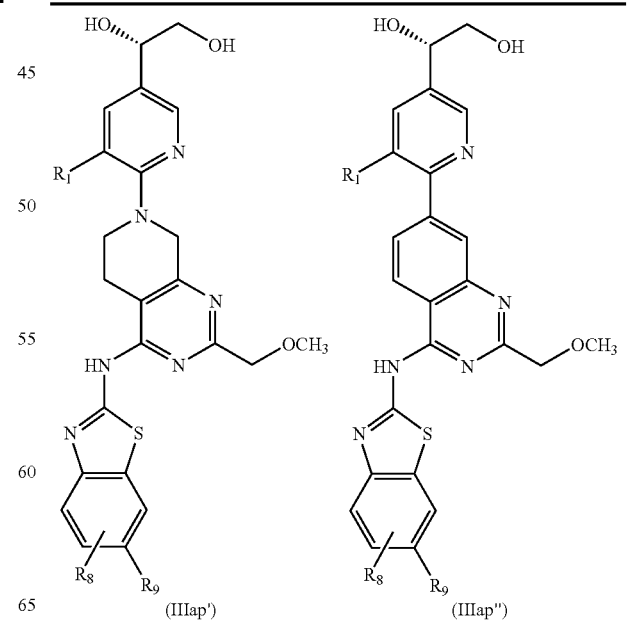

(IIIap')        (IIIap'')

TABLE 42-continued

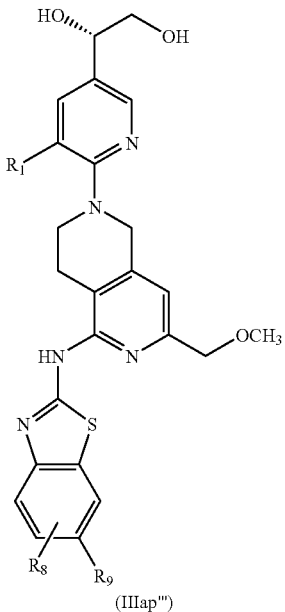

(IIIap''')

and pharmaceutically acceptable derivatives thereof, where:

| Compound | R₁ | R₉ |
|---|---|---|
| FAJ (ap', ap'', or ap''') | —Cl | —Cl |
| FAK (ap', ap'', or ap''') | —Cl | —F |
| FAL (ap', ap'', or ap''') | —Cl | —CH₃ |
| FAM (ap', ap'', or ap''') | —F | —Cl |
| FAN (ap', ap'', or ap''') | —F | —F |
| FAO (ap', ap'', or ap''') | —F | —CH₃ |
| FAP (ap', ap'', or ap''') | —CF₃ | —Cl |
| FAQ (ap', ap'', or ap''') | —CF₃ | —F |
| FAR (ap', ap'', or ap''') | —CF₃ | —CH₃ | and R₈ is —H.

TABLE 43

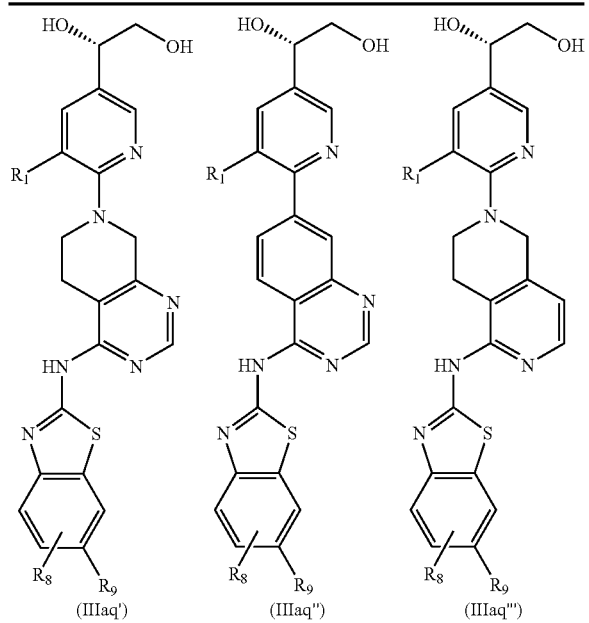

(IIIaq')  (IIIaq'')  (IIIaq''')

and pharmaceutically acceptable derivatives thereof, where:

| Compound | R₁ | R₈ | R₉ |
|---|---|---|---|
| FAS1 (aq', aq'', or aq''') | —Cl | —H | —H |
| FAS2 (aq', aq'', or aq''') | —Cl | —H | —Cl |
| FAS3 (aq', aq'', or aq''') | —Cl | —H | —Br |
| FAS4 (aq', aq'', or aq''') | —Cl | —H | —F |
| FAS5 (aq', aq'', or aq''') | —Cl | —H | —CH₃ |
| FAS6 (aq', aq'', or aq''') | —Cl | —H | —OCH₃ |
| FAS7 (aq', aq'', or aq''') | —Cl | —H | —OCH₂CH₃ |
| FAS8 (aq', aq'', or aq''') | —Cl | —H | —CF₃ |
| FAS9 (aq', aq'', or aq''') | —Cl | —H | —OCF₃ |
| FAS10 (aq', aq'', or aq''') | —Cl | —H | -iso-propyl |
| FAS11 (aq', aq'', or aq''') | —Cl | —H | -tert-butyl |
| FAS12 (aq', aq'', or aq''') | —Cl | —Cl | —H |
| FAS13 (aq', aq'', or aq''') | —Cl | —Cl | —Cl |
| FAS14 (aq', aq'', or aq''') | —Cl | —Cl | —Br |
| FAS15 (aq', aq'', or aq''') | —Cl | —Cl | —F |
| FAS16 (aq', aq'', or aq''') | —Cl | —Cl | —CH₃ |
| FAS17 (aq', aq'', or aq''') | —Cl | —Cl | —OCH₃ |
| FAS18 (aq', aq'', or aq''') | —Cl | —Cl | —OCH₂CH₃ |
| FAS19 (aq', aq'', or aq''') | —Cl | —Cl | —CF₃ |
| FAS20 (aq', aq'', or aq''') | —Cl | —Cl | —OCF₃ |
| FAS21 (aq', aq'', or aq''') | —Cl | —Cl | -iso-propyl |
| FAS22 (aq', aq'', or aq''') | —Cl | —Cl | -tert-butyl |
| FAS23 (aq', aq'', or aq''') | —Cl | —Br | —H |
| FAS24 (aq', aq'', or aq''') | —Cl | —Br | —Cl |
| FAS25 (aq', aq'', or aq''') | —Cl | —Br | —Br |
| FAS26 (aq', aq'', or aq''') | —Cl | —Br | —F |
| FAS27 (aq', aq'', or aq''') | —Cl | —Br | —CH₃ |
| FAS28 (aq', aq'', or aq''') | —Cl | —Br | —OCH₃ |
| FAS29 (aq', aq'', or aq''') | —Cl | —Br | —OCH₂CH₃ |
| FAS30 (aq', aq'', or aq''') | —Cl | —Br | —CF₃ |
| FAS31 (aq', aq'', or aq''') | —Cl | —Br | —OCF₃ |
| FAS32 (aq', aq'', or aq''') | —Cl | —Br | -iso-propyl |
| FAS33 (aq', aq'', or aq''') | —Cl | —Br | -tert-butyl |
| FAS34 (aq', aq'', or aq''') | —Cl | —F | —H |
| FAS35 (aq', aq'', or aq''') | —Cl | —F | —Cl |
| FAS36 (aq', aq'', or aq''') | —Cl | —F | —Br |
| FAS37 (aq', aq'', or aq''') | —Cl | —F | —F |
| FAS38 (aq', aq'', or aq''') | —Cl | —F | —CH₃ |
| FAS39 (aq', aq'', or aq''') | —Cl | —F | —OCH₃ |
| FAS40 (aq', aq'', or aq''') | —Cl | —F | —OCH₂CH₃ |
| FAS41 (aq', aq'', or aq''') | —Cl | —F | —CF₃ |
| FAS42 (aq', aq'', or aq''') | —Cl | —F | —OCF₃ |
| FAS43 (aq', aq'', or aq''') | —Cl | —F | -iso-propyl |
| FAS44 (aq', aq'', or aq''') | —Cl | —F | -tert-butyl |
| FAS45 (aq', aq'', or aq''') | —Cl | —CH₃ | —H |
| FAS46 (aq', aq'', or aq''') | —Cl | —CH₃ | —Cl |
| FAS47 (aq', aq'', or aq''') | —Cl | —CH₃ | —Br |
| FAS48 (aq', aq'', or aq''') | —Cl | —CH₃ | —F |
| FAS49 (aq', aq'', or aq''') | —Cl | —CH₃ | —CH₃ |
| FAS50 (aq', aq'', or aq''') | —Cl | —CH₃ | —OCH₃ |
| FAS51 (aq', aq'', or aq''') | —Cl | —CH₃ | —OCH₂CH₃ |
| FAS52 (aq', aq'', or aq''') | —Cl | —CH₃ | —CF₃ |
| FAS53 (aq', aq'', or aq''') | —Cl | —CH₃ | —OCF₃ |
| FAS54 (aq', aq'', or aq''') | —Cl | —CH₃ | -iso-propyl |
| FAS55 (aq', aq'', or aq''') | —Cl | —CH₃ | -tert-butyl |
| FAS56 (aq', aq'', or aq''') | —Cl | —OCH₃ | —H |
| FAS57 (aq', aq'', or aq''') | —Cl | —OCH₃ | —Cl |
| FAS58 (aq', aq'', or aq''') | —Cl | —OCH₃ | —Br |
| FAS59 (aq', aq'', or aq''') | —Cl | —OCH₃ | —F |
| FAS60 (aq', aq'', or aq''') | —Cl | —OCH₃ | —CH₃ |
| FAS61 (aq', aq'', or aq''') | —Cl | —OCH₃ | —OCH₃ |
| FAS62 (aq', aq'', or aq''') | —Cl | —OCH₃ | —OCH₂CH₃ |
| FAS63 (aq', aq'', or aq''') | —Cl | —OCH₃ | —CF₃ |
| FAS64 (aq', aq'', or aq''') | —Cl | —OCH₃ | —OCF₃ |
| FAS65 (aq', aq'', or aq''') | —Cl | —OCH₃ | -iso-propyl |
| FAS66 (aq', aq'', or aq''') | —Cl | —OCH₃ | -tert-butyl |
| FAS67 (aq', aq'', or aq''') | —Cl | —OCH₂CH₃ | —H |
| FAS68 (aq', aq'', or aq''') | —Cl | —OCH₂CH₃ | —Cl |
| FAS69 (aq', aq'', or aq''') | —Cl | —OCH₂CH₃ | —Br |
| FAS70 (aq', aq'', or aq''') | —Cl | —OCH₂CH₃ | —F |
| FAS71 (aq', aq'', or aq''') | —Cl | —OCH₂CH₃ | —CH₃ |
| FAS72 (aq', aq'', or aq''') | —Cl | —OCH₂CH₃ | —OCH₃ |
| FAS73 (aq', aq'', or aq''') | —Cl | —OCH₂CH₃ | —OCH₂CH₃ |
| FAS74 (aq', aq'', or aq''') | —Cl | —OCH₂CH₃ | —CF₃ |
| FAS75 (aq', aq'', or aq''') | —Cl | —OCH₂CH₃ | —OCF₃ |
| FAS76 (aq', aq'', or aq''') | —Cl | —OCH₂CH₃ | -iso-propyl |
| FAS77 (aq', aq'', or aq''') | —Cl | —OCH₂CH₃ | -tert-butyl |

TABLE 43-continued

| | | | |
|---|---|---|---|
| FAS78 (aq', aq'', or aq''') | —Cl | —CF$_3$ | —H |
| FAS79 (aq', aq'', or aq''') | —Cl | —CF$_3$ | —Cl |
| FAS80 (aq', aq'', or aq''') | —Cl | —CF$_3$ | —Br |
| FAS81 (aq', aq'', or aq''') | —Cl | —CF$_3$ | —F |
| FAS82 (aq', aq'', or aq''') | —Cl | —CF$_3$ | —CH$_3$ |
| FAS83 (aq', aq'', or aq''') | —Cl | —CF$_3$ | —OCH$_3$ |
| FAS84 (aq', aq'', or aq''') | —Cl | —CF$_3$ | —OCH$_2$CH$_3$ |
| FAS85 (aq', aq'', or aq''') | —Cl | —CF$_3$ | —CF$_3$ |
| FAS86 (aq', aq'', or aq''') | —Cl | —CF$_3$ | —OCF$_3$ |
| FAS87 (aq', aq'', or aq''') | —Cl | —CF$_3$ | -iso-propyl |
| FAS88 (aq', aq'', or aq''') | —Cl | —CF$_3$ | -tert-butyl |
| FAS89 (aq', aq'', or aq''') | —Cl | —OCF$_3$ | —H |
| FAS90 (aq', aq'', or aq''') | —Cl | —OCF$_3$ | —Cl |
| FAS91 (aq', aq'', or aq''') | —Cl | —OCF$_3$ | —Br |
| FAS92 (aq', aq'', or aq''') | —Cl | —OCF$_3$ | —F |
| FAS93 (aq', aq'', or aq''') | —Cl | —OCF$_3$ | —CH$_3$ |
| FAS94 (aq', aq'', or aq''') | —Cl | —OCF$_3$ | —OCH$_3$ |
| FAS95 (aq', aq'', or aq''') | —Cl | —OCF$_3$ | —OCH$_2$CH$_3$ |
| FAS96 (aq', aq'', or aq''') | —Cl | —OCF$_3$ | —CF$_3$ |
| FAS97 (aq', aq'', or aq''') | —Cl | —OCF$_3$ | —OCF$_3$ |
| FAS98 (aq', aq'', or aq''') | —Cl | —OCF$_3$ | -iso-propyl |
| FAS99 (aq', aq'', or aq''') | —Cl | —OCF$_3$ | -tert-butyl |
| FAS100 (aq', aq'', or aq''') | —Cl | -iso-propyl | —H |
| FAS101 (aq', aq'', or aq''') | —Cl | -iso-propyl | —Cl |
| FAS102 (aq', aq'', or aq''') | —Cl | -iso-propyl | —Br |
| FAS103 (aq', aq'', or aq''') | —Cl | -iso-propyl | —F |
| FAS104 (aq', aq'', or aq''') | —Cl | -iso-propyl | —CH$_3$ |
| FAS105 (aq', aq'', or aq''') | —Cl | -iso-propyl | —OCH$_3$ |
| FAS106 (aq', aq'', or aq''') | —Cl | -iso-propyl | —OCH$_2$CH$_3$ |
| FAS107 (aq', aq'', or aq''') | —Cl | -iso-propyl | —CF$_3$ |
| FAS108 (aq', aq'', or aq''') | —Cl | -iso-propyl | —OCF$_3$ |
| FAS109 (aq', aq'', or aq''') | —Cl | -iso-propyl | -iso-propyl |
| FAS110 (aq', aq'', or aq''') | —Cl | -iso-propyl | -tert-butyl |
| FAS111 (aq', aq'', or aq''') | —Cl | -tert-butyl | —H |
| FAS112 (aq', aq'', or aq''') | —Cl | -tert-butyl | —Cl |
| FAS113 (aq', aq'', or aq''') | —Cl | -tert-butyl | —Br |
| FAS114 (aq', aq'', or aq''') | —Cl | -tert-butyl | —F |
| FAS115 (aq', aq'', or aq''') | —Cl | -tert-butyl | —CH$_3$ |
| FAS116 (aq', aq'', or aq''') | —Cl | -tert-butyl | —OCH$_3$ |
| FAS117 (aq', aq'', or aq''') | —Cl | -tert-butyl | —OCH$_2$CH$_3$ |
| FAS118 (aq', aq'', or aq''') | —Cl | -tert-butyl | —CF$_3$ |
| FAS119 (aq', aq'', or aq''') | —Cl | -tert-butyl | —OCF$_3$ |
| FAS120 (aq', aq'', or aq''') | —Cl | -tert-butyl | -iso-propyl |
| FAS121 (aq', aq'', or aq''') | —Cl | -tert-butyl | -tert-butyl |
| FAT1 (aq', aq'', or aq''') | —F | —H | —H |
| FAT2 (aq', aq'', or aq''') | —F | —H | —Cl |
| FAT3 (aq', aq'', or aq''') | —F | —H | —Br |
| FAT4 (aq', aq'', or aq''') | —F | —H | —F |
| FAT5 (aq', aq'', or aq''') | —F | —H | —CH$_3$ |
| FAT6 (aq', aq'', or aq''') | —F | —H | —OCH$_3$ |
| FAT7 (aq', aq'', or aq''') | —F | —H | —OCH$_2$CH$_3$ |
| FAT8 (aq', aq'', or aq''') | —F | —H | —CF$_3$ |
| FAT9 (aq', aq'', or aq''') | —F | —H | —OCF$_3$ |
| FAT10 (aq', aq'', or aq''') | —F | —H | -iso-propyl |
| FAT11 (aq', aq'', or aq''') | —F | —H | -tert-butyl |
| FAT12 (aq', aq'', or aq''') | —F | —Cl | —H |
| FAT13 (aq', aq'', or aq''') | —F | —Cl | —Cl |
| FAT14 (aq', aq'', or aq''') | —F | —Cl | —Br |
| FAT15 (aq', aq'', or aq''') | —F | —Cl | —F |
| FAT16 (aq', aq'', or aq''') | —F | —Cl | —CH$_3$ |
| FAT17 (aq', aq'', or aq''') | —F | —Cl | —OCH$_3$ |
| FAT18 (aq', aq'', or aq''') | —F | —Cl | —OCH$_2$CH$_3$ |
| FAT19 (aq', aq'', or aq''') | —F | —Cl | —CF$_3$ |
| FAT20 (aq', aq'', or aq''') | —F | —Cl | —OCF$_3$ |
| FAT21 (aq', aq'', or aq''') | —F | —Cl | -iso-propyl |
| FAT22 (aq', aq'', or aq''') | —F | —Cl | -tert-butyl |
| FAT23 (aq', aq'', or aq''') | —F | —Br | —H |
| FAT24 (aq', aq'', or aq''') | —F | —Br | —Cl |
| FAT25 (aq', aq'', or aq''') | —F | —Br | —Br |
| FAT26 (aq', aq'', or aq''') | —F | —Br | —F |
| FAT27 (aq', aq'', or aq''') | —F | —Br | —CH$_3$ |
| FAT28 (aq', aq'', or aq''') | —F | —Br | —OCH$_3$ |
| FAT29 (aq', aq'', or aq''') | —F | —Br | —OCH$_2$CH$_3$ |
| FAT30 (aq', aq'', or aq''') | —F | —Br | —CF$_3$ |
| FAT31 (aq', aq'', or aq''') | —F | —Br | —OCF$_3$ |
| FAT32 (aq', aq'', or aq''') | —F | —Br | -iso-propyl |
| FAT33 (aq', aq'', or aq''') | —F | —Br | -tert-butyl |
| FAT34 (aq', aq'', or aq''') | —F | —F | —H |
| FAT35 (aq', aq'', or aq''') | —F | —F | —Cl |
| FAT36 (aq', aq'', or aq''') | —F | —F | —Br |
| FAT37 (aq', aq'', or aq''') | —F | —F | —F |
| FAT38 (aq', aq'', or aq''') | —F | —F | —CH$_3$ |
| FAT39 (aq', aq'', or aq''') | —F | —F | —OCH$_3$ |
| FAT40 (aq', aq'', or aq''') | —F | —F | —OCH$_2$CH$_3$ |
| FAT41 (aq', aq'', or aq''') | —F | —F | —CF$_3$ |
| FAT42 (aq', aq'', or aq''') | —F | —F | —OCF$_3$ |
| FAT43 (aq', aq'', or aq''') | —F | —F | -iso-propyl |
| FAT44 (aq', aq'', or aq''') | —F | —F | -tert-butyl |
| FAT45 (aq', aq'', or aq''') | —F | —CH$_3$ | —H |
| FAT46 (aq', aq'', or aq''') | —F | —CH$_3$ | —Cl |
| FAT47 (aq', aq'', or aq''') | —F | —CH$_3$ | —Br |
| FAT48 (aq', aq'', or aq''') | —F | —CH$_3$ | —F |
| FAT49 (aq', aq'', or aq''') | —F | —CH$_3$ | —CH$_3$ |
| FAT50 (aq', aq'', or aq''') | —F | —CH$_3$ | —OCH$_3$ |
| FAT51 (aq', aq'', or aq''') | —F | —CH$_3$ | —OCH$_2$CH$_3$ |
| FAT52 (aq', aq'', or aq''') | —F | —CH$_3$ | —CF$_3$ |
| FAT53 (aq', aq'', or aq''') | —F | —CH$_3$ | —OCF$_3$ |
| FAT54 (aq', aq'', or aq''') | —F | —CH$_3$ | -iso-propyl |
| FAT55 (aq', aq'', or aq''') | —F | —CH$_3$ | -tert-butyl |
| FAT56 (aq', aq'', or aq''') | —F | —OCH$_3$ | —H |
| FAT57 (aq', aq'', or aq''') | —F | —OCH$_3$ | —Cl |
| FAT58 (aq', aq'', or aq''') | —F | —OCH$_3$ | —Br |
| FAT59 (aq', aq'', or aq''') | —F | —OCH$_3$ | —F |
| FAT60 (aq', aq'', or aq''') | —F | —OCH$_3$ | —CH$_3$ |
| FAT61 (aq', aq'', or aq''') | —F | —OCH$_3$ | —OCH$_3$ |
| FAT62 (aq', aq'', or aq''') | —F | —OCH$_3$ | —OCH$_2$CH$_3$ |
| FAT63 (aq', aq'', or aq''') | —F | —OCH$_3$ | —CF$_3$ |
| FAT64 (aq', aq'', or aq''') | —F | —OCH$_3$ | —OCF$_3$ |
| FAT65 (aq', aq'', or aq''') | —F | —OCH$_3$ | -iso-propyl |
| FAT66 (aq', aq'', or aq''') | —F | —OCH$_3$ | -tert-butyl |
| FAT67 (aq', aq'', or aq''') | —F | —OCH$_2$CH$_3$ | —H |
| FAT68 (aq', aq'', or aq''') | —F | —OCH$_2$CH$_3$ | —Cl |
| FAT69 (aq', aq'', or aq''') | —F | —OCH$_2$CH$_3$ | —Br |
| FAT70 (aq', aq'', or aq''') | —F | —OCH$_2$CH$_3$ | —F |
| FAT71 (aq', aq'', or aq''') | —F | —OCH$_2$CH$_3$ | —CH$_3$ |
| FAT72 (aq', aq'', or aq''') | —F | —OCH$_2$CH$_3$ | —OCH$_3$ |
| FAT73 (aq', aq'', or aq''') | —F | —OCH$_2$CH$_3$ | —OCH$_2$CH$_3$ |
| FAT74 (aq', aq'', or aq''') | —F | —OCH$_2$CH$_3$ | —CF$_3$ |
| FAT75 (aq', aq'', or aq''') | —F | —OCH$_2$CH$_3$ | —OCF$_3$ |
| FAT76 (aq', aq'', or aq''') | —F | —OCH$_2$CH$_3$ | -iso-propyl |
| FAT77 (aq', aq'', or aq''') | —F | —OCH$_2$CH$_3$ | -tert-butyl |
| FAT78 (aq', aq'', or aq''') | —F | —CF$_3$ | —H |
| FAT79 (aq', aq'', or aq''') | —F | —CF$_3$ | —Cl |
| FAT80 (aq', aq'', or aq''') | —F | —CF$_3$ | —Br |
| FAT81 (aq', aq'', or aq''') | —F | —CF$_3$ | —F |
| FAT82 (aq', aq'', or aq''') | —F | —CF$_3$ | —CH$_3$ |
| FAT83 (aq', aq'', or aq''') | —F | —CF$_3$ | —OCH$_3$ |
| FAT84 (aq', aq'', or aq''') | —F | —CF$_3$ | —OCH$_2$CH$_3$ |
| FAT85 (aq', aq'', or aq''') | —F | —CF$_3$ | —CF$_3$ |
| FAT86 (aq', aq'', or aq''') | —F | —CF$_3$ | —OCF$_3$ |
| FAT87 (aq', aq'', or aq''') | —F | —CF$_3$ | -iso-propyl |
| FAT88 (aq', aq'', or aq''') | —F | —CF$_3$ | -tert-butyl |
| FAT89 (aq', aq'', or aq''') | —F | —OCF$_3$ | —H |
| FAT90 (aq', aq'', or aq''') | —F | —OCF$_3$ | —Cl |
| FAT91 (aq', aq'', or aq''') | —F | —OCF$_3$ | —Br |
| FAT92 (aq', aq'', or aq''') | —F | —OCF$_3$ | —F |
| FAT93 (aq', aq'', or aq''') | —F | —OCF$_3$ | —CH$_3$ |
| FAT94 (aq', aq'', or aq''') | —F | —OCF$_3$ | —OCH$_3$ |
| FAT95 (aq', aq'', or aq''') | —F | —OCF$_3$ | —OCH$_2$CH$_3$ |
| FAT96 (aq', aq'', or aq''') | —F | —OCF$_3$ | —CF$_3$ |
| FAT97 (aq', aq'', or aq''') | —F | —OCF$_3$ | —OCF$_3$ |
| FAT98 (aq', aq'', or aq''') | —F | —OCF$_3$ | -iso-propyl |
| FAT99 (aq', aq'', or aq''') | —F | —OCF$_3$ | -tert-butyl |
| FAT100 (aq', aq'', or aq''') | —F | -iso-propyl | —H |
| FAT101 (aq', aq'', or aq''') | —F | -iso-propyl | —Cl |
| FAT102 (aq', aq'', or aq''') | —F | -iso-propyl | —Br |
| FAT103 (aq', aq'', or aq''') | —F | -iso-propyl | —F |
| FAT104 (aq', aq'', or aq''') | —F | -iso-propyl | —CH$_3$ |
| FAT105 (aq', aq'', or aq''') | —F | -iso-propyl | —OCH$_3$ |
| FAT106 (aq', aq'', or aq''') | —F | -iso-propyl | —OCH$_2$CH$_3$ |
| FAT107 (aq', aq'', or aq''') | —F | -iso-propyl | —CF$_3$ |
| FAT108 (aq', aq'', or aq''') | —F | -iso-propyl | —OCF$_3$ |
| FAT109 (aq', aq'', or aq''') | —F | -iso-propyl | -iso-propyl |
| FAT110 (aq', aq'', or aq''') | —F | -iso-propyl | -tert-butyl |
| FAT111 (aq', aq'', or aq''') | —F | -tert-butyl | —H |
| FAT112 (aq', aq'', or aq''') | —F | -tert-butyl | —Cl |
| FAT113 (aq', aq'', or aq''') | —F | -tert-butyl | —Br |
| FAT114 (aq', aq'', or aq''') | —F | -tert-butyl | —F |
| FAT115 (aq', aq'', or aq''') | —F | -tert-butyl | —CH$_3$ |
| FAT116 (aq', aq'', or aq''') | —F | -tert-butyl | —OCH$_3$ |

TABLE 43-continued

| | | | |
|---|---|---|---|
| FAT117 (aq', aq", or aq''') | —F | -tert-butyl | —OCH$_2$CH$_3$ |
| FAT118 (aq', aq", or aq''') | —F | -tert-butyl | —CF$_3$ |
| FAT119 (aq', aq", or aq''') | —F | -tert-butyl | —OCF$_3$ |
| FAT120 (aq', aq", or aq''') | —F | -tert-butyl | -iso-propyl |
| FAT121 (aq', aq", or aq''') | —F | -tert-butyl | -tert-butyl |
| FAU1 (aq', aq", or aq''') | —CF$_3$ | —H | —H |
| FAU2 (aq', aq", or aq''') | —CF$_3$ | —H | —Cl |
| FAU3 (aq', aq", or aq''') | —CF$_3$ | —H | —Br |
| FAU4 (aq', aq", or aq''') | —CF$_3$ | —H | —F |
| FAU5 (aq', aq", or aq''') | —CF$_3$ | —H | —CH$_3$ |
| FAU6 (aq', aq", or aq''') | —CF$_3$ | —H | —OCH$_3$ |
| FAU7 (aq', aq", or aq''') | —CF$_3$ | —H | —OCH$_2$CH$_3$ |
| FAU8 (aq', aq", or aq''') | —CF$_3$ | —H | —CF$_3$ |
| FAU9 (aq', aq", or aq''') | —CF$_3$ | —H | —OCF$_3$ |
| FAU10 (aq', aq", or aq''') | —CF$_3$ | —H | -iso-propyl |
| FAU11 (aq', aq", or aq''') | —CF$_3$ | —H | -tert-butyl |
| FAU12 (aq', aq", or aq''') | —CF$_3$ | —Cl | —H |
| FAU13 (aq', aq", or aq''') | —CF$_3$ | —Cl | —Cl |
| FAU14 (aq', aq", or aq''') | —CF$_3$ | —Cl | —Br |
| FAU15 (aq', aq", or aq''') | —CF$_3$ | —Cl | —F |
| FAU16 (aq', aq", or aq''') | —CF$_3$ | —Cl | —CH$_3$ |
| FAU17 (aq', aq", or aq''') | —CF$_3$ | —Cl | —OCH$_3$ |
| FAU18 (aq', aq", or aq''') | —CF$_3$ | —Cl | —OCH$_2$CH$_3$ |
| FAU19 (aq', aq", or aq''') | —CF$_3$ | —Cl | —CF$_3$ |
| FAU20 (aq', aq", or aq''') | —CF$_3$ | —Cl | —OCF$_3$ |
| FAU21 (aq', aq", or aq''') | —CF$_3$ | —Cl | -iso-propyl |
| FAU22 (aq', aq", or aq''') | —CF$_3$ | —Cl | -tert-butyl |
| FAU23 (aq', aq", or aq''') | —CF$_3$ | —Br | —H |
| FAU24 (aq', aq", or aq''') | —CF$_3$ | —Br | —Cl |
| FAU25 (aq', aq", or aq''') | —CF$_3$ | —Br | —Br |
| FAU26 (aq', aq", or aq''') | —CF$_3$ | —Br | —F |
| FAU27 (aq', aq", or aq''') | —CF$_3$ | —Br | —CH$_3$ |
| FAU28 (aq', aq", or aq''') | —CF$_3$ | —Br | —OCH$_3$ |
| FAU29 (aq', aq", or aq''') | —CF$_3$ | —Br | —OCH$_2$CH$_3$ |
| FAU30 (aq', aq", or aq''') | —CF$_3$ | —Br | —CF$_3$ |
| FAU31 (aq', aq", or aq''') | —CF$_3$ | —Br | —OCF$_3$ |
| FAU32 (aq', aq", or aq''') | —CF$_3$ | —Br | -iso-propyl |
| FAU33 (aq', aq", or aq''') | —CF$_3$ | —Br | -tert-butyl |
| FAU34 (aq', aq", or aq''') | —CF$_3$ | —F | —H |
| FAU35 (aq', aq", or aq''') | —CF$_3$ | —F | —Cl |
| FAU36 (aq', aq", or aq''') | —CF$_3$ | —F | —Br |
| FAU37 (aq', aq", or aq''') | —CF$_3$ | —F | —F |
| FAU38 (aq', aq", or aq''') | —CF$_3$ | —F | —CH$_3$ |
| FAU39 (aq', aq", or aq''') | —CF$_3$ | —F | —OCH$_3$ |
| FAU40 (aq', aq", or aq''') | —CF$_3$ | —F | —OCH$_2$CH$_3$ |
| FAU41 (aq', aq", or aq''') | —CF$_3$ | —F | —CF$_3$ |
| FAU42 (aq', aq", or aq''') | —CF$_3$ | —F | —OCF$_3$ |
| FAU43 (aq', aq", or aq''') | —CF$_3$ | —F | -iso-propyl |
| FAU44 (aq', aq", or aq''') | —CF$_3$ | —F | -tert-butyl |
| FAU45 (aq', aq", or aq''') | —CF$_3$ | —CH$_3$ | —H |
| FAU46 (aq', aq", or aq''') | —CF$_3$ | —CH$_3$ | —Cl |
| FAU47 (aq', aq", or aq''') | —CF$_3$ | —CH$_3$ | —Br |
| FAU48 (aq', aq", or aq''') | —CF$_3$ | —CH$_3$ | —F |
| FAU49 (aq', aq", or aq''') | —CF$_3$ | —CH$_3$ | —CH$_3$ |
| FAU50 (aq', aq", or aq''') | —CF$_3$ | —CH$_3$ | —OCH$_3$ |
| FAU51 (aq', aq", or aq''') | —CF$_3$ | —CH$_3$ | —OCH$_2$CH$_3$ |
| FAU52 (aq', aq", or aq''') | —CF$_3$ | —CH$_3$ | —CF$_3$ |
| FAU53 (aq', aq", or aq''') | —CF$_3$ | —CH$_3$ | —OCF$_3$ |
| FAU54 (aq', aq", or aq''') | —CF$_3$ | —CH$_3$ | -iso-propyl |
| FAU55 (aq', aq", or aq''') | —CF$_3$ | —CH$_3$ | -tert-butyl |
| FAU56 (aq', aq", or aq''') | —CF$_3$ | —OCH$_3$ | —H |
| FAU57 (aq', aq", or aq''') | —CF$_3$ | —OCH$_3$ | —Cl |
| FAU58 (aq', aq", or aq''') | —CF$_3$ | —OCH$_3$ | —Br |
| FAU59 (aq', aq", or aq''') | —CF$_3$ | —OCH$_3$ | —F |
| FAU60 (aq', aq", or aq''') | —CF$_3$ | —OCH$_3$ | —CH$_3$ |
| FAU61 (aq', aq", or aq''') | —CF$_3$ | —OCH$_3$ | —OCH$_3$ |
| FAU62 (aq', aq", or aq''') | —CF$_3$ | —OCH$_3$ | —OCH$_2$CH$_3$ |
| FAU63 (aq', aq", or aq''') | —CF$_3$ | —OCH$_3$ | —CF$_3$ |
| FAU64 (aq', aq", or aq''') | —CF$_3$ | —OCH$_3$ | —OCF$_3$ |
| FAU65 (aq', aq", or aq''') | —CF$_3$ | —OCH$_3$ | -iso-propyl |
| FAU66 (aq', aq", or aq''') | —CF$_3$ | —OCH$_3$ | -tert-butyl |
| FAU67 (aq', aq", or aq''') | —CF$_3$ | —OCH$_2$CH$_3$ | —H |
| FAU68 (aq', aq", or aq''') | —CF$_3$ | —OCH$_2$CH$_3$ | —Cl |
| FAU69 (aq', aq", or aq''') | —CF$_3$ | —OCH$_2$CH$_3$ | —Br |
| FAU70 (aq', aq", or aq''') | —CF$_3$ | —OCH$_2$CH$_3$ | —F |
| FAU71 (aq', aq", or aq''') | —CF$_3$ | —OCH$_2$CH$_3$ | —CH$_3$ |
| FAU72 (aq', aq", or aq''') | —CF$_3$ | —OCH$_2$CH$_3$ | —OCH$_3$ |
| FAU73 (aq', aq", or aq''') | —CF$_3$ | —OCH$_2$CH$_3$ | —OCH$_2$CH$_3$ |
| FAU74 (aq', aq", or aq''') | —CF$_3$ | —OCH$_2$CH$_3$ | —CF$_3$ |
| FAU75 (aq', aq", or aq''') | —CF$_3$ | —OCH$_2$CH$_3$ | —OCF$_3$ |
| FAU76 (aq', aq", or aq''') | —CF$_3$ | —OCH$_2$CH$_3$ | -iso-propyl |
| FAU77 (aq', aq", or aq''') | —CF$_3$ | —OCH$_2$CH$_3$ | -tert-butyl |
| FAU78 (aq', aq", or aq''') | —CF$_3$ | —CF$_3$ | —H |
| FAU79 (aq', aq", or aq''') | —CF$_3$ | —CF$_3$ | —Cl |
| FAU80 (aq', aq", or aq''') | —CF$_3$ | —CF$_3$ | —Br |
| FAU81 (aq', aq", or aq''') | —CF$_3$ | —CF$_3$ | —F |
| FAU82 (aq', aq", or aq''') | —CF$_3$ | —CF$_3$ | —CH$_3$ |
| FAU83 (aq', aq", or aq''') | —CF$_3$ | —CF$_3$ | —OCH$_3$ |
| FAU84 (aq', aq", or aq''') | —CF$_3$ | —CF$_3$ | —OCH$_2$CH$_3$ |
| FAU85 (aq', aq", or aq''') | —CF$_3$ | —CF$_3$ | —CF$_3$ |
| FAU86 (aq', aq", or aq''') | —CF$_3$ | —CF$_3$ | —OCF$_3$ |
| FAU87 (aq', aq", or aq''') | —CF$_3$ | —CF$_3$ | -iso-propyl |
| FAU88 (aq', aq", or aq''') | —CF$_3$ | —CF$_3$ | -tert-butyl |
| FAU89 (aq', aq", or aq''') | —CF$_3$ | —OCF$_3$ | —H |
| FAU90 (aq', aq", or aq''') | —CF$_3$ | —OCF$_3$ | —Cl |
| FAU91 (aq', aq", or aq''') | —CF$_3$ | —OCF$_3$ | —Br |
| FAU92 (aq', aq", or aq''') | —CF$_3$ | —OCF$_3$ | —F |
| FAU93 (aq', aq", or aq''') | —CF$_3$ | —OCF$_3$ | —CH$_3$ |
| FAU94 (aq', aq", or aq''') | —CF$_3$ | —OCF$_3$ | —OCH$_3$ |
| FAU95 (aq', aq", or aq''') | —CF$_3$ | —OCF$_3$ | —OCH$_2$CH$_3$ |
| FAU96 (aq', aq", or aq''') | —CF$_3$ | —OCF$_3$ | —CF$_3$ |
| FAU97 (aq', aq", or aq''') | —CF$_3$ | —OCF$_3$ | —OCF$_3$ |
| FAU98 (aq', aq", or aq''') | —CF$_3$ | —OCF$_3$ | -iso-propyl |
| FAU99 (aq', aq", or aq''') | —CF$_3$ | —OCF$_3$ | -tert-butyl |
| FAU100 (aq', aq", or aq''') | —CF$_3$ | -iso-propyl | —H |
| FAU101 (aq', aq", or aq''') | —CF$_3$ | -iso-propyl | —Cl |
| FAU102 (aq', aq", or aq''') | —CF$_3$ | -iso-propyl | —Br |
| FAU103 (aq', aq", or aq''') | —CF$_3$ | -iso-propyl | —F |
| FAU104 (aq', aq", or aq''') | —CF$_3$ | -iso-propyl | —CH$_3$ |
| FAU105 (aq', aq", or aq''') | —CF$_3$ | -iso-propyl | —OCH$_3$ |
| FAU106 (aq', aq", or aq''') | —CF$_3$ | -iso-propyl | —OCH$_2$CH$_3$ |
| FAU107 (aq', aq", or aq''') | —CF$_3$ | -iso-propyl | —CF$_3$ |
| FAU108 (aq', aq", or aq''') | —CF$_3$ | -iso-propyl | —OCF$_3$ |
| FAU109 (aq', aq", or aq''') | —CF$_3$ | -iso-propyl | -iso-propyl |
| FAU110 (aq', aq", or aq''') | —CF$_3$ | -iso-propyl | -tert-butyl |
| FAU111 (aq', aq", or aq''') | —CF$_3$ | -tert-butyl | —H |
| FAU112 (aq', aq", or aq''') | —CF$_3$ | -tert-butyl | —Cl |
| FAU113 (aq', aq", or aq''') | —CF$_3$ | -tert-butyl | —Br |
| FAU114 (aq', aq", or aq''') | —CF$_3$ | -tert-butyl | —F |
| FAU115 (aq', aq", or aq''') | —CF$_3$ | -tert-butyl | —CH$_3$ |
| FAU116 (aq', aq", or aq''') | —CF$_3$ | -tert-butyl | —OCH$_3$ |
| FAU117 (aq', aq", or aq''') | —CF$_3$ | -tert-butyl | —OCH$_2$CH$_3$ |
| FAU118 (aq', aq", or aq''') | —CF$_3$ | -tert-butyl | —CF$_3$ |
| FAU119 (aq', aq", or aq''') | —CF$_3$ | -tert-butyl | —OCF$_3$ |
| FAU120 (aq', aq", or aq''') | —CF$_3$ | -tert-butyl | -iso-propyl |
| FAU121 (aq', aq", or aq''') | —CF$_3$ | -tert-butyl | -tert-butyl |
| FAV1 (aq', aq", or aq''') | —CH$_3$ | —H | —H |
| FAV2 (aq', aq", or aq''') | —CH$_3$ | —H | —Cl |
| FAV3 (aq', aq", or aq''') | —CH$_3$ | —H | —Br |
| FAV4 (aq', aq", or aq''') | —CH$_3$ | —H | —F |
| FAV5 (aq', aq", or aq''') | —CH$_3$ | —H | —CH$_3$ |
| FAV6 (aq', aq", or aq''') | —CH$_3$ | —H | —OCH$_3$ |
| FAV7 (aq', aq", or aq''') | —CH$_3$ | —H | —OCH$_2$CH$_3$ |
| FAV8 (aq', aq", or aq''') | —CH$_3$ | —H | —CF$_3$ |
| FAV9 (aq', aq", or aq''') | —CH$_3$ | —H | —OCF$_3$ |
| FAV10 (aq', aq", or aq''') | —CH$_3$ | —H | -iso-propyl |
| FAV11 (aq', aq", or aq''') | —CH$_3$ | —H | -tert-butyl |
| FAV12 (aq', aq", or aq''') | —CH$_3$ | —Cl | —H |
| FAV13 (aq', aq", or aq''') | —CH$_3$ | —Cl | —Cl |
| FAV14 (aq', aq", or aq''') | —CH$_3$ | —Cl | —Br |
| FAV15 (aq', aq", or aq''') | —CH$_3$ | —Cl | —F |
| FAV16 (aq', aq", or aq''') | —CH$_3$ | —Cl | —CH$_3$ |
| FAV17 (aq', aq", or aq''') | —CH$_3$ | —Cl | —OCH$_3$ |
| FAV18 (aq', aq", or aq''') | —CH$_3$ | —Cl | —OCH$_2$CH$_3$ |
| FAV19 (aq', aq", or aq''') | —CH$_3$ | —Cl | —CF$_3$ |
| FAV20 (aq', aq", or aq''') | —CH$_3$ | —Cl | —OCF$_3$ |
| FAV21 (aq', aq", or aq''') | —CH$_3$ | —Cl | -iso-propyl |
| FAV22 (aq', aq", or aq''') | —CH$_3$ | —Cl | -tert-butyl |
| FAV23 (aq', aq", or aq''') | —CH$_3$ | —Br | —H |
| FAV24 (aq', aq", or aq''') | —CH$_3$ | —Br | —Cl |
| FAV25 (aq', aq", or aq''') | —CH$_3$ | —Br | —Br |
| FAV26 (aq', aq", or aq''') | —CH$_3$ | —Br | —F |
| FAV27 (aq', aq", or aq''') | —CH$_3$ | —Br | —CH$_3$ |
| FAV28 (aq', aq", or aq''') | —CH$_3$ | —Br | —OCH$_3$ |
| FAV29 (aq', aq", or aq''') | —CH$_3$ | —Br | —OCH$_2$CH$_3$ |
| FAV30 (aq', aq", or aq''') | —CH$_3$ | —Br | —CF$_3$ |
| FAV31 (aq', aq", or aq''') | —CH$_3$ | —Br | —OCF$_3$ |
| FAV32 (aq', aq", or aq''') | —CH$_3$ | —Br | -iso-propyl |
| FAV33 (aq', aq", or aq''') | —CH$_3$ | —Br | -tert-butyl |
| FAV34 (aq', aq", or aq''') | —CH$_3$ | —F | —H |

TABLE 43-continued

| | | | |
|---|---|---|---|
| FAV35 (aq', aq'', or aq''') | —CH₃ | —F | —Cl |
| FAV36 (aq', aq'', or aq''') | —CH₃ | —F | —Br |
| FAV37 (aq', aq'', or aq''') | —CH₃ | —F | —F |
| FAV38 (aq', aq'', or aq''') | —CH₃ | —F | —CH₃ |
| FAV39 (aq', aq'', or aq''') | —CH₃ | —F | —OCH₃ |
| FAV40 (aq', aq'', or aq''') | —CH₃ | —F | —OCH₂CH₃ |
| FAV41 (aq', aq'', or aq''') | —CH₃ | —F | —CF₃ |
| FAV42 (aq', aq'', or aq''') | —CH₃ | —F | —OCF₃ |
| FAV43 (aq', aq'', or aq''') | —CH₃ | —F | -iso-propyl |
| FAV44 (aq', aq'', or aq''') | —CH₃ | —F | -tert-butyl |
| FAV45 (aq', aq'', or aq''') | —CH₃ | —CH₃ | —H |
| FAV46 (aq', aq'', or aq''') | —CH₃ | —CH₃ | —Cl |
| FAV47 (aq', aq'', or aq''') | —CH₃ | —CH₃ | —Br |
| FAV48 (aq', aq'', or aq''') | —CH₃ | —CH₃ | —F |
| FAV49 (aq', aq'', or aq''') | —CH₃ | —CH₃ | —CH₃ |
| FAV50 (aq', aq'', or aq''') | —CH₃ | —CH₃ | —OCH₃ |
| FAV51 (aq', aq'', or aq''') | —CH₃ | —CH₃ | —OCH₂CH₃ |
| FAV52 (aq', aq'', or aq''') | —CH₃ | —CH₃ | —CF₃ |
| FAV53 (aq', aq'', or aq''') | —CH₃ | —CH₃ | —OCF₃ |
| FAV54 (aq', aq'', or aq''') | —CH₃ | —CH₃ | -iso-propyl |
| FAV55 (aq', aq'', or aq''') | —CH₃ | —CH₃ | -tert-butyl |
| FAV56 (aq', aq'', or aq''') | —CH₃ | —OCH₃ | —H |
| FAV57 (aq', aq'', or aq''') | —CH₃ | —OCH₃ | —Cl |
| FAV58 (aq', aq'', or aq''') | —CH₃ | —OCH₃ | —Br |
| FAV59 (aq', aq'', or aq''') | —CH₃ | —OCH₃ | —F |
| FAV60 (aq', aq'', or aq''') | —CH₃ | —OCH₃ | —CH₃ |
| FAV61 (aq', aq'', or aq''') | —CH₃ | —OCH₃ | —OCH₃ |
| FAV62 (aq', aq'', or aq''') | —CH₃ | —OCH₃ | —OCH₂CH₃ |
| FAV63 (aq', aq'', or aq''') | —CH₃ | —OCH₃ | —CF₃ |
| FAV64 (aq', aq'', or aq''') | —CH₃ | —OCH₃ | —OCF₃ |
| FAV65 (aq', aq'', or aq''') | —CH₃ | —OCH₃ | -iso-propyl |
| FAV66 (aq', aq'', or aq''') | —CH₃ | —OCH₃ | -tert-butyl |
| FAV67 (aq', aq'', or aq''') | —CH₃ | —OCH₂CH₃ | —H |
| FAV68 (aq', aq'', or aq''') | —CH₃ | —OCH₂CH₃ | —Cl |
| FAV69 (aq', aq'', or aq''') | —CH₃ | —OCH₂CH₃ | —Br |
| FAV70 (aq', aq'', or aq''') | —CH₃ | —OCH₂CH₃ | —F |
| FAV71 (aq', aq'', or aq''') | —CH₃ | —OCH₂CH₃ | —CH₃ |
| FAV72 (aq', aq'', or aq''') | —CH₃ | —OCH₂CH₃ | —OCH₃ |
| FAV73 (aq', aq'', or aq''') | —CH₃ | —OCH₂CH₃ | —OCH₂CH₃ |
| FAV74 (aq', aq'', or aq''') | —CH₃ | —OCH₂CH₃ | —CF₃ |
| FAV75 (aq', aq'', or aq''') | —CH₃ | —OCH₂CH₃ | —OCF₃ |
| FAV76 (aq', aq'', or aq''') | —CH₃ | —OCH₂CH₃ | -iso-propyl |
| FAV77 (aq', aq'', or aq''') | —CH₃ | —OCH₂CH₃ | -tert-butyl |
| FAV78 (aq', aq'', or aq''') | —CH₃ | —CF₃ | —H |
| FAV79 (aq', aq'', or aq''') | —CH₃ | —CF₃ | —Cl |
| FAV80 (aq', aq'', or aq''') | —CH₃ | —CF₃ | —Br |
| FAV81 (aq', aq'', or aq''') | —CH₃ | —CF₃ | —F |
| FAV82 (aq', aq'', or aq''') | —CH₃ | —CF₃ | —CH₃ |
| FAV83 (aq', aq'', or aq''') | —CH₃ | —CF₃ | —OCH₃ |
| FAV84 (aq', aq'', or aq''') | —CH₃ | —CF₃ | —OCH₂CH₃ |
| FAV85 (aq', aq'', or aq''') | —CH₃ | —CF₃ | —CF₃ |
| FAV86 (aq', aq'', or aq''') | —CH₃ | —CF₃ | —OCF₃ |
| FAV87 (aq', aq'', or aq''') | —CH₃ | —CF₃ | -iso-propyl |
| FAV88 (aq', aq'', or aq''') | —CH₃ | —CF₃ | -tert-butyl |
| FAV89 (aq', aq'', or aq''') | —CH₃ | —OCF₃ | —H |
| FAV90 (aq', aq'', or aq''') | —CH₃ | —OCF₃ | —Cl |
| FAV91 (aq', aq'', or aq''') | —CH₃ | —OCF₃ | —Br |
| FAV92 (aq', aq'', or aq''') | —CH₃ | —OCF₃ | —F |
| FAV93 (aq', aq'', or aq''') | —CH₃ | —OCF₃ | —CH₃ |
| FAV94 (aq', aq'', or aq''') | —CH₃ | —OCF₃ | —OCH₃ |
| FAV95 (aq', aq'', or aq''') | —CH₃ | —OCF₃ | —OCH₂CH₃ |
| FAV96 (aq', aq'', or aq''') | —CH₃ | —OCF₃ | —CF₃ |
| FAV97 (aq', aq'', or aq''') | —CH₃ | —OCF₃ | —OCF₃ |
| FAV98 (aq', aq'', or aq''') | —CH₃ | —OCF₃ | -iso-propyl |
| FAV99 (aq', aq'', or aq''') | —CH₃ | —OCF₃ | -tert-butyl |
| FAV100 (aq', aq'', or aq''') | —CH₃ | -iso-propyl | —H |
| FAV101 (aq', aq'', or aq''') | —CH₃ | -iso-propyl | —Cl |
| FAV102 (aq', aq'', or aq''') | —CH₃ | -iso-propyl | —Br |
| FAV103 (aq', aq'', or aq''') | —CH₃ | -iso-propyl | —F |
| FAV104 (aq', aq'', or aq''') | —CH₃ | -iso-propyl | —CH₃ |
| FAV105 (aq', aq'', or aq''') | —CH₃ | -iso-propyl | —OCH₃ |
| FAV106 (aq', aq'', or aq''') | —CH₃ | -iso-propyl | —OCH₂CH₃ |
| FAV107 (aq', aq'', or aq''') | —CH₃ | -iso-propyl | —CF₃ |
| FAV108 (aq', aq'', or aq''') | —CH₃ | -iso-propyl | —OCF₃ |
| FAV109 (aq', aq'', or aq''') | —CH₃ | -iso-propyl | -iso-propyl |
| FAV110 (aq', aq'', or aq''') | —CH₃ | -iso-propyl | -tert-butyl |
| FAV111 (aq', aq'', or aq''') | —CH₃ | -tert-butyl | —H |
| FAV112 (aq', aq'', or aq''') | —CH₃ | -tert-butyl | —Cl |
| FAV113 (aq', aq'', or aq''') | —CH₃ | -tert-butyl | —Br |
| FAV114 (aq', aq'', or aq''') | —CH₃ | -tert-butyl | —F |
| FAV115 (aq', aq'', or aq''') | —CH₃ | -tert-butyl | —CH₃ |
| FAV116 (aq', aq'', or aq''') | —CH₃ | -tert-butyl | —OCH₃ |
| FAV117 (aq', aq'', or aq''') | —CH₃ | -tert-butyl | —OCH₂CH₃ |
| FAV118 (aq', aq'', or aq''') | —CH₃ | -tert-butyl | —CF₃ |
| FAV119 (aq', aq'', or aq''') | —CH₃ | -tert-butyl | —OCF₃ |
| FAV120 (aq', aq'', or aq''') | —CH₃ | -tert-butyl | -iso-propyl |
| FAV121 (aq', aq'', or aq''') | —CH₃ | -tert-butyl | -tert-butyl |

TABLE 44

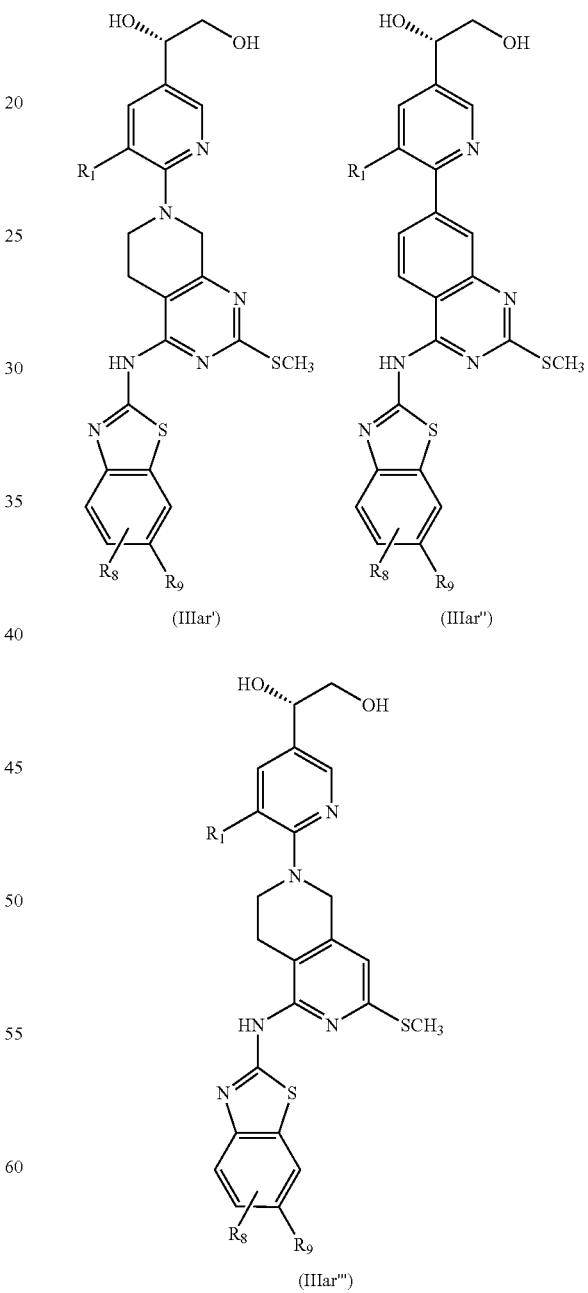

TABLE 44-continued and pharmaceutically acceptable derivatives thereof, where:

| Compound | $R_1$ | $R_9$ |
|---|---|---|
| FBB (ar', ar", or ar''') | —Cl | —Cl |
| FBC (ar', ar", or ar''') | —Cl | —F |
| FBD (ar', ar", or ar''') | —Cl | —CH$_3$ |
| FBE (ar', ar", or ar''') | —F | —Cl |
| FBF (ar', ar", or ar''') | —F | —F |
| FBG (ar', ar", or ar''') | —F | —CH$_3$ |
| FBH (ar', ar", or ar''') | —CF$_3$ | —Cl |
| FBI (ar', ar", or ar''') | —CF$_3$ | —F |
| FBJ (ar', ar", or ar''') | —CF$_3$ | —CF$_3$ | and $R_8$ is —H.

TABLE 45

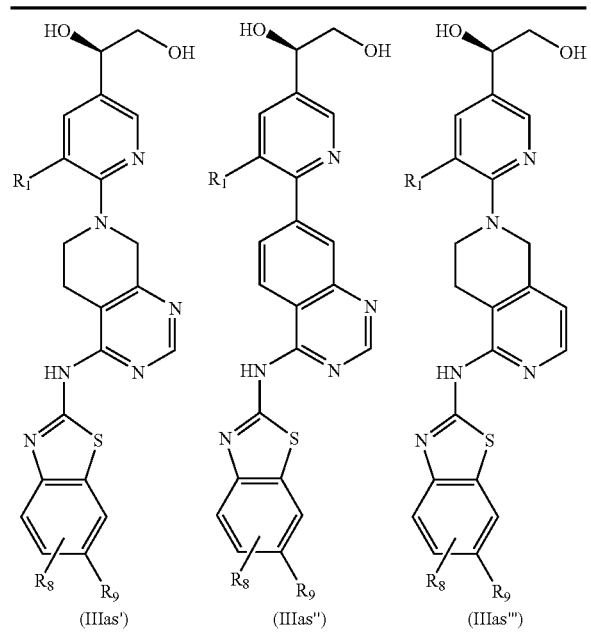

(IIIas')  (IIIas")  (IIIas''')

and pharmaceutically acceptable derivatives thereof, where:

| Compound | $R_1$ | $R_9$ |
|---|---|---|
| FBK (as', as", or as''') | —Cl | —Cl |
| FBL (as', as", or as''') | —Cl | —F |
| FBM (as', as", or as''') | —Cl | —CH$_3$ |
| FBN (as', as", or as''') | —F | —Cl |
| FBO (as', as", or as''') | —F | —F |
| FBP (as', as", or as''') | —F | —CH$_3$ |
| FBQ (as', as", or as''') | —CF$_3$ | Cl |
| FBR (as', as", or as''') | —CF$_3$ | —F |
| FBS (as', as", or as''') | —CF$_3$ | —CH$_3$ | and $R_8$ is —H.

TABLE 46

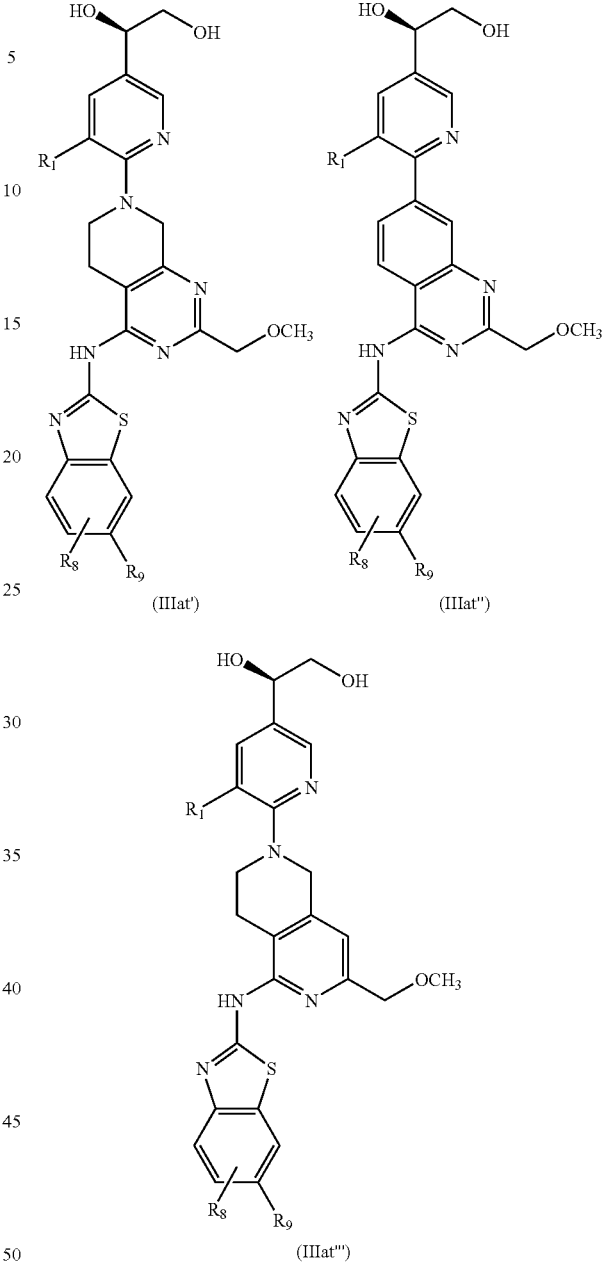

(IIIat')  (IIIat")

(IIIat''')

and pharmaceutically acceptable derivatives thereof, where:

| Compound | $R_1$ | $R_9$ |
|---|---|---|
| FBT (at', at", or at''') | —Cl | —Cl |
| FBU (at', at", or at''') | —Cl | —F |
| FBV (at', at", or at''') | —Cl | —CH$_3$ |
| FBW (at', at", or at''') | —F | —Cl |
| FBX (at', at", or at''') | —F | —F |
| FBY (at', at", or at''') | —F | —CH$_3$ |
| FBZ (at', at", or at''') | —CF$_3$ | —Cl |
| FCA (at', at", or at''') | —CF$_3$ | —F |
| FCB (at', at", or at''') | —CF$_3$ | —CH$_3$ | and $R_8$ is —H.

TABLE 47

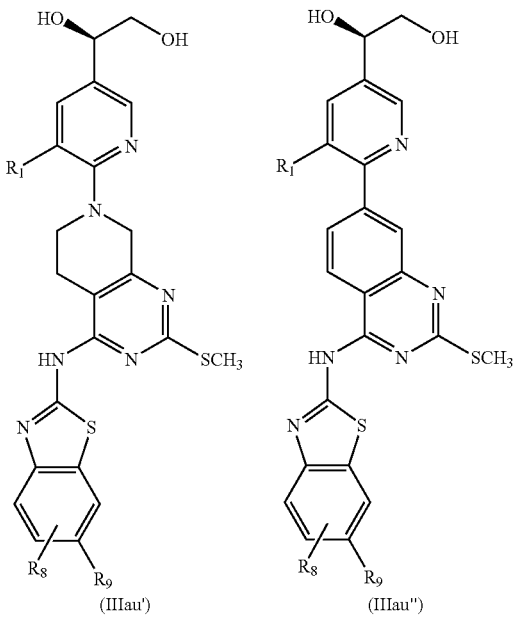

(IIIau')   (IIIau'')

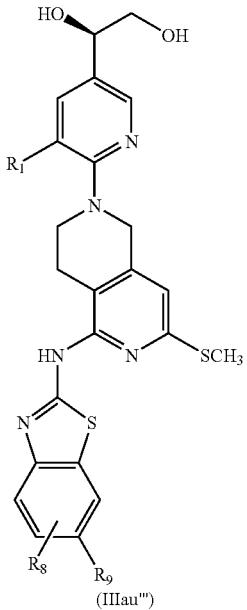

(IIIau''')

and pharmaceutically acceptable derivatives thereof, where:

| Compound | R₁ | R₉ |
|---|---|---|
| FCC (au', au'', or au''') | —Cl | —Cl |
| FCD (au', au'', or au''') | —Cl | —F |
| FCE (au', au'', or au''') | —Cl | —CH₃ |
| FCF (au', au'', or au''') | —F | —Cl |
| FCG (au', au'', or au''') | —F | —F |
| FCH (au', au'', or au''') | —F | —CH₃ |
| FCI (au', au'', or au''') | —CF₃ | —Cl |
| FCJ (au', au'', or au''') | —CF₃ | —F |
| FCK (au', au'', or au''') | —CF₃ | —CH₃ | and R₈ is —H.

4.4. Compounds of Formula IV

Preferred compounds of formula III are compounds of formula IV:

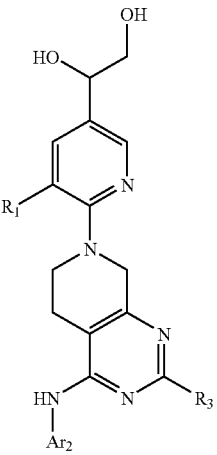

(IV)

or a pharmaceutically acceptable derivative thereof, where $R_3$ is as defined above for compounds of formula I;

$R_1$ is —Cl, —F, —CH$_3$, —CF$_3$, or —OCF$_3$;

Ar$_2$ is:

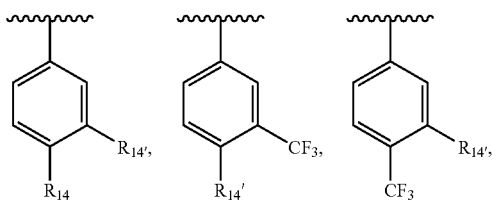

each $R_8$ and $R_9$ is independently selected from:

(a) —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, and -phenyl, each of which is unsubstituted or substituted with 1 or 2 —OH groups; or (b) —H, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —SC(halo)$_3$, —SCH(halo)$_2$, —SCH$_2$(halo), —CN, —O—CN, —OH, -halo, —N$_3$, —NO$_2$, —CH=NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, —S(O)$_2$R$_7$; and each $R_{14}$ and $R_{14'}$ is independently selected from —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, —(C$_1$-C$_6$)

alkoxy, —($C_1$-$C_6$)alkoxy-($C_1$-$C_6$)alkyl, -phenyl, —C(halo)$_3$, —CH(halo)$_2$, —CH$_2$(halo), -(3- to 7-membered)heterocycle, -(5- to 10-membered)heteroaryl, —($C_1$-$C_6$)haloalkyl, —($C_2$-$C_6$)haloalkenyl, —($C_2$-$C_6$)haloalkynyl, —($C_2$-$C_6$)hydroxyalkenyl, —($C_2$-$C_6$)hydroxyalkynyl, —($C_1$-$C_6$)alkoxy($C_2$-$C_6$)alkyl, —($C_1$-$C_6$)alkoxy($C_2$-$C_6$)alkenyl, —($C_1$-$C_6$)alkoxy($C_2$-$C_6$)alkynyl, —($C_1$-$C_6$)alkoxy($C_3$-$C_8$)cycloalkyl, —CN, —OH, -halo, —OC(halo)$_3$, —N$_3$, —NO$_2$, —CH=R$_7$, —N(R$_7$)$_2$, —NR$_7$OH, —OR$_7$, —SR$_7$, —O(CH$_2$)$_b$OR$_7$, —O(CH$_2$)$_b$SR$_7$, —O(CH$_2$)$_b$N(R$_7$)$_2$, —N(R$_7$)(CH$_2$)$_b$OR$_7$, —N(R$_7$)(CH$_2$)$_b$SR$_7$, —N(R$_7$)(CH$_2$)$_b$N(R$_7$)$_2$, —N(R$_7$)COR$_7$, —N(R$_7$)—S(O)$_2$—($C_1$-$C_6$)alkyl, —C(O)—N(R$_7$)$_2$, —C(O)R$_7$, —C(O)OR$_7$, —OC(O)R$_7$, —OC(O)OR$_7$, —S(O)R$_7$, —S(O)$_2$R$_7$, —S(O)$_2$N(R$_7$)$_2$, —S(O)$_2$C(halo)$_3$, —S(O)$_2$(3- to 7-membered)heterocycle, —CON(R$_7$)$_2$, —($C_1$-$C_5$)alkyl-C=NOR$_7$, —($C_1$-$C_5$)alkyl-C(O)—N(R$_7$)$_2$, —($C_1$-$C_6$)alkyl-N(H)S(O)$_2$N(R$_7$)$_2$, and —($C_1$-$C_6$)alkyl-C(=NH)—N(R$_7$)$_2$.

Certain embodiments of formula IV are presented below.

In one embodiment, a compound of formula IV is a pharmaceutically acceptable derivative of a compound of formula IV.

In another embodiment, a compound of formula IV is a compound of formula IV where the derivative is a pharmaceutically acceptable salt.

In another embodiment, a compound of formula IV is a pharmaceutically acceptable salt of a compound of formula IV.

In another embodiment, Ar$_2$ is:

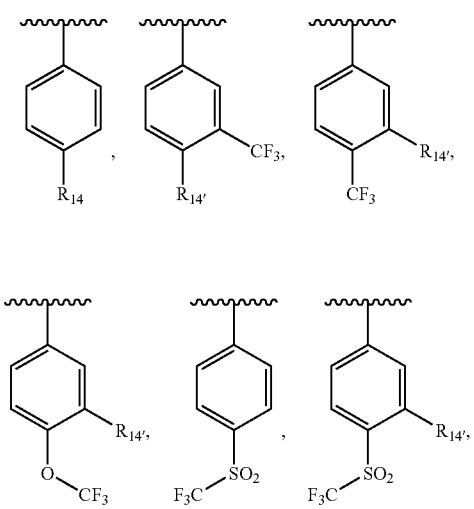

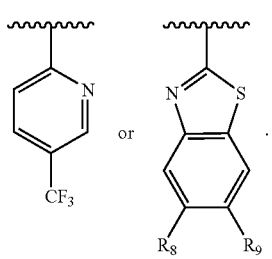

In another embodiment, Ar$_2$ is:

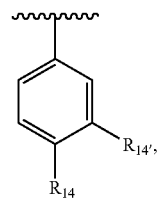

where R$_{14}$ is —H, —Cl, —F, —Br, —OCF$_3$, —($C_1$-$C_6$)alkyl, —S(O)$_2$CF$_3$, —S(O)$_2$($C_1$-$C_6$)alkyl, —OCH$_3$, —OCH$_2$CH$_3$, or —OCH(CH$_3$)$_2$, and preferably is —CF$_3$, —OCF$_3$, —Cl, or —F;

R$_{14'}$ is —H, —Cl, —F, Br, —CH$_3$, —CH$_2$CH$_3$, —OCH$_3$, —OCF$_3$, or —OCH$_2$CH$_3$.

In another embodiment, Ar$_2$ is:

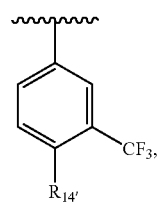

where R$_{14'}$ is —H, —Cl, —F, Br, —CH$_3$, —CH$_2$CH$_3$, —OCH$_3$, —OCF$_3$, or —OCH$_2$CH$_3$.

In another embodiment, Ar$_2$ is:

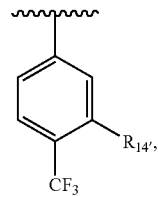

where R$_{14'}$ is —H, —Cl, —F, Br, —CH$_3$, —CH$_2$CH$_3$, —OCH$_3$, —OCF$_3$, or —OCH$_2$CH$_3$.

In another embodiment, Ar$_2$ is:

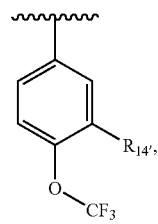

where R$_{14'}$ is —H, —Cl, —F, Br, —CH$_3$, —CH$_2$CH$_3$, —OCH$_3$, —OCF$_3$, or —OCH$_2$CH$_3$.

In another embodiment, Ar$_2$ is:

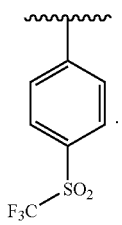

In another embodiment, Ar$_2$ is:

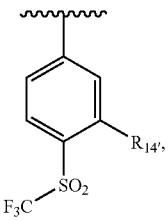

where R$_{14'}$ is —H, —Cl, —F, Br, —CH$_3$, —CH$_2$CH$_3$, —OCH$_3$, —OCF$_3$, or —OCH$_2$CH$_3$.

In another embodiment, Ar$_2$ is:

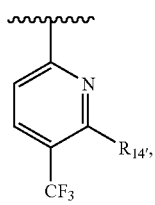

where R$_{14'}$ is —H, —Cl, —F, Br, —CH$_3$, —CH$_2$CH$_3$, —OCH$_3$, —OCF$_3$, or —OCH$_2$CH$_3$.

In another embodiment, Ar$_2$ is:

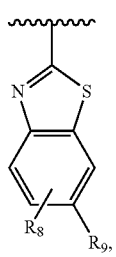

where each R$_8$ and R$_9$ is independently —H, —Cl, —Br, —F, —CH$_3$, —OCH$_3$, —OCH$_2$CH$_3$, —CF$_3$, —OCF$_3$, iso-propyl, or tert-butyl.

In another embodiment, R$_3$ is —H.
In another embodiment, R$_3$ is -halo.
In another embodiment, R$_3$ is —CN.
In another embodiment, R$_3$ is —C(halo)$_3$.
In another embodiment, R$_3$ is —CH(halo)$_2$.
In another embodiment, R$_3$ is —CH$_2$Cl.
In another embodiment, R$_3$ is CH$_2$(halo).
In another embodiment, R$_3$ is —(C$_1$-C$_6$)alkoxy.
In another embodiment, R$_3$ is —OCH$_3$.
In another embodiment, R$_3$ is —OC$_2$H$_5$.
In another embodiment, R$_3$ is —(C$_1$-C$_6$)alkyl-N(R$_7$)$_2$.
In another embodiment, R$_3$ is —(C$_1$-C$_6$)thioalkoxy.
In another embodiment, R$_3$ is S—CH$_3$.
In another embodiment, R$_3$ is —(C$_1$-C$_6$)alkyl-(C$_1$-C$_6$)alkoxy.
In another embodiment, R$_3$ is —CH$_2$—O—CH$_3$.
In another embodiment, R$_3$ is —(C$_1$-C$_6$)alkyl-(3- to 7-membered)heterocycle.
In another embodiment, R$_3$ is —CH$_2$-piperidyl.
In another embodiment, R$_3$ is —S(O)$_2$—(C$_1$-C$_6$)alkyl.
In another embodiment, R$_3$ is —S(O)$_2$—CH$_3$.
In another embodiment, R$_3$ is —OH.
In another embodiment, each R$_3$ is —N(R$_7$)—(C$_1$-C$_6$)alkyl-R$_{14}$.
In another embodiment, R$_3$ is —NH—C$_2$H$_4$-morpholinyl.
In another embodiment, R$_3$ is —NH—C$_2$H$_4$—N(CH$_3$)$_2$.
In another embodiment, R$_3$ is —N(R$_7$)$_2$.
In another embodiment, R$_3$ is —NH$_2$.
In another embodiment, R$_3$ is —SH.
In another embodiment, Ar$_1$ is:

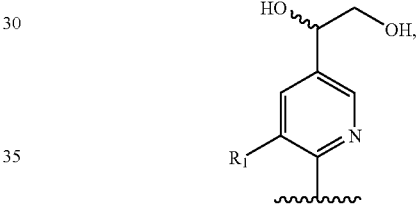

where the compound of formula IV is racemic.

In another embodiment, Ar$_1$ is:

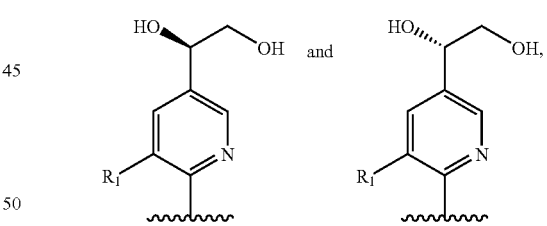

where the % ee of the R enantiomer is greater than 60%.

In another embodiment, Ar$_1$ is:

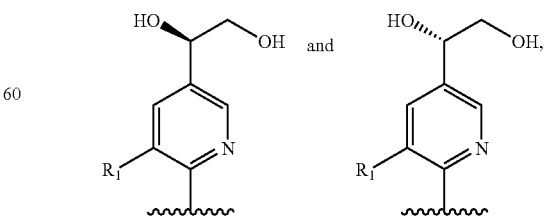

where the % ee of the R enantiomer is greater than 70%.

In another embodiment, Ar$_1$ is:

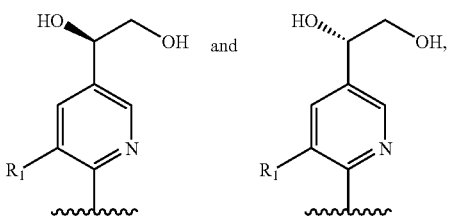

where the % ee of the R enantiomer is greater than 80%.
In another embodiment, Ar$_1$ is:

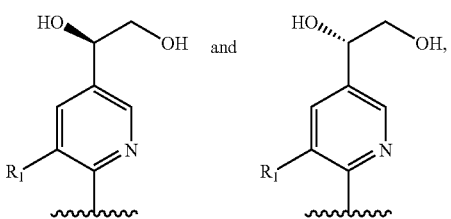

where the % ee of the R enantiomer is greater than 90%.
In another embodiment, Ar$_1$ is:

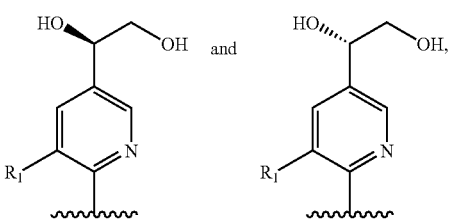

where the % ee of the R enantiomer is greater than 99%.
In another embodiment, Ar$_1$ is:

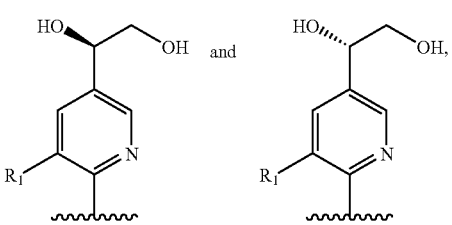

where the % ee of the S enantiomer is greater than 60%.
In another embodiment, Ar$_1$ is:

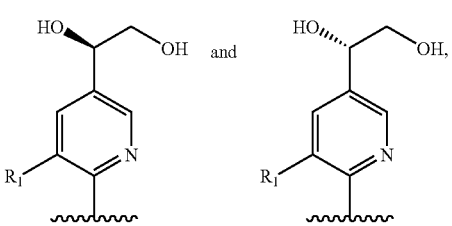

where the % ee of the S enantiomer is greater than 70%.

In another embodiment, Ar$_1$ is:

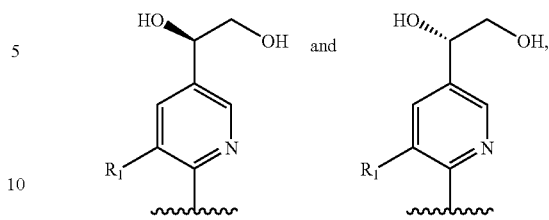

where the % ee of the S enantiomer is greater than 80%.
In another embodiment, Ar$_1$ is:

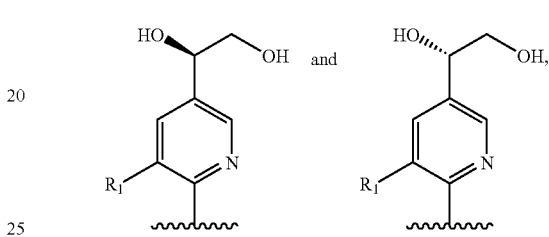

where the % ee of the S enantiomer is greater than 90%.
In another embodiment, Ar$_1$ is:

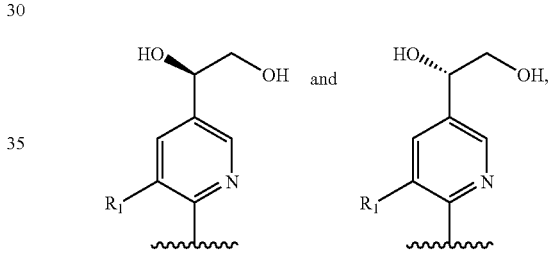

where the % ee of the S enantiomer is greater than 99%.
In another embodiment, Ar$_1$ is:

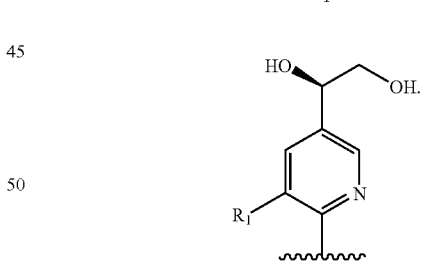

In another embodiment, Ar$_1$ is:

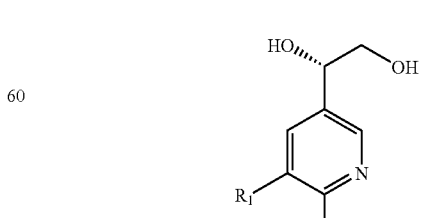

4.5. Definitions

As used herein, the terms used above having following meaning:

"—($C_1$-$C_{10}$)alkyl" means a straight chain or branched non-cyclic hydrocarbon having from 1 to 10 carbon atoms. Representative straight chain —($C_1$-$C_{10}$)alkyls include -methyl, -ethyl, -n-propyl, -n-butyl, -n-pentyl, -n-hexyl, -n-heptyl, -n-octyl, -n-nonyl, and -n-decyl. Representative branched —($C_1$-$C_{10}$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—($C_1$-$C_6$)alkyl" means a straight chain or branched non-cyclic hydrocarbon having from 1 to 6 carbon atoms. Representative straight chain —($C_1$-$C_6$)alkyls include -methyl, -ethyl, -n-propyl, -n-butyl, -n-pentyl, and -n-hexyl. Representative branched —($C_1$-$C_6$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—($C_1$-$C_5$)alkyl" means a straight chain or branched non-cyclic hydrocarbon having from 1 to 5 carbon atoms. Representative straight chain —($C_1$-$C_5$)alkyls include -methyl, -ethyl, -n-propyl, -n-butyl, and -n-pentyl. Representative branched —($C_1$-$C_5$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, and 1,2-dimethylpropyl.

"—($C_1$-$C_4$)alkyl" means a straight chain or branched non-cyclic hydrocarbon having from 1 to 4 carbon atoms. Representative straight chain —($C_1$-$C_4$)alkyls include -methyl, -ethyl, -n-propyl, and -n-butyl. Representative branched —($C_1$-$C_4$)alkyls include -iso-propyl, -sec-butyl, -iso-butyl, and -tert-butyl.

"—($C_1$-$C_6$)haloalkyl" means a straight chain or branched non-cyclic hydrocarbon having from 1 to 6 carbon atoms as defined above for —($C_1$-$C_6$)alkyl that is substituted with 1, 2, 3, 4, 5 or 6 independently selected -halo groups or where each hydrogen of the —($C_1$-$C_6$)alkyl is replaced with an independently selected -halo group. Representative ($C_1$-$C_6$)haloalkyls include trifluoromethyl, perfluoroethyl, 4-bromo-2-fluoro-3-iodobutyl, and 1,1,4,4,4-pentaiodo-3-(iodomethyl)-3-methylbutyl.

"—($C_1$-$C_6$)heteroalkyl" means a straight chain or branched non-cyclic hydrocarbon having from 1 to 6 carbon atoms as defined above for —($C_1$-$C_6$)alkyl in which 1, 2, 3 or 4 carbon atoms have been replaced by an atom independently selected from nitrogen, oxygen and sulfur. Representative —($C_1$-$C_6$)heteroalkyls include (2-methylbutoxy)methyl, and (2-methoxypropoxy)methyl, methyl(isobutyl)sulfane).

"—($C_1$-$C_6$)hydroxyalkyl" means a straight chain or branched non-cyclic hydrocarbon having from 1 to 6 carbon atoms as defined above for —($C_1$-$C_6$)alkyl that is substituted with 1, 2 or 3 hydroxyl groups. Representative —($C_1$-$C_6$) hydroxyalkyls include 1,3-dihydroxybutyl, 2-(methyl)-2-(hydroxymethyl)propane-1,3-diol, and 2-ethyl-2-methyl-propane-1,3-diol.

"—($C_2$-$C_{10}$)alkenyl" means a straight chain or branched non-cyclic hydrocarbon having from 2 to 10 carbon atoms and including at least one carbon-carbon double bond. Representative straight chain and branched ($C_2$-$C_{10}$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, and -3-decenyl.

"—($C_2$-$C_6$)alkenyl" means a straight chain or branched non-cyclic hydrocarbon having from 2 to 6 carbon atoms and including at least one carbon-carbon double bond. Representative straight chain and branched ($C_2$-$C_6$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, and -3-hexenyl.

"—($C_2$-$C_5$)alkenyl" means a straight chain or branched non-cyclic hydrocarbon having from 2 to 5 carbon atoms and including at least one carbon-carbon double bond. Representative straight chain and branched ($C_2$-$C_5$)alkenyls include -vinyl, -allyl, -1-butenyl, -2-butenyl, -iso-butylenyl, -1-pentenyl, -2-pentenyl, -3-methyl-1-butenyl, and -2-methyl-2-butenyl.

"—($C_2$-$C_6$)haloalkenyl" means a straight chain or branched non-cyclic hydrocarbon having from 2 to 6 carbon atoms and including at least one carbon-carbon double bond as defined above for —($C_2$-$C_6$)alkenyl that is substituted with 1, 2 or 3 independently selected -halo groups. Representative —($C_2$-$C_6$)haloalkenyls include 2-(fluoromethyl)but-3-enyl, 2-(bromofluoromethyl)but-3-enyl, and 1,1-dichlorobut-3-en-2-yl.

"—($C_2$-$C_6$)hydroxyalkenyl" means a straight chain or branched non-cyclic hydrocarbon having from 2 to 6 carbon atoms and including at least one carbon-carbon double bond as defined above for —($C_2$-$C_6$)alkenyl that is substituted with 1, 2 or 3 hydroxyl groups. Representative —($C_2$-$C_6$)hydroxyalkenyls include 2-(methyl)-2-vinylpropane-1,3-diol, and 2-(methyl)but-3-en-1-ol.

"—($C_2$-$C_{10}$)alkynyl" means a straight chain or branched non-cyclic hydrocarbon having from 2 to 10 carbon atoms and including at least one carbon-carbon triple bond. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butyryl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, and -9-decynyl.

"—($C_2$-$C_6$)alkynyl" means a straight chain or branched non-cyclic hydrocarbon having from 2 to 6 carbon atoms and including at least one carbon-carbon triple bond. Representative straight chain and branched ($C_2$-$C_6$)alkynyls include -acetylenyl, -propynyl, -1-butynyl, -2-butyryl, -1-pentynyl, -2-pentynyl, -3-methyl-1-butynyl, -4-pentynyl, -1-hexynyl, -2-hexynyl, and -5-hexynyl.

"—($C_2$-$C_6$)haloalkynyl" means a straight chain or branched non-cyclic hydrocarbon having from 2 to 6 carbon atoms and including at least one carbon-carbon triple bond that is substituted with 1, 2 or 3 independently selected -halo groups. Representative —($C_2$-$C_6$)haloalkynyls include 2-(fluoromethyl)but-3-ynyl, 2-(bromofluoromethyl)but-3-ynyl, and 1,1-dichlorobut-3-yn-2-yl.

"—$(C_2-C_6)$hydroxyalkynyl" means a straight chain or branched non-cyclic hydrocarbon having from 2 to 6 carbon atoms and including at least one carbon-carbon triple bond that is substituted with 1, 2 or 3 hydroxyl groups. Representative —$(C_2-C_6)$hydroxyalkynyls include 2-(methyl)-2-ethynyl-propane-1,3-diol, and 2-(methyl)but-3-yn-1-ol.

"—$(C_1-C_6)$alkoxy" means a straight chain or branched non cyclic hydrocarbon having one or more ether groups and from 1 to 6 carbon atoms. Representative straight chain and branched —$(C_1-C_6)$alkoxys include methoxy, ethoxy, propoxy, butoxy, pentoxy, hexoxy, methoxymethyl, 2-methoxyethyl, 5-methoxypentyl, and 3-ethoxybutyl.

"—$(C_1-C_6)$thioalkoxy" means a straight chain or branched non cyclic hydrocarbon having one or more thioether groups and from 1 to 6 carbon atoms. Representative straight chain and branched —$(C_1-C_6)$thioalkoxys include thiomethoxy, thioethoxy, thiopropoxy, thiobutoxy, thiopentoxy, thiohexoxy, thiomethoxymethyl, 2-thiomethoxyethyl, 5-thiomethoxypentyl, and 3-thioethoxybutyl.

"—$(C_1-C_6)$alkoxy$(C_2-C_6)$alkyl" means a straight chain or branched non cyclic hydrocarbon having one or more ether groups and from 1 to 6 carbon atoms as defined above for —$(C_1-C_6)$alkoxy group that is substituted with a —$(C_2-C_6)$alkyl group. Representative —$(C_1-C_6)$alkoxy$(C_2-C_6)$alkyls include 2-methyl-3-(3-methylpentan-2-yloxy)butyl, 2-methyl-3-(3-methylenepent-4-yn-2-yloxy)butyl, 2-methyl-3-(3-methylenepent-4-yn-2-yloxy)butyl, and 3-isopropoxy-2-methylbutyl.

"—$(C_1-C_6)$alkoxy$(C_2-C_6)$alkenyl" means a straight chain or branched non cyclic hydrocarbon having one or more ether groups and from 1 to 6 carbon atoms as defined above for —$(C_1-C_6)$alkoxy group that is substituted with a —$(C_2-C_6)$alkenyl group. Representative —$(C_1-C_6)$alkoxy$(C_2-C_6)$alkenyls include 2-methyl-3-(3-methylenepentan-2-yloxy)butyl, 2-methyl-3-(3-methylpent-3-en-2-yloxy)butyl, and 2-methyl-3-(3-methylenepent-4-en-2-yloxy)butyl.

"—$(C_1-C_6)$alkoxy$(C_2-C_6)$alkynyl" means a straight chain or branched non cyclic hydrocarbon having one or more ether groups and from 1 to 6 carbon atoms that is substituted with a —$(C_2-C_6)$alkynyl group. Representative —$(C_1-C_6)$alkoxy$(C_2-C_6)$alkynyls include 2-methyl-3-(3-methylnepentan-2-yloxy)butyl, 2-methyl-3-(3-methylpent-3-yn-2-yloxy)butyl, and 2-methyl-3-(3-methylenepent-4-yn-2-yloxy)butyl.

"—$(C_1-C_6)$alkoxy$(C_3-C_8)$cycloalkyl" means a straight chain or branched non cyclic hydrocarbon having one or more ether groups and from 1 to 6 carbon atoms as defined above for —$(C_1-C_6)$alkyl group that is substituted with a —$(C_3-C_8)$cycloalkyl group. Representative —$(C_1-C_6)$alkoxy$(C_3-C_8)$cycloalkyls include 3-(cyclohexyloxy)butyl, 1-cyclopropoxypentan-3-yl, and 1-(2-cyclopropylethoxy)propyl, (cyclopentylmethoxy)(methoxy)methyl.

"—$(C_3-C_{10})$cycloalkyl" means a saturated cyclic hydrocarbon having from 3 to 10 carbon atoms. Representative $(C_3-C_{10})$cycloalkyls are -cyclopropyl, -cyclobutyl, -cyclopentyl, -cyclohexyl, -cycloheptyl, -cyclooctyl, -cyclononyl, and -cyclodecyl.

"—$(C_3-C_8)$cycloalkyl" means a saturated cyclic hydrocarbon having from 3 to 8 carbon atoms. Representative $(C_3-C_8)$ cycloalkyls include -cyclopropyl, -cyclobutyl, -cyclopentyl, -cyclohexyl, -cycloheptyl, and -cyclooctyl.

"—$(C_6-C_{14})$bicycloalkyl" means a bi-cyclic hydrocarbon ring system having from 6 to 14 carbon atoms and at least one saturated cyclic alkyl ring. Representative —$(C_6-C_{14})$bicycloalkyls include -indanyl, -norbornyl, -1,2,3,4-tetrahydronaphthalenyl, -5,6,7,8-tetrahydronaphthalenyl, -perhydronaphthalenyl, bicyclo[2.2.1]hexyl, bicyclo[2.2.1.]heptyl, bicyclo[2.2.2]octyl, bicyclo[3.3.1]heptyl, bicyclo[3.2.1]octyl, bicyclo[3.3.1]nonyl, bicyclo[3.3.2]decyl, bicyclo[3.3.3]undecyl, bicyclo[4.2.2]decyl, bicyclo[4.3.2]undecyl, and bicyclo[4.3.1]decyl.

"—$(C_3-C_8)$cycloheteroalkyl" means a saturated cyclic hydrocarbon having from 3 to 8 carbon atoms where 1, 2, 3, 4 or 5 carbon atoms have been replaced by a heteroatom. A 3-membered cyclic ring system can contain up to 1 heteroatom, a 4-membered ring system can contain up to 2 heteroatoms, a 5-membered ring system can contain up to 4 heteroatoms, a 6-membered ring system can contain up to 4 heteroatoms, and a 7- or 8-membered ring system can contain up to 5 heteroatoms. Each heteroatom is independently selected from nitrogen, which can be quaternized; oxygen; and sulfur, including sulfoxide and sulfone. The —$(C_3-C_8)$ cycloheteroalkyl can be attached via a nitrogen or carbon atom. Representative —$(C_3-C_8)$cycloheteroalkyls include 2-oxiranyl, 1-azetidinyl, 2-(1,3-dioxolanyl), 3-thiomorpholinyl, 1-(1,3,5-triazepanyl), 2-(1,3,5-triazepanyl), 6-(1,3,5-triazepanyl), and 2-(1,5,3,7-dioxadithiocanyl).

"—$(C_5-C_8)$cycloalkenyl" means a cyclic non-aromatic hydrocarbon having at least one carbon-carbon double bond in the cyclic system and from 5 to 8 carbon atoms. Representative —$(C_5-C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, and -cyclooctatetraenyl.

"-(3- to 7-membered)heterocycle" or "-(3- to 7-membered) heterocyclo" means a 3- to 7-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, a 5-membered heterocycle can contain up to 4 heteroatoms, a 6-membered heterocycle can contain up to 4 heteroatoms, and a 7-membered heterocycle can contain up to 5 heteroatoms. Each heteroatom is independently selected from nitrogen, which can be quaternized; oxygen; and sulfur, including sulfoxide and sulfone. The -(3- to 7-membered) heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, and tetrahydrothiopyranyl.

"-(7- to 10-membered)bicycloheterocycle" or "-(7- to 10-membered)bicycloheterocyclo" means a 7- to 10-membered bicyclic, heterocyclic ring which is either saturated, unsaturated non-aromatic, or aromatic. A -(7- to 10-membered)bicycloheterocycle contains from 1 to 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, -indolinyl, -isoindolinyl, -1,2,3,4-tetrahydroquinolinyl, -1,2,3,4-tetrahydroisoquinolinyl, and pyrrolopyrrolyl.

"—$(C_6-C_{14})$aryl" means an aromatic carbocyclic ring of 6 to 14 carbon atoms, including mono-, bi- and tricyclic ring systems. Representative —$(C_6-C_{14})$aryls include phenyl, naphthyl, anthryl, and phenanthryl.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, the -(5- or 6-membered)heteroaryl's ring contains at least one carbon atom. Representative -(5- or 6-membered) heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—CH$_2$(halo)" means a methyl group where one of the hydrogens of the methyl group has been replaced with a halogen. Representative —CH$_2$(halo) groups include —CH$_2$F, —CH$_2$Cl, —CH$_2$Br, and —CH$_2$I.

"—CH(halo)$_2$" means a methyl group where two of the hydrogens of the methyl group have been replaced with a halogen. Representative —CH(halo)$_2$ groups include —CHF$_2$, —CHCl$_2$, —CHBr$_2$, —CHBrCl, —CHClI, and —CHI$_2$.

"—C(halo)$_3$" means a methyl group where each of the hydrogens of the methyl group has been replaced with a halogen. Representative —C(halo)$_3$ groups include —CF$_3$, —CCl$_3$, —CBr$_3$, —CI$_3$, —CClF$_2$, —CFCl$_2$, —CClBr$_2$, —CBrCl$_2$, and —CFClBr.

"amino" means —NH$_2$.

"azido" means —N$_3$.

"carbamoyl" means —C(O)N(R)$_2$ where each R group is independently hydrogen, —(C$_1$-C$_6$)alkyl, cycloalkyl or —(C$_6$-C$_{14}$)aryl, as defined herein, which can be optionally substituted as defined herein.

"carboxyl" means —C(O)OH.

"cyano" means —CN.

"halogen" or "-halo" means —F, —Cl, —Br, or —I.

"Hetero" when used to describe a group means that 1, 2, 3, 4 or 5 carbon atoms in the group have been replaced by an atom independently selected from nitrogen, which can be quaternized, oxygen, and sulfur, including sulfoxide and sulfone. Hetero can be applied to, e.g., a —(C$_1$-C$_6$)alkyl group, representing —(C$_1$-C$_6$)heteroalkyl, or a —(C$_3$-C$_8$)cycloalkyl group, representing —(C$_3$-C$_8$)cycloheteroalkyl, or a —(C$_6$-C$_{14}$)aryl group, representing -(6- to 14-membered)heteroaryl, and the like. Particularly preferred are hetero groups having from 1 to 3 heteroatoms.

In connection with the Ar$_2$ group

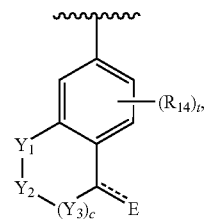

when E is —NH(C$_1$-C$_6$)alkyl it is to be understood that the dashed line in the above Ar$_2$ group is absent, i.e., the Ar$_2$ group is

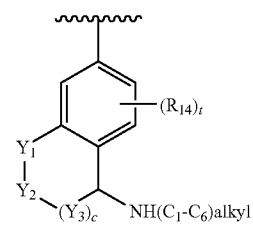

where Y$_1$, Y$_2$, Y$_3$, R$_{14}$, c and t are as defined above for compounds of formula I. When E is =O, =S, =CH(C$_1$-C$_5$)alkyl, =CH(C$_2$-C$_5$)alkenyl, or =N—OR$_{20}$, it is to be understood that the dashed line in the above Ar$_2$ group is present, i.e., the Ar$_2$ group is

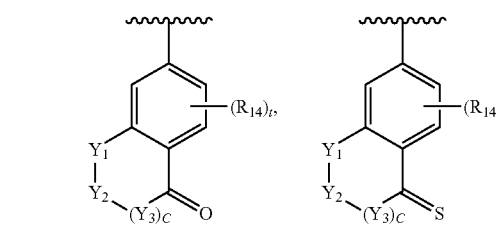

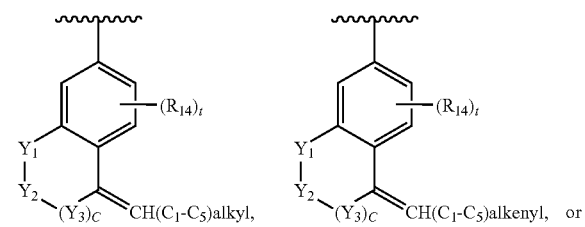

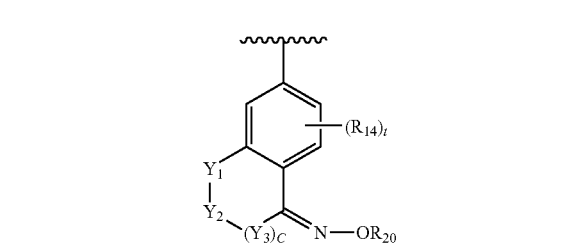

respectively, where Y$_1$, Y$_2$, Y$_3$, R$_{14}$, R$_{20}$, c and t are as defined above for compounds of formula I.

The term "pyridyl group" means

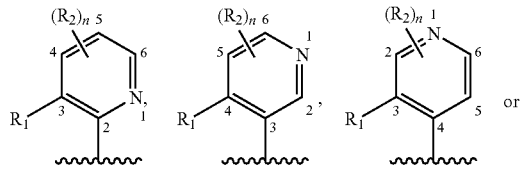

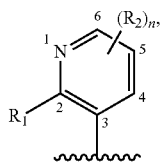

where $R_1$, $R_2$, and n are as defined above for compounds of formula I, and where the numbers designate the position of each atom in the ring.

The term "pyrazinyl group" means

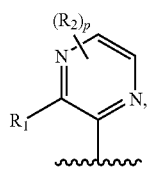

where $R_1$, $R_2$, and p are as defined above for compounds of formula I.

The term "pyrimidinyl group" means

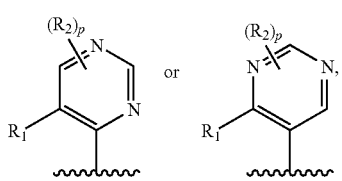

where $R_1$, $R_2$, and p are as defined above for compounds of formula I.

The term "pyridazinyl group" means

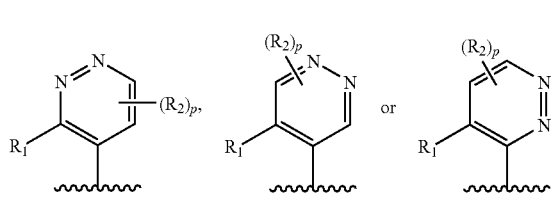

where $R_1$, $R_2$, and p are as defined above for compounds of formula I.

The term "benzoimidazolyl group" means

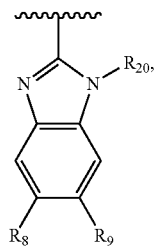

where $R_8$, $R_9$, and $R_{20}$ are as defined above for compounds of formula I.

The term "benzothiazolyl group" means

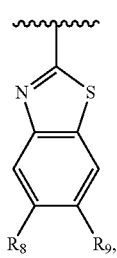

where $R_8$ and $R_9$ are as defined above for compounds of formula I.

The term "benzooxazolyl group" means

where $R_8$ and $R_9$ are as defined above for compounds of formula I.

The term phenyl group means

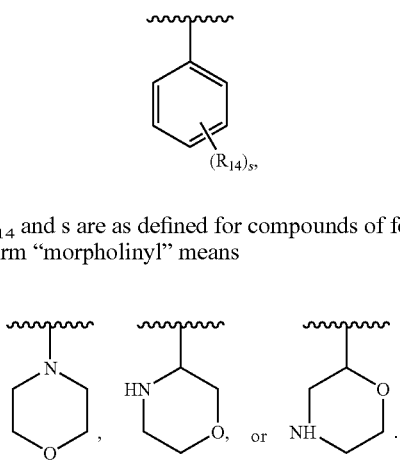

where $R_{14}$ and s are as defined for compounds of formula I.

The term "morpholinyl" means

In connection with the compounds of (73), the term "—CH$_2$-morpholino" means

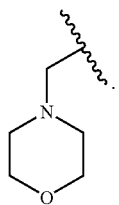 [SMILES: *CN1CCOCC1]

The term "animal," includes, but is not limited to, a cow, monkey, baboon, chimpanzee, horse, sheep, pig, chicken, turkey, quail, cat, dog, mouse, rat, rabbit, guinea pig, and human.

The term "pharmaceutically acceptable derivative," as used herein, includes any pharmaceutically acceptable salt, solvate, radiolabeled, stereoisomer, enantiomer, diastereomer, other stereoisomeric form, racemic mixture, geometric isomer, and/or tautomer, e.g., of a compound of formula I of the invention. In one embodiment, the pharmaceutically acceptable derivative is a pharmaceutically acceptable salt, solvate, radiolabeled, stereoisomer, enantiomer, diastereomer, other stereoisomeric form, racemic mixture, geometric isomer, and/or tautomer, e.g., of a compound of formula I of the invention. In another embodiment, the pharmaceutically acceptable derivative is a pharmaceutically acceptable salt, e.g., of a compound of formula I of the invention.

The term "pharmaceutically acceptable salt," as used herein, is any pharmaceutically acceptable salt that can be prepared from a compound of formula I including a salt formed from an acid and a basic functional group, such as a nitrogen group, of a compound of formula I. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound of formula I having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl,N-ethylamine; diethylamine; triethylamine; mono-, bis-, or tris-(2-hydroxy-(C$_1$-C$_3$)alkyl amines), such as mono-, bis-, or tris-(2-hydroxyethyl)amine, 2-hydroxy-tert-butylamine, or tris-(hydroxymethyl)methylamine, N,N-di-[(C$_1$-C$_3$)alkyl]-N-(hydroxy-(C$_1$-C$_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. One in the art will recognize that, e.g., acid addition salts of a compound of formula I can be prepared by reaction of the compounds with the appropriate acid by a variety of known methods.

Compounds of formula I encompass all solvates of compounds of formula I. "Solvates" are known in the art and are considered to be a combination, physical association and/or solvation of a compound of formula I with a solvent molecule, e.g., a disolvate, monosolvate or hemisolvate when the ratio of the solvent molecule to the molecule of the compound of formula I is 2:1, 1:1 or 1:2, respectively. This physical association involves varying degrees of ionic and covalent bonding, including hydrogen bonding. In certain instances, the solvate can be isolated, for example when one or more solvent molecules are incorporated into the crystal lattice of a crystalline solid. Thus, "solvate," as used herein, encompasses both solution-phase and isolatable solvates. A compound of formula I of the invention can be present as a solvated form with a pharmaceutically acceptable solvent, such as water, methanol, ethanol, and the like, and it is intended that the invention include both solvated and unsolvated compound of formula I forms. As "hydrate" relates to a particular subgroup of solvates, i.e., where the solvent molecule is water, hydrates are included within the solvates of the invention. Preparation of solvates is known in the art. For example, M. Caira et al., *J. Pharmaceut. Sci.*, 93(3):601-611 (2004), describes the preparation of solvates of fluconazole with ethyl acetate and with water. Similar preparations of solvates, hemisolvate, hydrates, and the like are described by E. C. van Tonder et al., *AAPS Pharm. Sci. Tech.*, 5(1), article 12 (2004), and A. L. Bingham et al., *Chem. Commun.*, 603-604 (2001). A typical, non-limiting, process involves dissolving the compound of formula I in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The invention disclosed herein is also meant to encompass all prodrugs of the compounds of the invention. "Prodrugs" are known in the art and, while not necessarily possessing any pharmaceutical activity as such, are considered to be any covalently bonded carrier(s) that releases the active parent drug in vivo. In general, such prodrugs will be a functional derivative of a compound of formula I, II and/or III which is readily convertible in vivo, e.g., by being metabolized, into the required compound of formula I, II and/or III. Conventional procedures for the selection and preparation of suitable prodrug derivatives are described in, for example, *Design of Prodrugs*, H. Bundgaard Ed., Elsevier (1985); "Drug and Enzyme Targeting, Part A," K. Widder et al. Eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard Eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984).

In addition, one or more hydrogen, carbon or other atoms of a compound of formula I can be replaced by an isotope of the hydrogen, carbon or other atoms. Compounds of formula I include all radiolabeled forms of compounds of formula I. Such a "radiolabeled," "radiolabeled form", and the like of a compound of formula I, each of which is encompassed by the invention, is useful as a research and/or diagnostic tool in metabolism pharmacokinetic studies and in binding assays. Examples of isotopes that can be incorporated into a compound of formula I of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Radiolabeled compounds of the invention can be prepared by methods known in the art. For example, tritiated compounds of formula I can be prepared by introducing tritium into the particular compound of formula I, for example, by catalytic dehalogenation with tritium. This method can include reacting a suitably halogen-substituted precursor of a compound of Formula I with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

A compound of formula I can contain one or more asymmetric centers and can thus give rise to enantiomers, diastereomers, conformers, rotamers, and other stereoisomeric forms. Compounds of formula I encompass all such possible forms as well as their racemic and resolved forms or any mixture thereof. When a compound of formula I contains an olefinic double bond or other center of geometric asymmetry, and unless specified otherwise, it is intended to include all "geometric isomers," e.g., both E and Z geometric isomers. All "tautomers," e.g., ketone-enol, amide-imidic acid, lactam-lactim, enamine-imine, amine-imine, and enamine-enimine tautomers, are intended to be encompassed by the invention as well.

As used herein, the terms "stereoisomer," "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule.

Stereoisomers, e.g., optical isomers, of a compound of formula I can be obtained by known techniques such as chiral chromatography or formation of diastereomeric salts from an optically active acid or base.

Stereoisomeric, e.g., optical, purity can be stated in terms of enantiomeric excess (% ee), which is determined by the formula:

$$\% \ ee \left[ \frac{\text{major enantiomer (mol)} - \text{minor enantiomer (mol)}}{\text{major enantiomer (mol)} + \text{minor enantiomer (mol)}} \right] \times 100$$

The term "effective amount," when used in connection with a compound of formula I means an amount effective for: (a) treating or preventing a Condition; or (b) detectably inhibiting TRPV1 receptor function in a cell.

The term "effective amount," when used in connection with a second therapeutic agent means an amount for providing the therapeutic effect of the therapeutic agent.

The term "therapeutic index," describes the gap between the dose that is effective, and the dose that induces adverse effects.

When a first group is "substituted" with one or more second groups, one or more hydrogen atoms of the first group are replaced with a corresponding number of second groups. When the number of second groups is two or greater, each second group can be the same or different. In one embodiment, the number of second groups is one or two. In another embodiment, the number of second groups is one. Typical substituents comprise, without intending to be exhaustive, —Y, —R$^{14}$, —O$^-$, =O, —OR$^{14}$, —SR$^{14}$, —S$^-$, =S, —NR$^{14}$, —NR$^{14}$R$^{15}$, —CY$_3$, —CF$_3$, —CN, —OCN, —SCN, —NO$_2$, =N$_2$, —N$_3$, —S(O)$_2$O$^-$, —S(O)$_2$OH, —S(O)$_2$R$^{14}$, —OS(O)$_2$O$^-$, —OS(O)$_2$R$^{14}$, —P(O)(O$^-$)$_2$, —P(O)(OR$^{14}$)(O$^-$), —OP(O)(OR$^{14}$)(OR$^{15}$), —C(O)R$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{14}$R$^{15}$ and —C(NR$^{16}$)NR$^{14}$R$^{15}$, where each Y is independently a halogen; each R$^{14}$ as defined for compounds of formula I; each R$^{15}$, R$^{16}$ and R$^{17}$ are independently hydrogen, or one of the substituted or unsubstituted groups listed in the following, e.g.: —(C$_2$-C$_6$) alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, —(C$_1$-C$_6$)alkoxy-(C$_1$-C$_6$)alkyl, -(5- to 10-membered)aryl, -(3- to 7-membered)heterocycle, —(C$_1$-C$_6$)heteroalkyl, -(5- to 10-membered)heteroaryl, —NR$^{18}$R$^{19}$, —C(O)R$^{18}$ or —S(O)$_2$R$^{18}$ or optionally R$^{18}$ and R$^{19}$ together with the atom to which they are both attached form a substituted or unsubstituted -(3- to 7-membered)heterocycle; and R$^{18}$ and R$^{19}$ are independently hydrogen, substituted or unsubstituted —(C$_2$-C$_6$) alkyl, substituted or unsubstituted -(5- to 10-membered)aryl, substituted or unsubstituted —(C$_3$-C$_8$)cycloalkyl, substituted or unsubstituted -(3- to 7-membered)heterocycle, substituted or unsubstituted —(C$_1$-C$_6$)heteroalkyl, substituted or unsubstituted -(5- to 10-membered)heteroaryl.

The term "EtOH" means ethanol, i.e., ethyl alcohol.
The term "t-BuOH" means tert-butyl alcohol, i.e., 2-methylpropan-2-ol.
The term "THF" means tetrahydrofuran.
The term "DMF" means N,N-dimethylformamide.
The term "TEA" means triethylamine.
The term "AcOH" means acetic acid.
The term "DMSO" means dimethylsulfoxide, i.e., methylsulfinylmethane.
The term "Bz" means benzyl, which is methylbenzene:

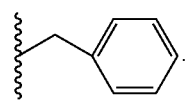

The term "DPPP" means 1,3-bis(diphenylphosphino)propane.

The term "BOC" means tert-butyloxycarbonyl:

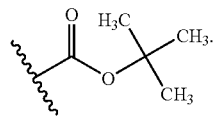

The term "TsOH" means p-toluenesulfonic acid or toluene-4-sulfonic acid.

The term "IBD" means inflammatory-bowel disease.

The term "IBS" means irritable-bowel syndrome.

The term "ALS" means amyotrophic lateral sclerosis.

The terms "treatment of," "treating" and the like include the amelioration or cessation of a Condition or a symptom thereof.

In one embodiment, treating includes inhibiting, for example, decreasing the overall frequency of episodes of a Condition or a symptom thereof.

The terms "prevention of," "preventing" and the like include the avoidance of the onset of a Condition or a symptom thereof.

4.6. Methods for Making the Compounds of the Invention

The compounds of the invention can be prepared from readily available starting materials using conventional organic synthesis methods and procedures known in the art and/or by the illustrative methods shown in the schemes below. Optimum reaction conditions can vary with the particular reactants or solvents used and such conditions can be determined by one in the art by routine optimization procedures. If desired, the product(s) can be isolated and purified by known standard procedures. Such procedures include, but are not limited to, recrystallization, column chromatography, thin-layer chromatography ("TLC"), preparative TLC, high pressure liquid chromatography ("HPLC") and/or preparative HPLC. If a single stereoisomer is desired, it is possible to use chiral separation techniques known in the art, such as chiral chromatography or chiral resolution, to isolate a single isomer or to use enantiomerically pure or enriched starting materials or enentioselective methods of synthesis.

Additionally, as will be apparent to those in the art, conventional protecting groups can be used to prevent certain functional groups from undergoing undesired reactions. The choice of a suitable protecting group(s) for a particular functional group as well as suitable conditions for protection and deprotection are well known in the art. For example, numerous protecting groups and their introduction and removal are described in T. W. Greene and P. G. M. Wuts, *Protecting Groups in Organic Synthesis*, 2$^{nd}$ Edition, Wiley, New York, 1991, and the references cited therein.

Procedures for obtaining compounds of the invention can be derived by appropriately modifying in view of the present disclosure the methods disclosed in, for example, U.S. Patent Application Publication Nos. US 2005/0165032 A1 and US 2005/0215572 A1, the entire disclosure of each of which is incorporated herein by reference in its entirety. In addition, U.S. Patent Application Publication No. US 2009/0170868 A1, the entire disclosure of which is incorporated herein by reference in its entirety, describes the synthesis of various Q-groups according to the invention.

In the following schemes, the Q group is typically depicted as 1,2-dihydroxyethyl for illustrative purposes only. However, any other Q group substituent as described in the invention can also be used. The exemplary 1,2-dihydroxyethyl group may be shown with only one stereochemical configuration. However any configuration selected from (S), (R), or a mixture thereof is possible. Methods for stereoselective synthesis are described in the examples below.

4.6.1. Methods for Making Compounds of Formula I where $A_1$ and $A_3$ are N, $A_2$ is $C(R_3)$, and the Dashed Lines are Absent The compounds of formula I where $A_1$ and $A_3$ are each nitrogen, $A_2$ is $C(R_3)$ and the dashed lines are absent can be made using conventional organic synthesis and/or by the illustrative methods shown in Schemes 1-5 below.

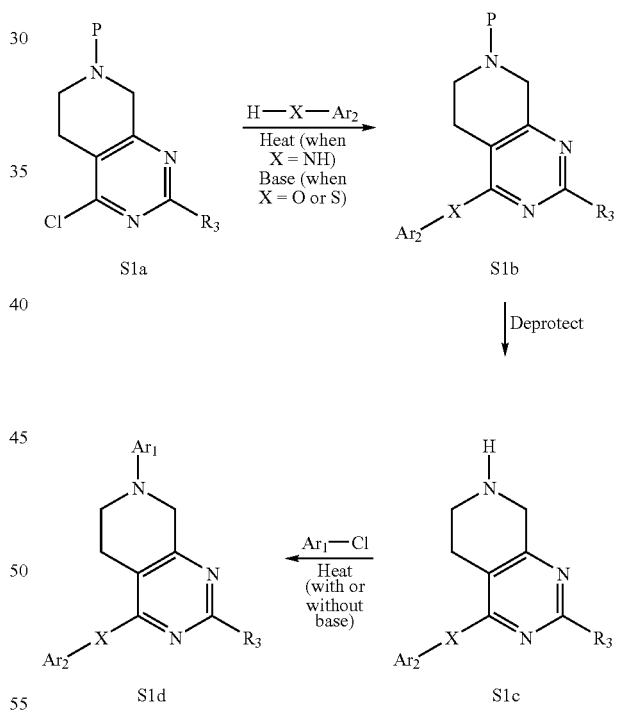

Scheme 1 where $Ar_1$, $Ar_2$, $R_3$ and X are defined above and P is an N-protecting group.

Compound S1a can be reacted with H—X—$Ar_2$ to provide compound S1b. If necessary, the reaction can be carried out in the presence of a base and/or heat. The protecting group P can be removed by methods known to those in the art. In a subsequent reaction step, the $Ar_1$ group can be attached to compound S1c to provide compound S1d.

Scheme 2

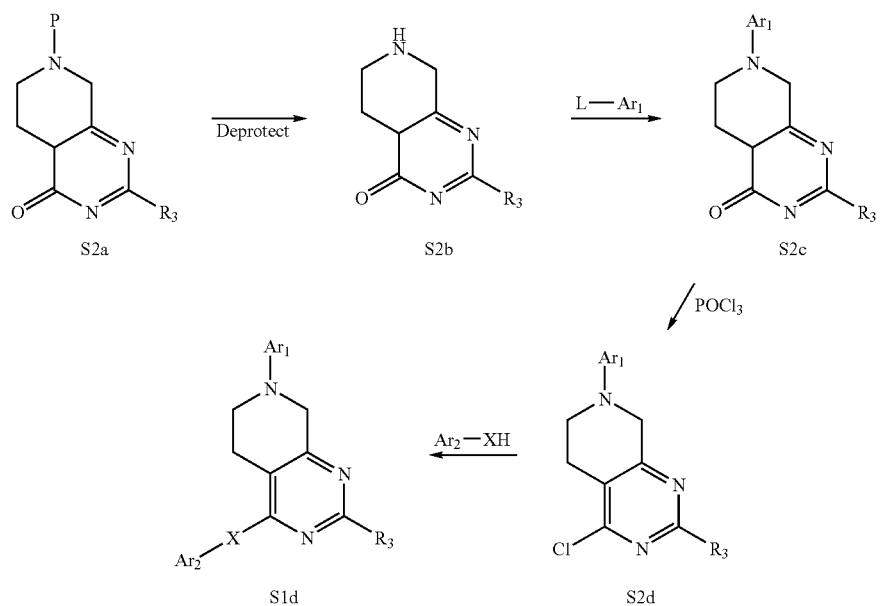

where $Ar_1$, $Ar_2$, $R_3$ and X are defined above, P is an N-protecting group, and L is Cl, Br or I.

N-protected with, e.g., benzyl, compound S2a can be deprotected by methods known in the art to provide the deprotected amine compound S2b. In a subsequent reaction, compound S2b can be reacted with, e.g., a chlorine-substituted $Ar_1$ group, such as:

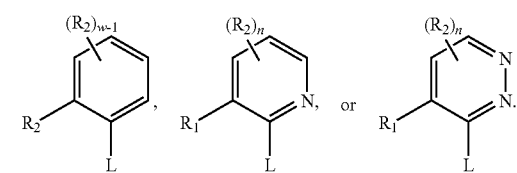

The resulting compound S2c can be reacted with $POCl_3$ to provide compound S2d, which can further be reacted with $Ar_2$—XH to form compound S1d. Furthermore, preferred $R_3$ groups for the synthetic procedure described in Scheme 2 are, e.g., —H, —($C_1$-$C_6$)alkyl and the like.

Scheme 3

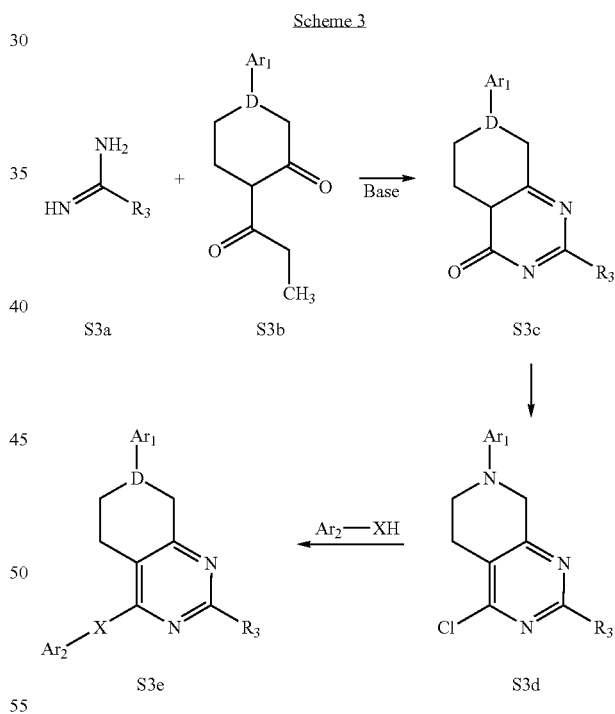

where $Ar_1$, $Ar_2$, $R_3$ and X are defined above and D is N or $C(R_D)$.

Formamidine compound S3a can be reacted with compound S3b in the presence of a base to provide the bicyclic compound S3c. Compound S3c can be converted to the chlorine containing compound S3d by reaction with $POCl_3$. In a final step, the X—$Ar_2$ group can be attached to the compound by reacting compound S3d with $Ar_2$—XH to provide compound S3e. Furthermore, preferred $R_3$ groups for the synthetic procedure described in Scheme 3 are, e.g., —H, —($C_1$-$C_6$)alkyl and the like.

Scheme 4

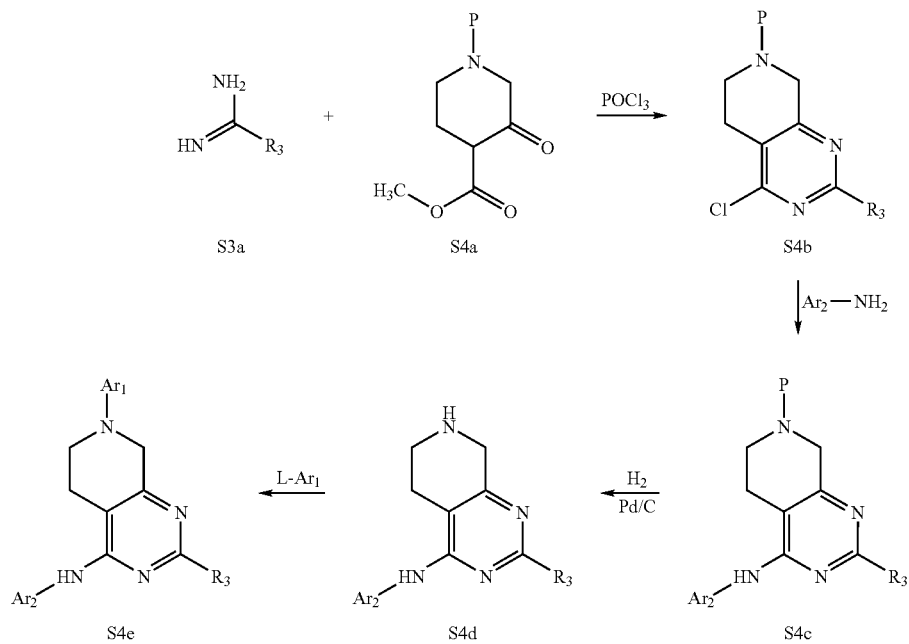

where $Ar_1$, $Ar_2$ and $R_3$ are defined above, P is an N-protecting group, and L is Cl, Br or I.

In the reaction sequence described in Scheme 4, the bicyclic ring system can be built up in a manner similar to Scheme 3. Formamidine compound S3a can be reacted with compound S4a and the product further reacted with POCl$_3$ to provide compound S4b. In a subsequent reaction step, an Ar$_2$NH— group can be attached to the ring system by reacting compound S4b with Ar$_2$—NH$_2$ to provide compound S4c. The N-protecting group, e.g., benzyl, can be removed from compound S4c by reaction with Pd/C and H$_2$ by methods known in the art to provide compound S4d. Finally, the Ar$_1$ group can be attached to compound S4d using, e.g., a chlorine-substituted Ar$_1$ group, such as:

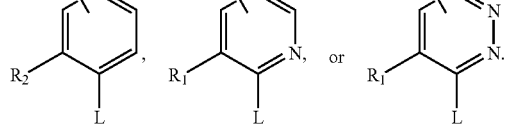

to provide compound S4e. Furthermore, preferred R$_3$ groups for the synthetic procedure described in Scheme 4 are, e.g., —H, —(C$_1$-C$_6$)alkyl, —(C$_1$-C$_6$)alkoxy, —O—(C$_1$-C$_6$)alkyl-OH, in particular —O—C$_2$H$_4$—OH, —O—(C$_1$-C$_6$)alkyl-COOH, in particular —O—C$_2$H$_4$—COOH, —O—(C$_1$-C$_6$)alkyl-S(O)$_2$CH$_3$ in particular —O—C$_2$H$_4$—S(O)$_2$CH$_3$, and —O—(C$_1$-C$_6$)alkyl-(3- to 7-membered)heterocycle, in particular —O—C$_2$H$_4$-morpholinyl.

Scheme 5

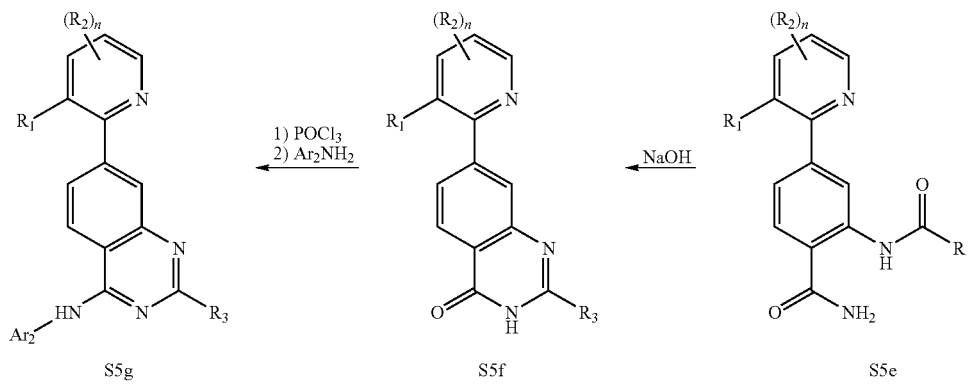

where $Ar_2$, $R_1$, $R_2$, $R_3$ and n are defined above and L is Cl, Br or I.

In Scheme 5, the synthesis of compounds where D is carbon and the dashed lines are present as part of double bonds is described. In a first step, the $Ar_1$ group, for example pyridyl compound S5b, can be reacted with compound S5a to provide compound S5c. Compound S5c can be converted to compound S5d by reaction with nitric acid followed by reduction. Compound S5d can be reacted with a suitable acyl compound to provide compound S5e. Compound S5e can then be cyclized to compound S5f. In a final reaction step, compound S5f is activated and reacted with $Ar_2NH_2$ to provide compound S5g. The $Ar_1$ group illustrated in Scheme 5 comprises a pyridyl ring; however, this example is provided for illustrative purposes only and shall not be construed to limit the scope of the invention. Similar techniques can be used when $Ar_1$ comprises a phenyl, pyrimidinyl, pyrazinyl or pyridazinyl ring.

4.6.2. Methods for Attaching an $R_2$ Group to $Ar_1$ when $R_2$ is Q

It can sometimes be advantageous to attach a Q-group to the $Ar_1$ group in a separate reaction step after the core molecule has been built up. As an example, the formation of a 1,2-dihydroxyethyl group on a 2-pyridyl substituent as the $Ar_1$ group is described, below. However, this example is provided for illustrative purposes only and shall not be construed to limit the scope of the invention.

The conversion of a halide (L) to a vinyl group by a Suzuki cross-coupling reaction is described in Scheme 6 below. While in Scheme 6 the conversion is illustrated for $Ar_1$ groups when L is in the 5-position of the pyridyl ring of compound S6a, the reaction can also be carried out when L is in other positions on any of the other $Ar_1$ aryl or heteroaryl ring as well. Thus, the same technique can be used when $Ar_1$ comprises a phenyl, pyrimidinyl, pyrazinyl or pyridazinyl ring.

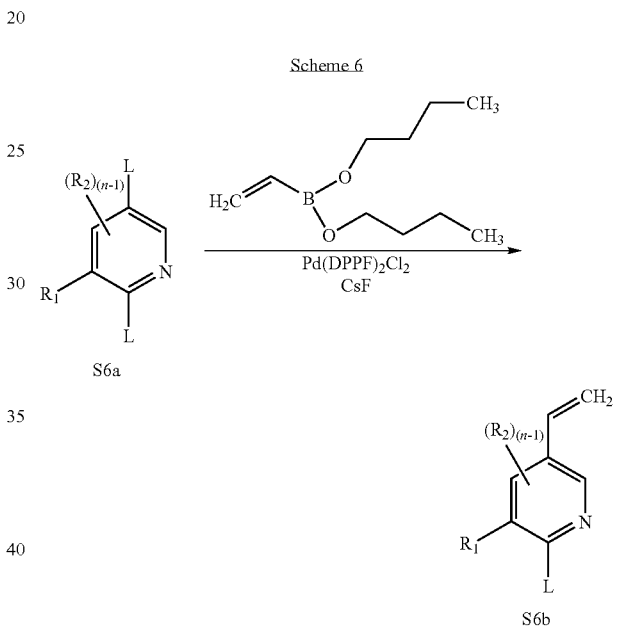

where $R_1$, $R_2$ and n are defined above and each L is independently Cl, Br or I.

In Scheme 6 where L is Cl, Br or I, compound S6a can be reacted with a di-n-butyl boronic ester in the presence of palladium diphenylphosphinoferrocene dichloride (Pd (DPPF)$_2$Cl$_2$) and CsF in a suitable solvent. The reaction mixture can then be reacted at elevated temperatures for a suitable time period and the expected product can be separated by conventional methods known to one in the art, such as column chromatography, to provide compound S6b.

Other suitable techniques for attaching a vinyl group are shown in Schemes 7 and 8. In Scheme 7, the first step can involve the oxidation of a benzylic alcohol to the corresponding aldehyde. This can be followed by a Wittig olefination to yield the vinyl group. Once again, while the starting benzylic alcohol illustrated is substituted in the 5-position of a pyridyl ring, similar reactions can be carried out when that alcohol is substituted at other positions of the aryl or heteroaryl ring. Moreover, the same technique can be used when $Ar_1$ comprises a phenyl, pyrimidinyl, pyrazinyl or pyridazinyl ring.

Scheme 7

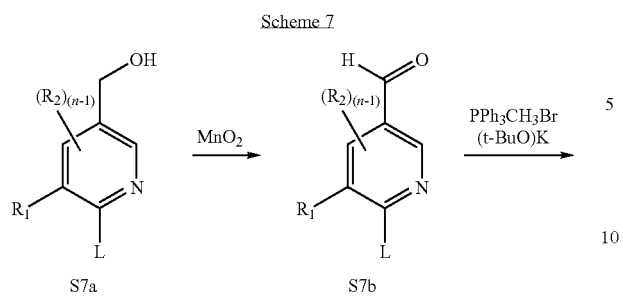

where $R_1$, $R_2$ and n are defined above and L is Cl, Br or I.

Manganese oxide can be added to a solution of compound S7a in a suitable solvent such as $CH_2Cl_2$. The resulting mixture can be stirred at a temperature of about 25° C. Product compound S7b can be separated by filtration and subsequent column chromatography.

To a cooled slurry of methyltriphenylphosphonium bromide in a suitable solvent such as toluene, potassium t-butoxide can be added. After stirring for 1-5 h at a temperature of about 25° C., the reaction mixture can be cooled to about −20° C. Thereafter, compound S7b dissolved in tetrahydrofuran can be added dropwise to the slurry. The reaction mixture is allowed to warm to about 0° C. and stirred for additional 1 hr. The resulting product can be worked up following standard procedures and can optionally be purified by column chromatography to provide compound S6b.

In Scheme 8, the first reaction step involves the reduction of a benzylic ketone to a hydroxyl. This can be followed by a dehydration reaction to yield a vinyl group.

Once again, while in Scheme 8 the starting benzylic ketone illustrated is substituted in the 5-position of a pyridyl ring, similar reactions can be carried out when the substitution is at other positions of the aryl or heteroaryl ring. Moreover, the same technique can be used when $Ar_1$ comprises a phenyl, pyrimidinyl, pyrazinyl or pyridazinyl ring.

Scheme 8

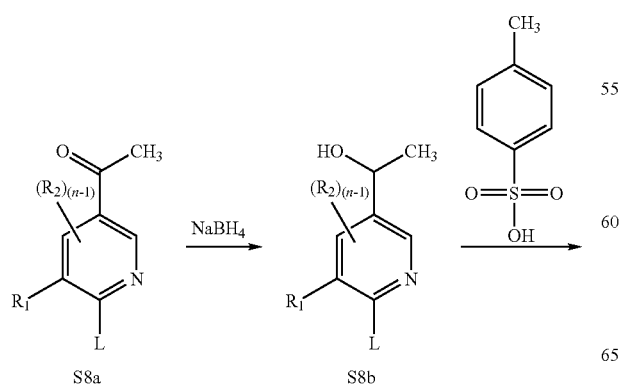

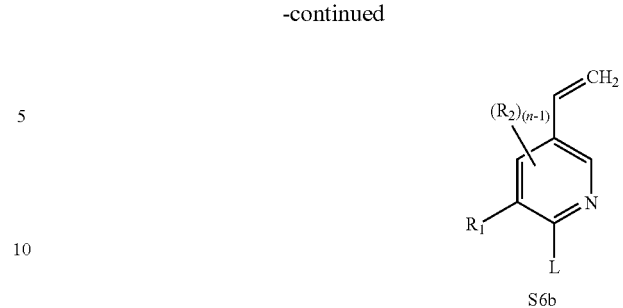

where $R_1$, $R_2$ and n are defined above and L is Cl, Br or I.

To a suspension of compound S8a at 0° C. in a suitable solvent, such as methanol, sodium borohydride can be added portionwise at a rate such that the reaction mixture temperature does not exceed 5° C. Subsequently, the reaction mixture can be stirred an additional 1 h at a temperature of about 25° C. The reaction mixture can be worked up following standard procedures, such as extraction and optionally purification by column chromatography, to provide compound S8b.

To a solution of compound S8b in a suitable solvent such as chlorobenzene can be added p-toluene sulfonic acid. The reaction mixture can be heated to reflux and water can be removed concurrently. At the completion of the reaction, the mixture is concentrated and extracted following standard procedures. Optionally, product compound S6b can then be purified, e.g., by column chromatography.

Vinyl groups are highly versatile, because they are a synthetic "handle" that can be further modified. For example, it is well known in synthetic organic chemistry that olefin hydrolysis provides a benzylic hydroxyl group, hydroboration gives a primary hydroxyl group, ozonolysis gives an aldehyde or ketone, oxidation gives a carboxylic acid, olefin metathesis extends the chain, and dihydroxylation gives a 1,2-diol. Many additional olefin functionalization techniques are available to those skilled in organic synthesis. Once functionalized, the group can undergo further reaction(s). In Scheme 9 an asymmetric dihydroxylation of the vinyl group is described.

Scheme 9

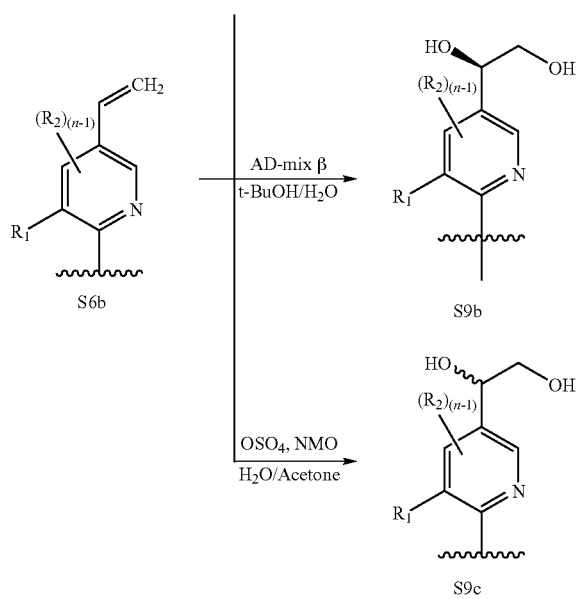

where R₁, R₂ and n are defined above.

A vinyl compound, e.g., the exemplary but non-limiting pyridyl compound S6b, can be reacted with AD-mix α (alpha) to provide compound S9a. As described in Scheme 9, the stereochemistry (R or S) of the resulting diol is dependent upon the chirality of the ligand used in the AD mix as described in Sharpless et al., *J. Org. Chem.* 57:2768-2771 (1992). AD-mix is composed of the following components: potassium osmate (K₂OsO₂(OH)₄), potassium ferricyanide (K₃Fe(CN)₆), potassium carbonate (K₂CO₃), and the chiral ligands shown in Scheme 10. The reaction of vinyl compounds with AD-mix is described in, e.g., U.S. Patent Application Publication No. US 2009/0170868 A1.

The other enantiomer S9b can be synthesized by the reaction of the vinyl compound S6b and AD-mix β (beta).

The racemic diol, compound S9c, can be synthesized by methods known in the art, e.g., reacting with osmium tetroxide (OsO₄) and N-methyl morpholine N-oxide (NMO) in an aqueous acetone solution.

Scheme 10

Ligand for AD-mix α:

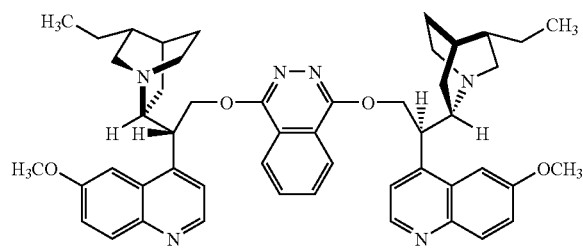

Ligand for AD-mix β:

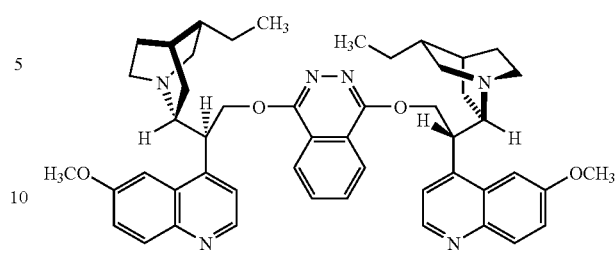

4.7. Therapeutic Uses of Compounds of Formula I

In accordance with the invention, the compounds of formula I are administered to an animal in need of treatment or prevention of a Condition.

In one embodiment, an effective amount of a compound of formula I can be used to treat or prevent any condition treatable or preventable by inhibiting TRPV1. Examples of Conditions that are treatable or preventable by inhibiting TRPV1 include, but are not limited to, pain, UI, an ulcer, IBD, and IBS.

The compounds of formula I, or a pharmaceutically acceptable derivative thereof, can be used to treat or prevent acute or chronic pain. Examples of pain treatable or preventable using the compounds of formula I include, but are not limited to, cancer pain, labor pain, myocardial infarction pain, pancreatic pain, colic pain, post-operative pain, headache pain, muscle pain, arthritic pain, and pain associated with a periodontal disease, including gingivitis and periodontitis.

The compounds of formula I, or a pharmaceutically acceptable derivative thereof, can also be used for treating or preventing pain associated with inflammation or with an inflammatory disease in an animal. Such pain can arise where there is an inflammation of the body tissue which can be a local inflammatory response and/or a systemic inflammation. For example, the compounds of formula I can be used to treat or prevent pain associated with inflammatory diseases including, but not limited to: organ transplant rejection; reoxygenation injury resulting from organ transplantation (see Grupp et al., *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The compounds of formula I can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The compounds of formula I, or a pharmaceutically acceptable derivative thereof, can be used to treat or prevent UI. Examples of UI treatable or preventable using the compounds of formula I include, but are not limited to, urge incontinence, stress incontinence, overflow incontinence, neurogenic incontinence, and total incontinence.

The compounds of formula I, or a pharmaceutically acceptable derivative thereof, can be used to treat or prevent an ulcer. Examples of ulcers treatable or preventable using the compounds of formula I include, but are not limited to, a duodenal ulcer, a gastric ulcer, a marginal ulcer, an esophageal ulcer, or a stress ulcer.

The compounds of formula I, or a pharmaceutically acceptable derivative thereof, can be used to treat or prevent IBD, including Crohn's disease and ulcerative colitis.

The compounds of formula I, or a pharmaceutically acceptable derivative thereof, can be used to treat or prevent IBS. Examples of IBS treatable or preventable using the compounds of formula I include, but are not limited to, spastic-colon-type IBS and constipation-predominant IBS.

Applicants believe that the compounds of formula I, or a pharmaceutically acceptable derivative thereof, are antagonists for TRPV1.

The invention also relates to methods for inhibiting TRPV1 function in a cell comprising contacting a cell capable of expressing TRPV1 with an effective amount of a compound of formula I, or a pharmaceutically acceptable derivative thereof. This method can be used in vitro, for example, as an assay to select cells that express TRPV1 and, accordingly, are useful as part of an assay to select compounds useful for treating or preventing pain, UI, an ulcer, IBD, or IBS. In another embodiment, the invention relates to an in vitro method for inhibiting TRPV1 function in a cell comprising contacting a cell expressing TRPV1 in vitro with a compound of formula I, or a pharmaceutically acceptable derivative thereof, in an amount sufficient to reduce calcium ion mobilization into a cell treated with an activator of TRPV1 as compared to a cell expressing TRPV1 in vitro treated with an activator of TRPV1 and not contacted with the compound. In another embodiment, the calcium ion mobilization is reduced by 50% or more.

The method is also useful for inhibiting TRPV1 function in a cell in vivo, in an animal, a human in one embodiment, by contacting a cell, in an animal, with an effective amount of a compound of formula I, or a pharmaceutically acceptable derivative thereof. In another embodiment, the invention relates to an in vivo method for inhibiting TRPV1 function in a cell comprising contacting a cell expressing TRPV1 in vivo with a compound of formula I, or a pharmaceutically acceptable derivative thereof, where the compound is capable, in an in vitro assay, of reducing calcium ion mobilization into a cell expressing TRPV1 and treated with an activator of TRPV1 by 50% or more as compared to a cell expressing TRPV1 treated with an activator of TRPV1 and not contacted with the compound. In another embodiment, the invention relates to an in vivo method for inhibiting TRPV1 function in a cell comprising contacting a cell expressing TRPV1 in vivo with a compound of formula I, or a pharmaceutically acceptable derivative thereof, where the compound is capable of reducing pain as or more effectively than a similar dose of one or more of the positive control analgesics celecoxib, indomethacin or naproxen, as measured by one or more of the in vivo pain tests consisting of an acute pain test, an inflammatory pain test, a neuropathic pain test, a mechanical stimuli pain test, a thermal stimuli pain test, or a tactile allodynia test.

In another embodiment, the method is useful for treating or preventing pain in an animal. In another embodiment, the invention relates to a method of treating pain in an animal, comprising administering to an animal in need of treatment for pain a compound of formula I, or a pharmaceutically acceptable derivative thereof, in an amount from 0.01 mg/kg body weight to 2500 mg/kg body weight where the compound is capable of reducing pain as or more effectively than a similar dose of one or more of the positive control analgesics celecoxib, indomethacin, or naproxen, as measured by one or more of the in vivo pain tests consisting of an acute pain test, an inflammatory pain test, a neuropathic pain test, a mechanical stimuli pain test, a thermal stimuli pain test, or a tactile allodynia test. In another embodiment, the method is useful for treating or preventing UI in an animal. In another embodiment, the method is useful for treating or preventing an ulcer in an animal. In another embodiment, the method is useful for treating or preventing IBD in an animal. In another embodiment, the method is useful for treating or preventing IBS in an animal.

Examples of tissue comprising cells capable of expressing TRPV1 include, but are not limited to, neuronal, brain, kidney, urothelium, and bladder tissue. Methods for assaying cells that express TRPV1 are known in the art.

4.8. Therapeutic/Prophylatic Administration and Composition of the Invention Due to their activity, compounds of formula I, or a pharmaceutically acceptable derivative thereof, are advantageously useful in veterinary and human medicine. As described above, compounds of formula I, or a pharmaceutically acceptable derivative thereof, are useful for treating or preventing a Condition.

When administered to an animal, compounds of formula I, or a pharmaceutically acceptable derivative thereof, are typically administered as a component of a composition that comprises a pharmaceutically acceptable carrier or excipient. The compositions, which comprise a compound of formula I, or a pharmaceutically acceptable derivative thereof, can be administered orally. Compounds of formula I, or a pharmaceutically acceptable derivative thereof, can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer the compound of formula I, or a pharmaceutically acceptable derivative thereof.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of compounds of formula I, or a pharmaceutically acceptable derivative thereof, into the bloodstream.

In specific embodiments, it can be desirable to administer the compounds of formula I, or a pharmaceutically acceptable derivative thereof, locally. This can be achieved, for example, and not by way of limitation, by local infusion during surgery, topical application, e.g., in conjunction with a wound dressing after surgery, by injection, by means of a catheter, by means of a suppository or enema, or by means of an implant, the implant being of a porous, non-porous, or gelatinous material, including membranes, such as sialastic membranes, or fibers.

In certain embodiments, it can be desirable to introduce the compounds of formula I, or a pharmaceutically acceptable derivative thereof, into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or by perfusion in a fluorocarbon or synthetic pulmonary surfactant. In certain embodiments, the compounds of formula I can be formulated as a suppository, with traditional binders and excipients such as triglycerides.

In another embodiment, the compounds of formula I, or a pharmaceutically acceptable derivative thereof, can be delivered in a vesicle, in particular a liposome (see Langer, *Science* 249:1527-1533 (1990) and Treat et al., *Liposomes in the Therapy of Infectious Disease and Cancer* 317-327 and 353-365 (1989)).

In yet another embodiment, the compounds of formula I, or a pharmaceutically acceptable derivative thereof, can be delivered in a controlled-release system or sustained-release system (see, e.g., Goodson, in Medical Applications of Controlled Release, supra, vol. 2, pp. 115-138 (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise Eds., 1974); *Controlled Drug Bioavailability, Drug Product Design and Performance* (Smolen and Ball Eds., 1984); Langer and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of the compounds of formula I, e.g., the spinal column, brain, or gastrointestinal tract, thus requiring only a fraction of the systemic dose.

The compositions can optionally comprise a suitable amount of a pharmaceutically acceptable excipient so as to provide the form for proper administration to the animal.

Such pharmaceutical excipients, can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Water is a particularly useful excipient when the compound of formula I is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The compositions, if desired, can also contain minor amounts of wetting or emulsifying agents, or can contain pH buffering agents.

The compositions can take the form of solutions, suspensions, emulsion, tablets, pills, pellets, multiparticulates, capsules, capsules containing liquids, powders, multiparticulates, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sciences* 1447-1676 (A. R. Gennaro Ed., 19th Ed. 1995), incorporated herein by reference.

In one embodiment, the compounds of formula I, or a pharmaceutically acceptable derivative thereof, are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, powdered or microcrystalline cellulose, cellulose derivatives, dibasic calcium hydrogen phosphate, colloidal silicon dioxide, magnesium carbonate, and other substances known from the pharmaceutical literature such as further lubricants, glidants, colorants, surfactants or flavors. In one embodiment, the excipients are of pharmaceutical grade.

The compounds of formula I, or a pharmaceutically acceptable derivative thereof, can be administered by controlled-release or sustained-release means or by delivery devices that are known to those in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained release counterparts. In one embodiment, a controlled- or sustained-release composition comprises a minimal amount of a compound of formula I to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the compound of formula I, and can thus reduce the occurrence of adverse side effects.

Controlled- or sustained-release compositions can be designed to immediately release an amount of a compound of formula I, or a pharmaceutically acceptable derivative thereof, that promptly produces the desired therapeutic or prophylactic effect, and gradually and continually release other amounts of the compound of formula I to maintain this level of therapeutic or prophylactic effect over an extended period of time. To maintain a constant level of the compound of formula I in the body, the compound of formula I can be released from the dosage form at a rate that will replace the amount of compound of formula I being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

In another embodiment, the compounds of formula I, or a pharmaceutically acceptable derivative thereof, can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compounds of formula I are to be administered by infusion, they can be dispensed, for example, with an infusion bottle containing sterile pharmaceutical grade water or saline. Where the compounds of formula I, or a pharmaceutically acceptable derivative thereof, are administered by injection, an ampoule of sterile water for injection or saline can be provided so that the ingredients can be mixed prior to administration.

The amount of the compound of formula I, or a pharmaceutically acceptable derivative thereof that is effective in the treatment or prevention of a Condition can be determined by standard clinical techniques. In addition, in vitro or in vivo assays can optionally be employed to help identify optimal dosage ranges. The precise dose to be employed will also depend on the route of administration and the seriousness of the Condition and can be decided according to the judgment of a practitioner and/or each animal's circumstances. Suitable effective dosage amounts, however, will typically range from about 0.01 mg/kg of body weight to about 2500 mg/kg of body weight, although they are typically about 100 mg/kg of body weight or less. In one embodiment, the effective dosage amount ranges from about 0.01 mg/kg of body weight to about 100 mg/kg of body weight of a compound of formula I; in another embodiment, about 0.02 mg/kg of body weight to about 50 mg/kg of body weight; and in another embodiment, about 0.025 mg/kg of body weight to about 20 mg/kg of body weight.

In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated.

The effective dosage amounts described herein refer to total amounts administered; that is, if more than one compound of formula I, or a pharmaceutically acceptable derivative thereof, is administered, the effective dosage amounts correspond to the total amount administered.

Where a cell capable of expressing TRPV1 is contacted with a compound of formula I in vitro, the amount effective for inhibiting the TRPV1 receptor function in a cell will typically range from about 0.01 µg/L to about 5 mg/L; in one embodiment, from about 0.01 µg/L to about 2.5 mg/L; in another embodiment, from about 0.01 µg/L to about 0.5 mg/L; and in another embodiment, from about 0.01 µg/L to about 0.25 mg/L, of a solution or suspension of a pharmaceutically acceptable carrier or excipient. In one embodiment, the volume of solution or suspension comprising the compound of formula I, or a pharmaceutically acceptable derivative thereof, is from about 0.01 µL to about 1 mL. In another embodiment, the volume of solution or suspension is about 200 µL.

The compounds of formula I, or a pharmaceutically acceptable derivative thereof, can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise co-administering to the animal being administered a compound of formula I, or a pharmaceutically acceptable derivative thereof (i.e., a first therapeutic agent), a second therapeutic agent. In one embodiment, the second therapeutic agent is administered in an effective amount.

An effective amount of the second therapeutic agent will be known to those in the art depending on the agent. However, it is well within the artisan's purview to determine the second therapeutic agent's optimal effective-amount range. A compound of formula I, or a pharmaceutically acceptable derivative thereof, and the second therapeutic agent combined can act either additively or synergistically to treat the same Condition, or they may act independently of each other such that the compound of formula I, or a pharmaceutically acceptable derivative thereof, treats or prevents a first Condition and the second therapeutic agent treats or prevents a second disorder, which can be the same as the first Condition or another disorder. In one embodiment of the invention, where a second therapeutic agent is administered to an animal for treatment of a Condition (e.g., pain), the minimal effective amount of the compound of formula I, or a pharmaceutically acceptable derivative thereof, will be less than its minimal effective amount would be where the second therapeutic agent is not administered. In this embodiment, the compound of formula I, or a pharmaceutically acceptable derivative thereof, and the second therapeutic agent can act synergistically to treat or prevent a Condition. In one embodiment, a compound of formula I, or a pharmaceutically acceptable derivative thereof, is administered concurrently with a second therapeutic agent as a single composition comprising an effective amount of a compound of formula I, or a pharmaceutically acceptable derivative thereof, and an effective amount of the second therapeutic agent. Alternatively, a composition comprising an effective amount of a compound of formula I, or a pharmaceutically acceptable derivative thereof, and a second composition comprising an effective amount of the second therapeutic agent are concurrently administered. In another embodiment, an effective amount of a compound of formula I, or a pharmaceutically acceptable derivative thereof, is administered prior or subsequent to administration of an effective amount of the second therapeutic agent. In this embodiment, the compound of formula I, or a pharmaceutically acceptable derivative thereof, is administered while the second therapeutic agent exerts its therapeutic effect, or the second therapeutic agent is administered while the compound of formula I, or a pharmaceutically acceptable derivative thereof, exerts its therapeutic effect for treating or preventing a Condition.

The second therapeutic agent can be, but is not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflunisal, flufenisal, piroxicam, sudoxicam, isoxicam, and pharmaceutically acceptable derivatives thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see P. A. Insel, *Analgesic-Antipyretic and Anti-inflammatory Agents and Drugs Employed in the Treatment of Gout*, in *Goodman & Gilman's The Pharmacological Basis of Therapeutics* 617-57 (P. B. Molinhoff and R. W. Ruddon Eds., 9th Ed. 1996) and G. R. Hanson, *Analgesic, Antipyretic and Anti-Inflammatory Drugs* in *Remington: The Science and Practice of Pharmacy Vol II* 1196-1221 (A. R. Gennaro Ed., 19th Ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

The second therapeutic agent can also be an agent useful for reducing any potential side effects of a compound of formula I. For example, the second therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; foteniustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazie; mesalamine; prednisone; azathioprine; mercaptopurine; and methotrexate.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsaprione, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrignine, phenobarbital, phenytoin, primidone, valproic acid, trimethadione, bemzodiaepines, gabapentin, lamotrigine, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a seizure include, but are not limited to, carbamazepine, ethosuximide, gabapentin, lamotrignine, phenobarbital, phenytoin, primidone, valproic acid, trimethadione, bemzodiaepines, gabapentin, lamotrigine, GABA, acetazolamide, and felbamate.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-$HT_3$ receptor antagonists such as ondansetron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotilinr, nefazadone, nortriptyline, protriptyline, trazodone, trimipramine, and venlaflaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A composition of the invention is prepared by a method comprising admixing a compound of formula I, or a pharmaceutically acceptable derivative thereof, with a pharmaceutically acceptable carrier or excipient. Admixing can be accomplished using methods known for admixing a compound (or derivative) and a pharmaceutically acceptable carrier or excipient. In one embodiment, the compound of formula I, or a pharmaceutically acceptable derivative thereof, is present in the composition in an effective amount.

4.9. Kits

The invention further encompasses kits that can simplify the handling and administration of a compound of formula I, or a pharmaceutically acceptable derivative thereof, to an animal.

A typical kit of the invention comprises a unit dosage form of a compound of formula I. In one embodiment, the unit dosage form is a container, which can be sterile, containing an effective amount of a compound of formula I and a pharmaceutically acceptable carrier or excipient. The kit can further comprise a label or printed instructions instructing the use of the compound of formula I to treat a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a compound of formula I, an effective amount of a second therapeutic agent and a pharmaceutically acceptable carrier or excipient. Examples of second therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, which would be within the purview of those in the art, and changes in formulation or minor changes in experimental design, are to be considered to fall within the scope of the invention incorporated herein.

5. EXAMPLES

The following examples illustrate various aspects of the invention, and are not to be construed to limit the claims in any manner whatsoever.

5.1. Example 1

Stereoselective Synthesis of Aromatic, Chiral Diol Compounds

The stereoselective synthesis of aromatic, chiral diol compounds (see in particular Schemes 6 to 9) is important. For the stereoselective synthesis, a vinyl substituted aromatic ring can be used as intermediate. The aromatic ring can also be heteroaromatic, containing one or more nitrogen atoms.

This approach is illustrated by the synthesis of (S)-1-(5,6-dichloropyridin-3-yl)ethane-1,2-diol and (R)-1-(5,6-dichloropyridin-3-yl)ethane-1,2-diol.

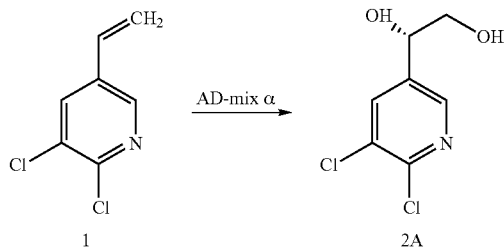

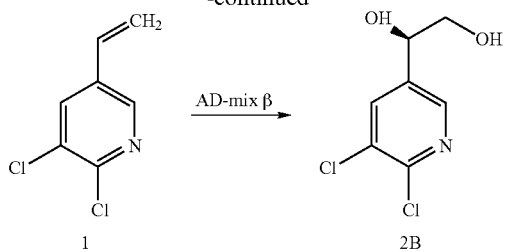

To a stirred slurry of AD-mix α (8.95 g) or AD-mix β (8.95 g) in water (32 mL) and tert-butyl alcohol (27 mL) at 0° C. was added a solution of 1 (0.909 g, 5.25 mmol) in tert-butyl alcohol (5 mL). After 24 hrs, solid sodium sulfite (9.57 g) was added and the resulting slurry was allowed to stir at a temperature of about 25° C. for 30 min. The mixture was extracted three times with ethyl acetate (50 mL for each extraction). The organic portions were combined, washed with brine, dried ($Na_2SO_4$), and concentrated under reduced pressure. The mixture was chromatographed by a silica gel chromatography column eluting with ethyl acetate (50%-100%)/hexanes to provide 0.75 g of product (2A for AD-mix α or 2B for AD-mix β) as a white solid (70% yield). $^1$H NMR (400 MHz, $CDCl_3$) δ 8.29 (1H, dd, J=0.44, 1.97 Hz), 7.87 (1H, dd, J=0.66, 2.19 Hz), 4.87 (1H, m), 3.84 (1H, M), 3.66 (1H, m), 2.83 (1H, d, J=5.92 Hz), 2.11 (1H, t, J=5.92 Hz). LC/MS (M+1): 208.

As demonstrated above, the stereochemistry (R or S) of the resulting diol, is dependent upon the chirality of the ligand used in the AD mix as described in Sharpless et al., *J. Org. Chem.* 57:2768-2771 (1992). AD-mix is composed of the following components: potassium osmate ($K_2OsO_2(OH)_4$), potassium ferricyanide ($K_3Fe(CN)_6$), potassium carbonate ($K_2CO_3$), and the chiral ligands are shown below Ligand for AD-mix α:

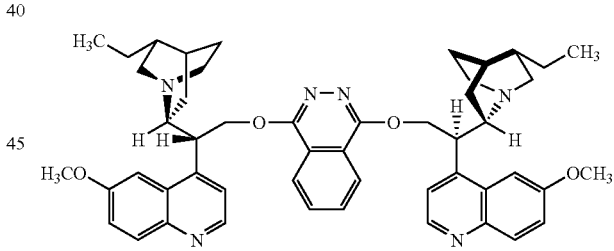

Ligand for AD-mix β:

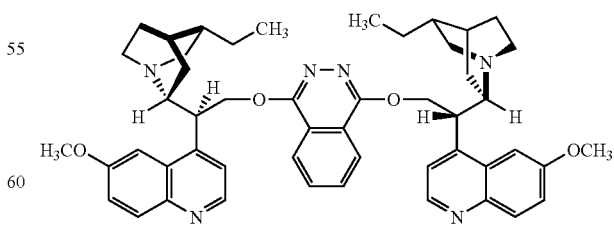

However, racemic diols can be synthesized by methods known in the art, using osmium tetroxide ($OsO_4$) and N-methyl morpholine N-oxide (NMO) in an aqueous acetone solution.

Intermediate 1 can be made from 2,3-dichloro-5-hydroxymethylpyridine 3 via intermediate 4:

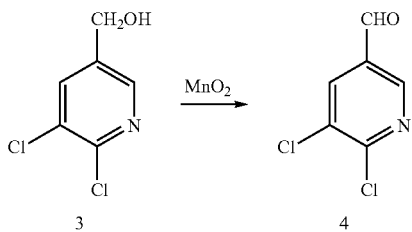

To a 500 mL round-bottom flask, manganese oxide (43.5 g, 0.50 mol) was added to a solution of 2,3-dichloro-5-hydroxylmethylpyridine (3, 8.10 g, 50.0 mmol, Sigma-Aldrich, St. Louis, Mo.) in anhydrous $CH_2Cl_2$ (150 mL). The reaction mixture was stirred at a temperature of about 25° C. for 48 h, filtered through CELITE, and concentrated under reduced pressure. The mixture was chromatographed by a silica gel chromatography column eluting with a gradient of ethyl acetate (0%-40%)/hexanes to provide 7.2 g of 4 (90% yield). $^1$H NMR (400 MHz, $CDCl_3$) δ 10.08 (1H, s), 8.77 (1H, d, J=1.97 Hz), 8.25 (1H, d, J=1.97 Hz). LC/MS (M+1): 176.

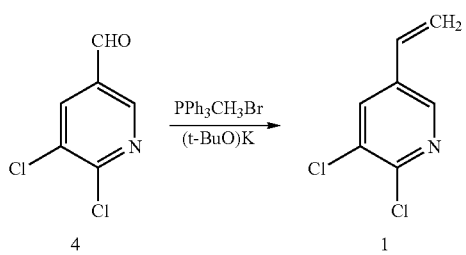

To a stirred slurry of methyltriphenylphosphonium bromide (10.0 g) in toluene (200 mL) at 0° C. was added potassium t-butoxide (3.07 g) portionwise to produce a yellow slurry. After 1 hr, the reaction mixture was cooled to −20° C. and 4 (4.0 grams, 22.72 mmol) dissolved in tetrahydrofuran (6 mL) was added dropwise to produce a purple colored slurry. The reaction mixture was heated to 0° C. and stirred for an additional 1 hr. Then the reaction mixture was treated with saturated aqueous brine (150 mL) and diluted with ethyl acetate (200 mL). The resulting organic portion was washed with brine, dried over anhydrous sodium sulfate, and concentrated under reduced pressure. The resulting product was chromatographed by silica gel chromatography column eluting with a gradient of ethyl acetate (0%-10%)/hexanes to provide 2.77 g of 1 (70% yield). $^1$H NMR (400 MHz, $CDCl_3$) δ 8.30 (1H, d, J=2.19 Hz), 7.80 (1H, d, J=2.19 Hz), 6.63 (1H, dd, J=10.96, 17.80 Hz), 5.86 (1H, d, J=17.80 Hz), 5.45 (1H, d, J=10.96 Hz). LC/MS (M+1): 174.

5.2. Example 2

Alternative Stereoselective Synthesis of Aromatic, Chiral Diol Compounds

An alternative approach for preparing aromatic, chiral diol compounds is illustrated below, using as an example the synthesis of 2,3-dichloro-5-vinyl-pyridine:

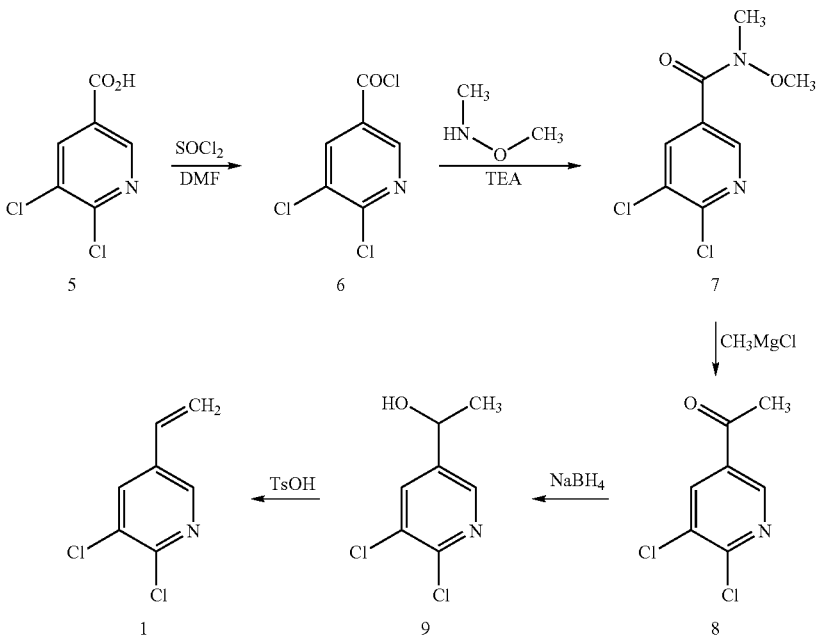

5,6-Dichloro-N-methoxy-N-methyl-nicotinamide (7)

To a well stirred suspension of 5,6-dichloronicotinic acid 5 (600 g, 3.125 mole, Sigma-Aldrich) and DMF (20.0 mL) in dichloroethane (1.2 L) was added drop wise with stirring thionyl chloride (743.56 g, 6.25 mole). The reaction mixture was set up for heating with reflux, fitted with a gas trap filled with saturated aqueous sodium bicarbonate and heated at a temperature of 75° C. until the reaction mixture formed a clear solution, about 3 h. LC/MS of a sample quenched in methanol showed only the presence of the methyl ester. The reaction mixture was cooled to a temperature of about 25° C. and concentrated under reduced pressure to provide 5,6-dichloronicotinoyl chloride 6 as a thick paste.

A suspension of N,O-dimethylhydroxylamine hydrochloride (350.53 g, 3.59 mole, Sigma-Aldrich) in methylene chloride was cooled to 0° C. (internal temp, dry ice/acetone bath), and triethyl amine (711.5 g, 7.03 mole) was added. The 5,6-dichloronicotinoyl chloride prepared above was dissolved in methylene chloride (2.4 L) and added to the mixture at a rate such that the internal temperature did not exceed 15° C. After addition of the acid chloride, the reaction mixture was allowed to warm slowly to a temperature of about 25° C. overnight.

The reaction mixture was poured into 2 L of water, the aqueous and organic portions were separated, and the aqueous portion was extracted twice (500 mL per extraction) with methylene chloride. The combined organic portions were dried ($MgSO_4$) and concentrated under reduced pressure to provide a brown solid. The solid was then treated with 1 L of boiling hexanes and heated at reflux for about 10 min. The resulting pale orange solution was decanted from the dark yellow-brown tar and allowed to cool. This step was repeated twice with the tar (500 mL boiling hexanes per step). The hexane mixtures were first allowed to cool to a temperature of about 25° C., then further cooled on ice/water baths. The resulting yellow needles were collected by vacuum filtration and air dried to provide 730 g of the amide 7 (99% yield), which was suitable to be carried on to the next step. $^1$H NMR (400 MHz, $CDCl_3$) δ 8.68 (m, 1H), 8.18 (m, 1H), 3.59 ($OCH_3$, 3H), 3.40 ($NCH_3$, 3H).

2-Propanol Recrystallization of 5,6-Dichloro-N-methoxy-N-methyl-nicotinamide (7)

The procedure above was followed using 600 g of 5,6-dichloronicotinic acid 5 and keeping all other reagents and ratios the same until the crude product was isolated. The crude product was dissolved in hot 2-propanol, 1.4 mL/g, and allowed to cool slowly to a temperature of about 25° C. The resulting pale yellow solid was isolated by filtration, and the resulting supernatant was cooled to 0° C. to provide a second crop. The supernatant was subsequently reduced in volume by approximately 70% and cooled to 0° C. to provide a slightly darker yellow third crop that was identical by LC/MS to the first two crops. Overall, 730 g was isolated (97% yield).

Preparation of 1-(5,6-dichloro-pyridin-3-yl)-ethanone (8)

To a solution of 5,6-dichloro-N-methoxy-N-methyl-nicotinamide 7 (549 g, 2.335 mole) in dry THF (2.335 L) cooled to −35° C. (internal temperature, dry ice/acetone bath) was added slowly drop wise methylmagnesium chloride solution (913 g, 2.68 mole) at a rate such that the internal temperature did not exceed −10° C. The reaction mixture was allowed to stir for 3 h between −25° C. and −15° C., at which point an aliquot was analyzed by LC/MS to insure the reaction had gone to completion.

The reaction mixture was poured into 2.3 L of 1N HCl. The aqueous and organic portions were separated, the aqueous portion was washed twice (500 mL per wash) with diethyl ether, and the combined organic portions were dried ($MgSO_4$) and concentrated under reduced pressure to provide a pale yellow solid.

The solid was taken up in about 450 mL of hot 2-propanol. Upon cooling, the solution deposited pale yellow needles. The mixture was further cooled (ice/water bath) and the resulting solid was collected by vacuum filtration and air dried. The 2-propanol supernatant was concentrated to produce an additional crop of needles. Total yield 431 g (97% yield). $^1$H NMR (400 MHz, $CDCl_3$) δ 8.82 (m, 1H), 8.29 (m, 1H), 2.62 ($COCH_3$, 3H).

Preparation of 1-(5,6-Dichloro-pyridin-3-yl)-ethanol (9)

To a well stirred suspension of sodium borohydride (66.21 g, 1.75 mole) in methanol (3.5 L) cooled to 0° C. with a dry ice/acetone bath was added 1-(5,6-dichloro-pyridin-3-yl)-ethanone 8 (665 g, 3.5 mole) at a rate such that the temperature remained at 0° C. After solid addition was complete, the reaction mixture was stirred an additional 1 h, after which time LC/MS analysis of an aliquot showed that the reaction was complete.

The methanol was removed under reduced pressure, and the residue was taken up in 2 L diethyl ether and 2 L 1N HCl. The aqueous and organic portions were separated, the aqueous portion was extracted twice (250 mL per extraction) with ether, and the combined organic portions were dried ($MgSO_4$) and concentrated under reduced pressure to provide 670 g of a pale yellow oil (99% yield). $^1$H NMR (400 MHz, $CDCl_3$) δ 8.20 (m, 1H), 7.82 (m, 1H) 4.96 (m, 1H), 3.57 (s, 1H), 1.51 (d, J=6.5 Hz, 3H).

1-(5,6-Dichloro-pyridin-3-yl)-ethanol (9) hydrochloride salt

To a solution of 1-(5,6-dichloro-pyridin-3-yl)-ethanol 9 (200 g, 1.04 mole) in ethyl acetate (200 mL) was added a solution of hydrogen chloride in dioxane/ethyl acetate prepared by diluting 4N HCl in dioxane (265 mL, 1.06 mole) in ethyl acetate (265 mL) with manual stirring. After a few minutes, a cream colored solid began to precipitate. The resulting mixture was allowed to cool to a temperature of about 25° C. and was then further cooled in an ice/water bath. The solid was isolated by vacuum filtration, washed with additional ethyl acetate (250 mL), and allowed to air dry for about 20 min. to provide 231 g of a solid (97% yield). This solid contained traces of ethyl acetate and was suitable for further reaction without additional drying. $^1$H NMR (400 MHz, $CD_3OD$) δ 8.36 (m, 1H), 8.03 (m, 1H) 4.92 (m, 1H), 1.47 (d, J=6.5 Hz, 3H).

Preparation of 2,3-Dichloro-5-vinyl-pyridine (1)

To a solution of 1-(5,6-dichloro-pyridin-3-yl)-ethanol 9 (311 g. 1.62 mole) in chlorobenzene (3 L) was added p-toluene sulfonic acid (431 g, 2.5 mole) and the reaction mixture was heated at reflux (about 140° C.) with concomitant removal of water. When the reaction was complete, the mixture was concentrated to about 500 mL, diluted with 2 L water, and extracted with three times (1 L per extraction) ethyl acetate. The organic portions were combined, dried (Na$_2$SO$_4$), concentrated under reduced pressure with low heat, dissolved in 500 mL methylene chloride, and applied to the top of 2 kg silica column. The purified vinyl pyridine was eluted with a 0% to 10% gradient of ethyl acetate in hexane. 178.55 g, of about 100% pure 2,3-dichloro-5-vinylpyridine was collected as a clear oil which solidified upon cooling to 4° C. (63% yield). $^1$H NMR (400 MHz, CDCl$_3$) δ 8.27 (m, 1H), 7.80 (dd, J=12, 18 Hz, 1H), 6.62 (d, J=18 Hz, 1H), 5.46 (d, J=12 Hz, 1H).

5.3. Example 3

In Vivo Assays for Prevention or Treatment of Pain

Test Animals:

Each experiment uses rats weighing between 200-260 g at the start of the experiment. The rats are group-housed and have free access to food and water at all times, except prior to oral administration of a compound of formula I when food is removed for 16 hours before dosing. A control group acts as a comparison to rats treated with a compound of formula I. The control group is administered the carrier for the compound of formula I. The volume of carrier administered to the control group is the same as the volume of carrier and compound of formula I administered to the test group.

Acute Pain:

To assess the actions of the compounds of formula I on the treatment or prevention of acute pain the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are as defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a compound of formula I. Data are expressed as tail flick latency(s) and the percentage of the maximal possible effect (% MPE), i.e., 20 seconds, is calculated as follows:

$$\% \, MPE = \frac{[(\text{post administration latency}) - (\text{pre-administration latency})]}{(20 \, s \, \text{pre-adminiatration latency})} \times 100$$

The rat tail flick test is described in F. E. D'Amour et al., "A Method for Determining Loss of Pain Sensation," *J. Pharmacol. Exp. Ther.* 72:74-79 (1941).

Inflammatory Pain:

To assess the actions of the compounds of formula I on the treatment or prevention of inflammatory pain the Freund's complete adjuvant ("FCA") model of inflammatory pain can be used. FCA-induced inflammation of the rat hind paw is associated with the development of persistent inflammatory mechanical and thermal hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the paw withdrawal threshold ("PWT"), or to noxious thermal stimuli by determining the paw withdrawal latencies ("PWL"), as described below. Rats may then be administered a single injection of 1, 3, 10 or 30 mg/kg of either a compound of formula I; 30 mg/kg of a control selected from celecoxib, indomethacin or naproxen; or carrier. Responses to noxious mechanical or thermal stimuli are determined 1, 3, 5 and 24 hours post administration. Percentage reversal of hyperalgesia for each animal is defined as:

$$\% \, \text{Reversal} = \frac{[(\text{post administration } PWT \text{ or } PWL) - (\text{pre-administration } PWT \text{ or } PWL)]}{[(\text{baseline } PWT \text{ or } PWL) - (\text{pre-administration } PWT \text{ or } PWL)]} \times 100$$

Neuropathic Pain:

To assess the actions of the compounds of formula I for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/O$_2$ inhalation anesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \, \text{Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain can be used to produce mechanical hyperalgesia, thermal hyperalgesia and tactile allodynia in rats. Surgery is performed under isoflurane/O$_2$ inhalation anesthesia. Following induction of anesthesia a 3 cm incision is made and the left paraspinal muscles are separated from the spinous process at the L$_4$-S$_2$ levels. The L$_6$ transverse process is carefully removed with a pair of small rongeurs to identify visually the L$_4$-L$_6$ spinal nerves. The left L$_5$ (or L$_5$ and L$_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then be returned to their home cages until behavioral testing begins. The animals are assessed for response to noxious mechanical stimuli by determining PWT, as described below, prior to surgery (baseline), then immediately prior to and 1, 3, and 5 hours after administration a compound of formula I for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia:

The plantar test can be used to assess thermal hyperalgesia. For this test, hind PWLs to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia:

To assess tactile allodynia, rats can be placed in clear, Plexiglas compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Capsaicin-Induced Eye Wipe Test:

To assess the effect of compounds of formula I on TRPV1 receptor-mediated pain, the capsaicin-induced eye wipe test can be used (N. R. Gavva et al., "AMG 9810 [(E)-3-(4-t-Butylphenyl)-N-(2,3-dihydrobenzo[b][1,4]dioxin-6-yl) acrylamide], a Novel Vanilloid Receptor 1 (TRPV1) Antagonist with Antihyperalgesic Properties", *Pharmacol. Exp. Ther.* 313:474-484 (2005)). The eye wipe test is a reliable high-throughput test of the effect of TRPV1 antagonists. Rats can be given a single injection of 1, 3, 10 or 30 mg/kg of either a compound of formula I; 30 mg/kg of a control selected from celecoxib, indomethacin or naproxen; or carrier. At 1, 3 or 5 hours after drug administration, 3 µL of a 100 µM capsaicin solution (in 10% EtOH/PBS) is instilled in one eye of each animal with a pipette. The number of forelimb movements (touching or wiping of the capsaicin-treated eye) are counted during a 2 minute period following instillation of capsaicin into the eye.

5.4. Example 4

Binding of Compounds of Formula I to TRPV1

Methods for assaying compounds capable of inhibiting TRPV1 are known in the art, for example, those methods disclosed in U.S. Pat. No. 6,239,267 to Duckworth et al., U.S. Pat. No. 6,406,908 to Mc Intyre et al., or U.S. Pat. No. 6,335,180 to Julius et al.

Protocol 1

Human TRPV1 Cloning:

Human spinal cord RNA (commercially available from Clontech, Palo Alto, Calif.) is used. Reverse transcription is conducted on 1.0 µg total RNA using Thermoscript Reverse Transcriptase (commercially available from Invitrogen, Carlsbad, Calif.) and oligo dT primers as detailed in its product description. Reverse transcription reactions are incubated at 55° C. for 1 h, heat-inactivated at 85° C. for 5 min, and RNase H-treated at 37° C. for 20 min.

Human TRPV1 cDNA sequence is obtained by comparison of the human genomic sequence, prior to annotation, to the published rat sequence. Intron sequences are removed and flanking exonic sequences are joined to generate the hypothetical human cDNA. Primers flanking the coding region of human TRPV1 are designed as follows: forward primer, 5'-GAAGATCTTCGCTGGTTGCACACTGGGCCACA-3' (SEQ ID NO: 1); and reverse primer, 5'-GAAGATCT-TCGGGGACAGTGACGGTTGGATGT-3' (SEQ ID NO: 2).

Using these primers, PCR of TRPV1 is performed on one tenth of the Reverse transcription reaction mixture using Expand Long Template Polymerase and Expand Buffer 2 in a final volume of 50 µL according to the manufacturer's instructions (Roche Applied Sciences, Indianapolis, Ind.). After denaturation at 94° C. for 2 min PCR amplification is performed for 25 cycles at 94° C. for 15 sec, 58° C. for 30 sec, and 68° C. for 3 min followed by a final incubation at 72° C. for 7 min to complete the amplification. The PCR product of about 2.8 kb is gel-isolated using a 1.0% agarose, Tris-Acetate gel containing 1.6 µg/mL of crystal violet and purified with a S.N.A.P. UV-Free Gel Purification Kit (commercially available from Invitrogen). The TRPV1 PCR product is cloned into the pIND/V5-His-TOPO vector (commercially available from Invitrogen) according to the manufacturer's instructions to result in the TRPV1-pIND construct. DNA preparations, restriction enzyme digestions, and preliminary DNA sequencing are performed according to standard protocols. Full-length sequencing confirms the identity of the human TRPV1.

Generation of Inducible Cell Lines:

Unless noted otherwise, cell culture reagents are purchased from Life Technologies of Rockville, Md. HEK293-EcR cells expressing the ecdysone receptor (commercially available from Invitrogen) are cultured in Growth Medium (Dulbecco's Modified Eagles Medium containing 10% fetal bovine serum (commercially available from HYCLONE, Logan, Utah), 1× penicillin/streptomycin, 1× glutamine, 1 mM sodium pyruvate and 400 µg/mL Zeocin (commercially available from Invitrogen)). The TRPV1-pIND constructs are transfected into the HEK293-EcR cell line using Fugene transfection reagent (commercially available from Roche Applied Sciences, Basel, Switzerland). After 48 h, cells are transferred to Selection Medium (Growth Medium containing 300 µg/mL G418 (commercially available from Invitrogen)). Approximately 3 weeks later individual Zeocin/G418 resistant colonies are isolated and expanded. To identify functional clones, multiple colonies are plated into 96-well plates and expression is induced for 48 h using Selection Medium supplemented with 5 µM ponasterone A ("PonA") (commercially available from Invitrogen). On the day of assay, cells are loaded with Fluo-4 (a calcium-sensitive dye that is commercially available from Molecular Probes, Eugene, Oreg.) and CAP-mediated calcium influx is measured using a Fluorescence Imaging Plate Reader ("FLIPR") as described below. Functional clones are re-assayed, expanded, and cryopreserved.

pH-Based Assay:

Two days prior to performing this assay, cells are seeded on poly-D-lysine-coated 96-well clear-bottom black plates (commercially available from Becton-Dickinson) at 75,000 cells/well in growth media containing 5 µM PonA (commercially available from Invitrogen) to induce expression of TRPV1. On the day of the assay, the plates are washed with 0.2 mL 1× Hank's Balanced Salt Solution (commercially available from Life Technologies) containing 1.6 mM $CaCl_2$ and 20 mM HEPES, pH 7.4 ("wash buffer"), and loaded using 0.1 mL of wash buffer containing Fluo-4 (3 µM final concentration, commercially available from Molecular Probes). After 1 h, the cells are washed twice with 0.2 mL wash buffer and resuspended in 0.05 mL 1× Hank's Balanced Salt Solution (commercially available from Life Technologies) containing 3.5 mM $CaCl_2$ and 10 mM Citrate, pH 7.4 ("assay buffer"). Plates are then transferred to a FLIPR for assay. The test compound is to be diluted in assay buffer, and 50 µL of the resultant solution can be added to the cell plates and the solution is monitored for two minutes. The final concentration of the test compound is to be adjusted to range from about 50 picoM to about 3 µM. Agonist buffer (wash buffer titrated with 1N HCl to provide a solution having a pH of 5.5 when mixed 1:1 with assay buffer) (0.1 mL) is then to be added to each well, and the plates are to be incubated for 1 additional minute. Data will be collected over the entire time course and analyzed using Excel and Graph Pad Prism to determine the $IC_{50}$.

Capsaicin-Based Assay:

Two days prior to performing this assay, cells are seeded in poly-D-lysine-coated 96-well clear-bottom black plates (50,000 cells/well) in growth media containing 5 µM PonA (commercially available from Invitrogen) to induce expression of TRPV1. On the day of the assay, the plates are washed with 0.2 mL 1× Hank's Balanced Salt Solution (commercially available from Life Technologies) containing 1 mM $CaCl_2$ and 20 mM HEPES, pH 7.4, and cells are loaded using 0.1 mL of wash buffer containing Fluo-4 (3 µM final). After one hour, the cells are washed twice with 0.2 mL of wash buffer and resuspended in 0.1 mL of wash buffer. The plates are transferred to a FLIPR for assay. 50 µL of test compound diluted with assay buffer (1× Hank's Balanced Salt Solution containing 1 mM $CaCl_2$ and 20 mM HEPES, pH 7.4) are added to the cell plates and incubated for 2 min. The final concentration of the compound is to be adjusted to range from about 50 picoM to about 3 µM. Human TRPV1 is to be activated by the addition of 50 µL of capsaicin (400 nM), and the plates are to be incubated for an additional 3 min. Data will be collected over the entire time course and analyzed using Excel and GraphPad Prism to determine the $IC_{50}$.

Protocol 2

For Protocol 2, a Chinese Hamster Ovary cell line (CHO) that has been engineered to constitutively express human recombinant TRPV1 is to be used (TRPV1/CHO cells). The TRPV1/CHO cell line can be generated as described below.

Human TRPV1 Cloning:

A cDNA for the human TRPV1 receptor (hTRPV1) is amplified by PCR (KOD-Plus DNA polymerase, ToYoBo, Japan) from a human brain cDNA library (BioChain) using primers designed surrounding the complete hTRPV1 open reading frame as follows: forward primer, 5'-GGATCCAG-CAAGGATGAAGAAATGG-3' (SEQ ID NO: 3), and reverse primer, 5'-TGTCTGCGTGACGTCCTCACTTCT-3' (SEQ ID NO: 4). The resulting PCR products are purified from agarose gels using Gel Band Purification Kit (GE Healthcare Bioscience) and are subcloned into pCR-Blunt vector (Invitrogen). The cloned cDNA is fully sequenced using a fluorescent dye-terminator reagent (BigDye Terminator ver3.1 Cycle Sequencing Kit, Applied Biosystems) and ABI Prism 3100 genetic analyzer (Applied Biosystems). The pCR-Blunt vector containing the hTRPV1 cDNA is subjected to restriction digestion with EcoR1. The restriction fragment is subcloned into expression vector pcDNA3.1(−) (Invitrogen) and named pcDNA3.1(−)-hVR1 plasmid. The sequence of the cDNA encoding TRPV1 is available at GenBank accession number AJ277028.

Generation of the TRPV1/CHO Cell Line:

CHO-K1 cells are maintained in growth medium consisting of α-MEM, 10% FBS (Hyclone), and 100 IU/mL of penicillin-100 µg/mL of streptomycin mixed solution (Nacalai Tesque, Japan) at 37° C. in an environment of humidified 95% air and 5% $CO_2$. The cells are transfected with the pcDNA3.1(−)-hVR1 plasmid using FuGENE6 (Roche) according to the manufacturer's protocol. 24 hr after transfection, neomycin-resistant cells are selected using 1 mg/mL G418 (Nacalai Tesque). After 2 weeks, individual colonies can be picked, expanded, and screened for the expression of hTRPV1 in the capsaicin-induced $Ca^{2+}$ influx assay (see below) with a FLIPR (Molecular Devices). A clone with the largest $Ca^{2+}$ response to capsaicin should be selected and re-cloned by the same procedure. The cells expressing hTRPV1 are cultured in the growth medium supplemented with 1 mg/mL G418. Approximately 1 month later, stable expression of functional TRPV1 receptors in the selected cell line is to be confirmed by validating $Ca^{2+}$ responses with or without capsazepine (Sigma, at 1 nM-10 µM) in capsaicin assay.

Capsaicin-Induced $Ca^{2+}$ Influx Assay for Cell Selection:

The following assay can be performed to identify cells with hTRPV1 expression. CHO-K1 cells transfected with pcDNA3.1(−)-hVR1 plasmid are seeded in 384-well black-wall clear-bottom plates (Corning) and cultivated in growth medium (see above) for 1 day. On the day of experiment, culture medium is exchanged to assay buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, pH 7.4) containing 4 µM Fluo-3-AM (Dojin, Japan). After the incubation at 37° C. for 1 hr, each well is washed 3 times with assay buffer using an EMBLA 384 plate washer (Molecular Devices) and refilled with assay buffer. The plates are incubated at a temperature of about 25° C. for 10 min. Subsequently, the plates are inserted into a FLIPR, and 1.5 μM capsaicin (Sigma) solution prepared in assay buffer is added to each well (final concentration is 500 nM). Cellular responses are monitored for 5 min.

Cell Culture:
1. Cell Culture Media
1. Alpha-MEM (Gibco, CAT: 12561-056, LOT: 1285752): 450 mL.
2. Fetal Bovine Serum (FBS), heat inactivated (Gibco, CAT: 16140-071, LOT: 1276457): 50 mL.
3. HEPES Buffer Solution, 1M stock (Gibco, CAT: 15630-080): 10 mL (final 20 mM).
4. Geneticin, 50 mg/mL stock (Gibco, CAT: 10135-035): 10 mL (final 1 mg/mL).
5. Antimicotic Antibiotic Mixed Solution, 100× stock (Nacalai Tesque, Japan, CAT: 02892-54): 5 mL.

Components 1-5 above are combined at the indicated amounts and stored at 4° C. The cell culture media are brought to about 37° C. before use. Optionally, component 5 can be replaced by penicillin-streptomycin solution (for example, Gibco 15140-122 or Sigma P-0781).

2. Thawing the Cells
TRPV1/CHO cells are frozen in Cellbanker™ (Juji-Field INC, Japan, CAT: BLC-1) and stored at −80° C. Optimized cryopreservation solution containing dimethyl sulphoxide and FBS can be used.

Vials containing the TRPV1/CHO cells are stored at −80° C. After removal from −80° C., the vial is immediately transferred to a 37° C. water bath to thaw for ca. 1-2 minutes. Once completely thawed, the contents of the vial (1 mL/vial) are transferred to a sterile 15 mL test tube and 9 mL warm culture media are slowly added. The test tube is subsequently centrifuged at 1000 rpm for 4 min at a temperature of about 25° C. The supernatant is removed and the pellet resuspended in 10 mL of culture media. The cell suspension is transferred to a sterile 75 cm² plastic flask and incubated at humidified 5% $CO_2$/95% air at 37° C. To monitor viability, the cells are visually inspected and/or counted, beginning at approximately 1 hr after incubation.

3. Passaging the Cells
The cells in a flask are close to confluence at the time of passaging. Cell culture media can be removed from the culture flask and 10 mL of sterile PBS(−), added and the flask gently shaken. The PBS is removed from the flask and 2 mL of trypsin/EDTA solution (0.05% trypsin with EDTA-4Na; Gibco, CAT: 25300-054) is added and the flask gently shaken. The flask is incubated at 37° C. for about 2 min. 8 mL cell culture media are subsequently added to the flask and the flask shaken to ensure that all cells are in solution. The cell suspension is then transferred to a sterile 15 mL or 50 mL plastic tube, centrifuged at 1,000 rpm for 4 min at a temperature of about 25° C. The supernatant is removed and the pellet resuspended in ca. 5 mL of culture media. The cell count is measured using the Burker-Turk hemocytometer.

The cells are seeded into a sterile 75 cm² plastic flask in ca. $0.8 \times 10^5$ cells/mL for 72 hr and incubated in humidified 5% $CO_2$/95% air at 37° C.

4. Freezing the Cells
The procedure up to the measurement of the cell count is the same as in the section Passaging the Cells above. Subsequently, the cell suspension can be centrifuged at 1,000 rpm for 4 min at a temperature of about 25° C. The supernatant can be removed and the pellet resuspended in Cellbanker™ solution to get a final concentration of from $5 \times 10^5$ to $5 \times 10^6$ cells/mL. The cell suspension can be transferred into appropriately labeled 1 mL cryovials and then placed into the −80° C. freezer.

pH-Based Assay:
The following assay can be conducted to determine the concentration of sulfuric acid that would give rise to a pH that induces a $Ca^{2+}$ response optimal to test compounds for their effect on TRPV1.

1. Cells
TRPV1/CHO cells can be seeded in the 96-well clear-bottom black-wall plate (Nunc) at densities of $1-2 \times 10^4$ cells/well and grown in 100 μL of culture medium (alpha-MEM supplemented with 10% FBS, 20 mM HEPES, 1 mg/mL geneticin and 1% antibiotic-antimycotic mixed stock solution) for 1-2 days before the experiment.

2. Determination of pH Sensitivity and Agonist Dose
2.1. Agonist Solution
Different agonist solutions with sulfuric acid concentrations of from 15 mM to 18 mM can be prepared by diluting 1M sulfuric acid with measuring buffer. The different sulfuric acid concentrations in the agonist solutions can be selected such that a 1:4 dilution would result in a final sulfuric acid concentration of between 3.0 mM to 3.6 mM, respectively.

2.2. Assay
$Ca^{2+}$ influx into TRPV1/CHO cells in response to low pH as measured by Fura-2 AM fluorescence is measured. The cells can be stimulated using 3.0 mM (well number B1-6), 3.1 mM (C1-6), 3.2 mM (D1-6), 3.3 mM (E1-6), 3.4 mM (F1-6), 3.5 mM (G1-6), or 3.6 mM (H1-6) $H_2SO_4$ or pH 7.2 measuring buffer without $H_2SO_4$ (A1-6).

(1) Culture medium can be removed using an 8-channel-pipette (Rainin, USA) from the 96-well plate and the wells can be refilled with 100 μL of loading buffer (20 mM HEPES, 115 mM NaCl, 5.4 mM KCl, 0.8 mM $MgCl_2$, 1.8 mM $CaCl_2$, 13.8 mM D-glucose, 2.5 mM probenecid, pH 7.4) containing 5 μM Fura-2 AM (Dojin, Japan).

(2) The 96-well plate can be incubated at 37° C. for 45 mm.
(3) The loading buffer can be removed from each well. The cells can be subsequently washed twice with 150 μL of measuring buffer (20 mM HEPES, 115 mM NaCl, 5.4 mM KCl, 0.8 mM $MgCl_2$, 5.0 mM $CaCl_2$, 13.8 mM D-glucose, 0.1% BSA, pH 7.4) (no probenecid). The wells can then be refilled with 80 μL of measuring buffer.

(4) After an incubation at 4° C. for 15 min, the 96-well plate can be transferred to FDSS-3000 (Hamamatsu Photonics, Japan).

(5) The Fura-2 fluorescent intensity can be monitored at a wavelength of 340 nm and at 380 nm, respectively, at a rate of 0.5 Hz for a total of 240 seconds. After 16 time points (32 sec) of baseline detection, 20 μL of agonist solution can be added to each well. The final volume is 100 μL/well.

(6) Fluorescence intensity ratio refers to the fluorescence intensity at 340 nm over the fluorescence intensity at 380 nm at a particular time point. The baseline can be set as the average of the fluorescent intensity ratios for the first 16 time points before the addition of agonist solution. The maximum response is the highest fluorescent intensity ratio during the 60 time points following addition of agonist solution.

(7) Maximal signal ratios from each well can be calculated as output data using the FDSS-3000 analysis program. Data is analyzed using Excel (Microsoft) and XLfit (idbs) software.

2.3. pH Determination
After the observation of $Ca^{2+}$ responses, the buffer of each lane (50 μL/well, 8-20 wells/plate) can be collected well by well and the pH values are measured using a portable pH meter (Shindengen, Japan).

Lanes optimal for testing the effects of the compounds on the TRPV1 calcium channel are selected. The final sulfuric acid concentrations in the wells of these lanes can be 3.2 mM and 3.3 mM, respectively. These final sulfuric acid concentrations can be obtained using agonist solutions with 16.0 mM and 16.5 mM sulfuric acid concentrations, respectively. The pH obtained using these sulfuric acid concentrations is ca. 5.0-5.1.

Thus, agonist solutions with 16.0 mM and 16.5 mM sulfuric acid concentrations, respectively, can be selected for the experiments described below in section 3.

3. pH Assay
3.1. Agonist

Two different agonist solutions with different $H_2SO_4$ concentrations can be used for the pH assay. For one half of a 96-well plate one agonist solution can be used, for the other half the other agonist solution. The agonist solutions can be obtained by diluting sulfuric acid ($H_2SO_4$, 1M) with measuring buffer. The concentrations for the two agonist solutions can be determined as described above in Section 2 of Protocol 2.

The sulfuric acid concentrations between the two agonist solutions may differ by 0.5 mM. In the experiment described in Section 2 of Protocol 2, the sulfuric acid concentrations in the agonist solutions can be determined to be 16 mM and 16.5 mM, respectively. After 1:4 dilution of the agonist solutions, the final sulfuric acid concentration can be 3.2 mM and 3.3 mM, respectively. The resulting pH value for the pH assay is 5.0 to 5.1.

3.2. Test Compounds

Test compounds are dissolved in DMSO to yield 1 mM stock solutions. The stock solutions are further diluted using DMSO in 1:3 serial dilution steps with 6 points (1000 µM, 250 µM, 62.5 µM, 15.625 µM, 3.9062 µM and 0.977 µM). The thereby-obtained solutions are further diluted in measuring buffer (1:100) as 10× stock serial dilutions with a DMSO concentration of 1%. 10 µL of a 10× stock is added into each well at step 3.3.(4) of Protocol 2. Thus, the final concentrations of antagonists ranges from 1000-0.977 nM containing 0.1% DMSO.

3.3. Assay

Steps (1) and (2) of this Assay can be the same as steps 2.2.(1) and 2.2.(2) of Protocol 2, respectively.

(3) The cells can be washed twice with 150 µL of measuring buffer (mentioned in 2.2.(3) of Protocol 2, no probenecid). The wells can be subsequently refilled with 70 µL of measuring buffer.

(4) Either 10 µL of measuring buffer or 10 µL of 10× stock serial dilution of test compound (described in 3.2. above) can be applied to each well. Usually, only one test compound can be tested per 96-well plate. The number of replicates per 96-well plate for a particular antagonist at a particular concentration is 7×2 since two different sulfuric acid concentrations can be used per 96-well plate (N=7×2).

Step (5) is the same as 2.2.(4) above.

(6) Fura-2 fluorescent intensity can be monitored as described in 2.2.(5) above. After 16 time points of baseline detection, 20 µL of agonist solution (measuring buffer titrated with $H_2SO_4$ to yield pH 5.0-5.1 when mixed 1:4 with the measuring buffer containing test compound) can be added to each well (final volume 100 µL/well).

Steps (7) and (8) are as described in 2.2.(6) and 2.2.(7) above, respectively.

3.4. pH Check (1) The pH values of the buffer in the wells of A1→H1 and A7→H7 (longitudinally) can be measured one by one using a portable pH meter.

(2) When a well is confirmed as pH 5.0 or 5.1, the next five wells to its right are checked one after another.

(3) For $IC_{50}$ calculation, only the data from wells with pH values of 5.0-5.1 are to be used. The number of wells tested for their pH varies among plates (about 16-60 wells/plate). The number depends on the results of 3.4.(1) above and the $Ca^{2+}$ responses.

Capsaicin-Based Assay:

One day prior to assay, TRPV1/CHO cells are seeded in 96-well clear-bottom black plates (20,000 cells/well) in growth media. On the day of the experiment, the cells are washed with 0.2 mL 1× Hank's Balanced Salt Solution (Life Technologies) containing 1.6 mM $CaCl_2$ and 20 mM HEPES, pH 7.4 ("wash buffer"). Subsequently, the cells are to be loaded by incubation in 0.1 mL of wash buffer containing Fluo-4 at 3 µM final concentration. After 1 hour, the cells can be washed twice with 0.2 mL wash buffer and resuspended in 0.1 mL wash buffer. The plates can then be transferred to a Fluorescence Imaging Plate Reader (Molecular Devices). Fluorescence intensity is monitored for 15 seconds to establish a baseline. Subsequently, test compounds diluted in assay buffer (1× Hank's Balanced Salt Solution containing 1 mM $CaCl_2$ and 20 mM HEPES, pH 7.4) containing 1% DMSO can be added to the cell plate and fluorescence is monitored for 2 minutes. The final concentration of the compound is adjusted to range from 100 µM to 1.5625 µM. If the test compound are an especially potent antagonist, the final concentration of the compound is to be adjusted to range from 10 µM to 1.5625 nM. Human TRPV1 can then be activated by the addition of 50 µL capsaicin (100 nM final concentration) and plates incubated for an additional 3 min. Data is collected over the entire time course and analyzed using Excel and the curve-fitting formula GraphPad Prism.

The invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those in the art and are intended to fall within the scope of the appended claims.

A number of references have been cited, the entire disclosures of which are incorporated herein by reference.

What is claimed:

1. A compound of formula I(d):

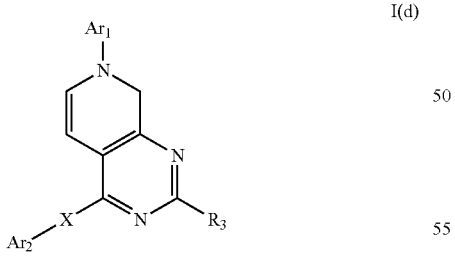

or a pharmaceutically acceptable salt thereof, wherein
X is —O—, —N($R_{20}$)—, —S—, —S(O)—, or —S(O)$_2$—;
$R_3$ is selected from
(a) —H, —$N_3$, -halo, —$NO_2$, —CN, —P(O)(OH)$_2$, —S(O)$_2$(OH), —S(O)$_2$(O)—($C_1$-$C_6$)alkyl, —SH, —OH, —C(O)O$R_7$, —C(halo)$_3$, —CH(halo)$_2$, and —CH$_2$(halo); and
(b) —($C_1$-$C_6$)alkyl, —($C_1$-$C_6$)alkoxy, —($C_3$-$C_8$)cycloalkyl, —($C_2$-$C_6$)alkenyl, —($C_2$-$C_6$)alkynyl, —($C_6$-$C_{14}$)aryl, —($C_1$-$C_6$)alkyl-N($R_7$)$_2$, —($C_1$-$C_6$)heteroalkyl, -(5- to 10-membered)heterocycle, -(5- to 10-membered)heteroaryl, —($C_6$-$C_{14}$)bicycloalkyl, —($C_1$-$C_6$)thioalkoxy, —($C_1$-$C_6$)alkyl-($C_1$-$C_6$)alkoxy, —($C_1$-$C_6$)alkyl-O—($C_6$-$C_{14}$)aryl, —($C_1$-$C_6$)alkyl-$R_7$, —($C_1$-$C_6$)alkyl-O—($C_3$-$C_8$)cycloalkyl, —($C_1$-$C_6$)alkyl-(3- to 7-membered)heterocycle, —($C_1$-$C_6$)alkyl-(5- to 10-membered)heteroaryl, —($C_1$-$C_6$)alkyl-N($R_7$)$_2$, —N($R_7$)$_2$, —N($R_7$)—($C_1$-$C_6$)alkyl-$R_{14}$, —S(O)—($C_1$-$C_6$)alkyl, —O—($C_1$-$C_6$)alkyl-$R_{14}$, —O—($C_1$-$C_6$)alkyl-S(O)$_2$—$R_{14}$, —O—($C_3$-$C_8$)cycloalkyl, —O$R_{14}$, —S$R_{14}$, —O—($C_1$-$C_6$)alkyl-O—$R_{14}$, —O—($C_1$-$C_6$)alkyl-C(O)—N($R_7$)—($C_1$-$C_6$)alkyl-O$R_7$, —O—($C_1$-$C_6$)alkyl-C(O)—$R_{14}$, —O—($C_1$-$C_6$)alkyl-C(O)—N($R_7$)$_2$, —C(O)$R_{14}$, —C(O)—($C_1$-$C_6$)alkyl, —C(O)-(3- to 7-membered)heterocycle, —C(O)-(5- to 10-membered)heteroaryl, —C(O)O—($C_1$-$C_6$)alkyl, —C(O)N($R_7$)—($C_1$-$C_6$)alkyl-(3- to 7-membered)heterocycle, —C(O)N($R_7$)—($C_1$-$C_6$)alkyl-(5- to 10-membered)heteroaryl, —C(O)N($R_7$)$_2$, —OC(O)N($R_7$)$_2$, —C(O)N($R_7$)—($C_1$-$C_6$)alkyl-N($R_7$)$_2$, —C(O)N($R_7$)—($C_1$-$C_6$)alkyl-$R_7$, —S(O)$_2$—($C_1$-$C_6$)alkyl, and —S(O)$_2$—N($R_7$)$_2$, each of which can be unsubstituted or substituted with 1, 2, 3 or 4 independently selected $R_{14}$;

Ar₁ is:

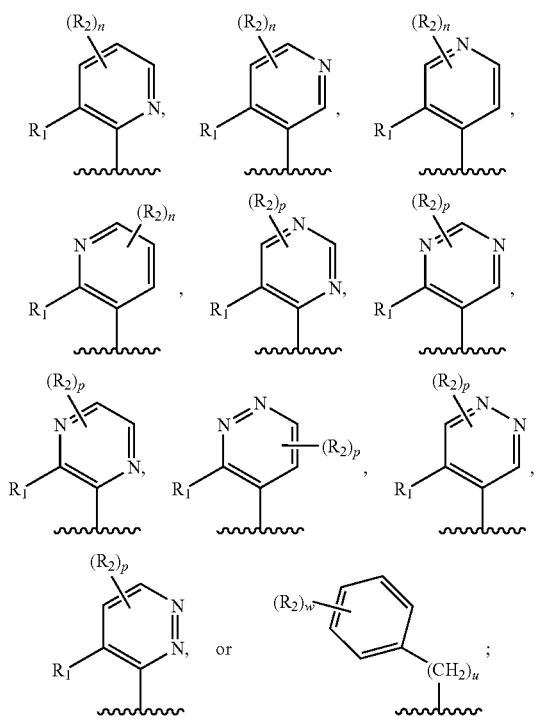

Ar₂ is:

(a) -(3- to 7-membered)heterocycle or -(7- to 10-membered)bicycloheterocycle, each of which can be unsubstituted or substituted with 1, 2, 3, or 4 independently selected R₃ groups; or (b)

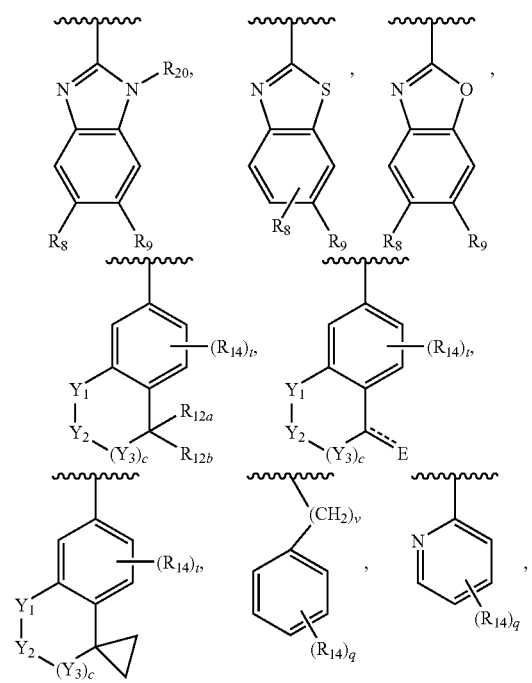

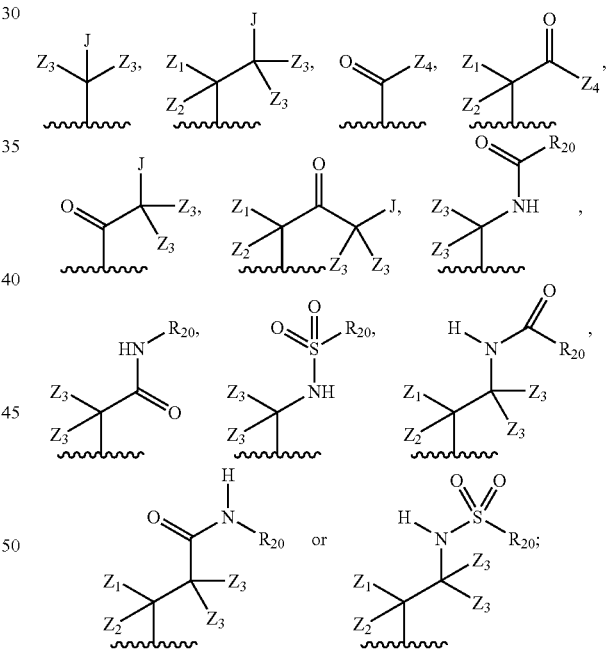

c is the integer 0, 1, or 2;
$Y_1$, $Y_2$, and $Y_3$ are each independently selected from C, N, and O, wherein no more than one of $Y_1$, $Y_2$, and $Y_3$ can be O, and for each $Y_1$; $Y_2$, or $Y_3$ that is N, the N is bonded to one $R_{21}$ group, and for each $Y_1$, $Y_2$, or $Y_3$ that is C, the C is bonded to two $R_{20}$ groups, provided that there are no more than a total of two $(C_1$-$C_6)$alkyl groups substituted on all of $Y_1$, $Y_2$, and $Y_3$;
E is =O, =S, =CH($C_1$-$C_6$)alkyl, =CH($C_2$-$C_6$)alkenyl, —NH($C_1$-$C_6$)alkyl, or =N—$OR_{20}$;
$R_1$ is —H, -halo, —($C_1$-$C_4$)alkyl, —$NO_2$, —CN, —OH, —$OCH_3$, —$NH_2$, —C(halo)$_3$, —CH(halo)$_2$, —$CH_2$(halo), —OC(halo)$_3$, —OCH(halo)$_2$, —$OCH_2$(halo), or —$S(O)_2$—($C_1$-$C_6$)alkyl;
each $R_2$ is independently selected from:
  (a) -halo, —OH, —O($C_1$-$C_4$)alkyl, —CN, —$NO_2$, —$NH_2$, —($C_1$-$C_{10}$)alkyl, —($C_2$-$C_{10}$)alkenyl, —($C_2$-$C_{10}$)alkynyl, and -phenyl; and
  (b) a group of formula Q, wherein Q is:

each $Z_1$ is independently selected from —H, —$OR_7$, —$CH_2OR_7$, —$CH_2SR_7$, —$CH_2N(R_{20})_2$, and -halo;
each $Z_2$ is independently selected from —H, —($C_1$-$C_6$)alkyl, —($C_2$-$C_6$)alkenyl, —($C_2$-$C_6$)alkynyl, —$CH_2OR_7$, -phenyl, and -halo;
each $Z_3$ is independently selected from —H, —($C_1$-$C_6$)alkyl, —($C_2$-$C_6$)alkenyl, —($C_2$-$C_6$)alkynyl, and -phenyl;
each $Z_4$ is independently selected from —H, —OH, —$OR_{20}$, —($C_1$-$C_6$)alkyl, and —$N(R_{20})_2$;
each J is independently selected from —$OR_{20}$, —$SR_{20}$, —$N(R_{20})_2$, and —CN;

provided that at least one R₂ group is a group of formula Q;

each R₇ is independently selected from —H, —OH, —(C₁-C₆)alkyl, —(C₁-C₆)alkoxy, —(C₁-C₆)alkyl-(C₆-C₁₄)aryl, —O—(C₆-C₁₄)aryl, —(C₂-C₆)alkenyl, —(C₂-C₆)alkynyl, —(C₃-C₈)cycloalkyl, —(C₅-C₈)cycloalkenyl, -phenyl, -benzyl, —(C₁-C₆)alkyl-(C₁-C₆)alkoxy, —(C₁-C₆)haloalkyl, —(C₁-C₆)hydroxyalkyl, —(C₁-C₆)alkoxy(C₁-C₆)alkyl, —(C₁-C₆)alkyl-N(R₂₀)₂, —C(O)N(R₂₀)₂, -(3- to 7-membered)heterocycle, -(7- to 10-membered) bicycloheterocycle, —(C₆-C₁₄)bicycloalkyl, and —S(O)₂—(C₁-C₆)alkyl;

each R₈ and R₉ is independently selected from:
(a) —(C₁-C₆)alkyl, —(C₂-C₆)alkenyl, —(C₂-C₆)alkynyl, —(C₃-C₈)cycloalkyl, —(C₅-C₈)cycloalkenyl, and -phenyl, each of which is unsubstituted or substituted with 1 or 2-OH groups; and
(b) —H, —CH₂C(halo)₃, —C(halo)₃, —CH(halo)₂, —CH₂(halo), —OC(halo)₃, —OCH(halo)₂, —OCH₂(halo), —SC(halo)₃, —SCH(halo)₂, —SCH₂(halo), —CN, —O—CN, —OH, -halo, —N₃, —NO₂, —CH=NR₇, —N(R₇)₂, —NR₇OH, —OR₇, —C(O)R₇, —C(O)OR₇, —OC(O)R₇, —OC(O)OR₇, —SR₇, —S(O)R₇, and —S(O)₂R₇;

each R₁₁ is independently selected from —CN, —OH, —(C₁-C₆)alkyl, —(C₂-C₆)alkenyl, -halo, —N₃, —NO₂, —N(R₇)₂, —CH=NR₇, —NR₇OH, —OR₇, —C(O)R₇, —C(O)OR₇, —OC(O)R₇, and —OC(O)OR₇;

R₁₂ₐ and R₁₂ᵦ are each independently selected from —H and —(C₁-C₆)alkyl;

each R₁₄ is independently selected from —H, —(C₁-C₆)alkyl, —(C₂-C₆)alkenyl, —(C₂-C₆)alkynyl, —(C₃-C₈)cycloalkyl, —(C₅-C₈)cycloalkenyl, —(C₁-C₆)alkoxy, —(C₁-C₆)alkoxy-(C₁-C₆)alkyl, -phenyl, —C(halo)₃, —CH(halo)₂, —CH₂(halo), -(3- to 7-membered)heterocycle, -(5- to 10-membered)heteroaryl, —(C₁-C₆)haloalkyl, —(C₂-C₆)haloalkenyl, —(C₂-C₆)haloalkynyl, —(C₂-C₆)hydroxyalkenyl, —(C₂-C₆)hydroxyalkynyl, —(C₁-C₆)alkoxy-(C₂-C₆)alkenyl, —(C₁-C₆)alkoxy(C₂-C₆)alkynyl, —(C₁-C₆)alkoxy-(C₃-C₈)cycloalkyl, —CN, —OH, -halo, —OC(halo)₃, —N₃, —NO₂, —CH=NR₇, —N(R₇)₂, —NR₇OH, —OR₇, —SR₇, —O(CH₂)ᵦOR₇, —O(CH₂)ᵦSR₇, —O(CH₂)ᵦN(R₇)₂, —N(R₇)(CH₂)ᵦOR₇, —N(R₇)(CH₂)ᵦSR₇, —N(R₇)(CH₂)ᵦN(R₇)₂, —N(R₇)C(O)R₇, —N(R₇)—S(O)₂—(C₁-C₆)alkyl, —C(O)—N(R₇)₂, —C(O)R₇, —C(O)OR₇, —OC(O)R₇, —OC(O)OR₇, —S(O)R₇, —S(O)₂R₇, —S(O)₂N(R₇)₂, —S(O)₂—C(halo)₃, —S(O)₂-(3- to 7-membered)heterocycle, —C(O)N(R₇)₂, —(C₁-C₅)alkyl-C=NOR₇, —(C₁-C₅)alkyl-C(O)—N(R₇)₂, —(C₁-C₆)alkyl-NHS(O)₂N(R₇)₂, and —(C₁-C₆)alkyl-C(=NH)—N(R₇)₂;

each R₂₀ is independently selected from —H, —(C₁-C₆)alkyl, and —(C₃-C₈)cycloalkyl;

each R₂₁ is independently selected from —H, —(C₁-C₆)alkyl,

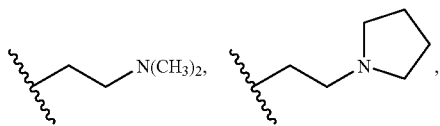

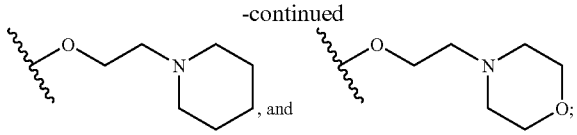, and each -halo is independently selected from —F, —Cl, —Br, and —I;
each b is independently selected from the integers 1 and 2;
n is the integer 1, 2, or 3;
p is the integer 1 or 2;
q is the integer 0, 1, 2, 3 or 4;
r is the integer 0, 1, 2, 3, 4, 5, or 6;
s is the integer 0, 1, 2, 3, 4, or 5;
t is the integer 1, 2, or 3;
u is the integer 1, 2, 3 or 4;
v is the integer 1, 2, 3 or 4; and
w is the integer 1, 2, 3, 4, or 5;
provided that when the R₃ group shown in formula I(d) is —H, and Ar₂ is substituted phenyl, then Q is not CH₂OH.

2. The compound of claim 1 or a pharmaceutically acceptable salt thereof, wherein n, p, or w is 1, and Q is:

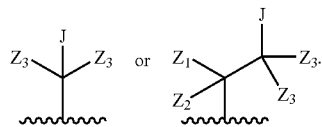

3. A compound of formula II(d):

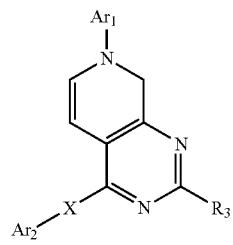

II(d)

or a pharmaceutically acceptable salt thereof, wherein
X is —O—, —N(R₂₀)—, —S—, —S(O)—, or —S(O)₂—;
R₃ is selected from:
(a) —H, —N₃, -halo, —NO₂, —CN, —P(O)(OH)₂, —S(O)₂(OH), —S(O)₂(O)—(C₁-C₆)alkyl, —SH, —OH, —C(O)OR₇, —C(halo)₃, —CH(halo)₂, and —CH₂(halo); and
(b) —(C₁-C₆)alkyl, —(C₁-C₆)alkoxy, —(C₃-C₈)cycloalkyl, —(C₂-C₆)alkenyl, —(C₂-C₆)alkynyl, —(C₆-C₁₄)aryl, —(C₁-C₆)alkyl-N(R₇)₂, —(C₁-C₆)heteroalkyl, -(5- to 10-membered)heterocycle, -(5- to 10-membered)heteroaryl, —(C₆-C₁₄)bicycloalkyl, —(C₁-C₆)thioalkoxy, —(C₁-C₆)alkyl-(C₁-C₆)alkoxy, —(C₁-C₆)alkyl-O—(C₆-C₁₄)aryl, —(C₁-C₆)alkyl-O—(C₃-C₈)cycloalkyl, —(C₁-C₆)alkyl-(3- to 7-membered)heterocycle, —(C₁-C₆)alkyl-(5- to 10-membered)heteroaryl, —(C₁-C₆)alkyl-N(R₇)₂, —N(R₇)₂, —N(R₇)—(C₁-C₆)alkyl-R₁₄, —S(O)—(C₁-C₆)alkyl, —O—(C₁-C₆)alkyl-R₁₄, —O—(C₁-C₆)alkyl-S(O)₂—R₁₄, O—(C₃-C₈)cycloalkyl, —OR₁₄, —SR₁₄, —O—(C₁-C₆)alkyl-O—R₁₄, —O—(C₁-C₆)alkyl-C(O)—N(R₇)—(C₁-C₆)alkyl- OR₇, —O—(C₁-C₆)alkyl-C(O)—R₁₄, —O—(C₁-C₆)alkyl-C(O)—N(R₇)₂, —C(O)R₁₄, —C(O)—(C₁-C₆)alkyl, —C(O)-(3- to 7-membered)heterocycle, —C(O)-(5- to 10-membered)heteroaryl, —C(O)O—(C₁-C₆)alkyl, —C(O)N(R₇)—(C₁-C₆)alkyl-(3- to 7-membered)heterocycle, —C(O)N(R₇)—(C₁-C₆)alkyl-(5- to 10-membered)heteroaryl, —C(O)N(R₇)₂, —OC(O)N(R₇)₂, —C(O)N(R₇)—(C₁-C₆)alkyl-N(R₇)₂, —C(O)N(R₇)—(C₁-C₆)alkyl-R₇, —S(O)₂—(C₁-C₆)alkyl, and —S(O)₂—N(R₇)₂, each of which can be unsubstituted or substituted with 1, 2, 3 or 4 independently selected R₁₄;

Ar₁ is:

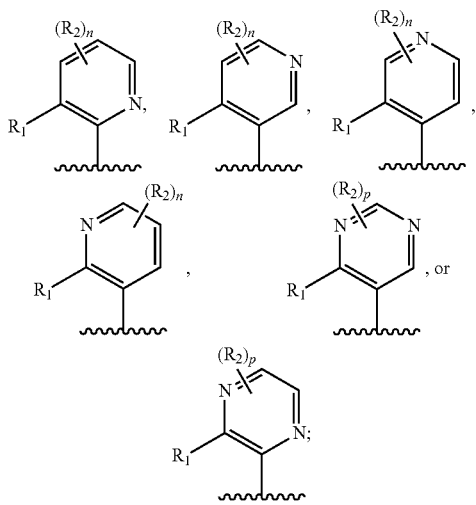

Ar₂ is:

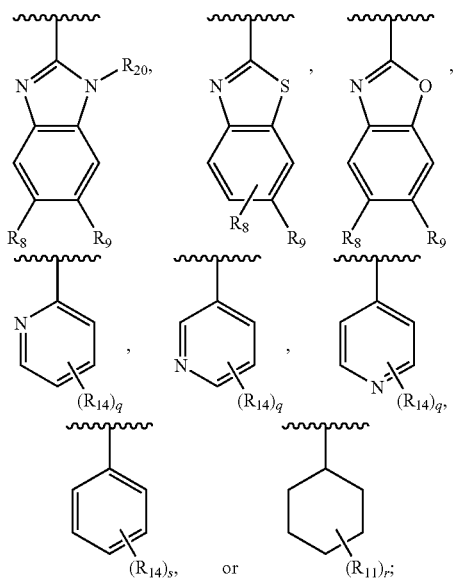

R₁ is —H, -halo, —(C₁-C₄)alkyl, —NO₂, —CN, —OH, —OCH₃, —NH₂, —C(halo)₃, —CH(halo)₂, —CH₂(halo), —OC(halo)₃, —OCH(halo)₂, —OCH₂(halo), or —S(O)₂—(C₁-C₆)alkyl;

each R₂ is independently selected from:
(a) -halo, —OH, —O(C₁-C₄)alkyl, —CN, —NO₂, —NH₂, —(C₁-C₁₀)alkyl, —(C₂-C₁₀)alkenyl, —(C₂-C₁₀)alkynyl, and -phenyl; and
(b) a group of formula Q, wherein Q is:

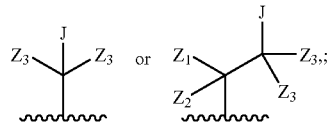

each Z₁ is independently selected from —H, —OR₇, —SR₇, —CH₂OR₇, —CH₂SR₇, —CH₂N(R₂₀)₂, and -halo;
each Z₂ is independently selected from —H, —(C₁-C₆)alkyl, —(C₂-C₆)alkenyl, —(C₂-C₆)alkynyl, —CH₂OR₇, -phenyl, and -halo;
each Z₃ is independently selected from —H, —(C₁-C₆)alkyl, —(C₂-C₆)alkenyl, —(C₂-C₆)alkynyl, and -phenyl;
each J is independently selected from —OR₂₀, —SR₂₀, —N(R₂₀)₂, and —CN;
provided that at least one R₂ group is a group of formula Q;
each R₇ is independently selected from —H, —OH, —(C₁-C₆)alkyl, —(C₁-C₆)alkoxy, —(C₁-C₆)alkyl-(C₆-C₁₄)aryl, —O—(C₆-C₁₄)aryl, —(C₂-C₆)alkenyl, —(C₂-C₆)alkynyl, —(C₃-C₈)cycloalkyl, —(C₅-C₈)cycloalkenyl, -phenyl, -benzyl, —(C₁-C₆)alkyl-(C₁-C₆)alkoxy, —(C₁-C₆)haloalkyl, —(C₁-C₆)hydroxyalkyl, —(C₁-C₆)alkoxy-(C₁-C₆)alkyl, —(C₁-C₆)alkyl-N(R₂₀)₂, —C(O)N(R₂₀)₂, -(3- to 7-membered)heterocycle, -(7- to 10-membered)bicycloheterocycle, —(C₆-C₁₄)bicycloalkyl, and —S(O)₂—(C₁-C₆)alkyl;
each R₈ and R₉ is independently selected from:
(a) —(C₁-C₆)alkyl, —(C₂-C₆)alkenyl, —(C₂-C₆)alkynyl, —(C₃-C₈)cycloalkyl, —(C₅-C₈)cycloalkenyl, and -phenyl, each of which is unsubstituted or substituted with 1 or 2 -OH groups; and
(b) —H, —CH₂C(halo)₃, —C(halo)₃, —CH(halo)₂, —CH₂(halo), —OC(halo)₃, —OCH(halo)₂, —OCH₂(halo), —SC(halo)₃, —SCH(halo)₂, —SCH₂(halo), —CN, —O—CN, —OH, -halo, —N₃, —NO₂, —CH═NR₇, —N(R₇)₂, —NR₇OH, —OR₇, —C(O)R₇, —C(O)OR₇, —OC(O)R₇, —OC(O)OR₇, —SR₇, —S(O)R₇, and —S(O)₂R₇;
each R₁₁ is independently selected from —CN, —OH, —(C₂-C₆)alkenyl, -halo, —N₃, —NO₂, —N(R₇)₂, —CH═NR₇, —NR₇OH, —OR₇, —C(O)R₇, —C(O)OR₇, —OC(O)R₇, and —OC(O)OR₇;
each R₁₄ is independently selected from —H, —(C₁-C₆)alkyl, —(C₂-C₆)alkenyl, —(C₂-C₆)alkynyl, —(C₃-C₈)cycloalkyl, —(C₅-C₈)cycloalkenyl, —(C₁-C₆)alkoxy, —(C₁-C₆)alkoxy-(C₁-C₆)alkyl, -phenyl, —C(halo)₃, —CH(halo)₂, —CH₂(halo), -(3- to 7-membered)heterocycle, -(5- to 10-membered)heteroaryl, —(C₁-C₆)haloalkyl, —(C₂-C₆)haloalkenyl, —(C₂-C₆)haloalkynyl, —(C₂-C₆)hydroxyalkenyl, —(C₂-C₆)hydroxyalkynyl, —(C₁-C₆)alkoxy(C₂-C₆)alkenyl, —(C₁-C₆)alkoxy(C₂-C₆)alkynyl, —(C₁-C₆)alkoxy(C₃-C₈)cycloalkyl, —CN, —OH, -halo, —OC(halo)₃, —N₃, —NO₂, —CH═NR₇, —N(R₇)₂, —NR₇OH, —OR₇, —SR₇, —O(CH₂)ᵦOR₇, —O(CH₂)ᵦSR₇, —O(CH₂)ᵦN(R₇)₂, —N(R₇)(CH₂)ᵦOR₇, —N(R₇)(CH₂)ᵦSR₇, —N(R₇)(CH₂)ᵦN(R₇)₂, —N(R₇)C(O)R₇, —N(R₇)—S(O)₂—

$(C_1-C_6)$alkyl, —C(O)—N$(R_7)_2$, —C(O)$R_7$, —C(O)O$R_7$, —OC(O)$R_7$, —OC(O)O$R_7$, —S(O)$R_7$, —S(O)$_2$$R_7$, —S(O)$_2$N$(R_7)_2$, —S(O)$_2$C(halo)$_3$, —S(O)$_2$(3- to 7-membered)heterocycle, —CON$(R_7)_2$, —$(C_1-C_5)$alkyl-C=NO$R_7$, —$(C_1-C_5)$alkyl-C(O)—N$(R_7)_2$, —$(C_1-C_6)$alkyl-N(H)S(O)$_2$N$(R_7)_2$, and —$(C_1-C_6)$alkyl-C(=NH)—N$(R_7)_2$;

each $R_{20}$ is independently selected from —H, —$(C_1-C_6)$alkyl, and —$(C_3-C_8)$cycloalkyl;

each $R_{21}$ is independently selected from —H, —$(C_1-C_6)$alkyl,

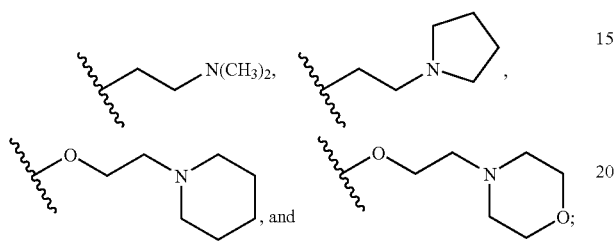

each -halo is independently selected from —F, —Cl, —Br, and —I;
each b is independently selected from the integers 1 and 2;
n is the integer 1, 2, or 3;
p is the integer 1 or 2;
q is the integer 0, 1, 2, 3 or 4;
r is the integer 0, 1, 2, 3, 4, 5, or 6; and
s is the integer 0, 1, 2, 3, 4, or 5;
provided that when $R_3$ is —H, and $Ar_2$ is substituted phenyl, then Q is not $CH_2OH$.

4. The compound of claim 3 or a pharmaceutically acceptable salt thereof, wherein the Q-group is selected from

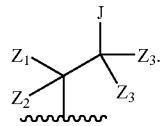

5. A compound of formula III(d):

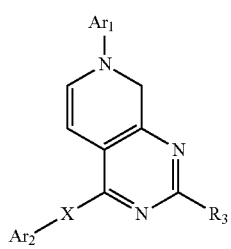

III(d)

or a pharmaceutically acceptable salt thereof, wherein
X is —N$(R_{20})$—;
$R_3$ is selected from:
(a) —H, —$N_3$, -halo, —$NO_2$, —CN, —P(O)(OH)$_2$, —S(O)$_2$(OH), —S(O)$_2$(O)—$(C_1-C_6)$alkyl, —SH, —OH, —COO$R_7$, —C(halo)$_3$, —CH(halo)$_2$, and —CH$_2$(halo); and
(b) —$(C_1-C_6)$alkyl, —$(C_1-C_6)$alkoxy, —$(C_3-C_8)$cycloalkyl, —$(C_2-C_6)$alkenyl, —$(C_2-C_6)$alkynyl, —$(C_6-C_{14})$aryl, —$(C_1-C_6)$alkyl-N$(R_7)_2$, —$(C_1-C_6)$heteroalkyl, -(3- to 7-membered)heterocycle, -(5- to 10-membered)heteroaryl, —$(C_6-C_{14})$bicycloalkyl, —$(C_1-C_6)$thioalkoxy, —$(C_1-C_6)$alkyl-$(C_1-C_6)$alkoxy, —$(C_1-C_6)$alkyl-O—$(C_6-C_{14})$aryl, —$(C_1-C_6)$alkyl-$R_7$, —$(C_1-C_6)$alkyl-O—$(C_3-C_8)$cycloalkyl, —$(C_1-C_6)$alkyl-(3- to 7-membered)-heterocycle, —$(C_1-C_6)$alkyl-(5- to 10-membered)heteroaryl, —$(C_1-C_6)$alkyl-N$(R_7)_2$, —N$(R_7)_2$, —N$(R_7)$—$(C_1-C_6)$alkyl-$R_{14}$, —S(O)—$(C_1-C_6)$alkyl, —O—$(C_1-C_6)$alkyl-$R_{14}$, —O—$(C_1-C_6)$alkyl-S(O)$_2$—$R_{14}$, O—$(C_3-C_8)$cycloalkyl, —O$R_{14}$, —S$R_{14}$, —O—$(C_1-C_6)$alkyl-O—$R_{14}$, —O—$(C_1-C_6)$alkyl-C(O)—N$(R_7)$—$(C_1-C_6)$alkyl-O$R_7$, —O—$(C_1-C_6)$alkyl-C(O)—$R_{14}$, —O—$(C_1-C_6)$alkyl-C(O)—N$(R_7)_2$, —C(O)$R_{14}$, —C(O)—$(C_1-C_6)$alkyl, —C(O)-(3- to 7-membered)heterocycle, —C(O)-(5- to 10-membered)heteroaryl, —C(O)O—$(C_1-C_6)$alkyl, —C(O)N$(R_7)$—$(C_1-C_6)$alkyl-(3- to 7-membered)heterocycle, —C(O)N$(R_7)$—$(C_1-C_6)$alkyl-(5- to 10-membered)heteroaryl, —C(O)N$(R_7)_2$, —OC(O)N$(R_7)_2$, —C(O)N$(R_7)$—$(C_1-C_6)$alkyl-N$(R_7)_2$, —C(O)N$(R_7)$—$(C_1-C_6)$alkyl-$R_7$, —S(O)$_2$—$(C_1-C_6)$alkyl, and —S(O)$_2$—N$(R_7)_2$, each of which can be unsubstituted or substituted with 1, 2, 3 or 4 independently selected $R_{14}$;

$Ar_1$ is:

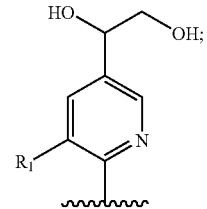

$Ar_2$ is:

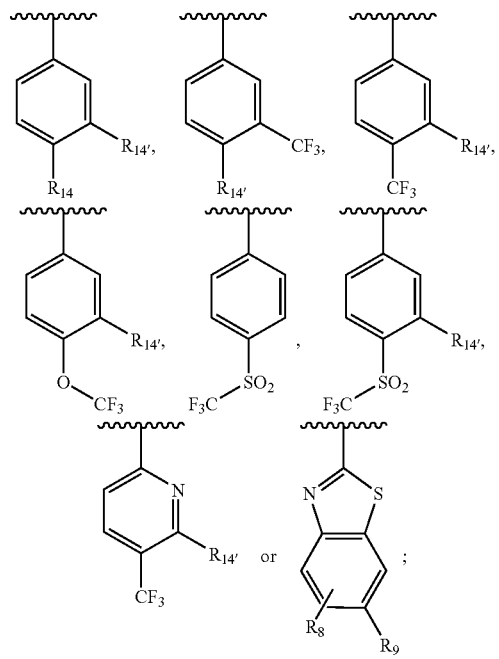

$R_1$ is —Cl, —F, —CH$_3$, —CF$_3$, or —OCF$_3$;

each $R_7$ is independently selected from —H, —OH, —(C$_1$-C$_6$)alkyl, —(C$_1$-C$_6$)alkoxy, —(C$_1$-C$_6$)alkyl-(C$_6$-C$_{14}$)aryl, —O—(C$_6$-C$_{14}$)aryl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, —(C$_1$-C$_6$)alkyl-(C$_1$-C$_6$)alkoxy, —(C$_1$-C$_6$)haloalkyl, —(C$_1$-C$_6$)hydroxyalkyl, —(C$_1$-C$_6$)—alkoxy(C$_1$-C$_6$)alkyl, —(C$_1$-C$_6$)alkyl-N(R$_{20}$)$_2$, —C(O)N(R$_{20}$)$_2$, -(3- to 7-membered)heterocycle, -(7- to 10-membered)bicycloheterocycle, —(C$_6$-C$_{14}$)bicycloalkyl, and —S(O)$_2$—(C$_1$-C$_6$)alkyl;

each $R_8$ and $R_9$ is independently selected from:
(a) —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, and -phenyl, each of which is unsubstituted or substituted with 1 or 2-OH groups; and
(b) —H, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —SC(halo)$_3$, —SCH(halo)$_2$, —SCH$_2$(halo), —CN, —O—CN, —OH, -halo, —N$_3$, —NO$_2$, —CH=NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, and —S(O)$_2$R$_7$;

each $R_{11}$ is independently selected from —CN, —OH, —(C$_1$-C$_6$)alkyl, —(C$_2$-C$_6$)alkenyl, -halo, —N$_3$, —NO$_2$, —N(R$_7$)$_2$, —CH=NR$_7$, —NR$_7$OH, —OR$_7$, —C(O)R$_7$, —C(O)OR$_7$, —OC(O)R$_7$, and —OC(O)OR$_7$;

each $R_{14}$ and $R_{14'}$ is independently selected from —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, —(C$_1$-C$_6$)alkoxy, —(C$_1$-C$_6$)alkoxy-(C$_1$-C$_6$)alkyl, -phenyl, —C(halo)$_3$, —CH(halo)$_2$, —CH$_2$(halo), -(3- to 7-membered)heterocycle, -(5- to 10-membered)heteroaryl, —(C$_1$-C$_6$)haloalkyl, —(C$_2$-C$_6$)haloalkenyl, —(C$_2$-C$_6$)haloalkynyl, —(C$_2$-C$_6$)hydroxyalkenyl, —(C$_2$-C$_6$)hydroxyalkynyl, —(C$_1$-C$_6$)alkoxy(C$_2$-C$_6$)alkenyl, —(C$_1$-C$_6$)alkoxy(C$_2$-C$_6$)alkynyl, —(C$_1$-C$_6$)alkoxy(C$_3$-C$_8$)cycloalkyl, —CN, —OH, -halo, —OC(halo)$_3$, —N$_3$, —NO$_2$, —CH=NR$_7$, —N(R$_7$)$_2$, —NR$_7$OH, —OR$_7$, —SR$_7$, —O(CH$_2$)$_b$OR$_7$, —O(CH$_2$)$_b$SR$_7$, —O(CH$_2$)$_b$N(R$_7$)$_2$, —N(R$_7$)(CH$_2$)$_b$OR$_7$, —N(R$_7$)(CH$_2$)$_b$SR$_7$, —N(R$_7$)(CH$_2$)$_b$N(R$_7$)$_2$, —N(R$_7$)C(O)R$_7$, —N(R$_7$)—S(O)$_2$—(C$_1$-C$_6$)alkyl, —C(O)—N(R$_2$)$_2$, —C(O)R$_7$, —C(O)OR$_7$, —OC(O)R$_7$, —OC(O)OR$_7$, —S(O)R$_7$, —S(O)$_2$R$_7$, —S(O)$_2$N(R$_7$)$_2$, —S(O)$_2$C(halo)$_3$, —S(O)$_2$(3- to 7-membered)heterocycle, —CON(R$_7$)$_2$, —(C$_1$-C$_5$)alkyl-C=NOR$_7$, —(C$_1$-C$_5$)alkyl-C(O)—N(R$_7$)$_2$, —(C$_1$-C$_6$)alkyl-NHS(O)$_2$N(R$_7$)$_2$, and —(C$_1$-C$_6$)alkyl-C(=NH)—N(R$_7$)$_2$;

each $R_{20}$ is independently selected from —H, —(C$_1$-C$_6$)alkyl, and —(C$_3$-C$_8$)cycloalkyl;

each $R_{21}$ is independently selected from —H, —(C$_1$-C$_6$)alkyl,

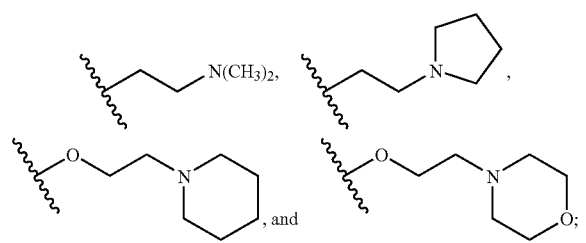

each -halo is independently selected from —F, —Cl, —Br, and —I; and each b is independently selected from the integers 1 and 2.

6. The compound of claim 2 or a pharmaceutically acceptable salt thereof, wherein Ar$_2$ is:

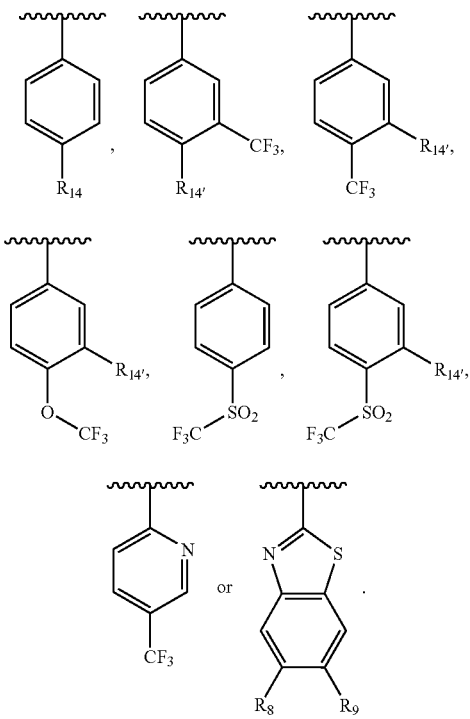

7. A composition comprising a compound of claim 1 or a pharmaceutically acceptable salt thereof and a pharmaceutically acceptable carrier or excipient.

8. The compound of claim 2 or a pharmaceutically acceptable salt thereof, wherein Ar$_2$ is:

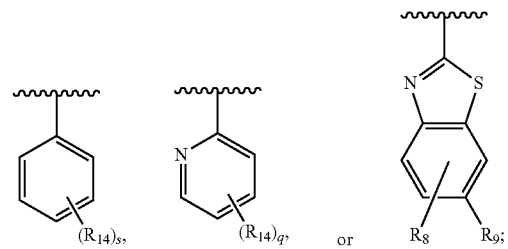

wherein $R_8$ and $R_9$ are independently selected from —H, -halo, and (C$_1$-C$_6$)alkyl;

each $R_{14}$ is independently selected from -halo, —C(halo)$_3$, —(C$_1$-C$_6$)alkyl, —OR$_7$, —OC(halo)$_3$, and —S(O$_2$)C(halo)$_3$; and s or q is 1 or 2.

9. The compound of claim 4 or a pharmaceutically acceptable salt thereof, wherein Ar$_2$ is:

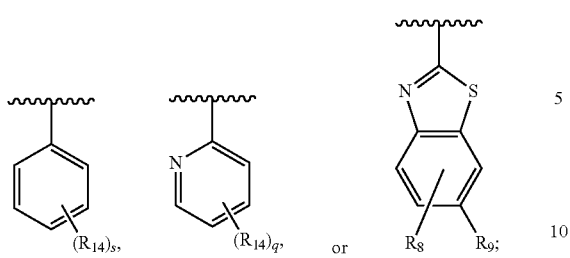

wherein $R_8$ and $R_9$ are independently selected from —H, -halo, and —$(C_1$-$C_6)$alkyl;

each $R_{14}$ is independently selected from -halo, —C(halo)$_3$, —$(C_1$-$C_6)$alkyl, —OR$_7$, —OC(halo)$_3$, and —S(O$_2$)C(halo)$_3$; and s or q is 1 or 2.

10. The compound of claim 5 or a pharmaceutically acceptable salt thereof, wherein $R_{20}$ is H and Ar$_2$ is:

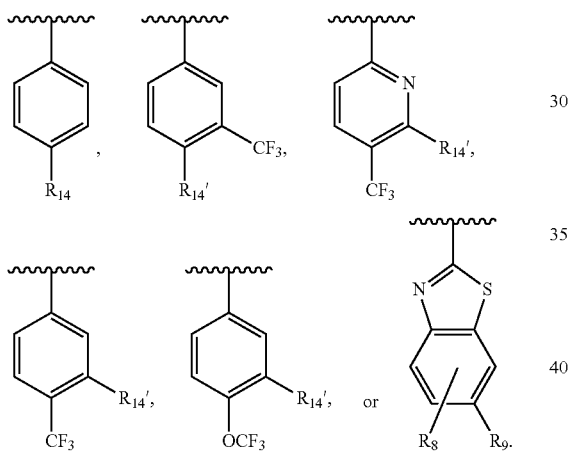

11. The compound of claim 1 or a pharmaceutically acceptable salt thereof, wherein Q is:

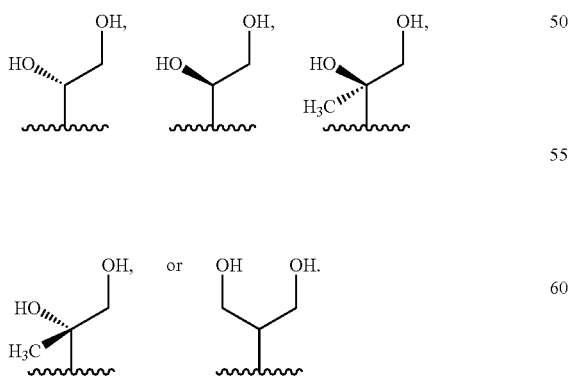

12. The compound of claim 11 or a pharmaceutically acceptable salt thereof, wherein Ar$_2$ is:

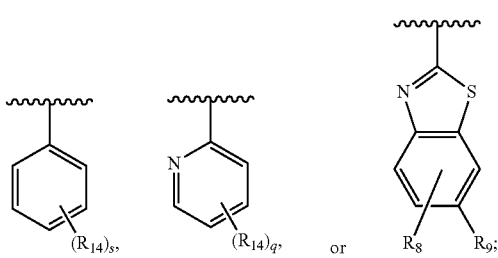

wherein $R_8$ and $R_9$ are independently selected from —H, -halo, and —$(C_1$-$C_6)$alkyl;

each $R_{14}$ is independently selected from -halo, —C(halo)$_3$, —$(C_1$-$C_6)$alkyl, —OR$_7$, —OC(halo)$_3$, and —S(O$_2$)C(halo)$_3$; and s or q is 1 or 2.

13. The compound of claim 1 or a pharmaceutically acceptable salt thereof, wherein Q is:

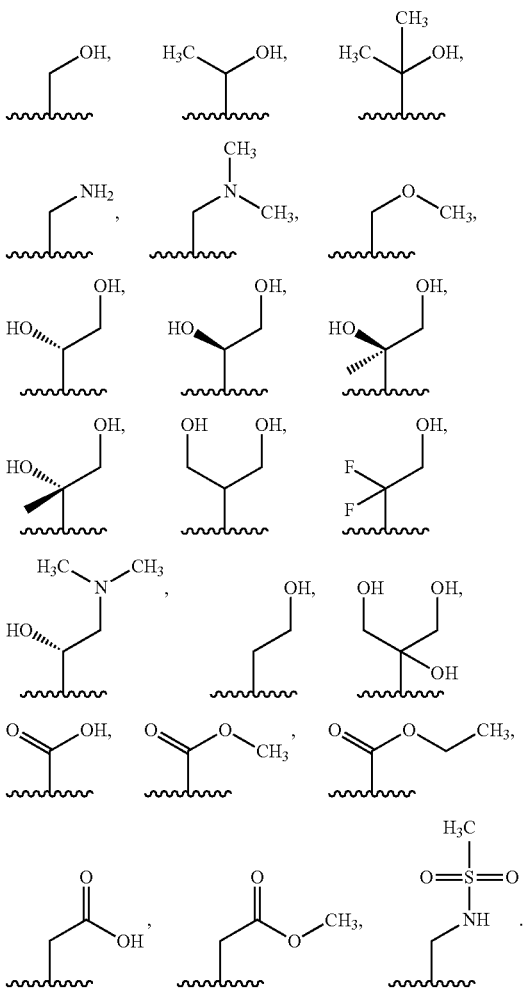

14. The compound of claim 13 or a pharmaceutically acceptable salt thereof, wherein Ar$_2$ is:

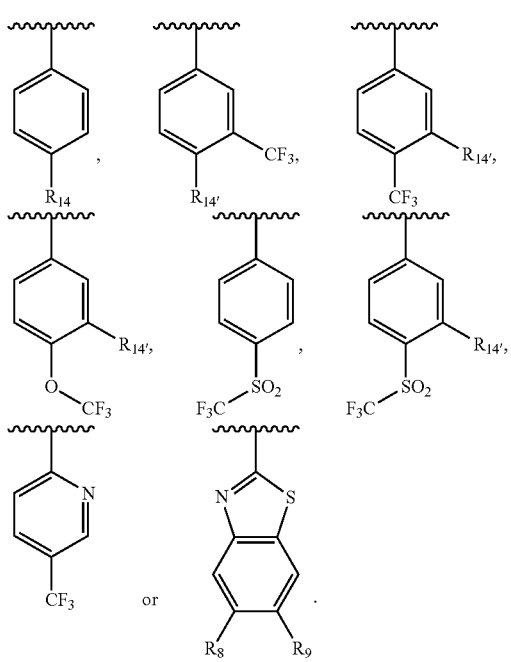

15. The compound of claim 2 or a pharmaceutically acceptable salt thereof, wherein Q is:

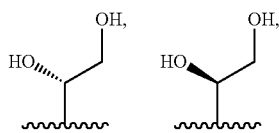 [SMILES: *[C@H](O)CO ; *[C@@H](O)CO]

or a mixture thereof.

16. The compound of claim 6 or a pharmaceutically acceptable salt thereof, wherein Q is:

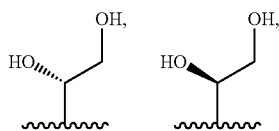

or a mixture thereof.

17. The compound of claim 8 or a pharmaceutically acceptable salt thereof, wherein Q is:

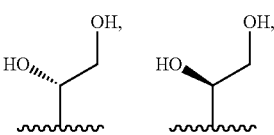 [SMILES: *[C@H](O)CO ; *[C@@H](O)CO]

or a mixture thereof.

18. The compound of claim 4 or a pharmaceutically acceptable salt thereof, wherein Q is:

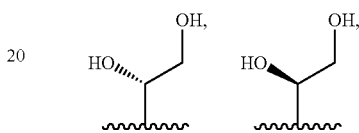

or a mixture thereof.

19. The compound of claim 9 or a pharmaceutically acceptable salt thereof, wherein Q is:

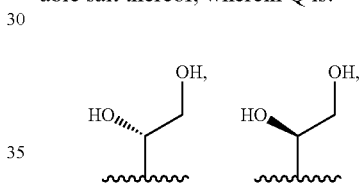

or a mixture thereof.

20. A composition comprising a compound of claim 3 or a pharmaceutically acceptable salt thereof and a pharmaceutically acceptable carrier or excipient.

21. A composition comprising a compound of claim 5 or a pharmaceutically acceptable salt thereof and a pharmaceutically acceptable carrier or excipient.

\* \* \* \* \*